US012558329B2

(12) United States Patent
Banh et al.

(10) Patent No.: US 12,558,329 B2
(45) Date of Patent: Feb. 24, 2026

(54) METHODS AND COMPOSITIONS FOR TREATING 4-HYDROXYPHENYLPYRUVATE DIOXYGENASE-LIKE (HPDL)-RELATED DISEASES OR DISORDERS

(71) Applicant: New York University, New York, NY (US)

(72) Inventors: Robert Banh, New York, NY (US); Michael Pacold, New York, NY (US); Quentin Spillier, New York, NY (US); Guangbin Shi, Mineola, NY (US)

(73) Assignee: NEW YORK UNIVERSITY, New York, NY (US)

( * ) Notice: Subject to any disclaimer, the term of this patent is extended or adjusted under 35 U.S.C. 154(b) by 397 days.

(21) Appl. No.: 18/273,397

(22) PCT Filed: Jan. 19, 2022

(86) PCT No.: PCT/US2022/012952
§ 371 (c)(1),
(2) Date: Jul. 20, 2023

(87) PCT Pub. No.: WO2022/159473
PCT Pub. Date: Jul. 28, 2022

(65) Prior Publication Data

US 2024/0130987 A1 Apr. 25, 2024

Related U.S. Application Data

(60) Provisional application No. 63/226,495, filed on Jul. 28, 2021, provisional application No. 63/139,559, filed on Jan. 20, 2021.

(51) Int. Cl.

| | |
|---|---|
| ***A61K 31/192*** | (2006.01) |
| ***A61K 31/11*** | (2006.01) |
| ***A61K 31/122*** | (2006.01) |
| ***A61K 31/375*** | (2006.01) |
| ***A61K 45/06*** | (2006.01) |
| ***C07B 59/00*** | (2006.01) |
| ***C12Q 1/6883*** | (2018.01) |
| ***G01N 33/574*** | (2006.01) |
| ***G01N 33/68*** | (2006.01) |

(52) U.S. Cl.
CPC ............ *A61K 31/192* (2013.01); *A61K 31/11* (2013.01); *A61K 31/122* (2013.01); *A61K 31/375* (2013.01); *A61K 45/06* (2013.01); *C07B 59/008* (2013.01); *C12Q 1/6883* (2013.01); *G01N 33/57438* (2013.01); *G01N 33/6848* (2013.01); *C07B 2200/05* (2013.01); *C12Q 2600/106* (2013.01); *C12Q 2600/156* (2013.01); *G01N 2333/90241* (2013.01); *G01N 2800/52* (2013.01)

(58) Field of Classification Search
CPC .... A61K 31/192; A61K 31/11; A61K 31/122; A61K 31/375
USPC .......................................................... 514/570
See application file for complete search history.

(56) References Cited

U.S. PATENT DOCUMENTS

| | | | |
|---|---|---|---|
| 8,114,775 | B2 | 2/2012 | Siddiqui et al. |
| 2008/0249030 | A1 | 10/2008 | Potier et al. |
| 2009/0170105 | A1 | 7/2009 | Kornman et al. |
| 2022/0251295 | A1 | 8/2022 | Patel et al. |

FOREIGN PATENT DOCUMENTS

| | | | |
|---|---|---|---|
| WO | 201004775 | A2 | 4/2010 |
| WO | 2022159473 | A1 | 7/2022 |
| WO | 2023/168053 | A2 | 9/2023 |
| WO | 2024105203 | A1 | 5/2024 |
| WO | 2025015136 | A1 | 1/2025 |
| WO | 2025137572 | A1 | 6/2025 |

OTHER PUBLICATIONS

International Search Report and Written Opinion mailed Nov. 15, 2023 in connection with PCT/US2023/14468.

Ye et al., "4-Hydroxyphenylpyruvate Dioxygenase-Like Protein Promotes Pancreatic Cancer Cell Progression and Is Associated With Glutamine-Mediated Redox Balance," Front. Oncol. 2021. 10:617190, 14 p. especially: abstract: p. 3, Figure 1.

Benzel et al., "Chemoprevention and Treatment of Pancreatic Cancer: Update and Review of the Literature," Digestion. 2018. 97: pp. 275-287, especially: p. 282, col. 1, para 5.

El-Shahawy et al., "DFT-Comparison of Anti-Cancer Effect of Ibuprofen Drug Anions and Breast Cancer Treatment by Ethanolic Solution of Nitrobenzaldehyde in Two Hours," Computational Chemistry. 2017. 5, pp. 9-21, especially: p. 10, para 2.

(Continued)

*Primary Examiner* — Raymond J Henley, III
(74) *Attorney, Agent, or Firm* — Troutman Pepper Locke LLP

(57) ABSTRACT

Various methods and compositions of treating 4-hydroxyphenylpyruvate dioxygenase-like (HPDL)-related diseases or disorders are presented herein. Also presented herein are methods of increasing CoQ10 biosynthesis, and methods of determining whether a subject will benefit from a CoQ10 or CoQ10 alternative treatment. Also presented herein are pharmaceutical compositions and dosage forms comprising 4-hydroxymandelic acid (4-HMA), and/or its metabolites. Further presented herein are compounds that inhibit 4-hydroxyphenylpyruvate dioxygenase-like (HPDL). Further presented herein are methods of identifying and/or assessing modulators of HPDL. Yet further presented herein are example methods and systems for isotopic labelling in cells by metabolizing cells in the presence of gaseous isotopic tracer.

14 Claims, 108 Drawing Sheets

Specification includes a Sequence Listing.

(56) References Cited

OTHER PUBLICATIONS

Banh et al., "The Polar Oxy-metabolome Reveals the 4-Hydroxymandelate CoQ10 Synthesis Pathway," Nature, (2021) 597(7876):420-425, entire document.

Ghosh et al., "Biallelic Variants in HPDL, Encoding 4-Hydroxyphenylpyruvate Dioxygenase-Like Protein, Lead to an Infantile Neurodegenerative Condition," Genet Med 23, 524-533, doi: 10.1038/s41436-020-01010-y (2021).

Morgan et al., "Evidence That Autosomal Recessive Spastic Cerebral Palsy-1 (CPSQ1) is Caused by a Missense Variant in HPDL," Brain Commun. 3, fcab002, doi:10.1093/braincomms/fcab002 (2021).

Husain et al., "Bi-allelic HPDL Variants Cause a Neurodegenerative Disease Ranging from Neonatal Encephalopathy to Adolescent-Onset Spastic Paraplegia," Am. J. Hum. Genet. 107:364-373, doi:10.1016/j.ajhg.2020.06.015 (2020).

International Search Report and Written Opinion mailed Oct. 23, 2024 in connection with PCT/US2024/037534.

Pubchem, SID 43898548, Modify Date: Dec. 5, 2007 [retrieved on Aug. 22, 2024]., Retrieved from the Internet <url: https:="" pubchem. ncbi.nlm.nih.gov="" substance="" 43898548=""> entire document</url:>.

Pubchem, SID 187564854, Modify Date: Oct. 4, 2017 [retrieved on Aug. 19, 2024]., Retrieved from the Internet <URL:https://pubchem.ncbi/nlm.nih.gov/substance/187564854>entire document.

International Search Report and Written Opinion mailed Apr. 15, 2025 in connection with PCT/US2024/061461.

Herebian et al., "4-Hydroxybenzoic Acid Restores CoQ10 Biosynthesis Inhuman COQ2 Deficiency," Annals of Clinical and Translational Neurology 4(12):902-908 (2017).

PCT International Application No. PCT/US25/13344, filed Jan. 28, 2025.

PCT International Application No. PCT/US25/20495, filed Mar. 19, 2025.

International Search Report and Written Opinion mailed Jun. 14, 2022 in connection with International Application No. PCT/US2022/12952.

Mendes et al., "Proteomic, metabolic and immunological changes in Biomphalaria glabrata Infected with Schistosoma mansoni", International Journal of Parasitology, 2019, 49, pp. 1049-1060, especially: p. 1053, col. 1, para 4.

O'Hare et al., "Conversion of hydroxyphenylpyruvate dioxigenases into hydroxymandelate synthases by directed evolution", FEBS Letters, 2006, 580, pp. 3445-3450, especiallly: p. 2445, col. 2, para 2, p. 3446, Fig 1.

Gallo et al., "From Microbial Proteomics to Synthetic Biology: Amycolatopsis balhimycina case" Chemical Engineering Transactions, 2012, 27, 7 pages, especially: p. 5, Table 1, row 1; p. 6, Figure 2, Scheme.

Stefely et al., "Mitochondrial protein functions elucidated by multiomic mass spectrometry profiling", Nat Biotechnol, 2016, 34(11): pp. 1191-1197, especially: p. 22, Figure 2, 4-HPP, 4-hydroxyphenylpyruvate.

Awad et al., "Coenzyme Q10 deficiencies: pathways in yeast and humans", Essays in Biochemistry, 2018, 62 pp. 361-376, especially: p. 361, para 2: p. 363 Figure 1.

Banh et al, "The Polar Oxy-metabolome Reveals the 4-Hydroxymandelate CoQ10 Synthesis Pathway", Nature, Sep. 2021: 597 (7876): pp. 420-425, entire document.

4-hydroxymandelate

FIG. 5G

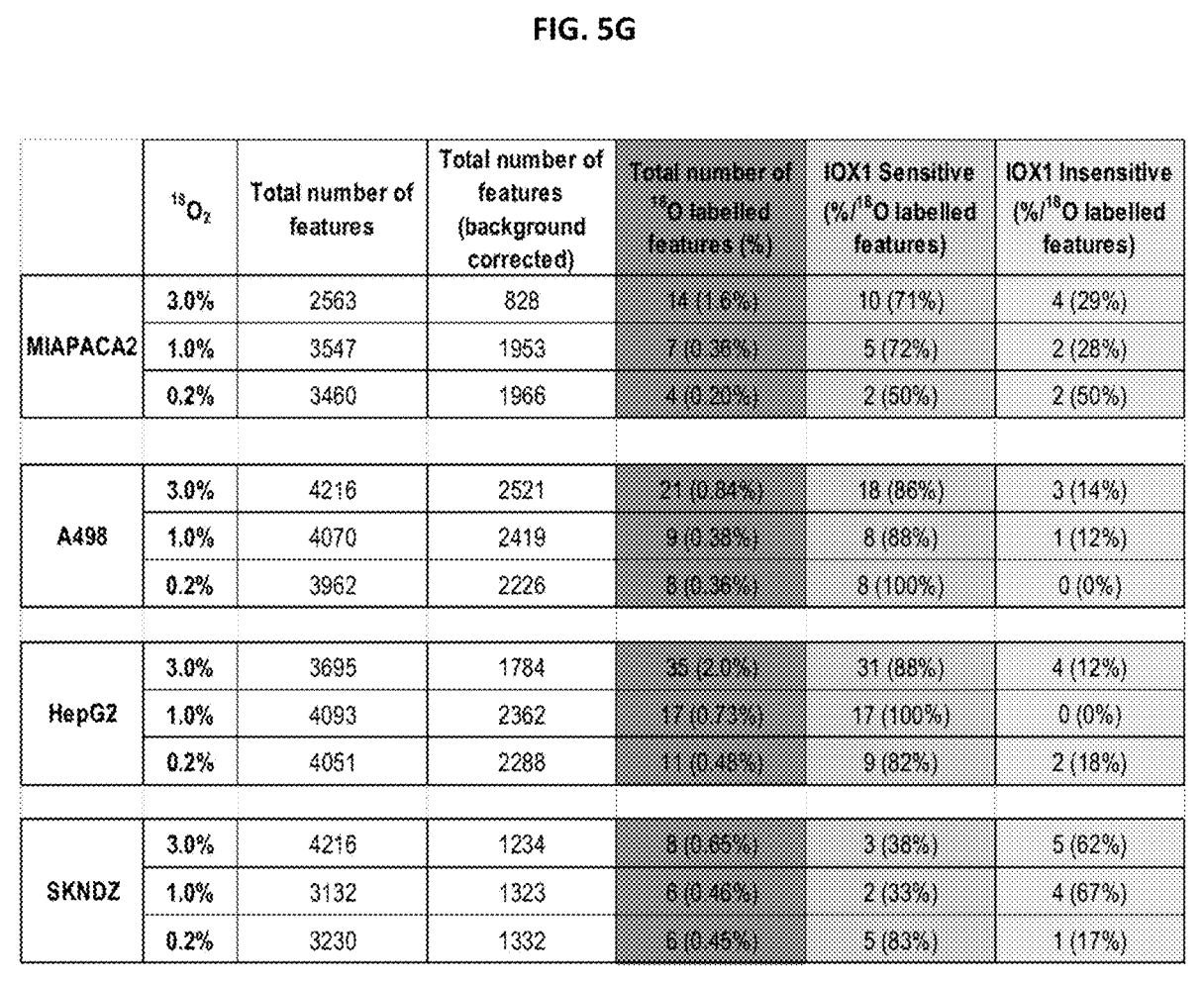

| | $^{18}O_2$ | Total number of features | Total number of features (background corrected) | Total number of $^{18}O$ labelled features (%) | IOX1 Sensitive (%/$^{18}O$ labelled features) | IOX1 Insensitive (%/$^{18}O$ labelled features) |
|---|---|---|---|---|---|---|
| MIAPACA2 | 3.0% | 2563 | 828 | 14 (1.6%) | 10 (71%) | 4 (29%) |
| | 1.0% | 3547 | 1953 | 7 (0.36%) | 5 (72%) | 2 (28%) |
| | 0.2% | 3460 | 1966 | 4 (0.20%) | 2 (50%) | 2 (50%) |
| | | | | | | |
| A498 | 3.0% | 4216 | 2521 | 21 (0.84%) | 18 (86%) | 3 (14%) |
| | 1.0% | 4070 | 2419 | 9 (0.38%) | 8 (88%) | 1 (12%) |
| | 0.2% | 3962 | 2226 | 8 (0.36%) | 8 (100%) | 0 (0%) |
| | | | | | | |
| HepG2 | 3.0% | 3695 | 1784 | 35 (2.0%) | 31 (88%) | 4 (12%) |
| | 1.0% | 4093 | 2362 | 17 (0.73%) | 17 (100%) | 0 (0%) |
| | 0.2% | 4051 | 2288 | 11 (0.48%) | 9 (82%) | 2 (18%) |
| | | | | | | |
| SKNDZ | 3.0% | 4216 | 1234 | 8 (0.65%) | 3 (38%) | 5 (62%) |
| | 1.0% | 3132 | 1323 | 6 (0.46%) | 2 (33%) | 4 (67%) |
| | 0.2% | 3230 | 1332 | 6 (0.45%) | 5 (83%) | 1 (17%) |

Trimethyllysine

Hydroxy-trimethyllysine

γ-Butyrobetaine

Carnitine

Methionine

Methionine Sulfoxide

Methionine Sulfone

Known and Proposed
4-Hydroxymandelate Biosynthesis Pathways

FIG. 10C

Protein Sequence Alignment

Conserved catalytic histidine

```
H.Sapiens HPD/1-393        1 MTTYSDKGAKPERGRFLHFHSVTFWVGNAKQAASFYCSKMGFEPLA-Y  47
A. orientalis HmaS/1-357   1 MQN-------------FEIDYVEMYVENLEVAAFSWVDKYAFAVAGTS  35
H.Sapiens HPDL/1-371       1 MAA-------PA----LRLCHIAFHVPAGQPLARNLQRLFGFQPLA-S  36

H.Sapiens HPD/1-393       48 RGLETGSREVVSHVIKQGKIVFVLSSALNPWNKEMGDHLVKHG-DGVK  94
A. orientalis HmaS/1-357  36 RSAD--HRSI---ALRQGQVTLVLTEPTSDRHPAAA-YLQTHG-DGVA  76
H.Sapiens HPDL/1-371      37 REVD-GWRQL---ALRSGDAVFLVNEGAGSGEPLYG-LDPRHAVPSAT  79

H.Sapiens HPD/1-393       95 DIAFEVEDCDYIVQKARERGAKIMREPWVEQDKFGKVKFAVLQT-YGD 141
A. orientalis HmaS/1-357  77 DIAMATSDVAAAYEAAVRAGAEAVRAP--GQHSEAAVTTATIGG-FGD 121
H.Sapiens HPDL/1-371      80 NLCFDVADAGAATRELAALGCSVPVPPVRVRDAQGAATYAVVSSPAGI 127

H.Sapiens HPD/1-393      142 TTHTLVEKMNYIGQFLPGYEAPAFMDPLLPKLPKCSLEMIDHIVGNQP 189
A. orientalis HmaS/1-357 122 VVHTLIQRDGTSAELPPGFTGS--MDVTNHGKGDVDLLGIDHFAICLN 167
H.Sapiens HPDL/1-371     128 LSLTLLERAGYRGPFLPGFRPV----SSAPGPGWS--RVDHLTLACT 169

H.Sapiens HPD/1-393      190 DQEMVSASEWYLKNLQFHRFWSV--DDTQVHTEYSS------LRSIVV 229
A. orientalis HmaS/1-357 168 AGDLGPTVEYYERALGFRQIF-----DEHIVVGAQA------MNSTVV 204
H.Sapiens HPDL/1-371      170 PGSSPTLLRWFHDCLGFCHLPLSPGEDPELGLEMTAGFGLGGLRLTAL 217

H.Sapiens HPD/1-393      230 ANYEESI--KMPINE--PAPGKKKSQIQEYVDYNGGAGVQHIALKTED 273
A. orientalis HmaS/1-357 205 QSASGAV--TL[illegible]L[illegible]E--PDRNADPGQIDEFLKDHQGAGVQHIAFNSND 248
H.Sapiens HPDL/1-371      218 QAQPGSIVPTLVLAESLPGATTRQDQVEQFLARHKGPGLQHVGLYTPN 265

H.Sapiens HPD/1-393      274 IITAIRHLRERGLEFLSVPSTYYKQLREKLKTAKIKVKENIDALEELK 321
A. orientalis HmaS/1-357 249 AVRAVKALSERGVEFLKTPGAYYDLLGERITLQ---THSLDDLRATN 292
H.Sapiens HPDL/1-371      266 IVEATEGVATAGGQFLAPPGAYYQQPGKERQIR--AAGHEPHLLARQG 311

H.Sapiens HPD/1-393      322 ILVDYDEKGYLLQIFTKPVQDRPTLFLEVIQRHNHQGFGAGNFNSLFK 369
A. orientalis HmaS/1-357 293 VLADEDHGGQLFQIFTASTHPRHTIFFEVIERQGAGTFGSSN[illegible]KALYE 340
H.Sapiens HPDL/1-371      312 ILLDGDKGKFLLQVFTKSLFTEDTFFLELIQRQGATGFGQGN[illegible]RALWQ 359

H.Sapiens HPD/1-393      370 AFEEEQNLRGNLTNMETNGVVPGM 393
A. orientalis HmaS/1-357 341 AVELERTGQSEFGAARR------- 357
H.Sapiens HPDL/1-371      360 SVQ-EQSARSQEA----------- 371
```

L-4HMA ((S)-2-hydroxy-2-(4-hydroxyphenyl)acetic acid)

D-4HMA ((R)-2-hydroxy-2-(4-hydroxyphenyl)acetic acid)

Nitisinone docking on HPDL homology model (Arabidopsis)

Sulcotrione docking on HPDL homology model (Arabidopsis)

IOX1 derivatives and scaffold

IOX1

Derivative 1

Derivative 2

Derivative 3

IOX1

-R1 should be H donnor
-R2 could be carboxylic acid, tetrazole
-Green aromatic can be replace (1, 2)
-IOX1 can be extended in R3, R4, R5 and R6 positions Derivative 4

Derivative5

Derivative 6

FIG. 22B

Nitisinone derivatives and scaffold

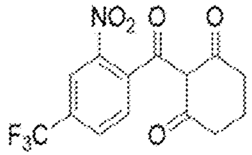

Nitisinone

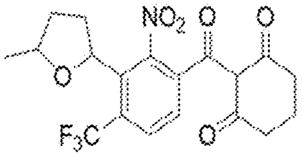

Derivative 1

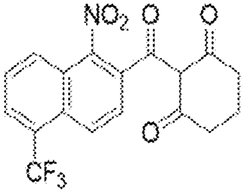

Derivative 2

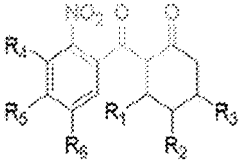

-Green part should remain or be replaced by chelator motifs or H acceptors
-R1 should be a H acceptor
-R2, R3, R5 and R6 can be slightly extended but nothing bigger than a 6 members ring
-No cyclisation allowed between R1 and the aromatic cycle
-R4 is the most promising position in order to extend the molecule (with preferentially non lipophilic motif)

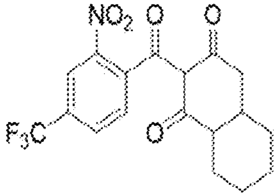

Derivative 3

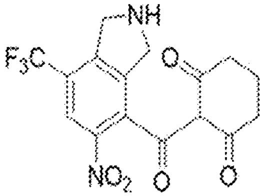

Derivative 4

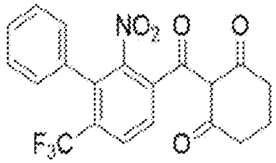

Derivative 5

FIG. 22C

Sulcotrione derivatives and scaffold

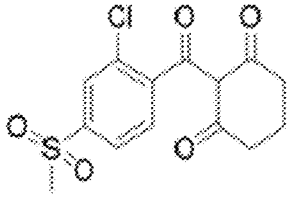

Sulcotrione

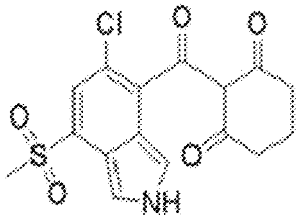

Derivative 1

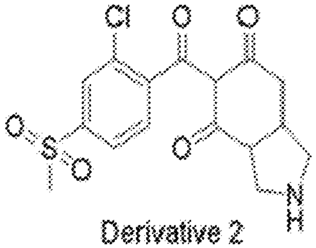

Derivative 2

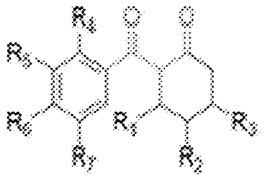

*Modifications similar to* *Nitisinone*

-Green part should remain or be replaced by chelator motifs or H acceptors

-R1 should be a H acceptor

-R2, R3, R6 and R7 can be slightly extended but nothing bigger than a 6 members ring -R4 can be extended to interact with a hydrophilic area -R5 can be slightly extended to interact with a lipophilic area

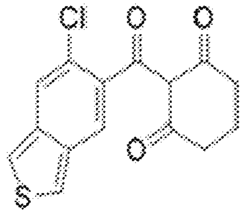

Sulcotrione

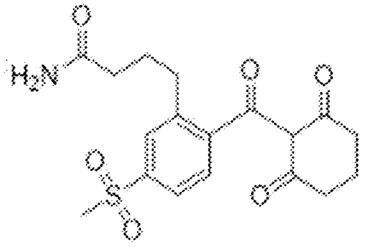

Derivative 1

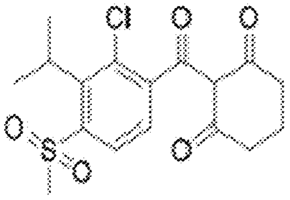

Derivative 2

Postpartum Day 29

Treat Day 21

METHODS AND COMPOSITIONS FOR TREATING 4-HYDROXYPHENYLPYRUVATE DIOXYGENASE-LIKE (HPDL)-RELATED DISEASES OR DISORDERS

STATEMENT REGARDING FEDERALLY SPONSORED RESEARCH OR DEVELOPMENT

This invention was made with government support under CA212059 awarded by the National Institutes of Health. The government has certain rights in the invention.

CROSS-REFERENCE TO RELATED APPLICATIONS

This patent application is a U.S. National Phase Application under 37 U.S.C. § 371 of International Application No. PCT/US22/12952, filed Jan. 19, 2022, which claims priority to U.S. Provisional Application No. 63,226,495, filed Jul. 28, 2021, and U.S. Provisional Application No. 63,139,559, filed Jan. 20, 2021, the disclosure of each of which is herein incorporated by reference in its entirety.

SEQUENCE LISTING

The instant application contains a Sequence Listing which has been submitted electronically in ASCII format and is hereby incorporated by reference in its entirety. Said ASCII copy, created on Jan. 17, 2022, is named 243735_000236_SL.txt and is 15,510 bytes in size.

FIELD OF THE INVENTION

Various aspects of the present invention relate to methods and compositions for the treating 4-hydroxyphenylpyruvate dioxygenase-like (HPDL)-related diseases or disorders. Some aspects of the present invention relate to methods of treating pancreatic cancer, methods of determining effectiveness of a treatment for pancreatic cancer, and methods of predicting prognosis of pancreatic cancer. Some aspects of the present invention relate to compounds that inhibit HPDL. Further aspects of the present invention relate to methods of identifying and/or assessing modulators of HPDL. Yet further aspects of the present invention relate to pharmaceutical compositions comprising 4-hydroxymandelic acid (4-HMA), methods of producing 4-HMA, and methods of using such compositions for the treatment of related diseases. Yet further aspects of the present invention relate to systems and methods for controlling gas composition in hermetically sealed chamber, and more specifically to controlling gas composition within the sealed chamber while a living animal and/or cells are contained therein.

BACKGROUND

Pancreatic ductal adenocarcinoma (PDAC) has a 5-year survival rate of 9%. No new targets for this disease have been discovered in the last 5 years. There is an urgent need for new therapeutics for this disease. Pancreatic cancers are amongst the most hypoxic of cancers, with oxygen tensions as low as 0.1% (for comparison, the ambient oxygen tension is 21%).

Gaseous oxygen ($O_2$) is essential for cellular respiration, the production of reactive oxygen species (ROS), and the activity of oxygen-dependent enzymes, such as dioxygenases. Oxygen-utilizing enzymes are essential for sensing, regulatory, and biosynthetic processes that are critical for cell growth and survival. Although the necessity of oxygen in sustaining life has been known since the late 1700s, the scope of oxygen-dependent processes in mammalian cells remains unknown as there are no established methods for systematically identifying the targets of oxygen or any other labelled gas in mammalian cells. Identification of the targets and site-specific modifications of ROS and measuring the activity of oxygen-dependent enzymes in a systematic manner using direct mass spectrometric methods, would reveal these fundamental oxygen-dependent processes and novel biology.

Coenzyme Q (CoQ) is an essential component of eukaryotic cells. It plays an important role in mitochondrial ATP synthesis and functions as an antioxidant in mitochondrial membranes. It is also involved in the biosynthesis of pyrimidines and the modulation of apoptosis. CoQ10 requires more than ten genes for its biosynthesis. Mutations in these genes cause primary CoQ10 deficiency, a clinically and genetically heterogeneous disorder. Deficiency of CoQ10 is also associated with a number of human diseases and age-related chronic conditions such as, but not limited to, metabolic syndrome and diabetes, neurodegenerative disorders, cardiovascular diseases, and human fertility[41-42]. Because the pharmacokinetics of CoQ10 are not well understood and it is not clear how much orally ingested CoQ10 is actually absorbed, alternative therapies to CoQ10 supplementation are needed.

Cerebral palsy (CP) is a progressive and disabling neurodevelopmental disease of childhood, with an incidence as high as 4 in 1000 live births. Although CP was initially thought to be due to hypoxia at birth, it is now thought to be mostly due to pre-natal insults, and up to 50% of cases have no known cause. Recently, it has been found that inherited disorders can present with CP, which is consistent with consanguinity as a risk factor for CP.

Mutations in 4-hydroxyphenylpyruvate dioxygenase (HPDL) that segregate with a spastic neurodevelopmental disorder with similarities to cerebral palsy[37-40]. These mutations have not been functionally characterized but are thought to inactivate HPDL, as at least some of them are missense mutations that result in decreased expression of the protein. An HPDL knockout mouse[37] recapitulates the phenotype of the disease.

As such, there is an unmet need for novel therapeutics for the treatment of pancreatic cancer, or for the treatment of diseases or disorders associated with CoQ10 deficiency and/or others that result from variations in the HPDL gene, including cerebral palsy. There is also a need for improved methods that allow isotopic labelling of oxygen or any other gas in cells.

SUMMARY OF THE INVENTION

In one aspect, provide herein is a method of treating a 4-hydroxyphenylpyruvate dioxygenase-like (HPDL)-related disease or disorder in a subject in need thereof, comprising administering to the subject a therapeutically effective amount of 4-hydroxymandelic acid (4-HMA), or a metabolite, pharmaceutically acceptable salt, prodrug, solvate, hydrate, or combinations thereof. In some embodiments, the metabolite is 4-hydroxybenzoylformate (4-HBF), 4-hydroxybenzaldehyde (4-HBz), 4-hydroxybenzoate (4-TB), and/or CoQ10.

In another aspect, provide herein is a method of increasing CoQ10 biosynthesis in a subject in need thereof, comprising administering to the subject a therapeutically effective amount of 4-hydroxymandelic acid (4-HMA), or a metabolite, pharmaceutically acceptable salt, prodrug, solvate, hydrate, or combinations thereof. In some embodiments, the metabolite is 4-hydroxybenzoylformate (4-HBF), 4-hydroxybenzaldehyde (4-HBz), or 4-hydroxybenzoate (4-HB).

In various embodiments of the methods described above, the 4-HMA is enantioentriched (R)-4-HMA. In some embodiments, the enantioentriched (R)-4-HMA has enantiomeric excess (ee) of at least about 20%, or at least about 30%, or at least about 40%, or at least about 50%, or at least about 60%, or at least about 70%, or at least about 80%, or at least about 85%, or at least about 90%, or at least about 95%, or at least about 98%, or at least about 99%. In various embodiments, the 4-HMA is enantiopure (R)-4-HMA.

In various embodiments of the methods described above, the method further comprises administering to the subject a therapeutically effective amount of an activator of HPDL. In some embodiments, the activator of HPDL is vitamin C, or a pharmaceutically acceptable salt, prodrug, solvate, or hydrate thereof.

In one aspect, provide herein is a method of treating a 4-hydroxyphenylpyruvate dioxygenase-like (HPDL)-related disease or disorder in a subject in need thereof, comprising administering to the subject a therapeutically effective amount of an activator of HPDL. In some embodiments, the activator of HPDL is vitamin C, or a pharmaceutically acceptable salt, prodrug, solvate, or hydrate thereof.

In various embodiments of the methods described above, the subject has one or more mutations in the HPDL gene. The one or more mutations in the HPDL gene may result in reduced or abolished activity and/or expression of the HPDL protein. In some embodiments, the one or more mutations in the HPDL gene is bi-allelic.

In some embodiments, the one or more mutations the HPDL gene may be selected from p. Leu176Pro (c.527 T>C; rs773333490), p.Ala78Thr, p.Gly126Ser, p.Leu164Pro, p.Gly301Val, p.Gly50Asp (c.149G>A), p.Trp157Arg (c.469T>C), p.Cys168Tyr (c.503G>A), p.Trp179Cys (c.537G>C), p.Leu217Pro (c.650T>C), p.Leu234Pro (c.701T>C), p.Leu248Pro (c.743T>C), p.His251Gln (c.753C>A), p.Gly260Glu (c.779G>A), p.Ile266Thr (c.797T>C), p.Tyr287His (c.859T>C), p.His163Ala, p.His258Ala, p.Gly319Argfs*15, p.Gln32*, p.Glu94Serfs*37 (c.280del). p.Ala115Cysfs*82 (c.342_343insTGCC), p.Leu234Glyfs*94 (c.698_699insTGGGCCAGCATTGTCCCCACTCTTGTTCTGGCTGAGTC (SEQ ID NO: 23)), p.Gln241* (c.721C>T), and p.Gln342* (c.1024C>T).

In various embodiments of the methods described above, the subject has one or more mutations in additional gene(s) involved in CoQ10 headgroup synthesis. The one or more mutations in additional gene(s) involved in CoQ10 headgroup synthesis may result in reduced or abolished activity and/or expression of the protein produced by said gene(s). In some embodiments, the additional gene(s) involved in CoQ10 headgroup synthesis is Tyrosine Aminotransferase (TAT), Lactate Dehydrogenase D (LDHD), D-2-Hydroxyglutarate Dehydrogenase (D2HGDH), Aldehyde Dehydrogenase 3 Family Member A1 (ALDH3A1), 4-hydroxybenzoate polyprenyltransferase, mitochondrial, (COQ2), Ubiquinone biosynthesis monooxygenase COQ6, mitochondrial (COQ6), Ubiquinone biosynthesis O-methyltransferase, mitochondrial (COQ3), 2-methoxy-6-polyprenyl-1,4-benzoquinol methylase, mitochondrial (COQ5), 5-demethoxyubiquinone hydroxylase, mitochondrial (COQ7), and/or Ubiquinone biosynthesis O-methyltransferase, mitochondrial (COQ3). In some embodiments, the one or more mutations in additional gene(s) involved in CoQ10 headgroup synthesis are selected from LDHD mutations Arg370Trp, Thr463Met, Trp376Cys; D2HGDH mutations Val444Ala, Ile147Ser, c.293-23A>G (IVS1AS, A-G, -23), c.685-2A>G (IVS4AS, A-G, -2), Asn439Asp, 326dupTC, Asp375Tyr; COQ2 mutations Tyr297Cys, Arg197His, Asn228Ser, Ser146Asn, Met128Val, Val393Ala, Arg387Ter, Arg387Gln, 1198delT; COQ5 mutation 9.6-kb Dup; and COQ7 mutation Val141Glu.

In some embodiments, the method further comprises detecting in a biological sample obtained from the subject the presence of the one or more mutations in the HPDL gene or additional gene(s) involved in CoQ10 headgroup synthesis prior to said administration. The biological sample may comprise peripheral blood mononuclear cells; or is a biopsy specimen. When the subject is a pregnant female and the unborn fetus is suspected to have a 4-hydroxyphenylpyruvate dioxygenase-like (HPDL)-related disease or disorder, or defective CoQ10 biosynthesis, the biological sample may be a fetal DNA sample. The fetal DNA sample can be obtained via any methods known to a skilled artisan, for example, by isolation of circulating fetal DNA, chorionic villus sampling, and/or amnioscentesis.

In some embodiments, the detection of one or more mutations in the HPDL gene or additional gene(s) involved in CoQ10 headgroup synthesis is conducted by sequencing of said gene(s) or immunohistochemistry (IHC) of the protein(s) produced by said gene(s).

In another aspect, provided herein is a method of determining whether a subject will benefit from a treatment with 4-hydroxymandelic acid (4-HMA), or a metabolite, pharmaceutically acceptable salt, prodrug, solvate, hydrate, or combinations thereof, comprising:

a) detecting the presence of one or more mutations in the HPDL gene and/or additional gene(s) involved in CoQ10 headgroup synthesis in a biological sample obtained from the subject, wherein the one or more mutations result in reduced or abolished activity and/or expression of the protein produced by said gene(s); and b) (i) determining that the subject will benefit from said treatment, when the one or more mutations are present in the HPDL gene and/or additional gene(s) involved in CoQ10 headgroup synthesis; or (ii) determining that the subject will not benefit from said treatment, when the one or more mutations are absent in the HPDL gene and/or additional gene(s) involved in CoQ10 headgroup synthesis.

In another aspect, provided herein is a method of treating a 4-hydroxyphenylpyruvate dioxygenase-like (HPDL)-related disease or disorder in a subject in need thereof, comprising:

a) detecting the presence of one or more mutations in the HPDL gene and/or additional gene(s) involved in CoQ10 headgroup synthesis in a biological sample obtained from the subject, wherein the one or more mutations result in reduced or abolished activity and/or expression of the protein(s) produced by said gene(s); and b) when the one or more mutations are present in the HPDL gene and/or additional gene(s) involved in CoQ10 headgroup synthesis, administering to the subject a therapeutically effective amount of 4-hydroxymandelic acid (4-HMA), or a metabolite, pharmaceutically acceptable salt, prodrug, solvate, hydrate, or combinations thereof.

In some embodiments of the method described above, when the one or more mutations are absent in the HPDL gene and/or additional gene(s) involved in CoQ10 headgroup synthesis, the method comprise not administering 4-hydroxymandelic acid (4-HMA), or a metabolite, pharmaceutically acceptable salt, prodrug, solvate, hydrate, or combinations thereof, to the subject.

In some embodiments of the methods described above, the metabolite is 4-hydroxybenzoylformate (4-HBF), 4-hydroxybenzaldehyde (4-HBz), 4-hydroxybenzoate (4-HB), and/or CoQ10.

In another aspect, provided herein is a method of increasing CoQ10 biosynthesis in a subject in need thereof, comprising:

a) detecting the presence of one or more mutations in the HPDL gene and/or additional gene(s) involved in CoQ10 headgroup synthesis in a biological sample obtained from the subject, wherein the one or more mutations result in reduced or abolished activity and/or expression of the protein produced by said gene(s), and/or reduced CoQ10 biosynthesis; and b) when the one or more mutations are present in the HPDL gene and/or additional gene(s) involved in CoQ10 headgroup synthesis, administering to the subject a therapeutically effective amount of 4-hydroxymandelic acid (4-HMA), or a metabolite, pharmaceutically acceptable salt, prodrug, solvate, hydrate, or combinations thereof.

In some embodiments of the method described above, when the one or more mutations are absent in the HPDL gene and/or additional gene(s) involved in CoQ10 headgroup synthesis, the method comprise not administering 4-hydroxymandelic acid (4-HMA), or a metabolite, pharmaceutically acceptable salt, prodrug, solvate, hydrate, or combinations thereof, to the subject.

In some embodiments of the method described above, the metabolite is 4-hydroxybenzoylformate (4-HBF), 4-hydroxybenzaldehyde (4-HBz), or 4-hydroxybenzoate (4-HB).

In some embodiments of the methods described above, the 4-HMA is enantioentriched (R)-4-HMA. In some embodiments, the enantioentriched (R)-4-HMA has enantiomeric excess (ee) of at least about 20%, or at least about 30%, or at least about 40%, or at least about 50%, or at least about 60%, or at least about 70%, or at least about 80%, or at least about 85%, or at least about 90%, or at least about 95%, or at least about 98%, or at least about 99%. In some embodiments, the 4-HMA is enantiopure (R)-4-HMA.

In some embodiments of the methods described above, the method further comprises administering to the subject a therapeutically effective amount of an activator of HPDL. In some embodiments, the activator of HPDL is vitamin C, or a pharmaceutically acceptable salt, prodrug, solvate, or hydrate thereof.

In another aspect, provided herein is a method of treating a 4-hydroxyphenylpyruvate dioxygenase-like (HPDL)-related disease or disorder in a subject in need thereof, comprising a) detecting the presence of one or more mutations in the HPDL gene and/or additional gene(s) involved in CoQ10 headgroup synthesis in a biological sample obtained from the subject, wherein the one or more mutations result in reduced or abolished activity and/or expression of the protein produced by said gene(s); and b) when the one or more mutations are present in the HPDL gene and/or additional gene(s) involved in CoQ10 headgroup synthesis, administering to the subject a therapeutically effective amount of an activator of HPDL.

In some embodiments of the method described above, when the one or more mutations are absent in the HPDL gene and/or additional gene(s) involved in CoQ10 headgroup synthesis, the method comprise not administering 4-hydroxymandelic acid (4-HMA), or a metabolite, pharmaceutically acceptable salt, prodrug, solvate, hydrate, or combinations thereof, to the subject.

In some embodiments, the activator of HPDL is vitamin C, or a pharmaceutically acceptable salt, prodrug, solvate, or hydrate thereof.

In various embodiments of the methods described above, the one or more mutations in the HPDL gene is bi-allelic.

In various embodiments of the methods described above, the one or more mutations in the HPDL gene is selected from p. Leu176Pro (c.527 T>C; rs773333490), p.Ala78Thr, p.Gly126Ser, p.Leu164Pro, p.Gly301Val, p.Gly50Asp (c.149G>A), p.Trp157Arg (c.469T>C), p.Cys168Tyr (c.503G>A), p.Trp179Cys (c.537G>C), p.Leu217Pro (c.650T>C), p.Leu234Pro (c.701T>C), p.Leu248Pro (c.743T>C), p.His251Gln (c.753C>A), p.Gly260Glu (c.779G>A), p.Ile266Thr (c.797T>C), p.Tyr287His (c.859T>C), p.His163Ala, p.His258Ala, p.Gly319Argfs*15, p.Gln32*, p.Glu94Serfs*37 (c.280del). p.Ala115Cysfs*82 (c.342_343insTGCC), p.Leu234Glyfs*94 (c.698_699insTGGGCCAGCATTGTCCCCACTCTTGTTCTGGCTGAGTC (SEQ ID NO: 23)), p.Gln241* (c.721C>T), and p.Gln342* (c.1024C>T).

In various embodiments of the methods described above, the additional gene(s) involved in CoQ10 headgroup synthesis is Tyrosine Aminotransferase (TAT), Lactate Dehydrogenase D (LDHD), D-2-Hydroxyglutarate Dehydrogenase (D2HGDH), Aldehyde Dehydrogenase 3 Family Member A1 (ALDH3A1), 4-hydroxybenzoate polyprenyltransferase, mitochondrial, (COQ2), Ubiquinone biosynthesis monooxygenase COQ6, mitochondrial (COQ6), Ubiquinone biosynthesis O-methyltransferase, mitochondrial (COQ3), 2-methoxy-6-polyprenyl-1,4-benzoquinol methylase, mitochondrial (COQ5), 5-demethoxyubiquinone hydroxylase, mitochondrial (COQ7), and/or Ubiquinone biosynthesis O-methyltransferase, mitochondrial (COQ3). In some embodiments, the one or more mutations are selected from LDHD mutations Arg370Trp, Thr463Met, Trp376Cys; D2HGDH mutations Val444Ala, Ile147Ser, c.293-23A>G (IVS1AS, A-G, -23), c.685-2A>G (IVS4AS, A-G, -2), Asn439Asp, 326dupTC, Asp375Tyr; COQ2 mutations Tyr297Cys, Arg197His, Asn228Ser, Ser146Asn, Met128Val, Val393Ala, Arg387Ter, Arg387Gln, 1198delT; COQ5 mutation 9.6-kb Dup; and COQ7 mutation Val141Glu.

In various embodiments of the methods described above, the detection of one or more mutations in the HPDL gene or additional gene(s) involved in CoQ10 headgroup synthesis is conducted by sequencing of said gene(s) or immunohistochemistry (IHC) of the protein produced by said gene(s).

In various embodiments of the methods described above, the biological sample comprises peripheral blood mononuclear cells, or a biopsy specimen.

In various embodiments of the methods described above, the subject is a pregnant female, and the biological sample is a fetal DNA sample. The fetal DNA sample may be obtained by circulating fetal DNA analysis, chorionic villus sampling, or amnioscentesis.

In various embodiments of the methods described above, the HPDL-related disease or disorder is a neurodegenerative or psychiatric disease, aging, obesity, cachexia, chronic fatigue syndrome, cardiac disease, immune deficiency, vitamin deficiency or infertility.

In some embodiments, the HPDL-related disease or disorder is a childhood neurodegenerative disease. In some embodiments, the childhood neurodegenerative disease is cerebral palsy, mitochondrial disease, neonatal encephalopathy, adolescent-onset spastic paraplegia, or pure and complicated hereditary spastic paraplegia. In one embodiment, the HPDL-related disease or disorder is cerebral palsy.

In some embodiments, the HPDL-related disease or disorder is an adult neurodegenerative disease. In some embodiments, the adult neurodegenerative disease is Alzheimer's disease or Parkinson's disease.

In some embodiments, the psychiatric disease is schizophrenia, major depressive disorder, or bipolar disorder.

In some embodiments, the cardiac disease is myocardial infarction or heart failure.

In some embodiments, the vitamin deficiency is scurvy.

In various embodiments of the methods described above, the subject is a mammal. In some embodiments, the subject is a human. In some embodiments, the subject is a child, including an unborn fetus, a newborn, an infant, or a toddler. In some embodiments, the subject is an adult. In some embodiments, treating an unborn fetus using methods described herein may involve treating a pregnant female carrying the unborn fetus. Accordingly, the subject can be a pregnant female and the one or more mutations in the HPDL gene and/or additional gene(s) involved in CoQ10 head-group synthesis can be present in the fetal DNA derived from the pregnant female.

In another aspect, provided herein is a method of inhibiting expression of 4-hydroxyphenylpyruvate dioxygenase-like (HPDL) in a subject in need thereof, comprising administering to the subject a therapeutically effective amount of (S)-4-HMA, or a metabolite, pharmaceutically acceptable salt, prodrug, solvate, hydrate, or combinations thereof.

In another aspect, provided herein is a method of treating a pancreatic cancer in a subject in need thereof, comprising the following steps:

a) determining expression level of 4-hydroxyphenylpyruvate dioxygenase-like (HPDL) in a sample obtained from the subject;
b) comparing the HPDL expression level determined in step (a) with a control level of HPDL expression; and
c) administering an effective amount of (S)-4-HMA, or a metabolite, pharmaceutically acceptable salt, prodrug, solvate, hydrate, or combinations thereof, to the subject exhibiting a higher level of HPDL expression as compared to the control level.

In some embodiments of the method described above, the sample comprises circulating tumor cells.

In some embodiments, the control level of HPDL expression is determined in normal tissue from the same subject, a sample from a normal subject, or is a predetermined value.

In some embodiments, the expression level of HPDL is determined by determining the level of 4-HMA in the sample.

In another aspect, presented herein is a method of treating a pancreatic cancer in a subject in need thereof, comprising the following steps:

a) determining expression level of 4-hydroxyphenylpyruvate dioxygenase-like (HPDL) in a sample obtained from the subject;
b) comparing the HPDL expression level determined in step (a) with a control level of HPDL expression; and
c) administering an effective amount of an HPDL inhibitor to the subject exhibiting a higher level of HPDL expression as compared to the control level.

In some embodiments, the sample is a tumor sample. In some embodiments, the sample is a fluid sample. In some embodiments, the sample comprises circulating tumor cells.

In some embodiments, the control level of HPDL expression is determined in normal tissue from the same subject, a sample from a normal subject, or is a predetermined value. In some embodiments, the expression level of HPDL is determined by determining the level of 4-HMA in the sample (e.g., in a fluid sample).

In some embodiments, the HPDL inhibitor is a small molecule, an antibody or antibody fragment, an siRNA, an shRNA, an antisense oligonucleotide, a site-specific nuclease, or a degron (e.g., a small molecule conjugated to a degrader).

In some embodiments, the small molecule is a compound having the structure of Formula (I):

(I)

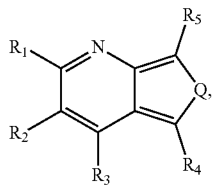

or a pharmaceutically acceptable salt thereof, wherein:

Q is selected from —O—, —NH—, and

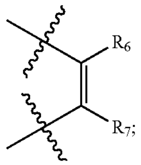

$R_1$, $R_2$, and $R_3$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of which optionally contains 1-8 heteroatoms selected from halogen, O, N, and S; —OH, =O, —$CO_2H$, —$NO_2$, —$NH_2$, —NHR*, —$NR^*_2$, —N—OH, —$HSO_3$, —$H_2PO_3$, —OR*, —(C=O)—R*, —$CO_2R^*$, —CO—$NH_2$, —CO—NHR*, —$SO_2$—NHR*, or adjacent two moieties combine to form a fused ring which may optionally contain 1-3 heteroatoms selected from halogen, O, N, and S and which may be further substituted by one or more R*;

$R_4$ and $R_5$ are independently selected from —OH and —$CO_2H$;

$R_6$ and $R_7$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of which optionally contains 1-8 heteroatoms selected from halogen, O, N, and S; —OH, =O, —$CO_2H$, —$NO_2$, —$NH_2$, —NHR*, —$NR^*_2$, —N—OH, —$HSO_3$, —$H_2PO_3$, —OR*, —(C=O)—R*, —$CO_2R^*$, —CO—$NH_2$, —CO—NHR*, —$SO_2$—NHR*, or $R_6$ and $R_7$ combine to form a fused ring, and R* is independently selected at each occurrence from hydrogen or $C_1$-$C_{12}$ hydrocarbons each of which optionally contains 1-8 heteroatoms selected from halogen, O, N, and S and combinations thereof.

In some embodiments, wherein when Q is

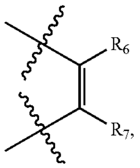

at least one of $R_1$, $R_2$, and $R_3$ is not H.

In some embodiments, the compound has the structure of Formula (IA):

(IA)

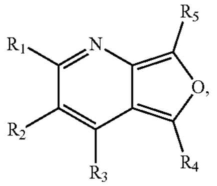

or a pharmaceutically acceptable salt thereof.

In some embodiments, the compound has the structure of Formula (IB):

(IB)

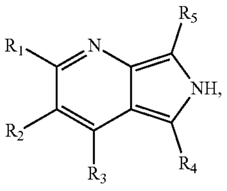

or a pharmaceutically acceptable salt thereof.

In some embodiments, the compound has the structure of Formula (IC):

(IC)

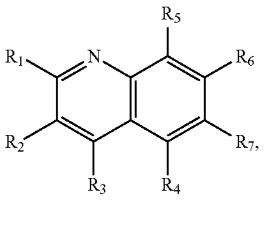

or a pharmaceutically acceptable salt thereof.

In some embodiments, the compound has the structure of Formula (ID):

(ID)

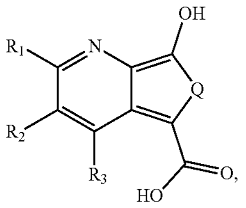

or a pharmaceutically acceptable salt thereof, wherein Q is —O— or —NH—.

In some embodiments, the compound has the structure of Formula (IE):

(IE)

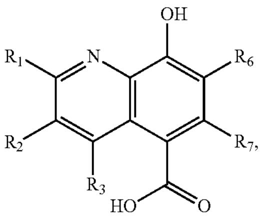

or a pharmaceutically acceptable salt thereof.

In some embodiments, the compound having the structure of Formula (I) is selected from the group consisting of:

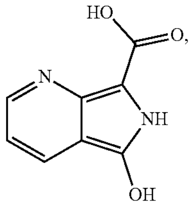

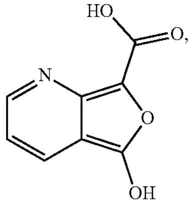

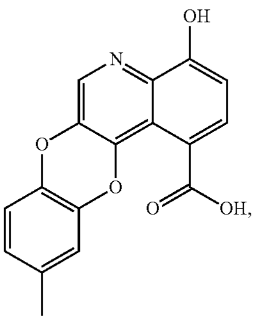

-continued

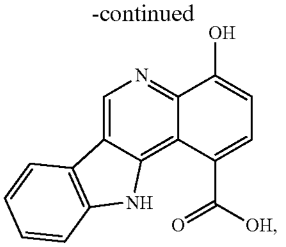

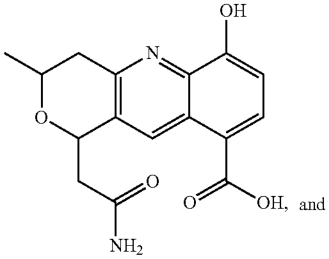

and

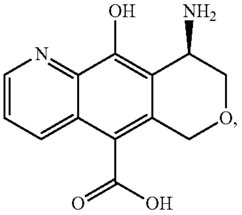

or a pharmaceutically acceptable salt thereof.

In some embodiments, the small molecule is a compound having the structure of Formula (II):

(II)

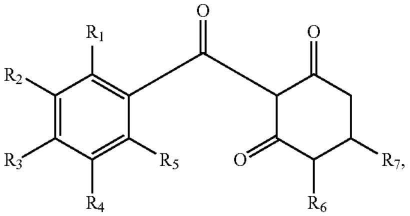

or a pharmaceutically acceptable salt thereof, wherein:

$R_1$ is selected from —$NO_2$, —Cl, and a $C_{1-12}$ alkyl which may be optionally substituted with one or more of —OH, =O, —$CO_2H$, —$NO_2$, —$NH_2$, —NHR*, —$NR*_2$, —N—OH, —$HSO_3$, —$H_2PO_3$, —OR*, —(C=O)—R*, —$CO_2R*$, —CO—$NH_2$, —CO—NHR*, and —$SO_2$—NHR*;

$R_2$, $R_3$, $R_4$, $R_5$, $R_6$ and $R_7$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of which optionally contains 1-8 heteroatoms selected from halogen, O, N, and S; —OH, =O, —$CO_2H$, —$NO_2$, —$NH_2$, —NHR*, —$NR*_2$, —N—OH, —$HSO_3$, —$H_2PO_3$, —OR*, —(C=O)—R*, —$CO_2R*$, —CO—$NH_2$, —CO—NHR*, —$SO_2R*$, —$SO_2$—NHR*, or adjacent two moieties combine to form a fused ring which may optionally contain 1-3 heteroatoms selected from halogen, O, N, and S and which may be further substituted by one or more R*, and R* is independently selected at each occurrence from hydrogen or $C_1$-$C_{12}$ hydrocarbons each of which optionally contains 1-8 heteroatoms selected from halogen, O, N, and S and combinations thereof.

In some embodiments, the compound does not have the structure selected from

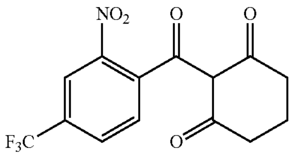

and (nitisinone)

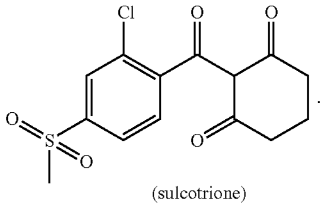

(sulcotrione)

In some embodiments, the compound has the structure of Formula (IIA):

(IIA)

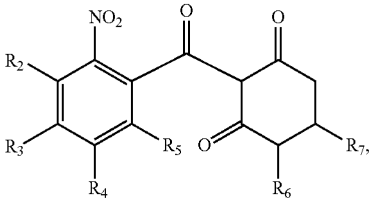

or a pharmaceutically acceptable salt thereof.

In some embodiments, the compound has the structure of Formula (IIB):

(IIB)

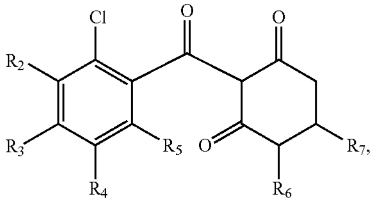

or a pharmaceutically acceptable salt thereof.

In some embodiments, $R_1$ is a $C_{1-12}$ alkyl substituted with one or more of —OH, =O, —$CO_2H$, —$NO_2$, —$NH_2$, —NHR*, —$NR*_2$, —N—OH, —$HSO_3$, —$H_2PO_3$, —OR*, —(C=O)—R*, —$CO_2R*$, —CO—$NH_2$, —CO—NHR*, and —$SO_2$—NHR*.

In some embodiments, the compound having the structure of Formula (II) is selected from the group consisting of:

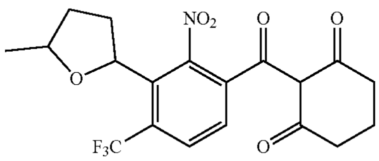
,
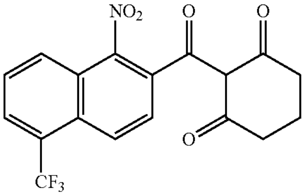
,
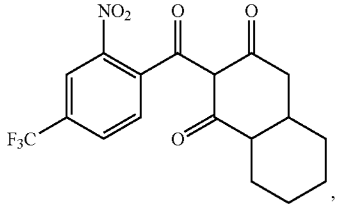
,
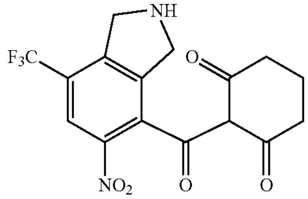
, and
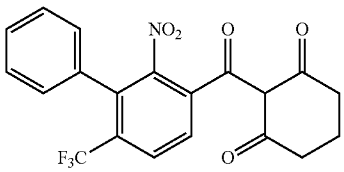
, or a pharmaceutically acceptable salt thereof.

In some embodiments, the compound having the structure of Formula (II) is selected from the group consisting of:

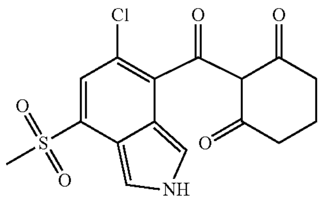
,
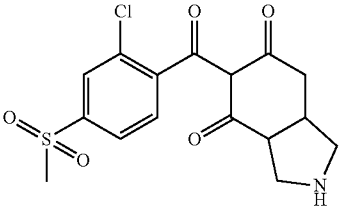
,
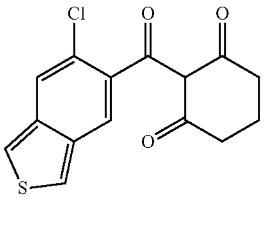
,

-continued

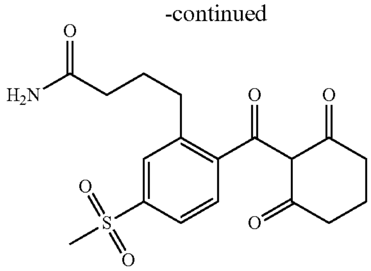
, and
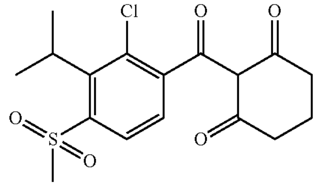
, or a pharmaceutically acceptable salt thereof.

In some embodiments, the small molecule is N-[5-[[4-[5-[acetyl(hydroxy)amino]pentylamino]-4-oxobutanoyl]-hydroxyamino]pentyl]-N'-(5-aminopentyl)-N'-hydroxybutanediamide (Deferoxamine; DFO).

In some embodiments, the site-specific nuclease comprises a Cas protein and a guide RNA (gRNA) comprising a sequence complementary to a region in the HPDL gene. For example, the guide RNA (gRNA) may comprise a nucleotide sequence of any one of SEQ ID NOs: 5-8, or a fragment thereof. In some embodiments, the Cas protein is a Cas9 protein. In some embodiments, the guide RNA is a single guide RNA (sgRNA). In further embodiments, the site-specific nuclease comprises a zinc finger nuclease (ZFN), a TALEN nuclease, or a mega-TALEN nuclease.

In some embodiments, the method described above comprises not administering an HPDL inhibitor to the subject exhibiting a lower or equivalent level of HPDL expression as compared to the control level.

In some embodiments, the method described above further comprises administering one or more additional treatments to the subject, wherein said additional treatments are selected from a chemotherapy, a chemoradiotherapy, a neoadjuvant chemoradiotherapy, a radiotherapy, a surgery, and any combination thereof. In some embodiments, the additional treatment is a platinum-based chemotherapy and the method further comprises administering an electron transport chain (ETC) inhibitor. In some embodiments, the electron transport chain (ETC) inhibitor is metformin, phenformin, BAY84-2243, carboxyamidotriazole, ME344, Fenofibrate, mIBG (meta-iodobenzylguanidine), Alpha-TOS, Lonidamine, Atovaquone, Arsenic trioxide, Nitric Oxide, or Hydrocortisone, or a combination thereof.

In some embodiments, the method of treating a pancreatic cancer further comprises administering one or more additional treatments to the subject. The additional treatments may be a chemotherapy, a chemoradiotherapy, a neoadjuvant chemoradiotherapy, a radiotherapy, a surgery, or any combination thereof. In one embodiment, the additional treatment is a platinum-based chemotherapy and the method further comprises administering an electron transport chain (ETC) inhibitor. Exemplary electron transport chain (ETC) inhibitors include, but are not limited to compounds that target Complex I such as metformin, phenformin, BAY84-2243, carboxyamidotriazole, ME344, Fenofibrate, mIBG (meta-iodobenzylguanidine), compounds that target Complex II such as Alpha-TOS, Lonidamine, compounds that target Complex III such as Atovaquone, mIBG (meta-iodobenzylguanidine) and compounds that target Complex IV such as Arsenic trioxide, Nitric Oxide, or Hydrocortisone, or a combination thereof.

In some embodiments, the HPDL expression level is determined at protein level via immunohistochemistry (IHC) staining or immunofluorescence. In some embodiments, the HPDL protein expression level is determined via chromogenic IHC staining using an anti-HPDL antibody as the primary antibody and an HRP-linked secondary antibody followed by DAB staining.

In some embodiments, the pancreatic cancer is pancreatic ductal adenocarcinoma (PDAC) or neuroendocrine pancreatic cancer.

In another aspect, presented herein is a method of determining effectiveness of a treatment for pancreatic cancer in a subject, comprising the following steps:

a) determining expression level of 4-hydroxyphenylpyruvate dioxygenase-like (HPDL) in a first sample obtained from the subject before the subject receives a treatment for pancreatic cancer;
b) determining expression level of HPDL in a second sample obtained from the subject after the subject has received the treatment for pancreatic cancer;
c) comparing the HPDL expression levels determined in the first sample and the second sample; and
d) determining that (i) the treatment is effective if the HPDL expression level in the second sample is lower than HPDL expression level in the first sample, or (ii) the treatment is not effective if the HPDL expression level in the second sample is not lower than the HPDL expression level in the first sample.

In some embodiments, the treatment for pancreatic cancer includes an HPDL inhibitor, a chemotherapy, a chemoradiotherapy, a neoadjuvant chemoradiotherapy, a radiotherapy, a surgery, or any combination thereof.

In another aspect, presented herein is a method of identifying and/or assessing a modulator of 4-hydroxyphenylpyruvate dioxygenase-like (HPDL), comprising the following steps:

a) in a test sample, contacting the sample with a test compound, wherein the sample is obtained from a subject having pancreatic cancer or is a pancreatic cancer cell line;
b) determining expression level of HPDL in the test sample;
c) comparing the HPDL expression level determined in step (b) to a control level of HPDL expression determined under the same conditions in a control sample without the test compound;
d) determining (i) the compound is an inhibitor of HPDL if the HPDL expression level in the test sample is lower than the control level, or (ii) the compound is not an inhibitor of HPDL if the HPDL expression level in the test sample is not lower than the control level, or (iii) the compound is an activator of HPDL if the HPDL expression level in the test sample is higher than the control level.

In some embodiments, the pancreatic cancer cell line is MIAPACA2, 8988T, Panc-1, or 8902. In some embodiments, the compound is a small molecule, an antibody or antibody fragment, an siRNA, an shRNA, an antisense oligonucleotide, a site-specific nuclease, or a degron (e.g., a small molecule conjugated to a degrader).

In another aspect, presented herein is a method of predicting prognosis of pancreatic cancer in a subject having pancreatic cancer, comprising the following steps:

a) determining expression level of 4-hydroxyphenylpyruvate dioxygenase-like (HPDL) protein in a sample obtained from the subject;
b) comparing the HPDL expression level determined in step (a) with a control level of HPDL expression; and
c) determining the subject (i) as having poor prognosis if the HPDL expression level is higher than the control level, or (ii) as having good prognosis if the HPDL expression level is lower than or equal to the control level.

In some embodiments, the control level of HPDL expression is determined in normal tissue from the same subject, a sample from a normal subject, or is a predetermined value.

In some embodiments, the subject has unresectable or borderline resectable pancreatic cancer. In some embodiments, the method further comprises administering to the subject an HPDL inhibitor, a single-agent chemotherapy and/or supportive care if the subject is determined to have poor prognosis.

In some embodiments, the HPDL inhibitor is a small molecule, an antibody or antibody fragment, an siRNA, an shRNA, an antisense oligonucleotide, a site-specific nuclease, or a degron (e.g., a small molecule conjugated to a degrader).

In some embodiments, the small molecule is a compound having the structure of Formula (I):

(I)

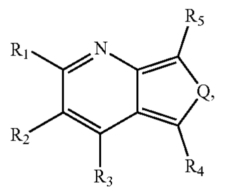

or a pharmaceutically acceptable salt thereof, wherein:

Q is selected from —O—, —NH—, and

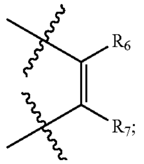

$R_1$, $R_2$, and $R_3$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of which optionally contains 1-8 heteroatoms selected from halogen, O, N, and S; —OH, =O, —$CO_2$H, —$NO_2$, —$NH_2$, —NHR*, —NR*$_2$, —N—OH, —$HSO_3$, —$H_2PO_3$, —OR*, —(C=O)—R*, —$CO_2$R*, —CO—$NH_2$, —CO—NHR*, —$SO_2$—NHR*, or adjacent two moieties combine to form a fused ring which may optionally contain 1-3 heteroatoms selected from halogen, O, N, and S and which may be further substituted by one or more R*, and wherein when Q is

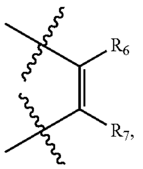

at least one of $R_1$, $R_2$, and $R_3$ is not H;

$R_4$ and $R_5$ are independently selected from —OH and —$CO_2H$;

$R_6$ and $R_7$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of which optionally contains 1-8 heteroatoms selected from halogen, O, N, and S; —OH, =O, —$CO_2H$, —$NO_2$, —$NH_2$, —NHR*, —$NR^*_2$, —N—OH, —$HSO_3$, —$H_2PO_3$, —OR*, —(C=O)—R*, —$CO_2R^*$, —CO—$NH_2$, —CO—NHR*, —$SO_2$—NHR*, or $R_6$ and $R_7$ combine to form a fused ring, and R* is independently selected at each occurrence from hydrogen or $C_1$-$C_{12}$ hydrocarbons each of which optionally contains 1-8 heteroatoms selected from halogen, O, N, and S and combinations thereof.

In some embodiments, when Q is

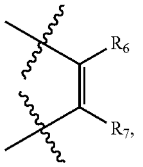

at least one of $R_1$, $R_2$, and $R_3$ is not H.

In some embodiments, the compound has the structure of Formula (IA):

(IA)

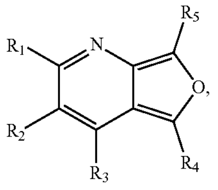

or a pharmaceutically acceptable salt thereof.

In some embodiments, the compound has the structure of Formula (IB):

(IB)

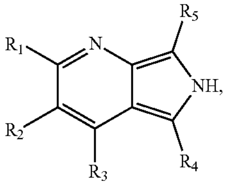

or a pharmaceutically acceptable salt thereof.

In some embodiments, the compound has the structure of Formula (IC):

(IC)

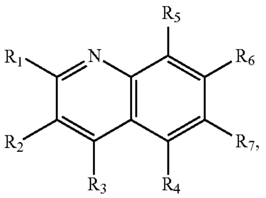

or a pharmaceutically acceptable salt thereof.

In some embodiments, the compound has the structure of Formula (ID):

(ID)

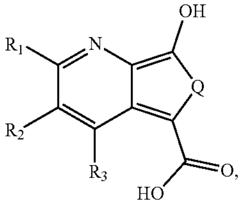

or a pharmaceutically acceptable salt thereof, wherein Q is —O— or —NH—.

In some embodiments, the compound has the structure of Formula (IE):

(IE)

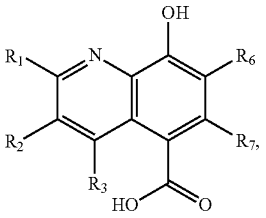

or a pharmaceutically acceptable salt thereof.

In some embodiments, the compound having the structure of Formula (I) is selected from the group consisting of:

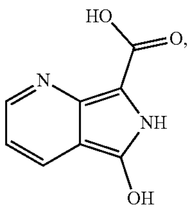
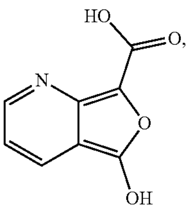
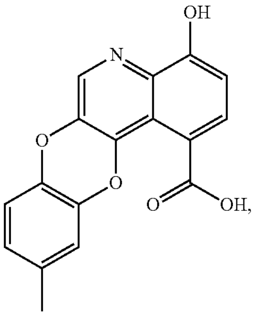
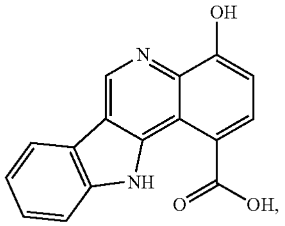

-continued

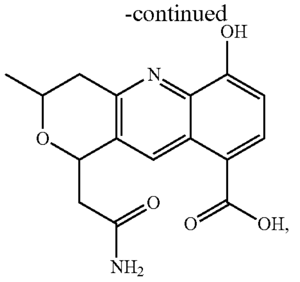

and

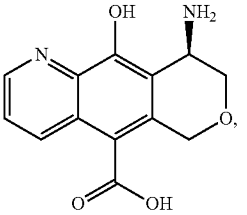

or a pharmaceutically acceptable salt thereof.

In some embodiments, the small molecule is a compound having the structure of Formula (II):

(II)

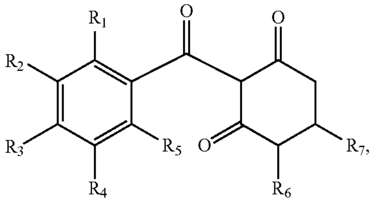

or a pharmaceutically acceptable salt thereof, wherein:

$R_1$ is selected from —$NO_2$, —Cl, and a $C_{1-12}$ alkyl which may be optionally substituted with one or more of —OH, =O, —$CO_2$H, —$NO_2$, —$NH_2$, —NHR*, —NR*$_2$, —N—OH, —$HSO_3$, —$H_2PO_3$, —OR*, —(C=O)—R*, —$CO_2$R*, —CO—$NH_2$, —CO—NHR*, and —$SO_2$—NHR*;

$R_2$, $R_3$, $R_4$, $R_5$, $R_6$ and $R_7$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of which optionally contains 1-8 heteroatoms selected from halogen, O, N, and S; —OH, =O, —$CO_2$H, —$NO_2$, —$NH_2$, —NHR*, —NR*$_2$—N—OH, —$HSO_3$, —$H_2PO_3$, —OR*, —(C=O)—R*, —$CO_2$R*, —CO—$NH_2$, —CO—NHR*, —$SO_2$R*, —$SO_2$—NHR*, or adjacent two moieties combine to form a fused ring which may optionally contain 1-3 heteroatoms selected from halogen, O, N, and S and which may be further substituted by one or more R*, and R* is independently selected at each occurrence from hydrogen or $C_1$-$C_{12}$ hydrocarbons each of which optionally contains 1-8 heteroatoms selected from halogen, O, N, and S and combinations thereof.

In some embodiments, the compound does not have the structure selected from

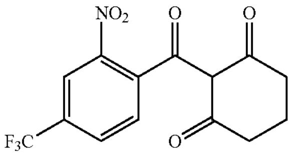

and (nitisinone)

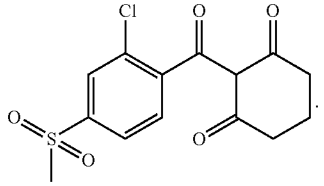

(sulcotrione)

In some embodiments, the compound has the structure of Formula (IIA):

(IIA)

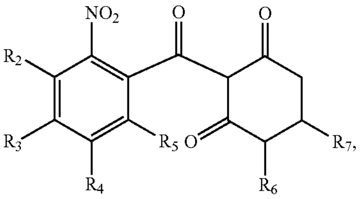

or a pharmaceutically acceptable salt thereof.

In some embodiments, the compound has the structure of Formula (IIB):

(IIB)

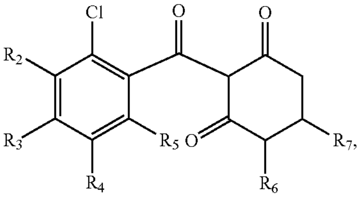

or a pharmaceutically acceptable salt thereof.

In some embodiments, $R_1$ is a $C_{1-12}$ alkyl substituted with one or more of —OH, =O, —$CO_2$H, —$NO_2$, —$NH_2$, —NHR*, —NR*$_2$, —N—OH, —$HSO_3$, —$H_2PO_3$, —OR*, —(C=O)—R*, —$CO_2$R*, —CO—$NH_2$, —CO—NHR*, and —$SO_2$—NHR*.

In some embodiments, the compound having the structure of Formula (II) is selected from the group consisting of:

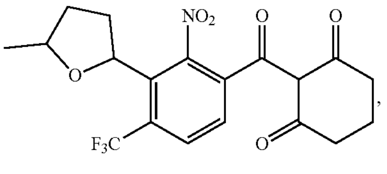

-continued

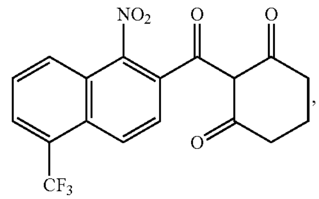

,

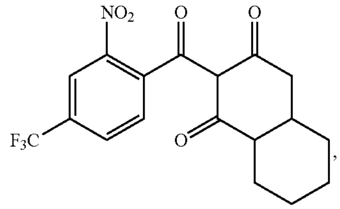

,

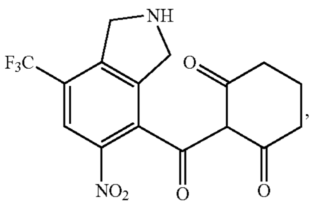

and

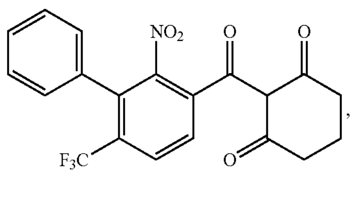

, or a pharmaceutically acceptable salt thereof.

In some embodiments, the compound having the structure of Formula (II) is selected from the group consisting of:

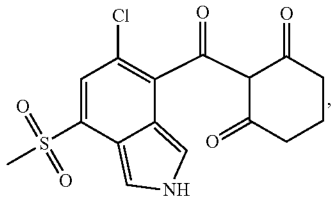

,

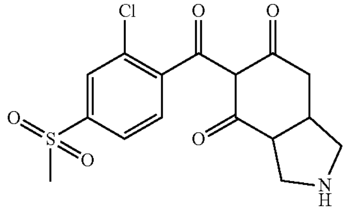

,

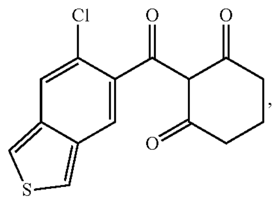

,

-continued

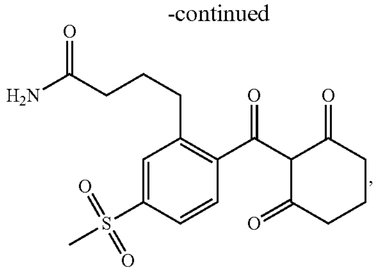

, and

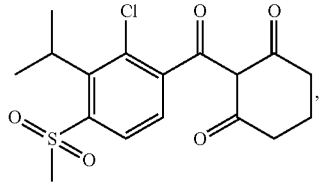

, or a pharmaceutically acceptable salt thereof.

In some embodiments, the small molecule is N-[5-[[4-[5-[acetyl(hydroxy)amino]pentylamino]-4-oxobutanoyl]-hydroxyamino]pentyl]-N'-(5-aminopentyl)-N'-hydroxybutanediamide (Deferoxamine; DFO).

In some embodiments, the site-specific nuclease comprises a Cas protein and a guide RNA (gRNA) comprising a sequence complementary to a region in the HPDL gene. For example, the guide RNA (gRNA) may comprise a nucleotide sequence of any one of SEQ ID NOs: 5-8, or a fragment thereof. In some embodiments, the Cas protein is a Cas9 protein. In some embodiments, the guide RNA is a single guide RNA (sgRNA). In further embodiments, the site-specific nuclease comprises a zine finger nuclease (ZFN), a TALEN nuclease, or a mega-TALEN nuclease.

In some embodiments, the single-agent chemotherapy is platinum-based chemotherapy. In some embodiments, the method further comprises administering an electron transport chain (ETC) inhibitor in combination with the single-agent chemotherapy. Exemplary electron transport chain (ETC) inhibitors include, but are not limited to compounds that target Complex I such as metformin, phenformin, BAY84-2243, carboxyamidotriazole, ME344, Fenofibrate, mIBG (meta-iodobenzylguanidine), compounds that target Complex II such as Alpha-TOS, Lonidamine, compounds that target Complex III such as Atovaquone, mIBG (meta-iodobenzylguanidine) and compounds that target Complex IV such as Arsenic trioxide, Nitric Oxide, or Hydrocortisone, or a combination thereof.

In some embodiments, the method of predicting prognosis of pancreatic cancer further comprises administering to the subject a multiagent chemotherapy, chemoradiotherapy, and/or neoadjuvant chemoradiotherapy if the subject is determined to have good prognosis. In some embodiments, the multiagent chemotherapy is FOLFIRINOX (Leucovorin calcium/Folinic acid, 5-fluorouracil, Irinotecan, Oxaliplatin).

In various embodiments of the methods described herein, the HPDL expression level is determined at mRNA level via RNA-seq, reverse transcription polymerase chain reaction (rt-PCR), or fluorescence in situ hybridization (FISH). In some embodiments, the HPDL expression level is determined at protein level via immunohistochemistry (IHC) staining or immunofluorescence. For example, the HPDL protein expression level may be determined via chromogenic IHC staining using an anti-HPDL antibody as the primary antibody and an HRP-linked secondary antibody followed by DAB staining.

In various embodiments of the methods described herein, the pancreatic cancer is pancreatic ductal adenocarcinoma (PDAC) or neuroendocrine pancreatic cancer.

In another aspect, presented herein is a method of treating coenzyme Q10 (CoQ10) deficiency or cachexia comprising administering to a subject in need thereof a therapeutically effective amount of 4-hydroxymandelic acid (4-HMA), 4-HPPA and/or 4-HB, or its pharmaceutically acceptable salts, prodrugs, solvates, or hydrates thereof. In some embodiments, the coenzyme Q10 (CoQ10) deficiency is induced by statins or by inborn errors of metabolism.

In another aspect, presented herein is a method of treating coenzyme Q10 (CoQ10) deficiency comprising administering to a subject in need thereof a therapeutically effective amount of an activator of 4-hydroxyphenylpyruvate dioxygenase-like (HPDL). In some embodiments, the activator of HPDL increases the HPDL protein activity. In some embodiments, the activator of HPDL increases the HPDL expression level.

In some embodiments, the subject is a mammal. In some embodiments, the subject is a human.

In another aspect, provided herein is a pharmaceutical composition comprising one or more of 1) 4-HMA as a racemic mixture of (R)-4-HMA and (S)-4-HMA, 2) enantioentriched (R)-4-HMA, 3) enantiopure (R)-4-HMA, or 4) enantioentriched (S)-4-HMA, or 5) enantiopure (S)-4-HMA, and a pharmaceutically acceptable carrier. In some embodiments, the pharmaceutical composition further comprises one or more of 4-hydroxybenzoylformate (4-HBF), 4-hydroxybenzaldehyde (4-HBz), 4-hydroxybenzoate (4-TB), and CoQ10. In some embodiments, the pharmaceutical composition further comprises one or more additional therapeutic agent. In some embodiments, the one or more additional therapeutic agent is selected from vitamin C, tyrosine, acetate, mevalonate, and other intermediates in the CoQ10 headgroup or tail synthesis pathways (e.g., those shown in FIG. 13).

In another aspect, provided herein is a dosage form comprising one or more of 1) 4-HMA as a racemic mixture of (R)-4-HMA and (S)-4-HMA, 2) enantioentriched (R)-4-HMA, 3) enantiopure (R)-4-HMA, or 4) enantioentriched (S)-4-HMA, or 5) enantiopure (S)-4-HMA, and a pharmaceutically acceptable carrier. In some embodiments, the dosage form further comprises one or more of 4-hydroxybenzoylformate (4-HBF), 4-hydroxybenzaldehyde (4-HBz), 4-hydroxybenzoate (4-HB), and CoQ10. In some embodiments, the dosage form further comprises one or more additional therapeutic agent. In some embodiments, the one or more additional therapeutic agent is selected from vitamin C, tyrosine, acetate, mevalonate, and other intermediates in the CoQ10 headgroup or tail synthesis pathways (e.g., those shown in FIG. 13).

In another aspect, presented herein is a method of producing 4-hydroxymandelic acid (4-HMA) comprising incubating 4-hydroxyphenylpyruvate (4-HPPA) with 4-hydroxyphenylpyruvate dioxygenase-like (HPDL) under conditions which permit production of 4-hydroxymandelic acid (4-HMA). The method may be used to produce the beta-blocker Atenolol as 4-HMA is a precursor of Atenolol.

In another aspect, presented herein is a compound having the structure of Formula (I):

(I)

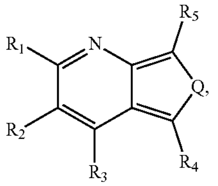

or a pharmaceutically acceptable salt thereof, wherein:

Q is selected from —O—, —NH—, and

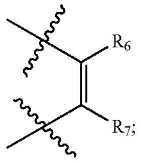

$R_1$, $R_2$, and $R_3$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of which optionally contains 1-8 heteroatoms selected from halogen, O, N, and S; —OH, =O, —$CO_2$H, —$NO_2$, —$NH_2$, —NHR*, —NR*$_2$, —N—OH, —$HSO_3$, —$H_2PO_3$, —OR*, —(C=O)—R*, —$CO_2$R*, —CO—$NH_2$, —CO—NHR*, —$SO_2$—NHR*, or adjacent two moieties combine to form a fused ring which may optionally contain 1-3 heteroatoms selected from halogen, O, N, and S and which may be further substituted by one or more R*, and wherein when Q is

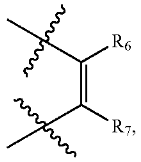

at least one of $R_1$, $R_2$, and $R_3$ is not H;

$R_4$ and $R_5$ are independently selected from —OH and —$CO_2$H;

$R_6$ and $R_7$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of which optionally contains 1-8 heteroatoms selected from halogen, O, N, and S; —OH, =O, —$CO_2$H, —$NO_2$, —$NH_2$, —NHR*, —NR*$_2$, —N—OH, —$HSO_3$, —$H_2PO_3$, —OR*, —(C=O)—R*, —$CO_2$R*, —CO—$NH_2$, —CO—NHR*, —$SO_2$—NHR*, or $R_6$ and $R_7$ combine to form a fused ring, and R* is independently selected at each occurrence from hydrogen or $C_1$-$C_{12}$ hydrocarbons each of which optionally contains 1-8 heteroatoms selected from halogen, O, N, and S and combinations thereof.

In some embodiments, the compound has the structure of Formula (IA):

(IA)

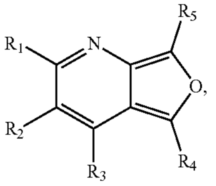

or a pharmaceutically acceptable salt thereof.

In some embodiments, the compound has the structure of Formula (IB):

(IB)

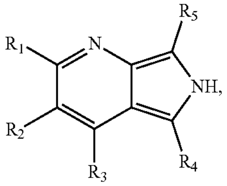

or a pharmaceutically acceptable salt thereof.

In some embodiments, the compound has the structure of Formula (IC):

(IC)

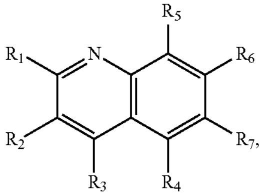

or a pharmaceutically acceptable salt thereof.

In some embodiments, the compound has the structure of Formula (ID):

(ID)

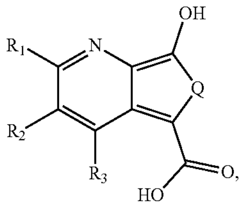

or a pharmaceutically acceptable salt thereof, wherein Q is —O— or —NH—.

In some embodiments, the compound has the structure of Formula (IE):

(IE)

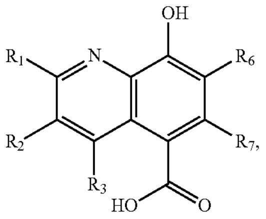

or a pharmaceutically acceptable salt thereof.

In some embodiments, the compound has the structure of Formula (I) selected from the group consisting of:

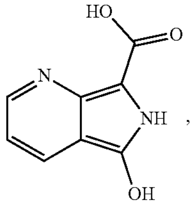 , 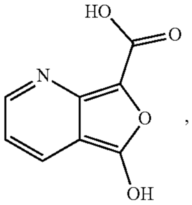 ,

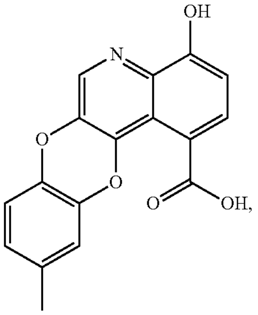

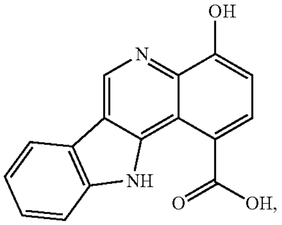

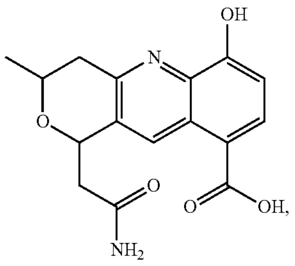 and

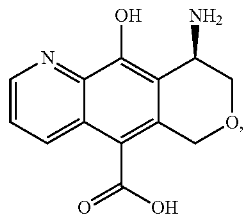

or a pharmaceutically acceptable salt thereof.

In another aspect, presented herein is a compound having the structure of Formula (II):

(II)

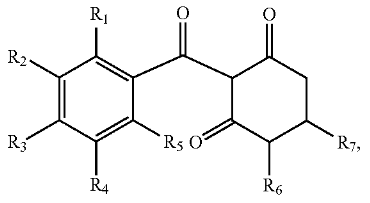

or a pharmaceutically acceptable salt thereof, wherein:

- $R_1$ is selected from —$NO_2$, —Cl, and a $C_{1-12}$ alkyl which may be optionally substituted with one or more of —OH, =O, —$CO_2H$, —$NO_2$, —$NH_2$, —NHR*, —$NR*_2$, —N—OH, —$HSO_3$, —$H_2PO_3$, —OR*, —(C=O)—R*, —$CO_2R*$, —CO—$NH_2$, —CO—NHR*, and —$SO_2$—NHR*;
- $R_2$, $R_3$, $R_4$, $R_5$, $R_6$ and $R_7$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of which optionally contains 1-8 heteroatoms selected from halogen, O, N, and S; —OH, =O, —$CO_2H$, —$NO_2$, —$NH_2$, —NHR*, —$NR*_2$—N—OH, —$HSO_3$, —$H_2PO_3$, —OR*, —(C=O)—R*, —$CO_2R*$, —CO—$NH_2$, —CO—NHR*, —$SO_2R*$, —$SO_2$—NHR*, or adjacent two moieties combine to form a fused ring which may optionally contain 1-3 heteroatoms selected from halogen, O, N, and S and which may be further substituted by one or more R*, and
- R* is independently selected at each occurrence from hydrogen or $C_1$-$C_{12}$ hydrocarbons each of which optionally contains 1-8 heteroatoms selected from halogen, O, N, and S and combinations thereof, wherein the compound does not have the structure selected from

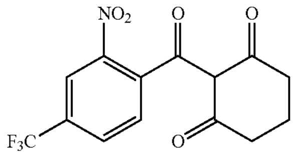

and (nitisinone)

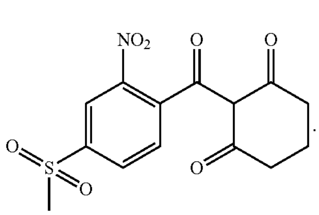

(sulcotrione)

In some embodiments, the compound has the structure of Formula (IIA):

(IIA)

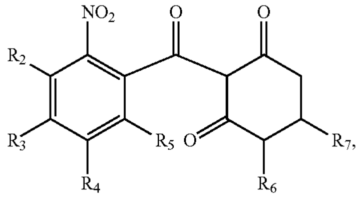

or a pharmaceutically acceptable salt thereof.

In some embodiments, the compound has the structure of Formula (IIB):

(IIB)

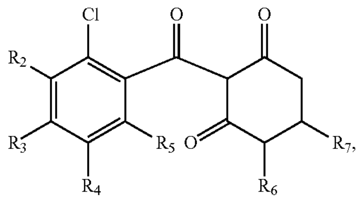

or a pharmaceutically acceptable salt thereof.

In some embodiments, $R_1$ is a $C_{1-12}$ alkyl substituted with one or more of —OH, =O, —$CO_2H$, —$NO_2$, —$NH_2$, —NHR*, —$NR*_2$, —N—OH, —$HSO_3$, —$H_2PO_3$, —OR*, —(C=O)—R*, —$CO_2R*$, —CO—$NH_2$, —CO—NHR*, and —$SO_2$—NHR*.

In some embodiments, the compound has the structure of Formula (II) selected from the group consisting of:

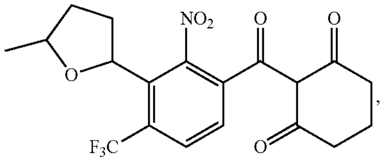

,

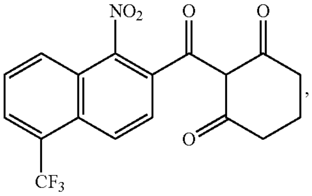

,

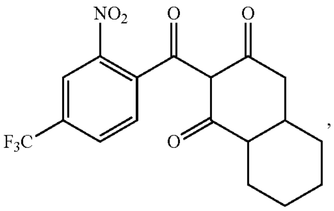

,

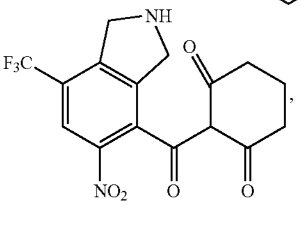

, and

-continued

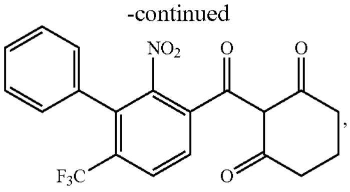

, and F or a pharmaceutically acceptable salt thereof.

In some embodiments, the compound has the structure of Formula (II) selected from the group consisting of.

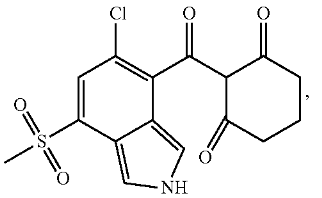

,

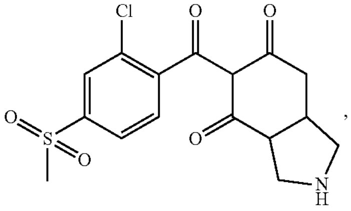

,

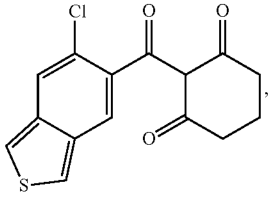

,

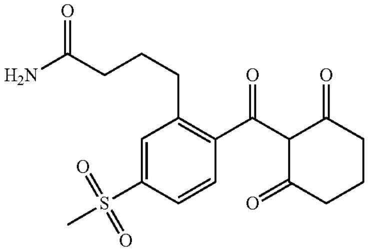

, and

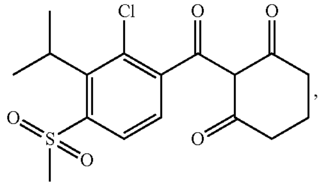

, or a pharmaceutically acceptable salt thereof.

In one aspect, example methods and systems for isotopic labelling in cells by metabolizing cells in the presence of gaseous isotopic tracer are presented herein.

An example method for isotopic labelling in cells includes allowing the cells to metabolize in the presence of a gaseous isotopic tracer and identifying metabolites in the cells based at least in part on detection of the isotopic tracer in the cells. The cells may also be animal cells, insect cells, bacteria, yeast, etc. In some embodiments, the cells may be mammalian cells.

In a first variant of the example method, the cells which are labelled are of a cell sample. The example method can further include positioning the sample of the cells within a primary chamber, hermetically sealing the primary chamber in a closed system while the cells are in the primary chamber, and replacing, by the closed system, gasses in the primary chamber with a predetermined concentration of the gaseous isotopic tracer while the cells are in the primary chamber and while the primary chamber is hermetically sealed in the closed system. The step of allowing the cells to metabolize in the presence of the gaseous isotopic tracer can further include allowing the cells to metabolize in the predetermined concentration of the gaseous isotopic tracer. The example method can further include extracting the cells from the primary chamber and detecting the isotopic tracer in the cells. The example method can further include positioning a plurality of samples of the cells respectively within a plurality of primary chambers that are hermetically isolated from each other within a singular housing, replacing, by the closed system, gasses in each of the plurality of primary chambers with a predetermined concentration of the gaseous isotopic tracer while each of the plurality of samples of the cells are in the plurality of primary chambers and while the plurality of primary chambers are hermetically sealed in a respective closed system, and extracting one of the plurality of samples of cells from the primary chamber in which it is positioned without opening the respective closed system of another primary chamber of the plurality of primary chambers.

In a second variant of the example method that is an alternative to the first variant, the cells are of a living experimental animal. The example method can include hermetically sealing a primary chamber in a closed system, replacing, by the closed system, gasses in the primary chamber with a predetermined concentration of the gaseous isotopic tracer while the primary chamber is hermetically sealed in the closed system, positioning a living experimental animal in a secondary chamber, and opening a passageway between the primary chamber and the secondary chamber to allow the living experimental animal to travel through the passageway into the primary chamber while the primary chamber contains the predetermined concentration of the gaseous isotopic tracer. The step of allowing the cells of the experimental animal to metabolize in the presence of the gaseous isotopic tracer includes allowing the living experimental animal to perform metabolic functions in the predetermined concentration of the gaseous isotopic tracer within the primary chamber. The example method can further include providing, by the closed system, additional gaseous isotopic tracer into the primary chamber while the living experimental animal is performing metabolic functions therein to thereby maintain the predetermined concentration of the gaseous isotopic tracer within the primary chamber, extracting the cells from the experimental animal, and detecting the isotopic tracer in components of the cells.

In either of the first variant and the second variant of the example method, the gaseous isotopic tracer can include at least one of $^{15}N$, $^{13}C$, $^{2}H$, $^{34}S$, and $^{18}O_2$. Preferably, the gaseous isotopic tracer includes $^{18}O_2$. The method can further include identifying molecules produced by reactive oxygen species modification of cellular components of the cells. The method can further include measuring activity of oxygen-dependent enzymes in the cells using direct mass spectrometry. The method can further include identifying oxygen dependent metabolic pathways in the cells based at least in part on detection of $^{18}O_2$ in the cells.

In either of the first variant and the second variant of the example method, the method can further include allowing the cells to metabolize in any desired gas mixture having any desired gas ratio totaling 100%. Specifically, the method can include allowing the cells to metabolize in a gas mixture comprising a ratio of $^{18}O_2$:$CO_2$:$N_2$ of approximately 5%:5%:90%. Alternatively, the method can further include allowing the cells to metabolize in a gas mixture comprising a ratio of $^{18}O_2$:$CO_2$:$N_2$ of approximately 1.5%:5%:93.5%. Alternatively, the method can further include allowing the cells to metabolize in a gas mixture comprising a ratio of $^{18}O_2$:$CO_2$:$N_2$ of approximately 0.5%:5%:94.5%.

In either of the first variant and the second variant of the example method, the method can further include purging oxygen from the primary chamber. The step of purging oxygen from the primary chamber can further include flowing approximately 80 liters of $N_2$ through the primary chamber for a time period of approximately 2 minutes.

A first example system can include a modular hermetically sealable apparatus and a gas flow control system. The modular hermetically sealable apparatus can include individually sealable chambers, gas inlet ports, gas exhaust ports, and hermetically sealable openings. The chambers can be mechanically interlocked to the apparatus. The gas inlet ports can be configured to provide a respective gas inlet path individually to each respective chamber. The gas exhaust ports can be configured to provide a respective gas exhaust path individually from each respective chamber. The hermetically sealable openings can each have a closed position and an open position such that in the closed position, the respective chamber associated with the respective opening is hermetically sealed, and such that in the closed position a solid sample can pass through the respective opening into the respective chamber. The gas flow control system can be in communication with at least a portion of the gas inlet ports and can be configured to provide a predetermined concentration of a gaseous isotopic tracer within the portion of the chambers. The gas flow control system can also be in communication with a corresponding portion of the gas exhaust ports associated with chambers having an inlet port in communication with the gas flow control system.

An internal volume of each of the plurality of chambers can be between about 0.25 liters and about 5 liters.

A second example system can include a primary chamber, a secondary chamber, a hermetically sealable passageway joining the secondary chamber to the primary chamber, and a gas flow control system. The primary chamber can include a gas inlet and a gas exhaust. The gas flow control system can be in communication with the gas inlet and the gas exhaust and can be configured to provide a predetermined concentration of a gaseous isotopic tracer within the primary chamber.

The primary chamber, the hermetically sealable passageway, and the secondary chamber can be configured such that a living experimental animal can be placed into the secondary chamber, the secondary chamber can be subsequently hermetically sealed, and while the primary and secondary chambers are each hermetically sealed, and the passageway can be opened to allow the living experimental animal to pass through the passageway.

An internal volume of the primary chamber can be between about 3 liters and about 10 liters. An internal volume of the secondary chamber can be between about 0.1 liters and about 0.5 liters.

The second example system can further include a gas sensor configured to measure concentration of the gaseous isotopic tracer within the primary chamber. The gas flow control system can be configured to provide the predetermined concentration of the gaseous isotopic tracer based at least in part on the concentration of gaseous isotopic tracer measured by the gas sensor.

The second example system can further include a carbon dioxide absorber positioned within the primary chamber.

The second example system can further include a drinking water dispenser within the primary chamber and a food dispenser within the primary chamber.

The primary chamber can include a hermetically sealable lid.

4K) were compared using the two-sided Log-rank (Mantel-Cox) test. Graphs (mean±s.e.m or median±max/min (FIG. 4I-4J)) were compared using two-tailed Student t-test (FIG. 4A, FIG. 4I), one- (FIGS. 4B-4C, 4F, 4H-4J) or two (FIGS. 4A, 4E, 4G) way ANOVA, followed by Bonferroni (FIG. 4A), Tukey (FIGS. 4B-4C, 4E-4H) or Holm-Sidak (FIGS. 4I, 4J) post-hoc test (*p<0.05, ^p<0.01, %p<0.005, #p<0.0001).

Figure 5A:
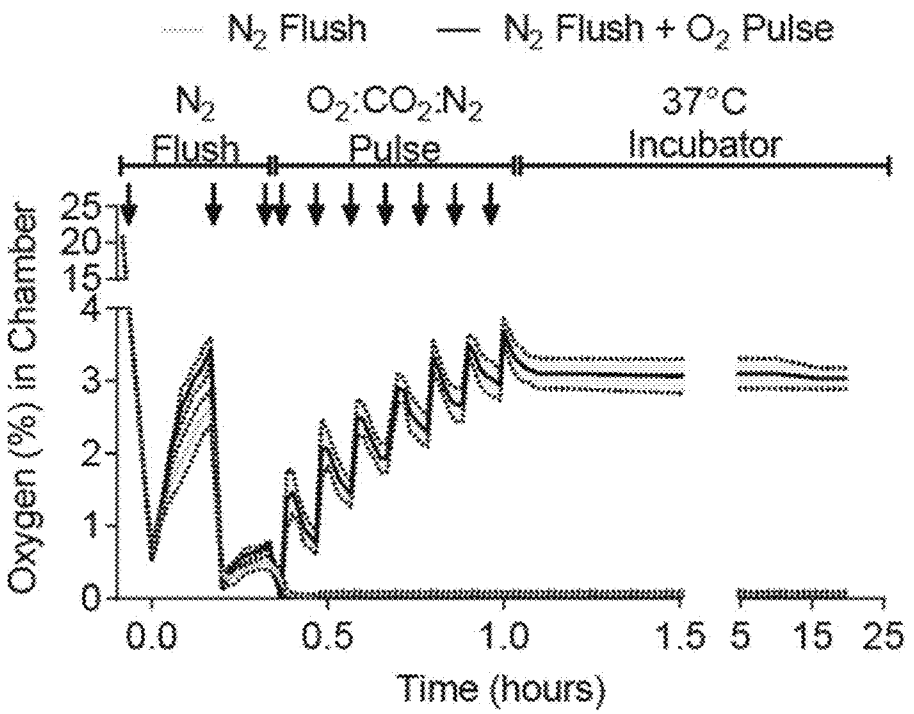
Figure 5B:
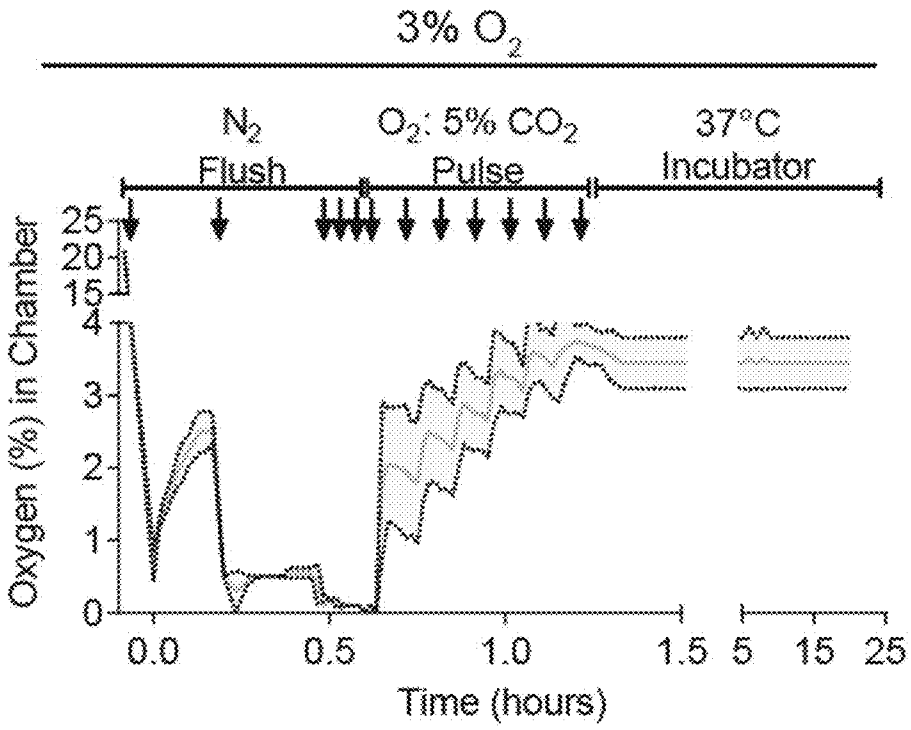
Figure 5C:
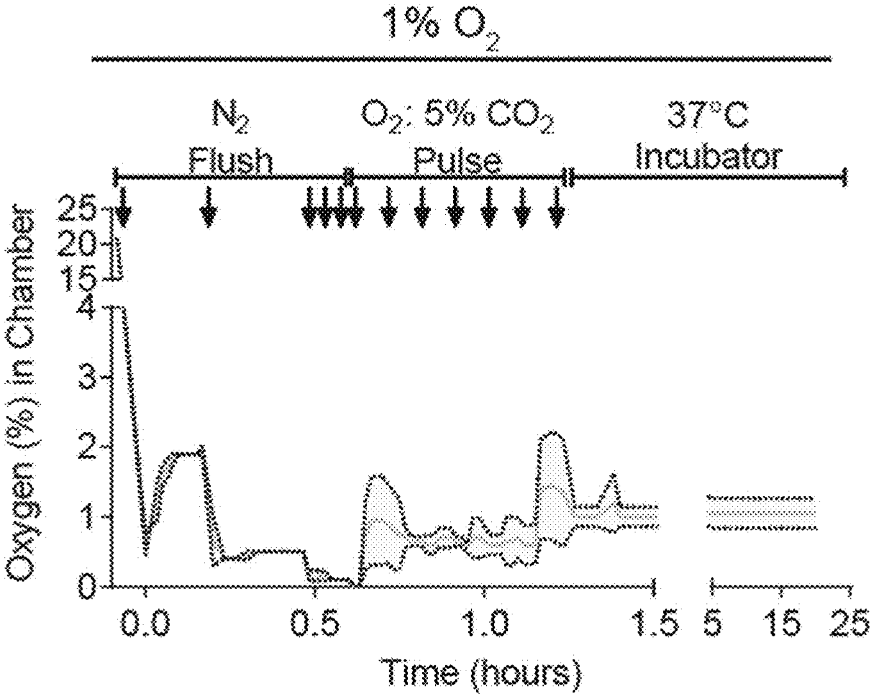
Figure 5D:
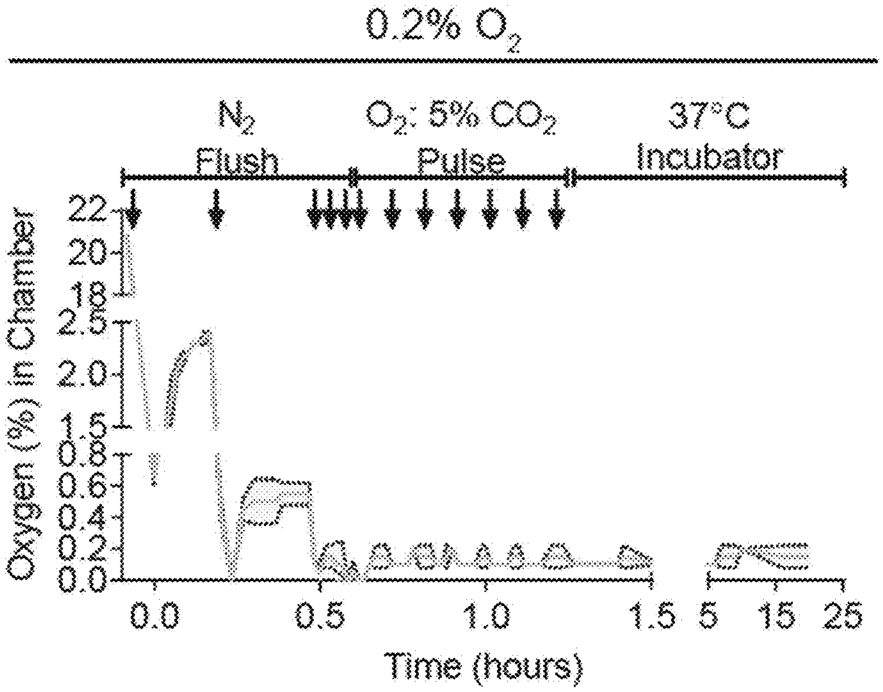
Figure 5E:
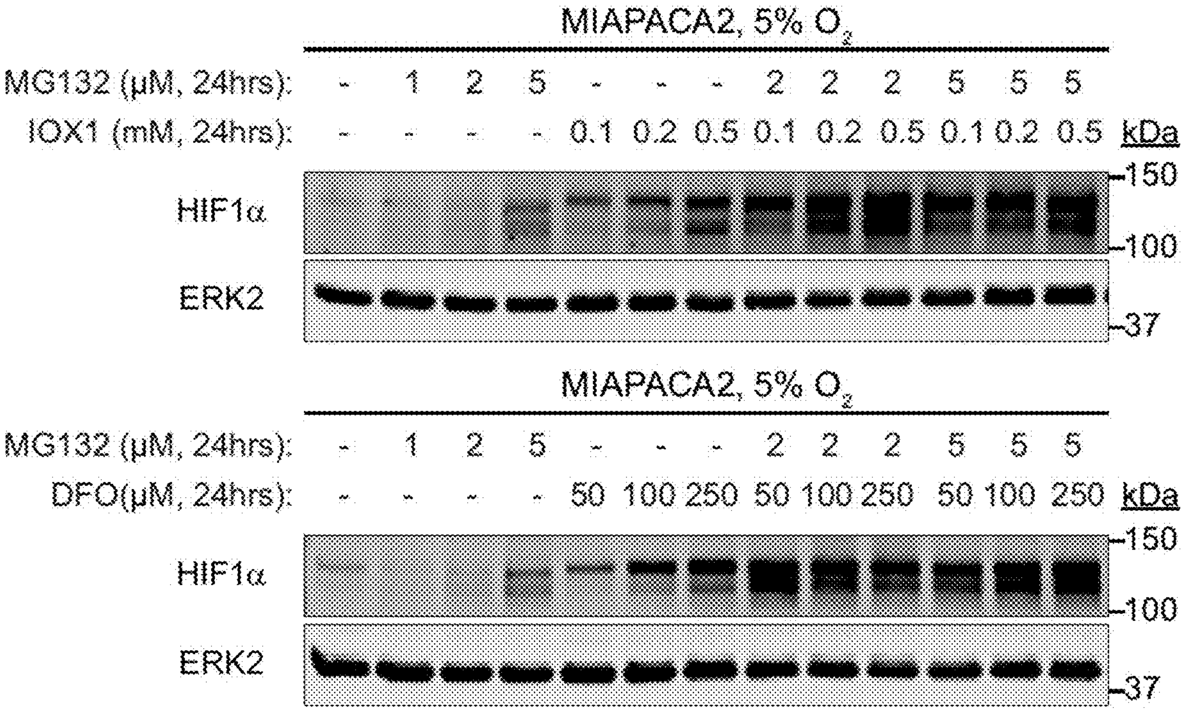
Figure 5F:
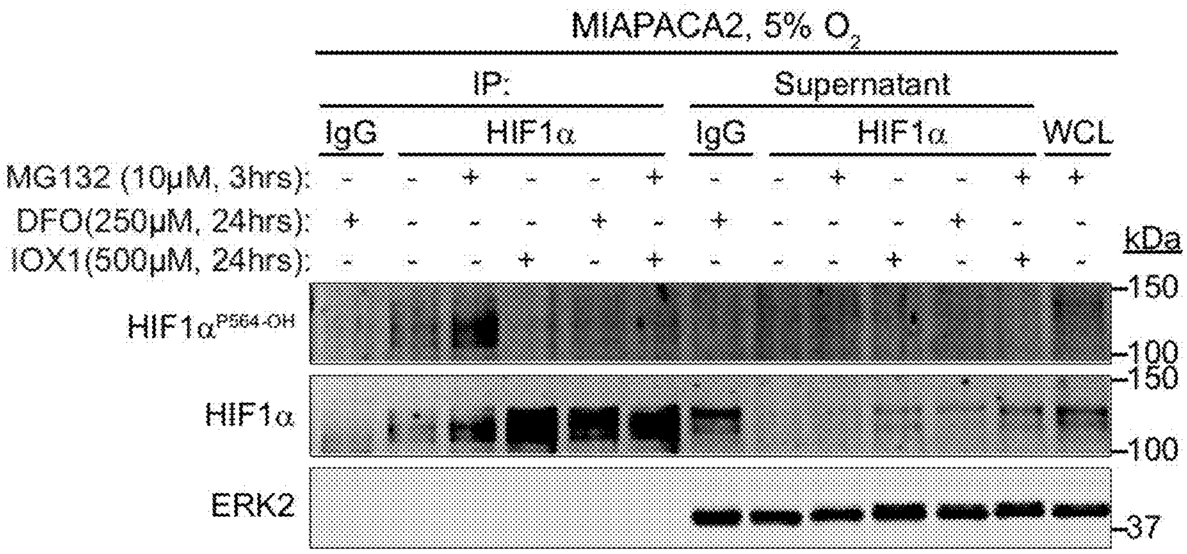
Figure 5H:
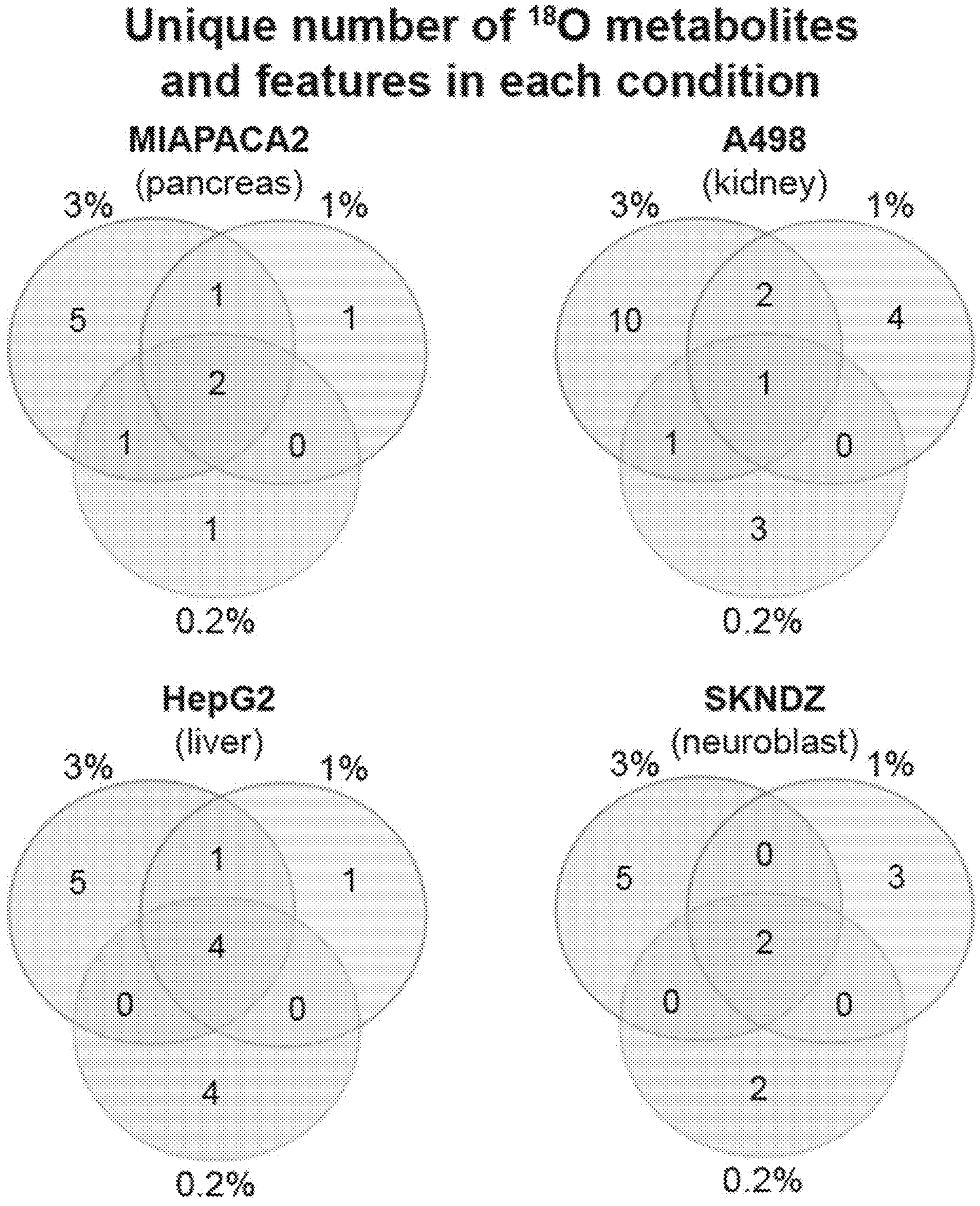
Figure 5I:
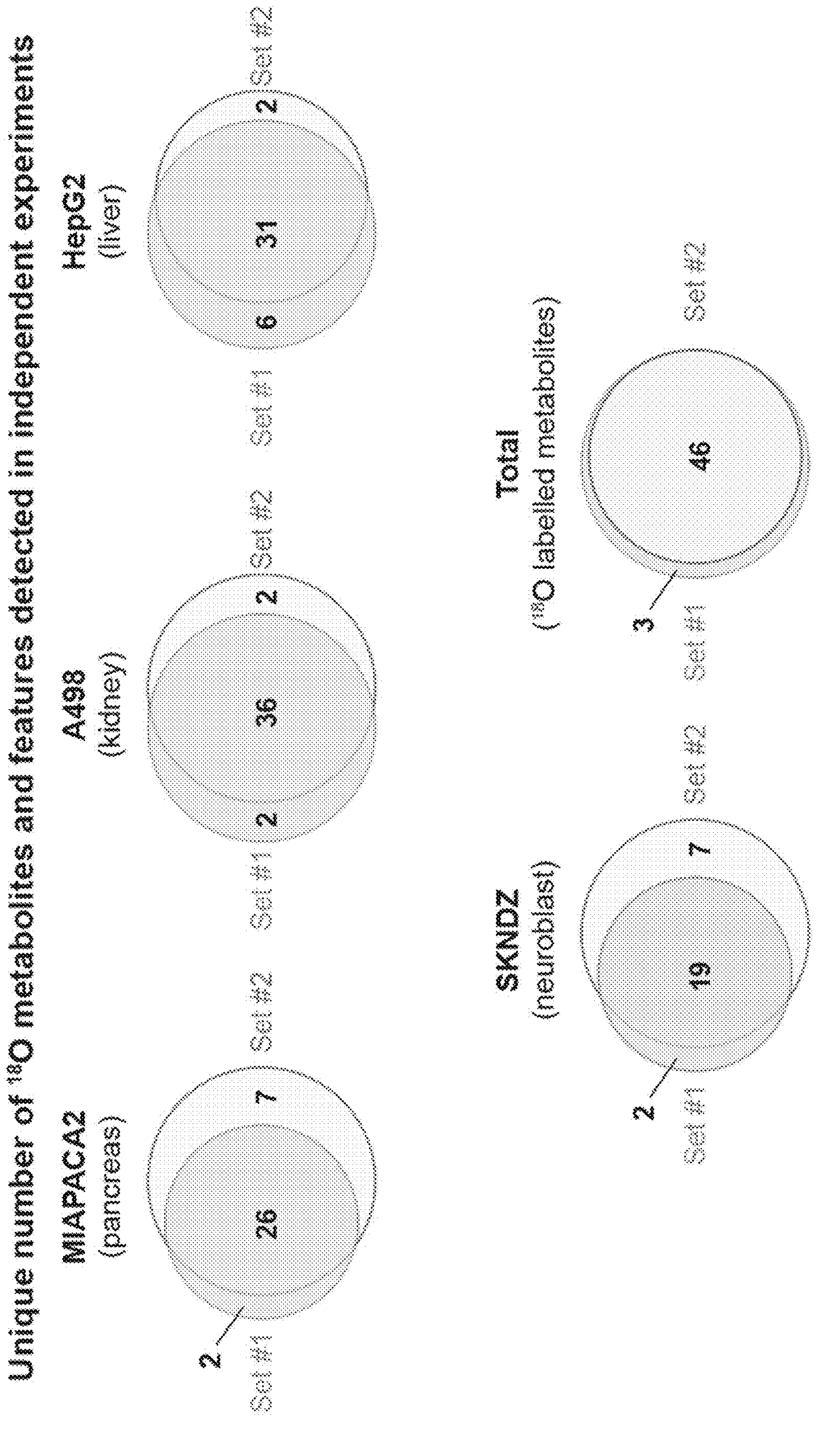

FIGS. 5A-5I show $^{18}O_2$-GASSP of human cells. Oxygen measurements after $N_2$ flush, followed with or without pulses of $O_2$:$CO_2$ gas mixture in the closed chamber containing tissue culture plates and media (n=3 technical replicates each) (FIG. 5A). The chamber maintained oxygen concentrations during the labeling run. Oxygen percentage of $O_2$-labelling experiments performed at 3% (FIG. 5B), 1% (FIG. 5C), and 0.2% (FIG. 5D) $^{16}O_2$ or $^{18}O_2$. (n=2 technical replicates each) (FIGS. 5B-5D). After oxygen had been added to the correct concentration, its concentration remained stable throughout the labeling run. Cells were treated with several concentrations of MG132, DFO (an iron chelator), IOX1 (a dioxygenase inhibitor), or in combination at 5% $O_2$ for 24 hours (FIG. 5E). Immunoblots were of HIF1α with ERK2 as a loading control. HIF1α stabilization was used as a measure of prolyl hydroxylase (PHD) inhibition. Immunoprecipitation of HIF1α to determine its hydroxylation (P564-OH) levels by the indicated inhibitors (FIG. 5F). Immunoblots of HIF1α and HIF1α P564-OH are shown, with ERK2 serving as a loading control. Experiments were performed once for optimization of drug concentrations (FIG. 5E, 5F). Summary of total and percentage of identified $^{18}O$ labelled features for each cell line and oxygen tension as described in FIG. 1B (FIG. 5G). Venn diagram demonstrating the overlap of unique $^{18}O$ labelled metabolite and features identified for each oxygen condition per cell line (FIG. 5H). Detected number of $^{18}O$-labelled metabolites in cells grown in 3%, 1%, and 0.2% $^{18}O_2$ for 24 hours in two sets of experiments. The overlap of the total number of detected $^{18}O$-labelled metabolites and features in both experimental sets are shown (FIG. 5I). Graphs represent mean±standard deviation (s.d.) (FIGS. 5A-5D).

Figure 6A:
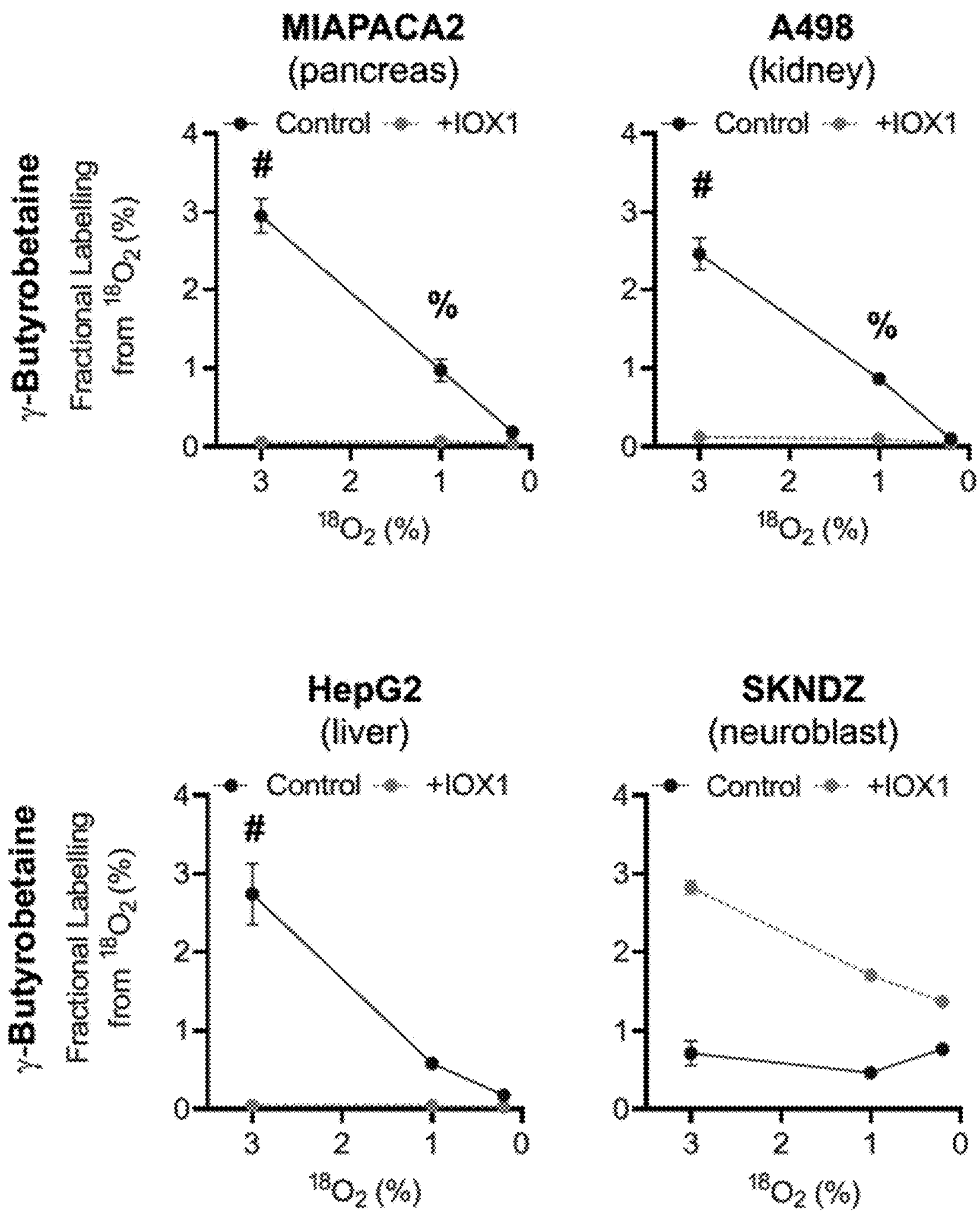
Figure 6B:
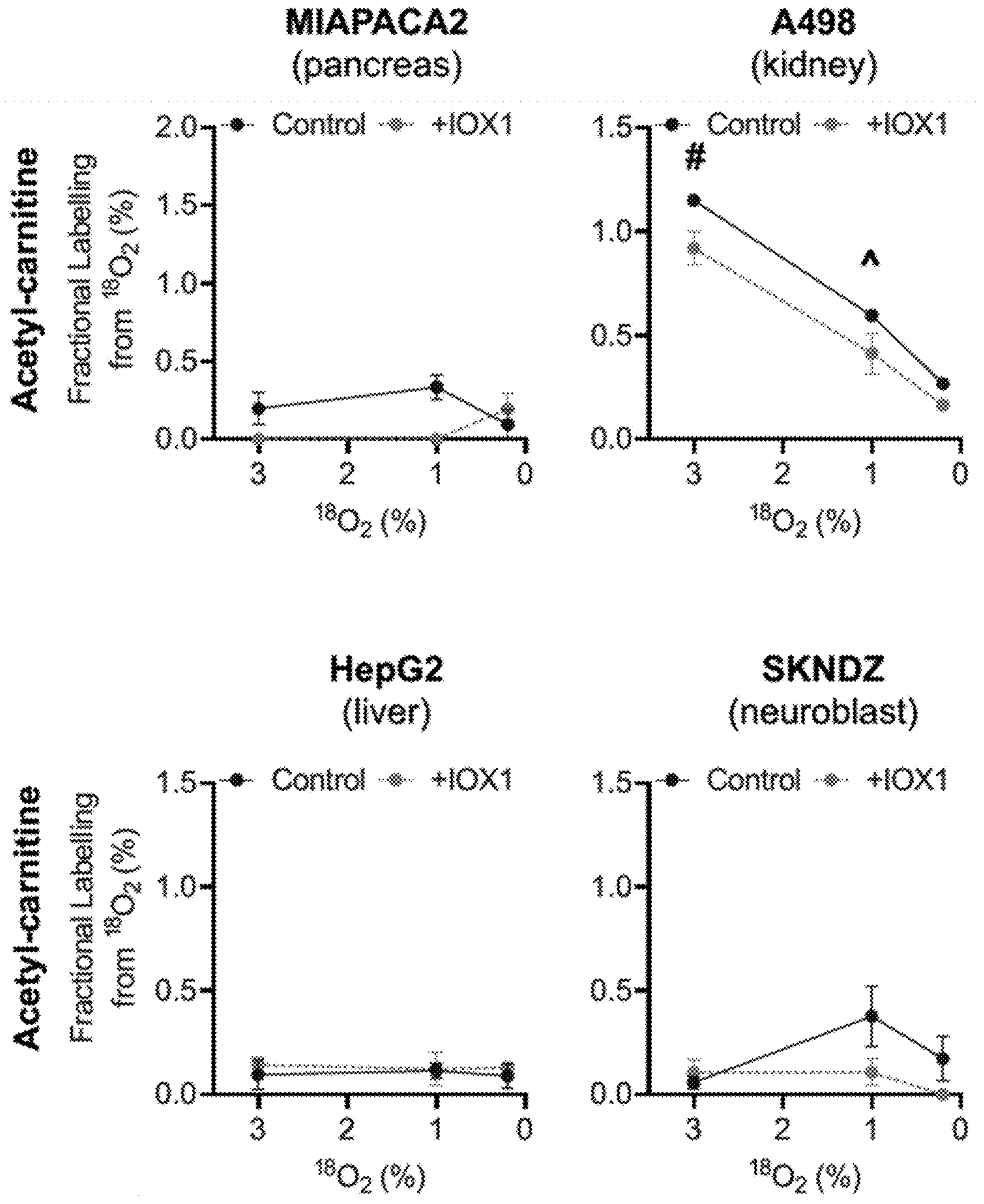
Figure 6C:
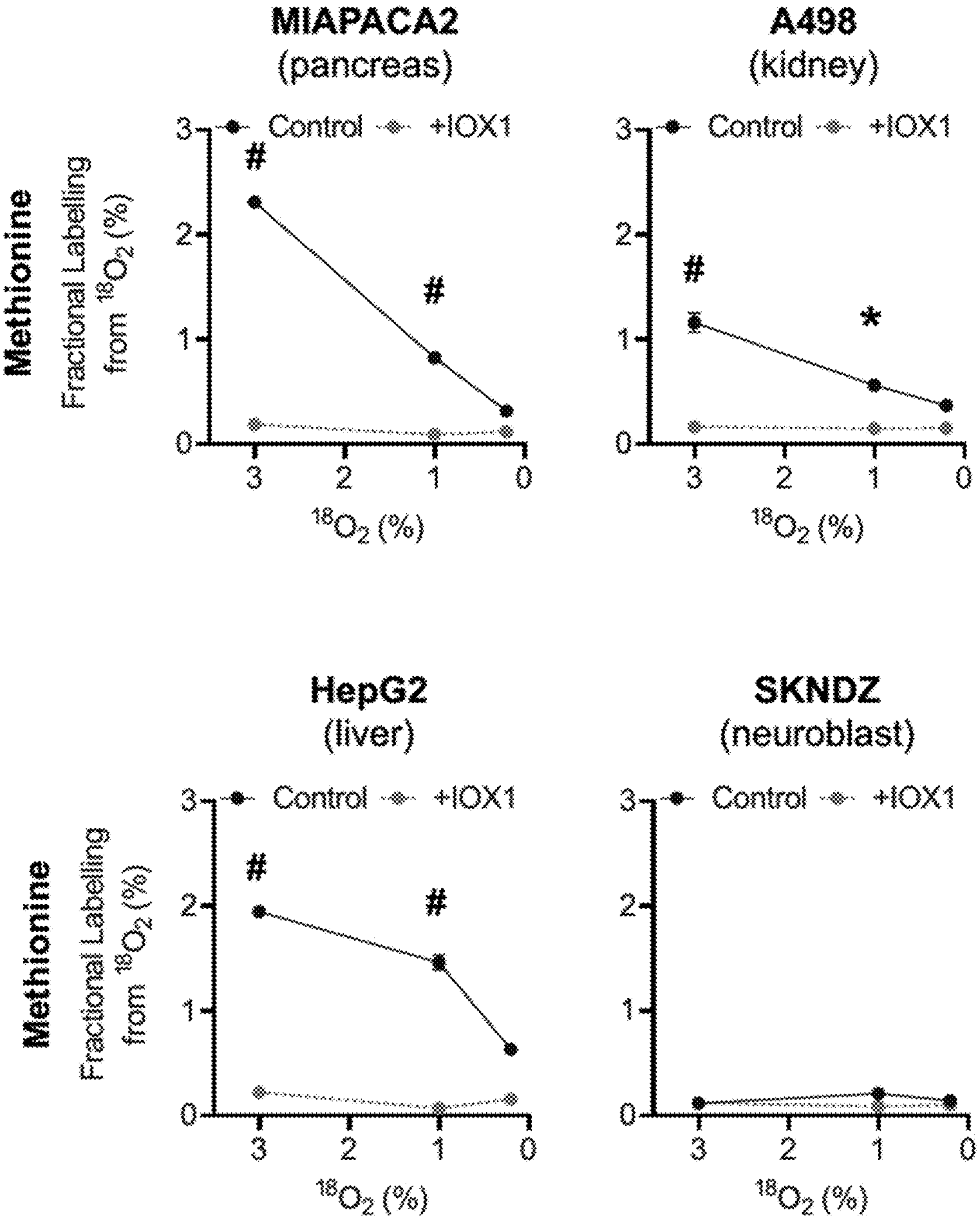
Figure 6D:
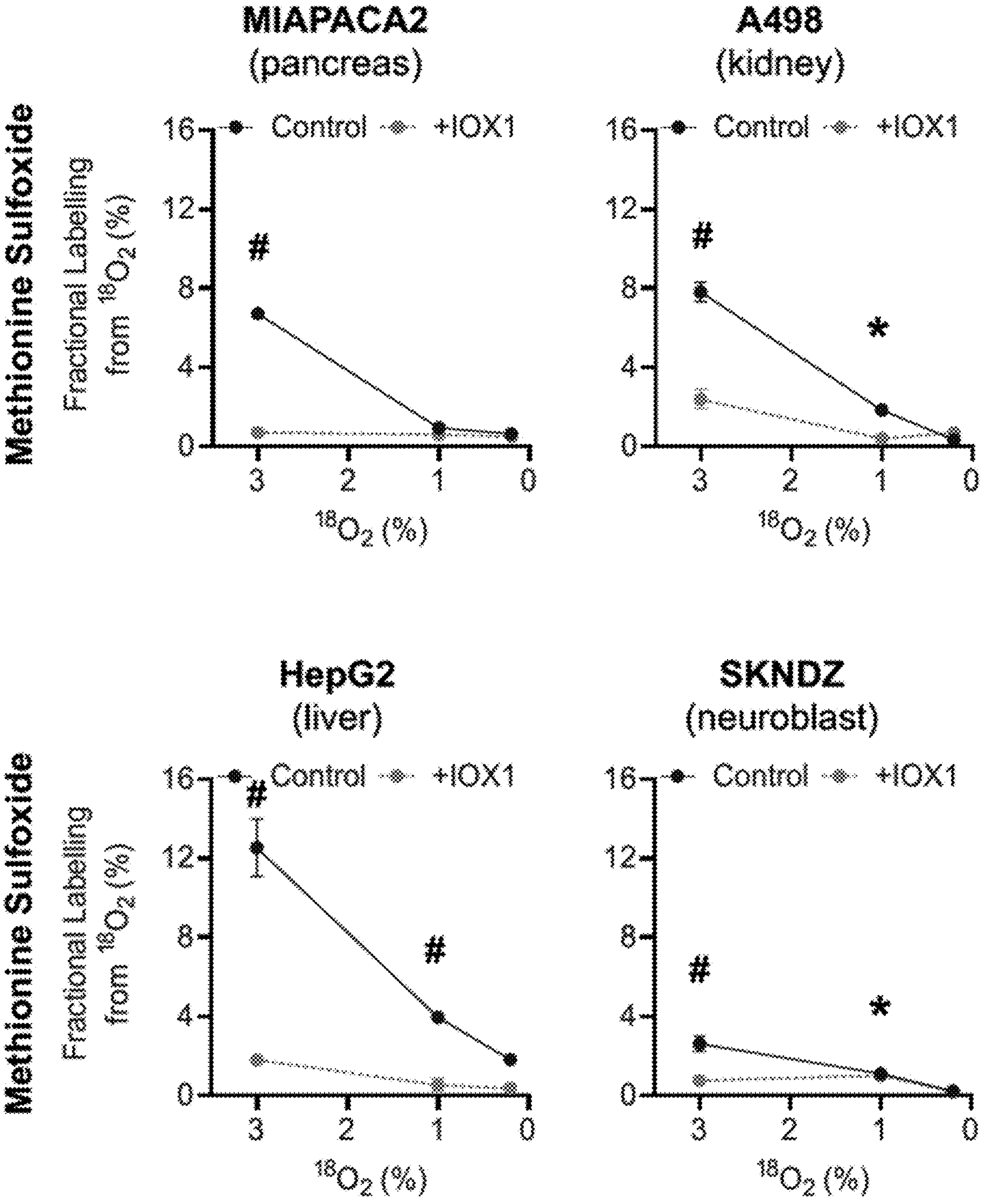
Figure 6E:
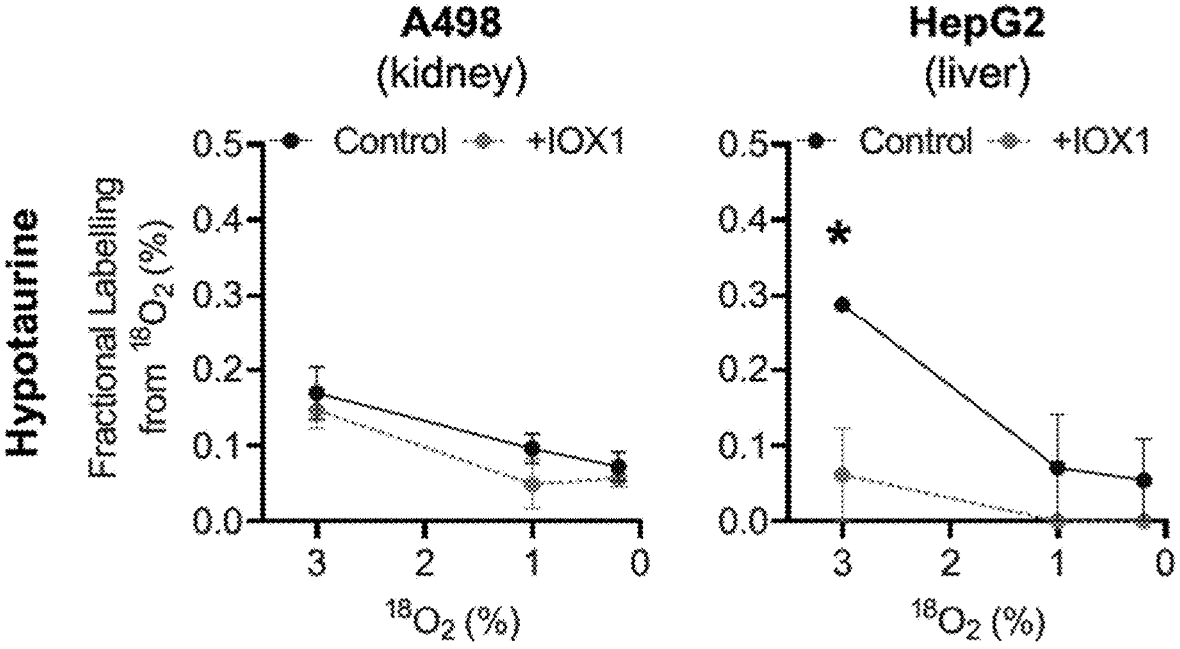
Figure 6F:
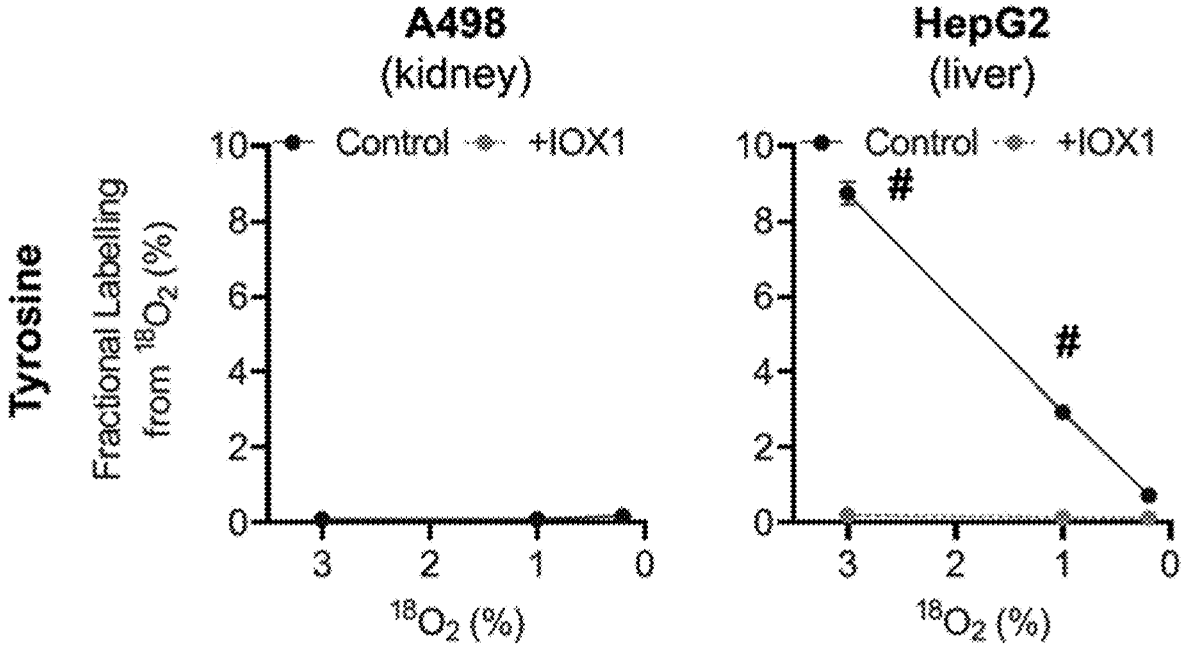
Figure 6G:
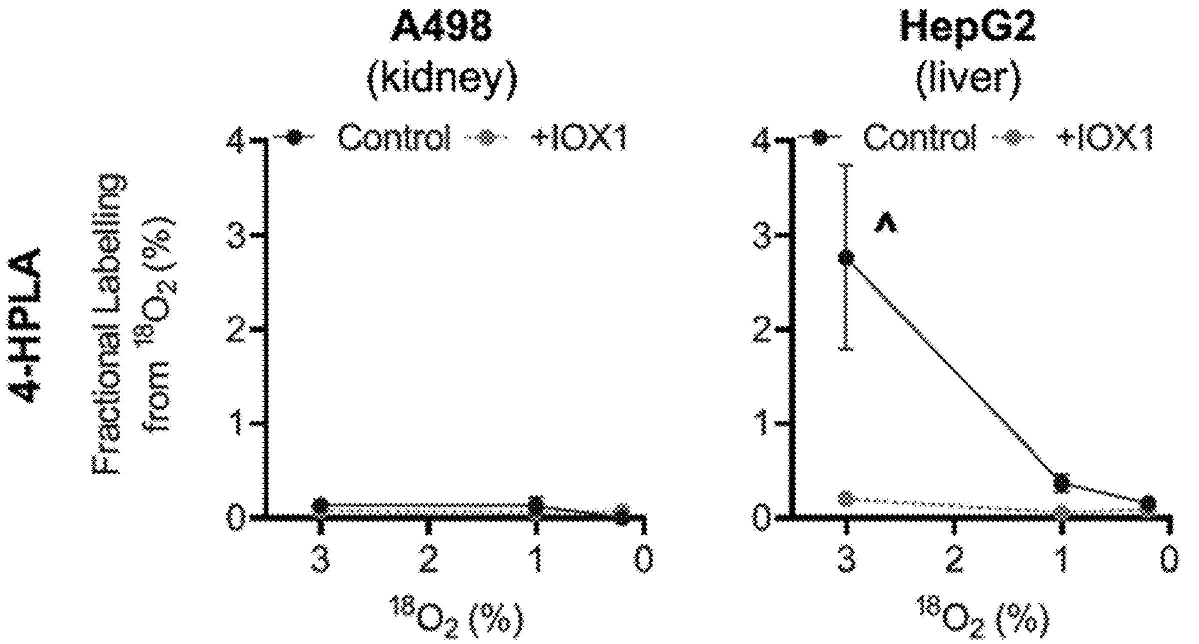
Figure 6H:
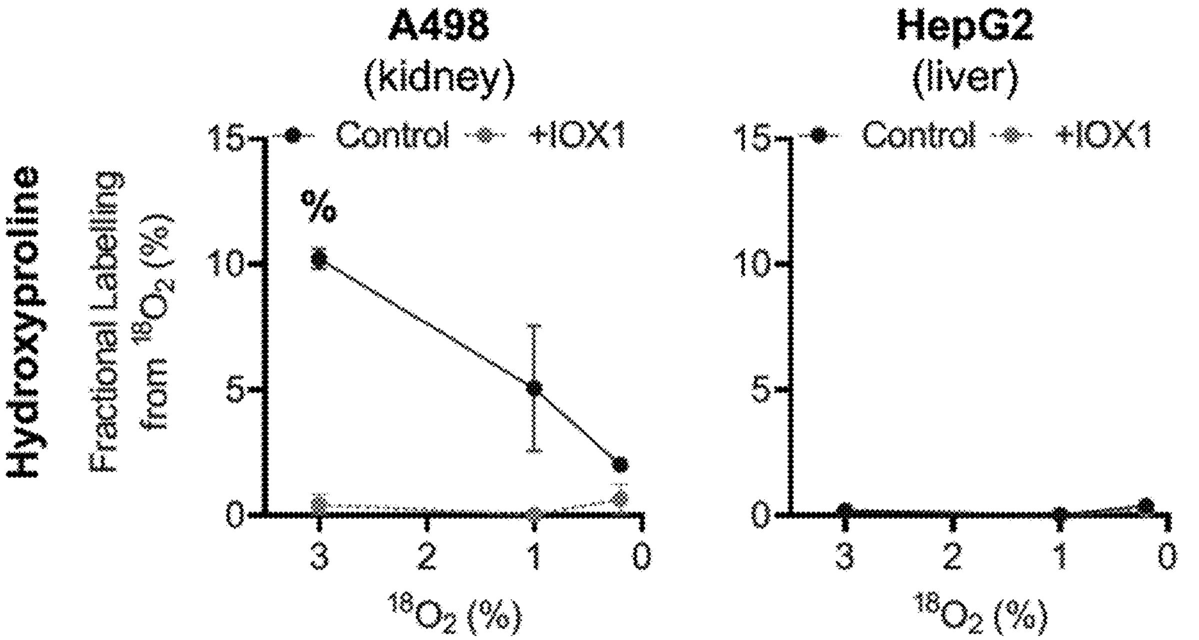
Figure 6I:
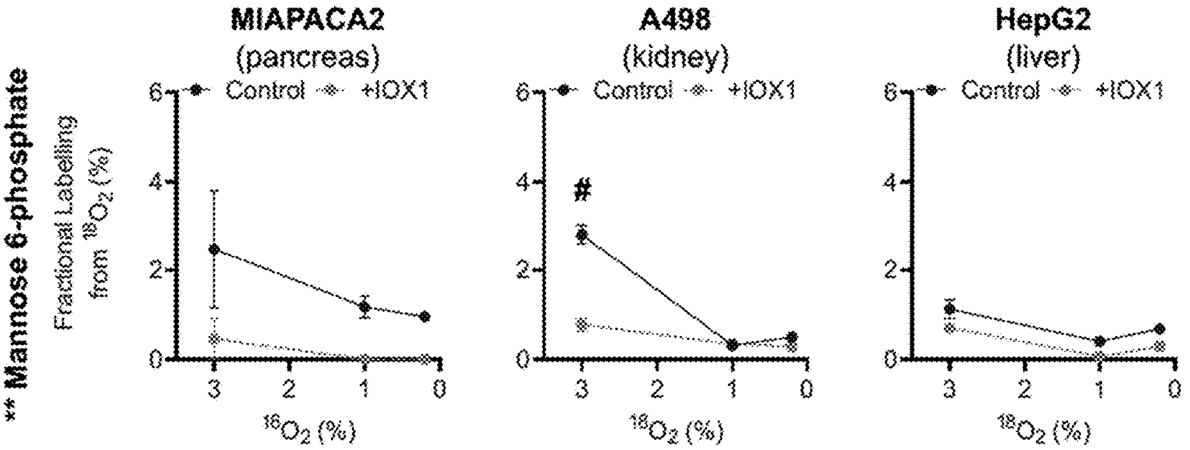
Figure 6J:
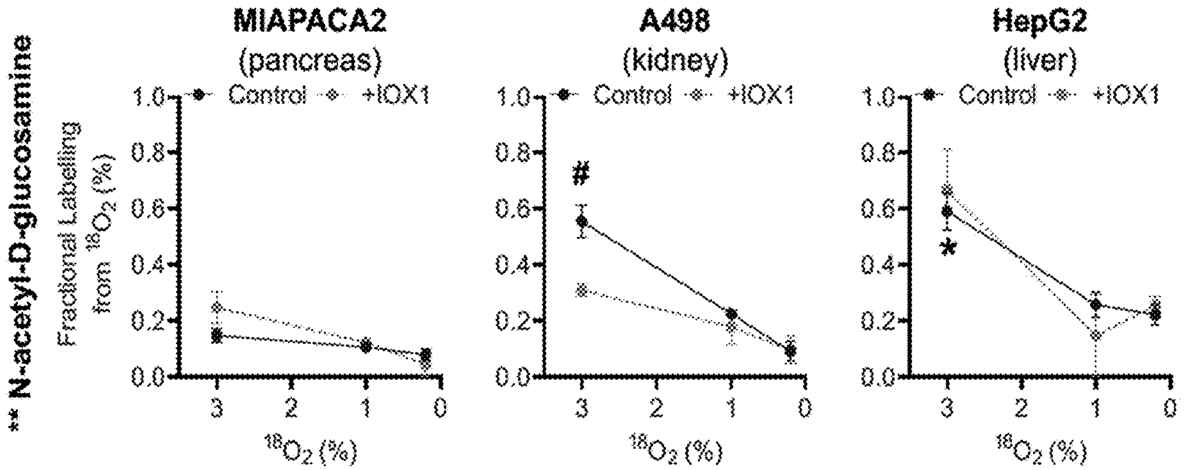

FIGS. 6A-6M show fractional $^{18}O$ labelling of metabolites and features identified in human cells by $^{18}O_2$-GASSP. Fractional $^{18}O$ labelling of metabolites by $^{18}O_2$ across multiple cell lines in response to different oxygen tensions, treated with or without IOX1 (dioxygenase inhibitor) for 24 hours (FIGS. 6A-6M). $^{18}O$ labelling of predicted (FIGS. 6A-6G), not predicted (FIGS. 6I-6K), and unknown (FIGS. 6L-6M) metabolites or features are shown for the indicated cell line. Cell line-specific $^{18}O$ labelling of known metabolites is shown in (FIGS. 6E-6H). ** represents metabolites that had matching MS2 spectra, but needed to be validated due to multiple metabolite isomers. Most metabolites exhibited decreased $^{18}O$ labelling with decreased $^{18}O_2$ tensions. A few unknown metabolites (FIGS. 6L-6M) exhibited increased labeling at lower oxygen tensions. n=3 biologically independent samples for each group and condition in all experiments except in FIGS. 6D and 6H where n=1. Graphs represent mean±s.e.m. and were compared using two-way ANOVA, followed by Tukeypost-hoc test (*p<0.05, ^p<0.01, %p<0.005, #p<0.0001).

Figure 7A:
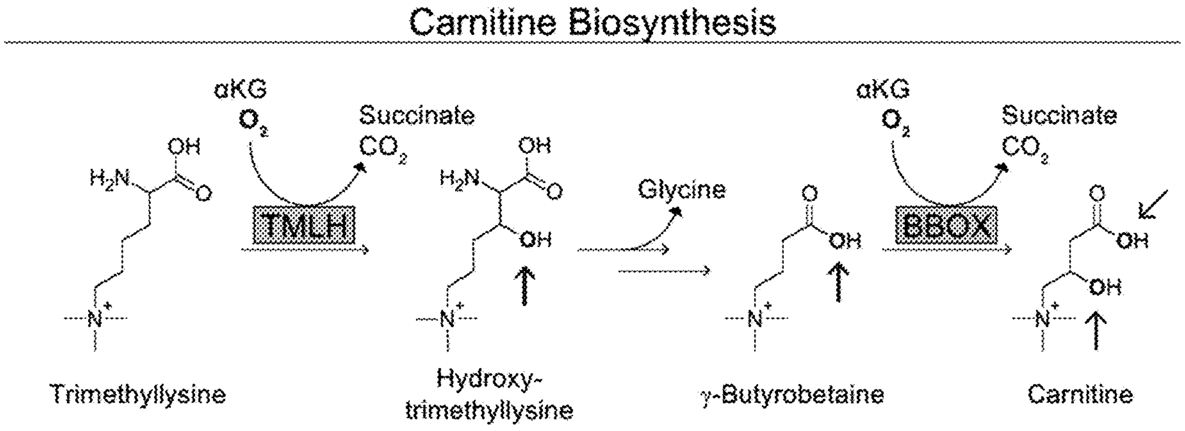
Figure 7B:
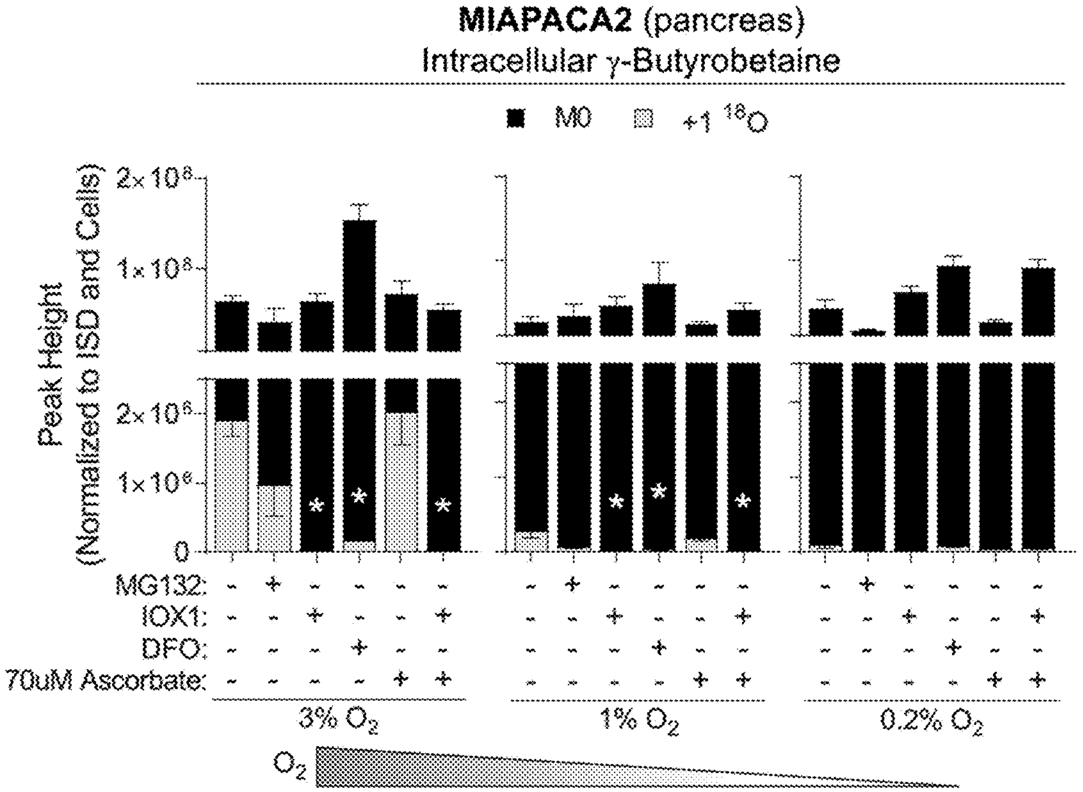
Figure 7C:
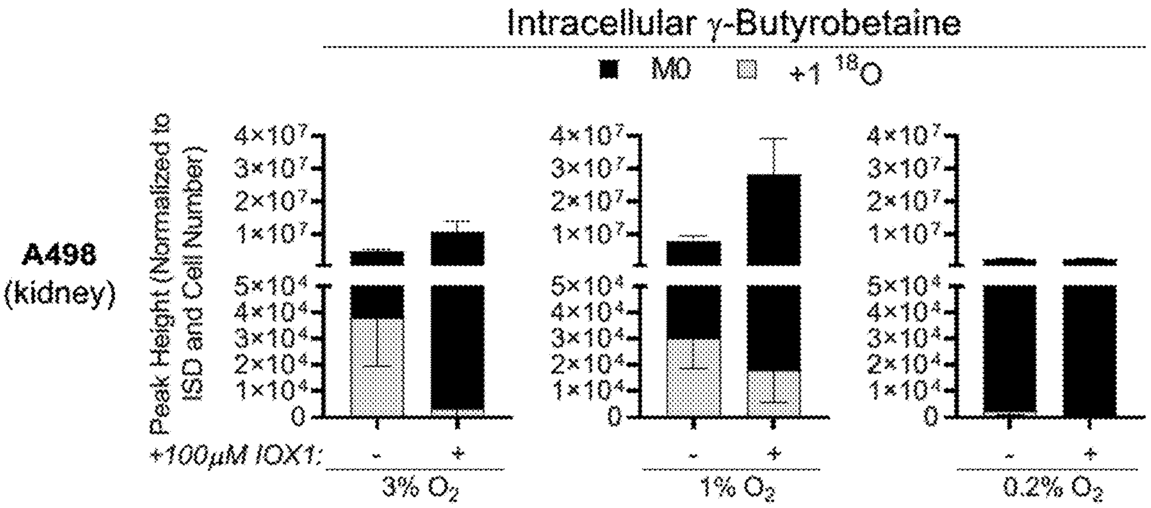
Figure 7D:
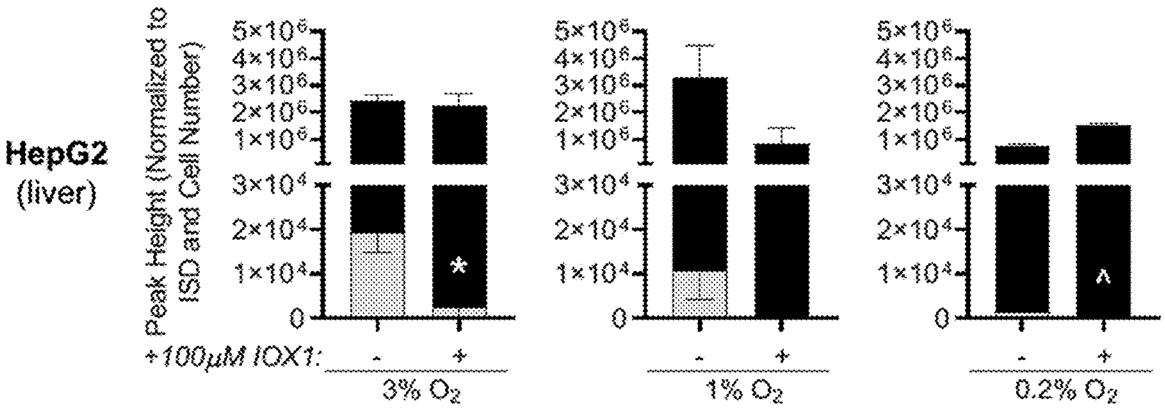
Figure 7E:
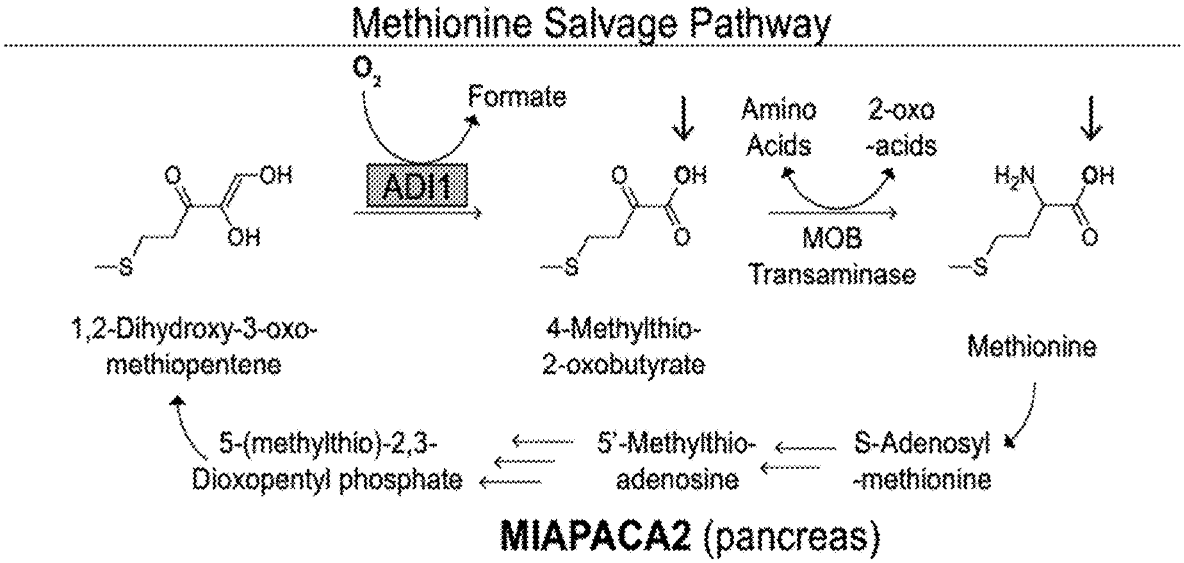
Figure 7F:
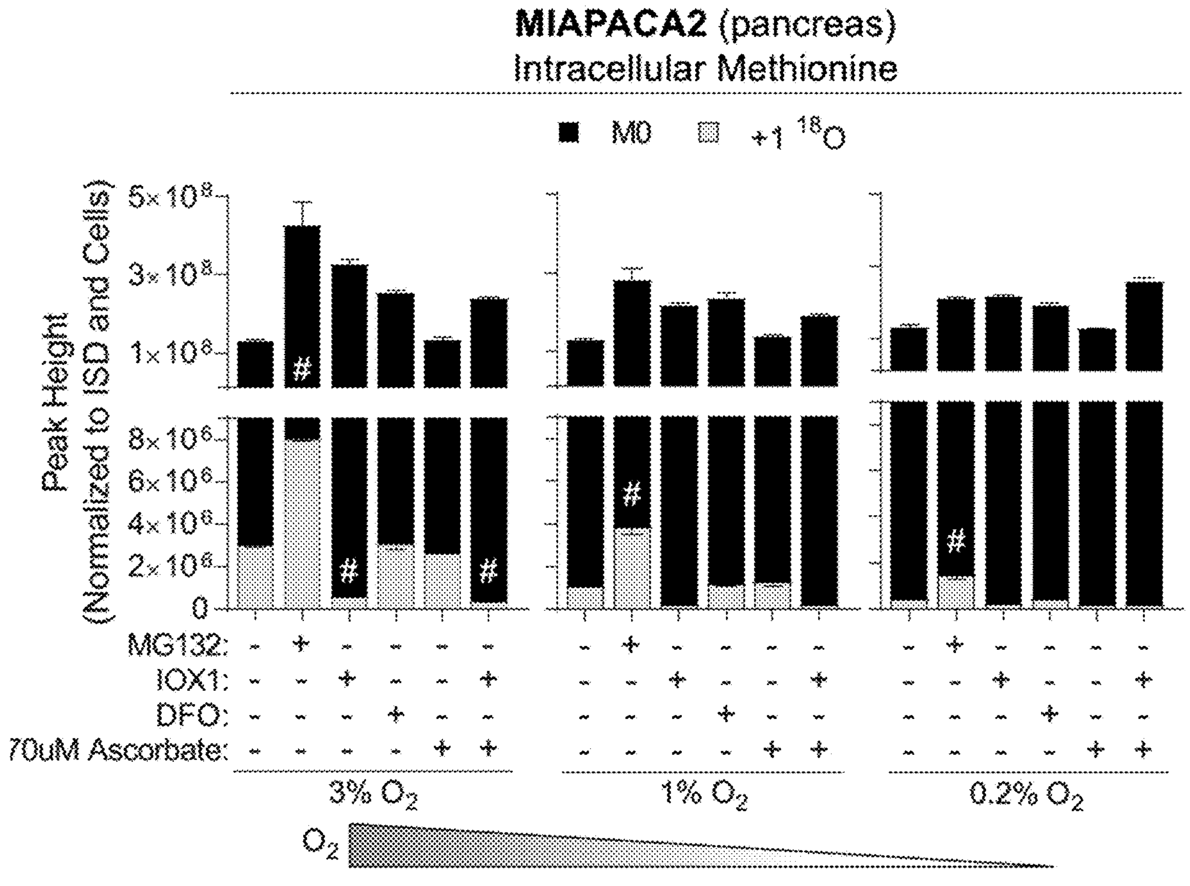
Figure 7G:
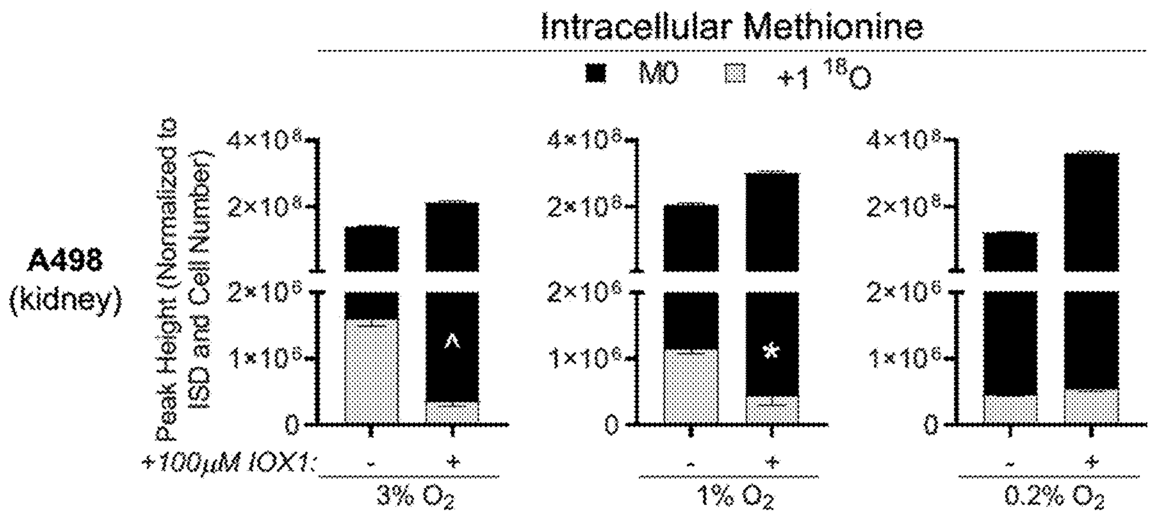
Figure 7H:
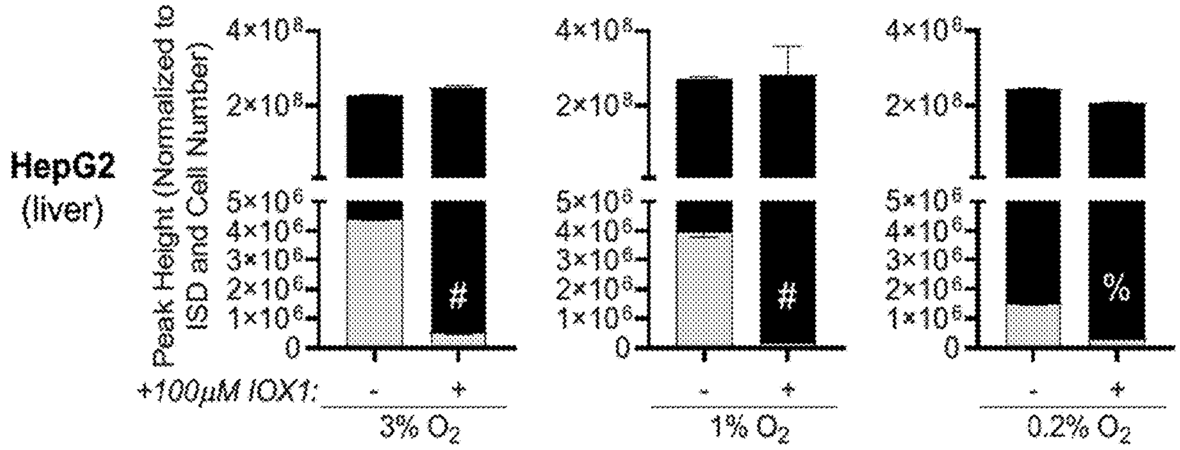
Figure 7I:
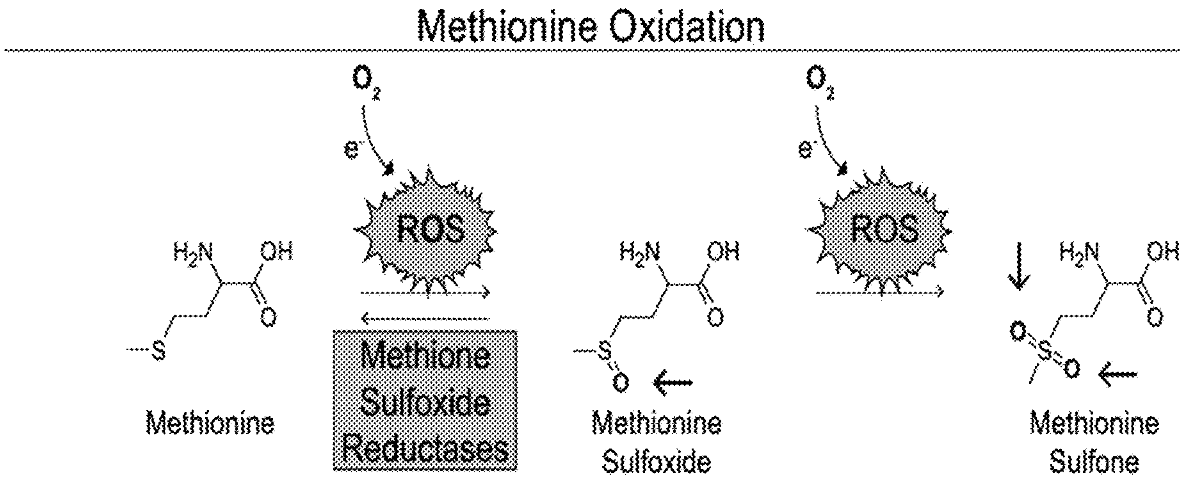
Figure 7J:
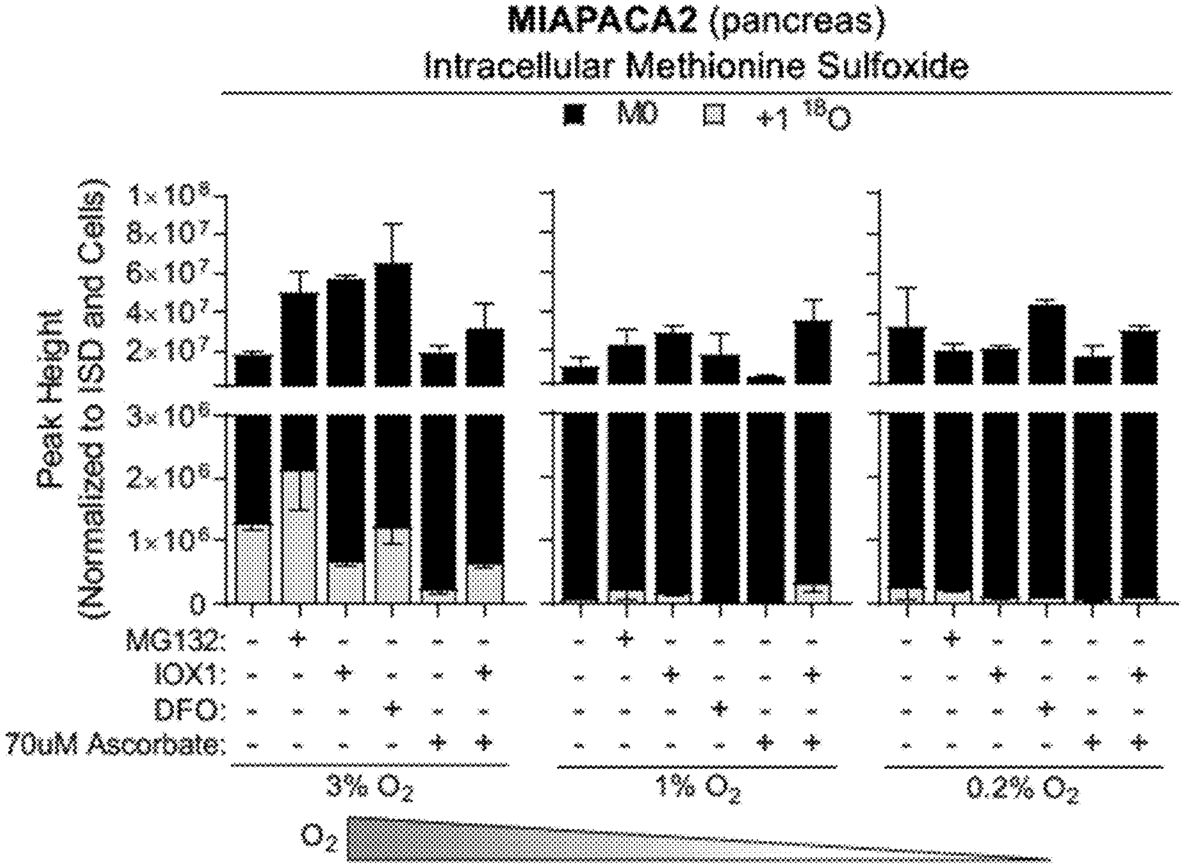
Figure 7K:
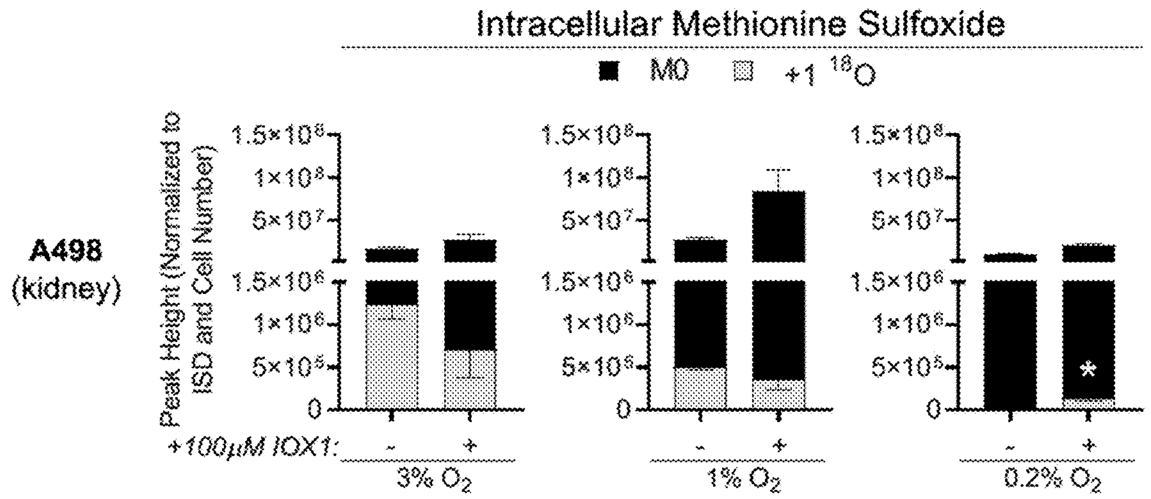
Figure 7L:
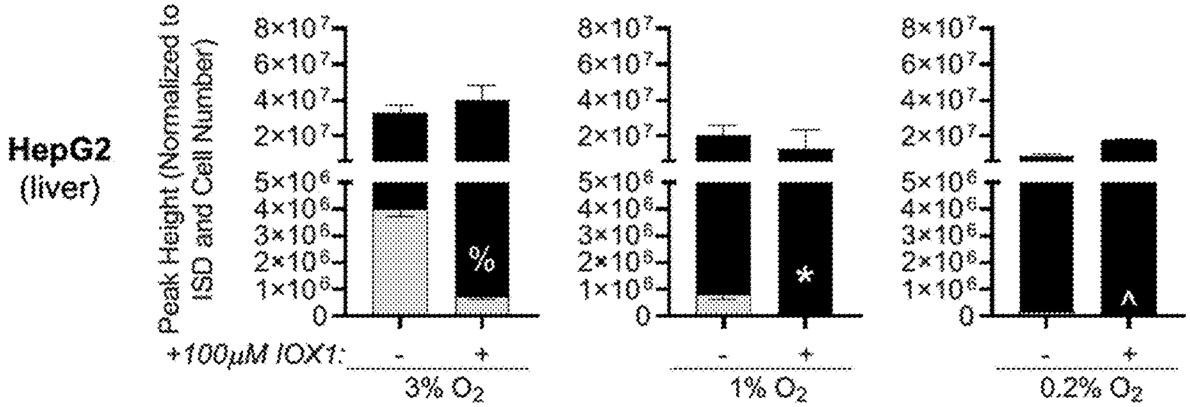
Figure 7M:
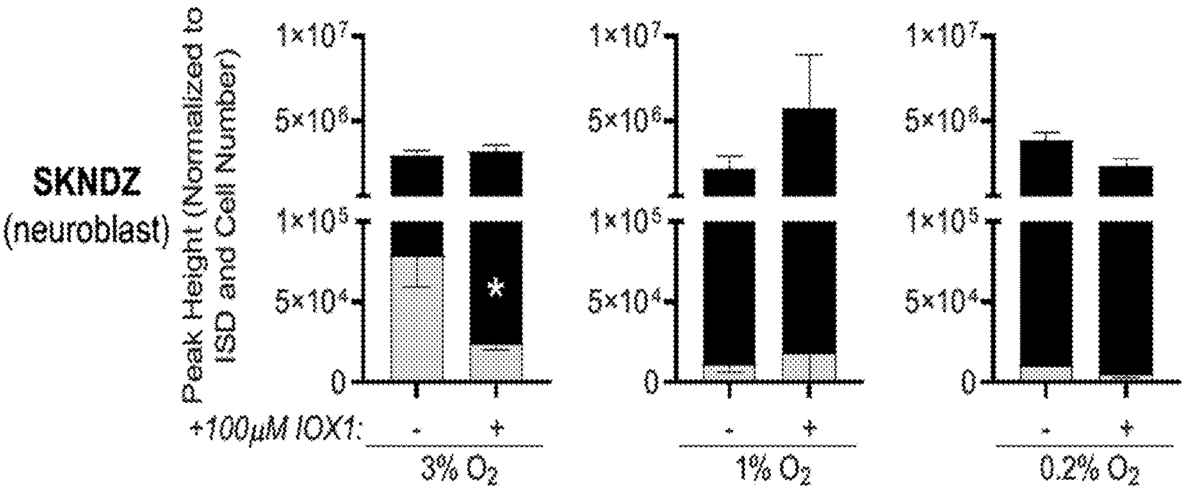

FIGS. 7A-7M show total levels of unlabelled and $^{18}O$ labelled metabolites identified in human cells by $^{18}O_2$-GASSP. Schematic of the carnitine biosynthesis pathway (FIG. 7A). Dioxygenases, TMLH (Trimethyllysine hydroxylase) and BBOX (butyrobetaine, 2-oxoglutarate dioxygenase), are shown in orange boxes, and $^{18}O$ labelling is indicated with arrows. Total intracellular levels of unlabelled and $^{18}O$ labelled γ-butyrobetaine from cells grown in 3%, 1%, and 0.2% $^{18}O_2$ with the indicated reagents for 24 hours (n=3) (FIGS. 7B-7D). γ-butyrobetaine was labelled with $^{18}O$ in an IOX1- and DFO-sensitive manner consistent with its production by an iron-dependent dioxygenase. Schematic of methionine salvage pathway (FIG. 7E). ADI1 (Acireductone dioxygenase 1), a dioxygenase, is shown in orange, and $^{18}O$ labelling is indicated with arrows. Total intracellular levels of unlabelled and $^{18}O$ labelled methionine from cells grown in 3%, 1%, and 0.2% $^{18}O_2$ with the indicated reagents for 24 hours (n=3) (FIGS. 7F-7H). Methionine was labelled with $^{18}O$ in an IOX1-sensitive manner but was less sensitive to DFO, consistent with the ability of ADI1 to use other metals to catalyze its reaction. Schematic of methionine oxidation by $^{18}O$ labelled reactive oxygen species with arrows (FIG. 7I). Total intracellular levels of unlabelled and $^{18}O$ labelled methionine sulfoxide from cells grown in 3%, 1%, and 0.2% $^{18}O_2$ with the indicated reagents for 24 hours (n=3) (FIG. 7J-7M). "n" represents the number of biologically independent experiments for each group and condition. Graphs (mean±s.e.m.) were compared using two-tailed Student t-test (FIGS. 7C-7D, FIGS. 7G-7H, FIGS. 7K-7M) or one-way (FIG. 7B, FIG. 7F, FIG. 7J) ANOVA, followed by Tukey post-hoc test (*p<0.05, ^<0.01, %p<0.005, #p<0.0001).

Figure 8A:
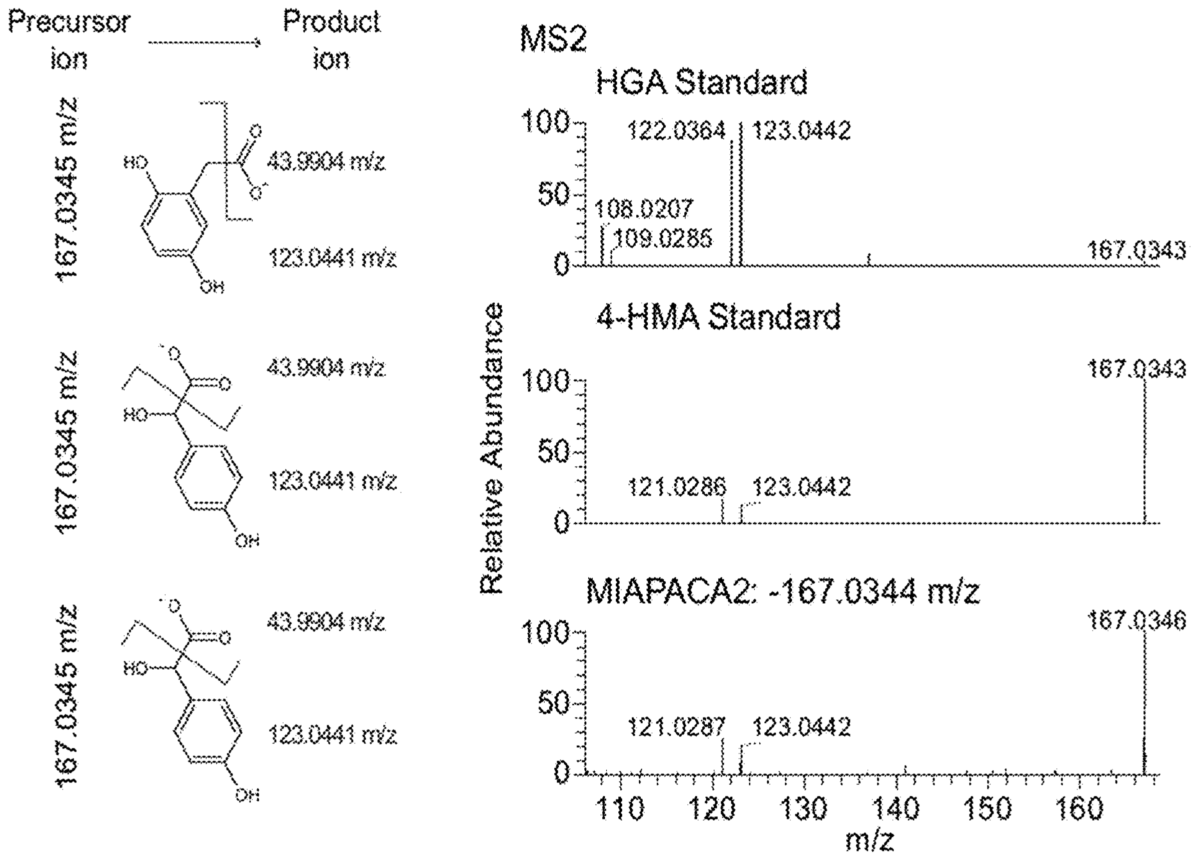
Figure 8B:
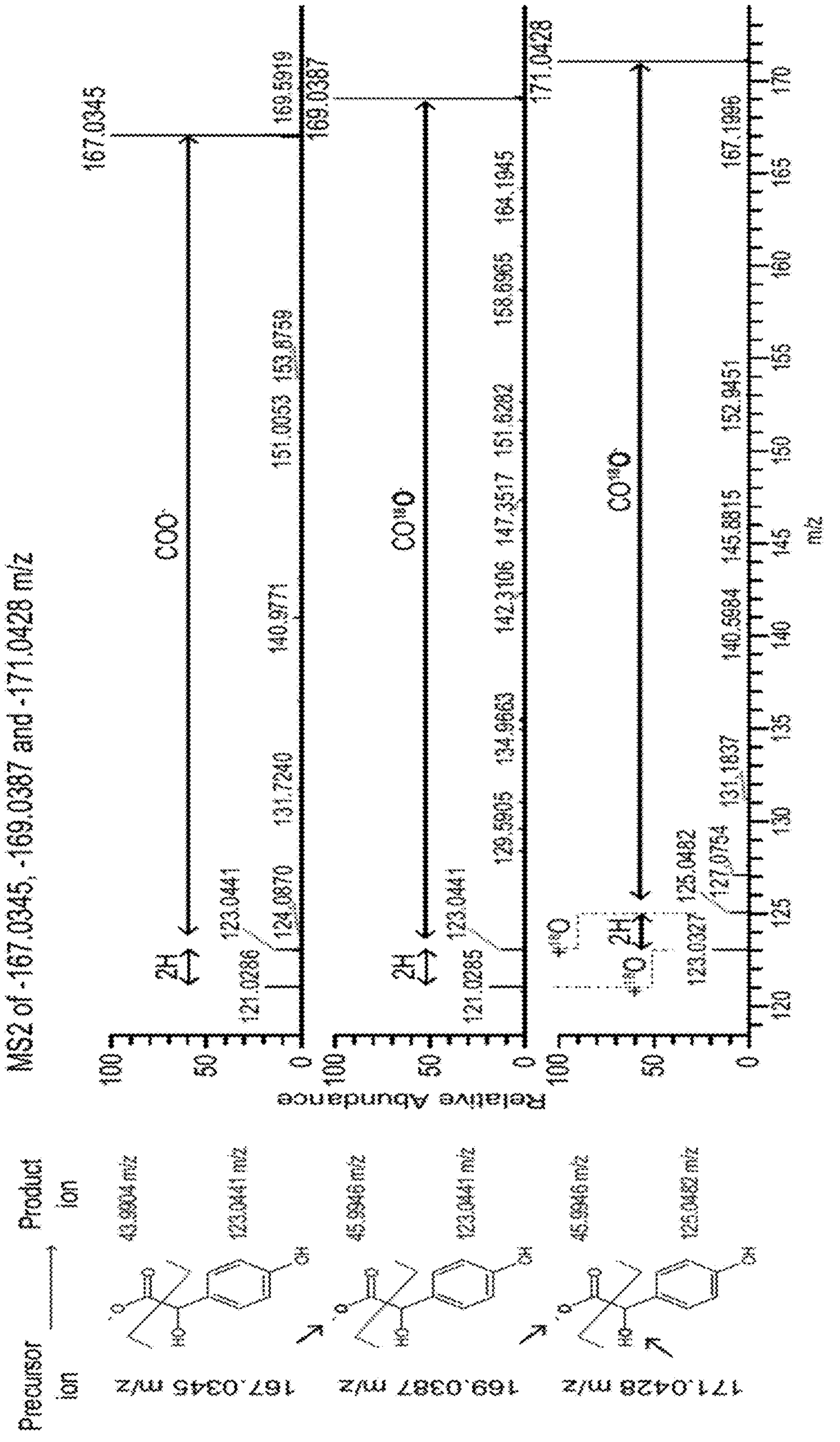
Figure 8C:
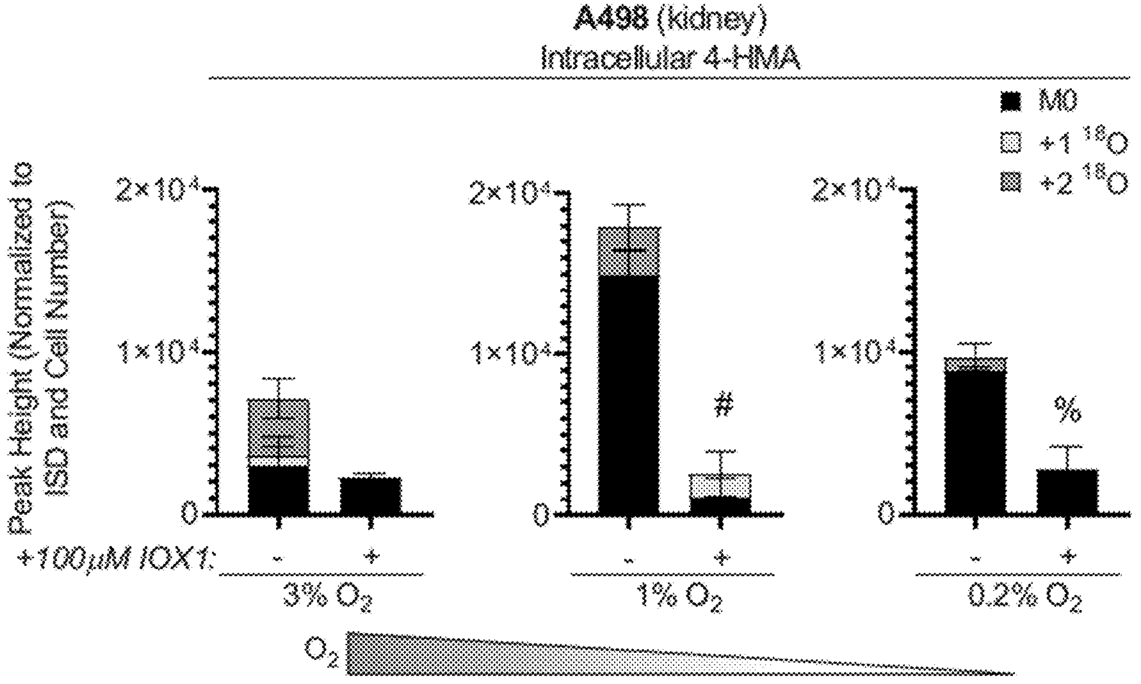
Figure 8D:
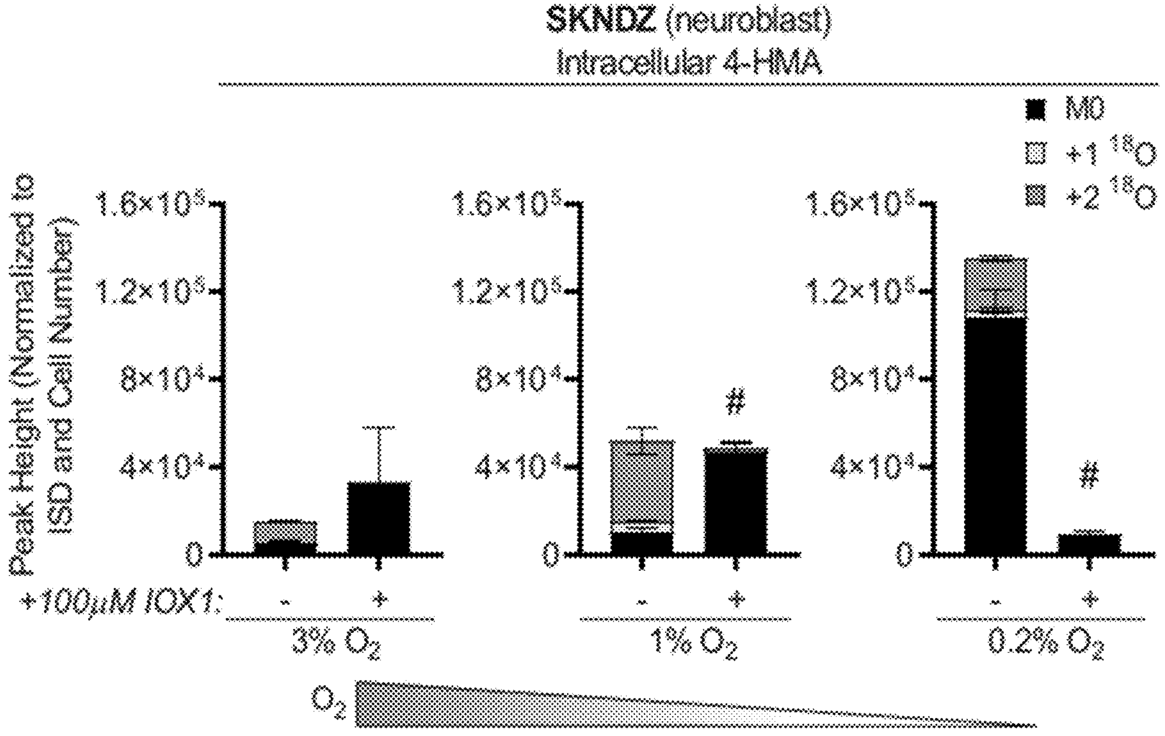

FIGS. 8A-8D show identification of $^{18}O$-labelled 4-HMA in human cells. Tandem mass spectra (MS2) of homogentisate (HGA) standard, 4-hydroxymandelate (4-HMA) standard, and unlabelled (167.0344 m/z) feature precursors, and the respective product fragments (FIG. 8A). Mass differences between the precursor and product ions reflected loss of one $CO_2$. The line in the structure indicates fragmentation of the precursor ion into the two product ions. The structure of the precursor and product ions are depicted on the left. MS2 of unlabelled (167.0344 m/z), +one $^{18}O$ (169.0387 m/z), and +two $^{18}O$ (171.0428 m/z) labelled 4-HMA precursors, and the respective product fragments (FIG. 8B). Mass differences between precursor and product ions reflected loss of unlabelled and +one $^{18}O$-labelled $CO_2$. The line in the structure indicates precursor ion fragmentation into two product ions. The structure and position of $^{18}O$ labelled (pointed arrow) 4-HMA are depicted on the left. Total levels of unlabelled and $^{18}O$ labelled 4-HMA levels in A498 (FIG. 8C) and SKNDZ (FIG. 8D) cells grown in 3%, 1%, and 0.2% $^{18}O_2$, and treated with or without IOX1 (dioxygenase inhibitor) for 24 hours (FIG. 8C-8D). 4-HMA $^{18}O$ labeling was decreased with IOX1 treatment. n=3 biologically independent replicates for each group and condition. Graphs represent mean±s.e.m. and were compared by two-way ANOVA (FIGS. 8C-8D), followed by Bonferroni post-hoc test (*p<0.05, ^p<0.01, %p<0.005, #p<0.0001). HCD: higher energy collision induced dissociation.

Figure 9A:
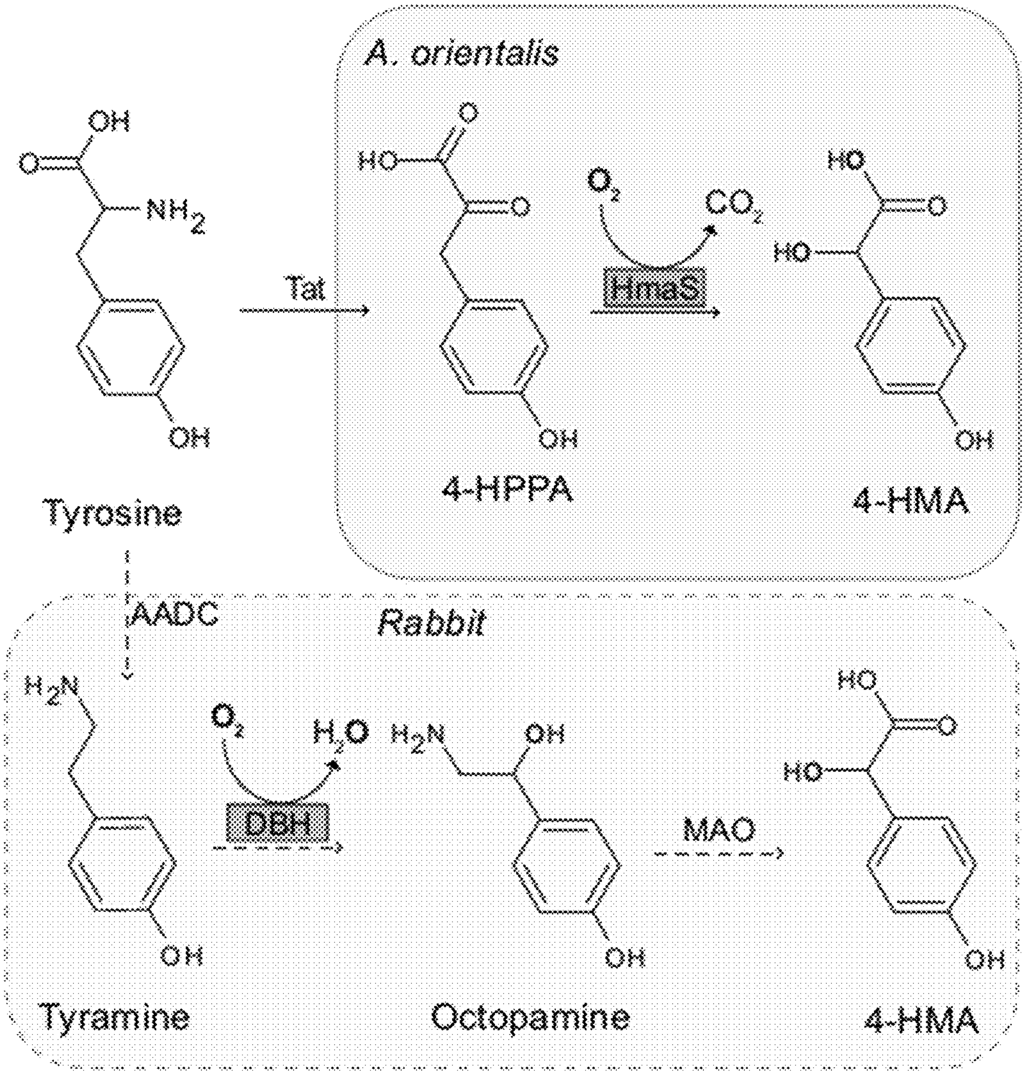
Figure 9B:
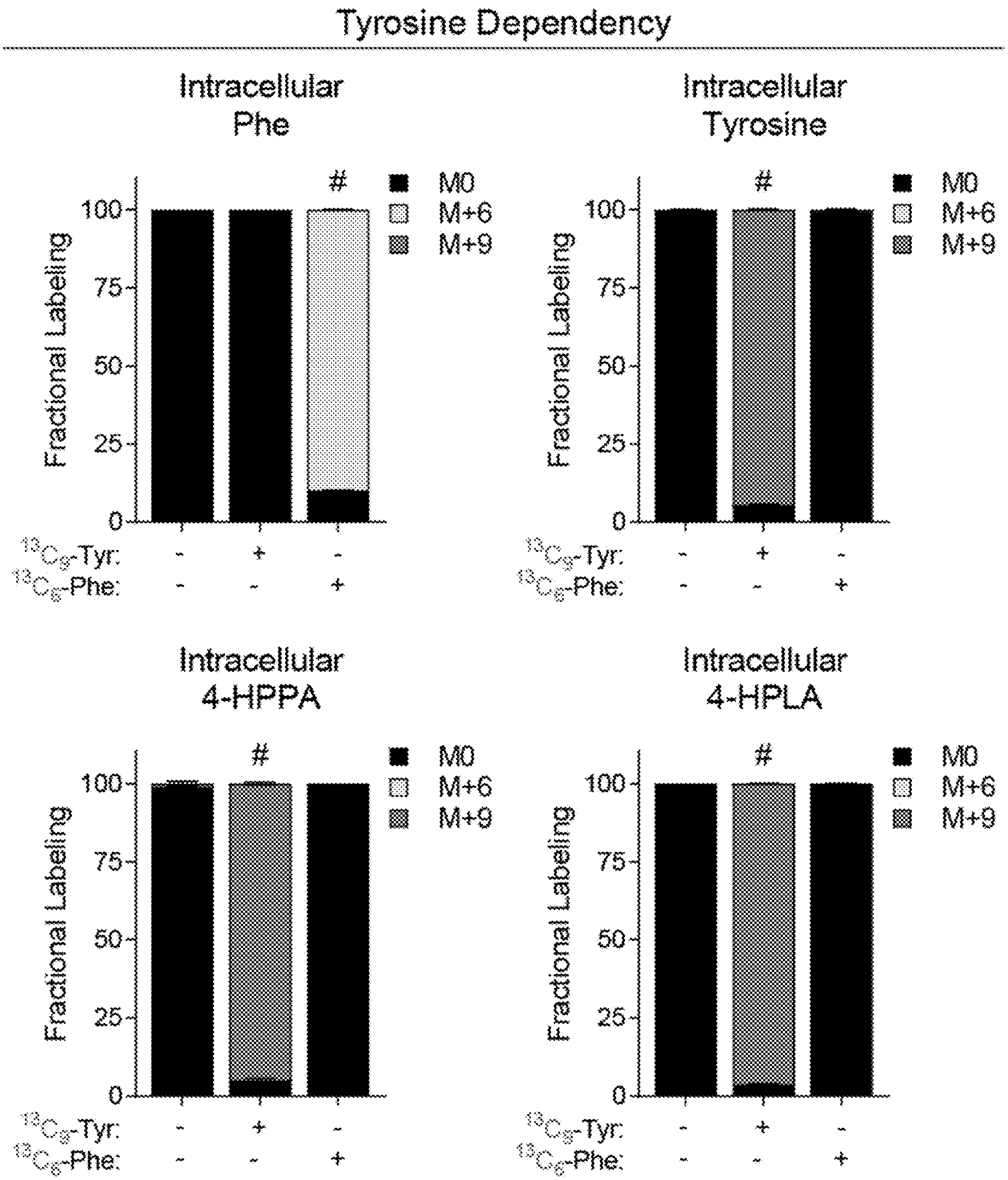
Figure 9C:
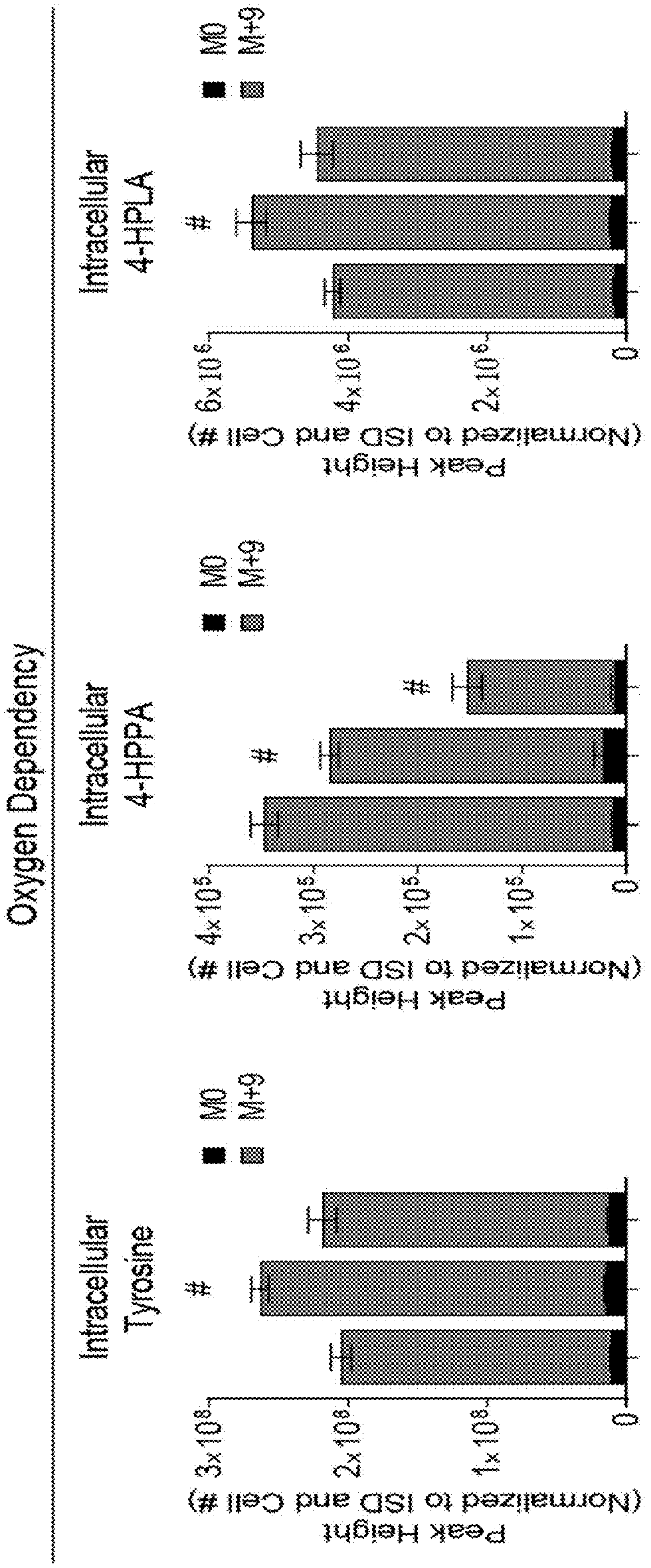
Figure 9D:
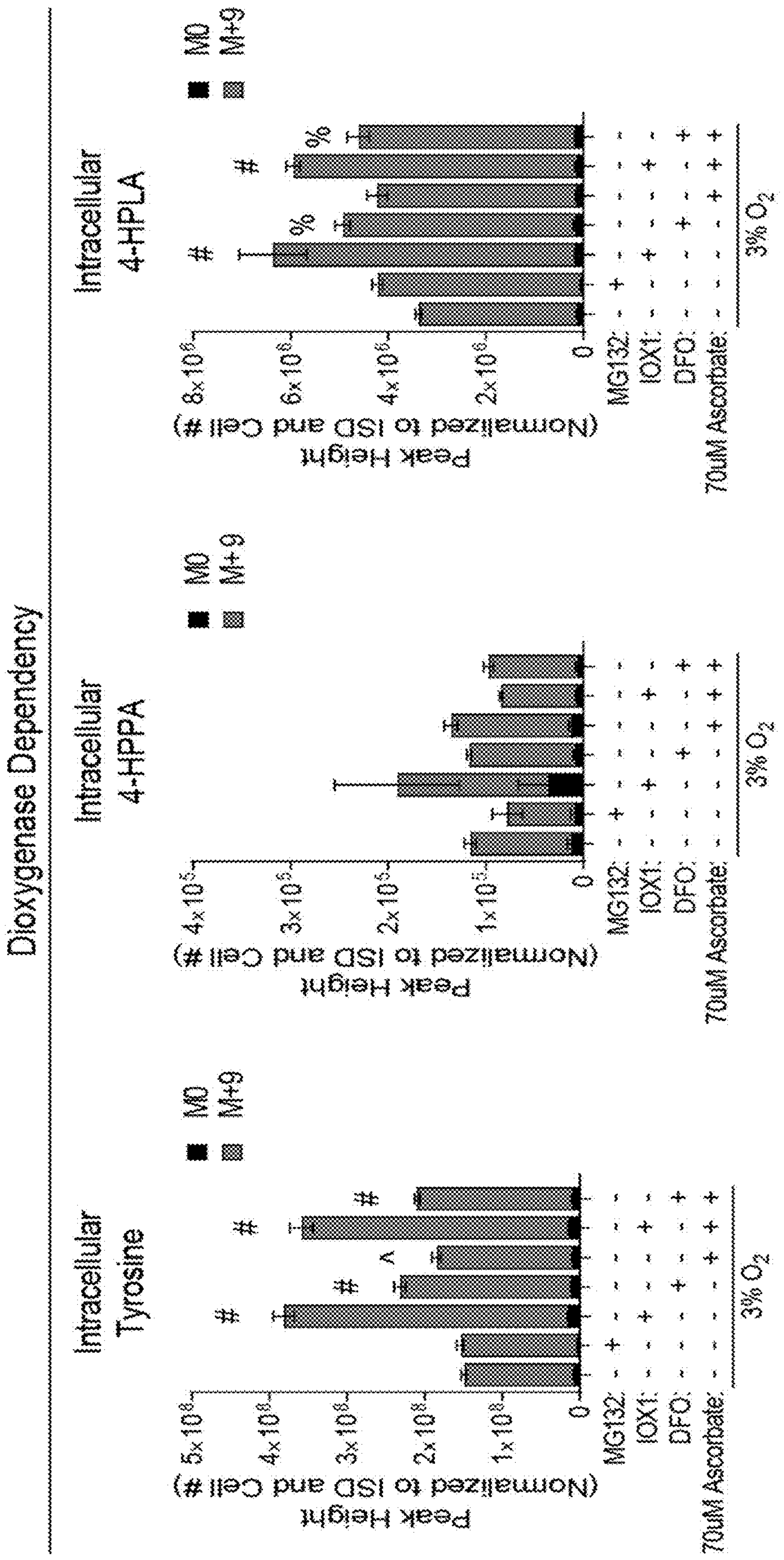

FIGS. 9A-9D show 4-HMA as a tyrosine-derived metabolite in human cells. Schematic of known and proposed pathways involved in 4-HMA biosynthesis found in the literature (FIG. 9A). *A. orientalis* biosynthesizes 4-HMA from 4-hydroxyphenylpyruvate (4-HPPA), via an iron-dependent dioxygenase, hydroxymandelate synthase (HmaS). 4-HMA also has been proposed to be made from tyramine in rabbits by radioactive tracing studies. However, the proposed pathway was never formally demonstrated, as indicated by the dotted lines and box. Fractional labelling of Phe, Tyr, 4-HPPA and 4-HPLA from cells grown at 3% $O_2$ with or without $^{13}C_9$-Tyr or $^{13}C_6$-Phe for 24 hours (from FIG. 3A) (n=5 for each group) (FIG. 9B). $^{13}C_9$-Tyr was incorporated into 4-HPPA and 4-HPLA while $^{13}C_6$-Phe was not. Total intracellular levels of unlabelled and $^{13}C$-labelled Tyr, 4-HPPA and 4-HPLA from cells grown at 3%, 1%, and 0.2% $O_2$ with $^{13}C$-Tyr for 24 hours (from FIG. 3B) (n=5 for each group) (FIG. 9C). Pools of 4-HPPA dropped with lower oxygen tensions. Total intracellular levels of unlabelled and $^{13}C$-labelled Tyr, 4-HPPA and 4-HPLA from cells grown in $^{13}C$-Tyr at 3% $O_2$ with the indicated reagents for 24 hours (from FIG. 3C) (n=5 for each group) (FIG. 9D). IOX1 and DFO increased 4-HPLA pools. "n" represents the number of biologically independent replicates for each group and condition. Graphs represent mean±s.e.m. and were compared by two-way ANOVA (FIGS. 9B-9D), followed by Tukey post-hoc test (^p<0.01, %p<0.005, #p<0.0001).

Figure 10A:
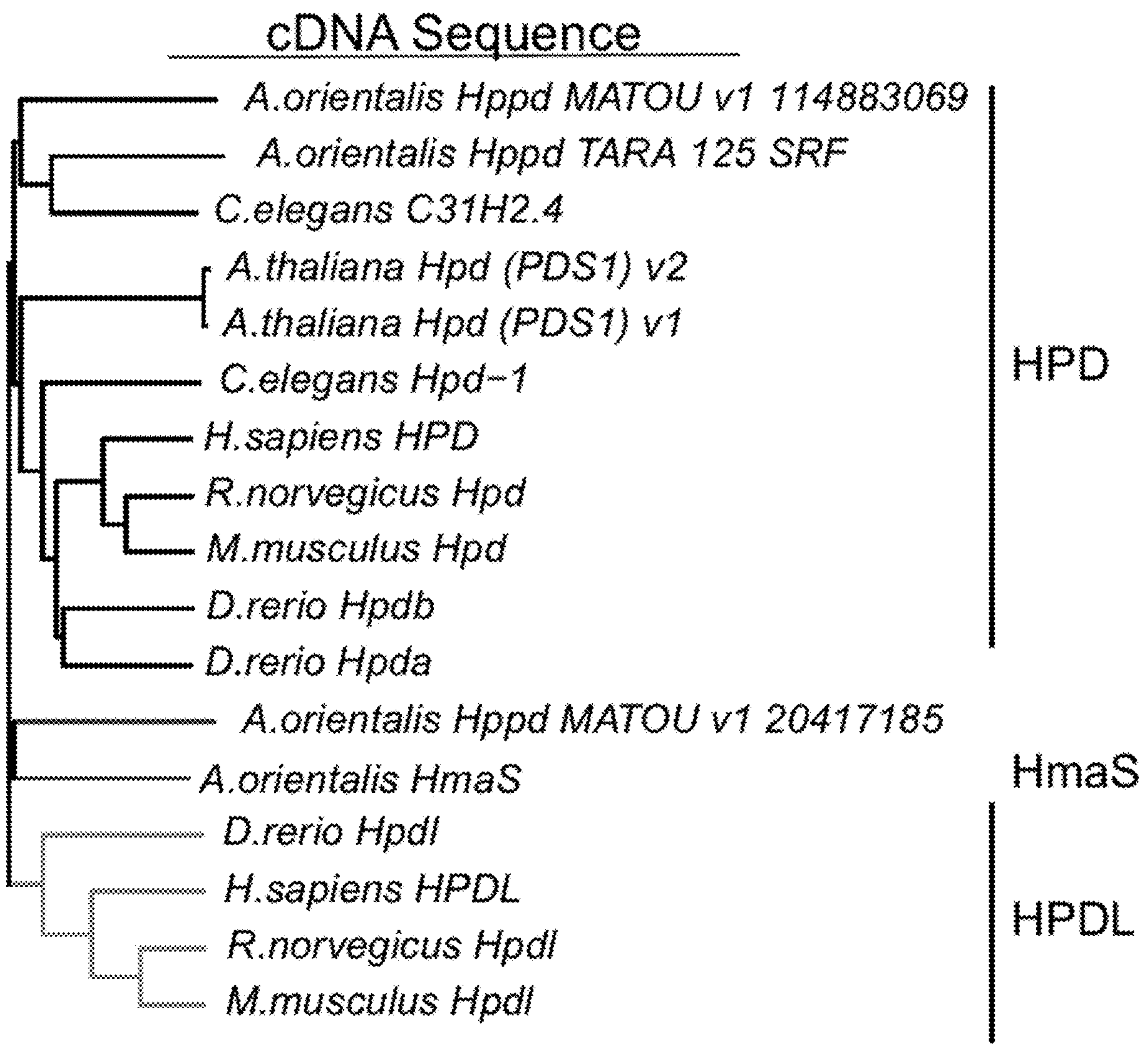
Figure 10B:
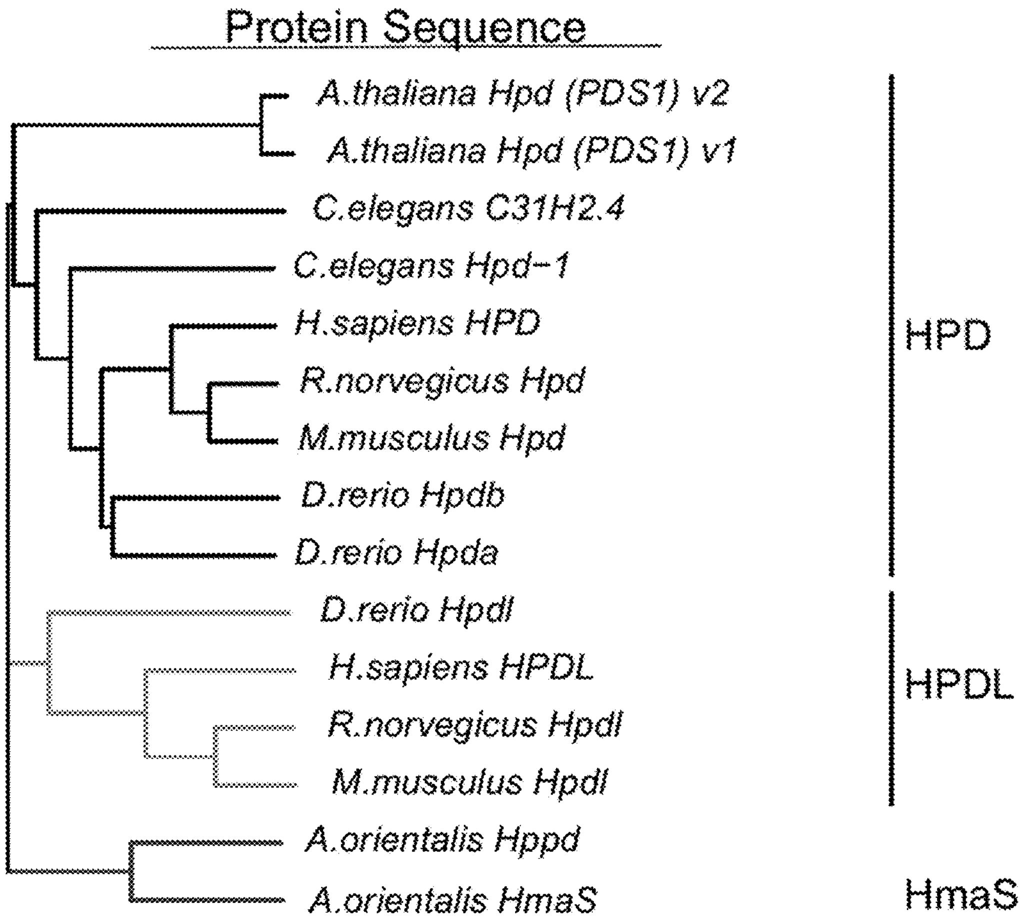
Figure 10D:
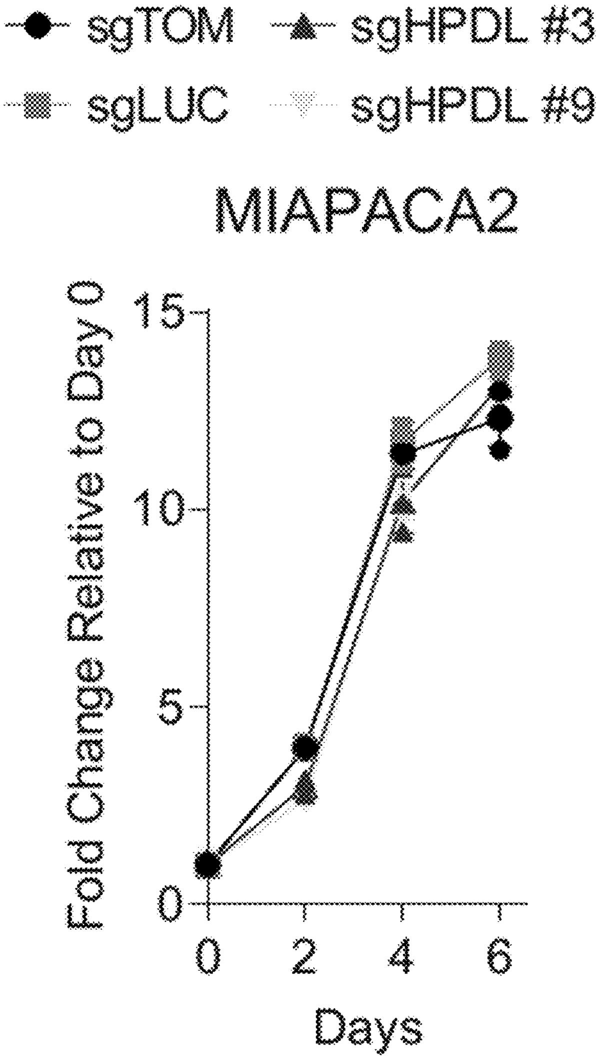
Figure 10E:
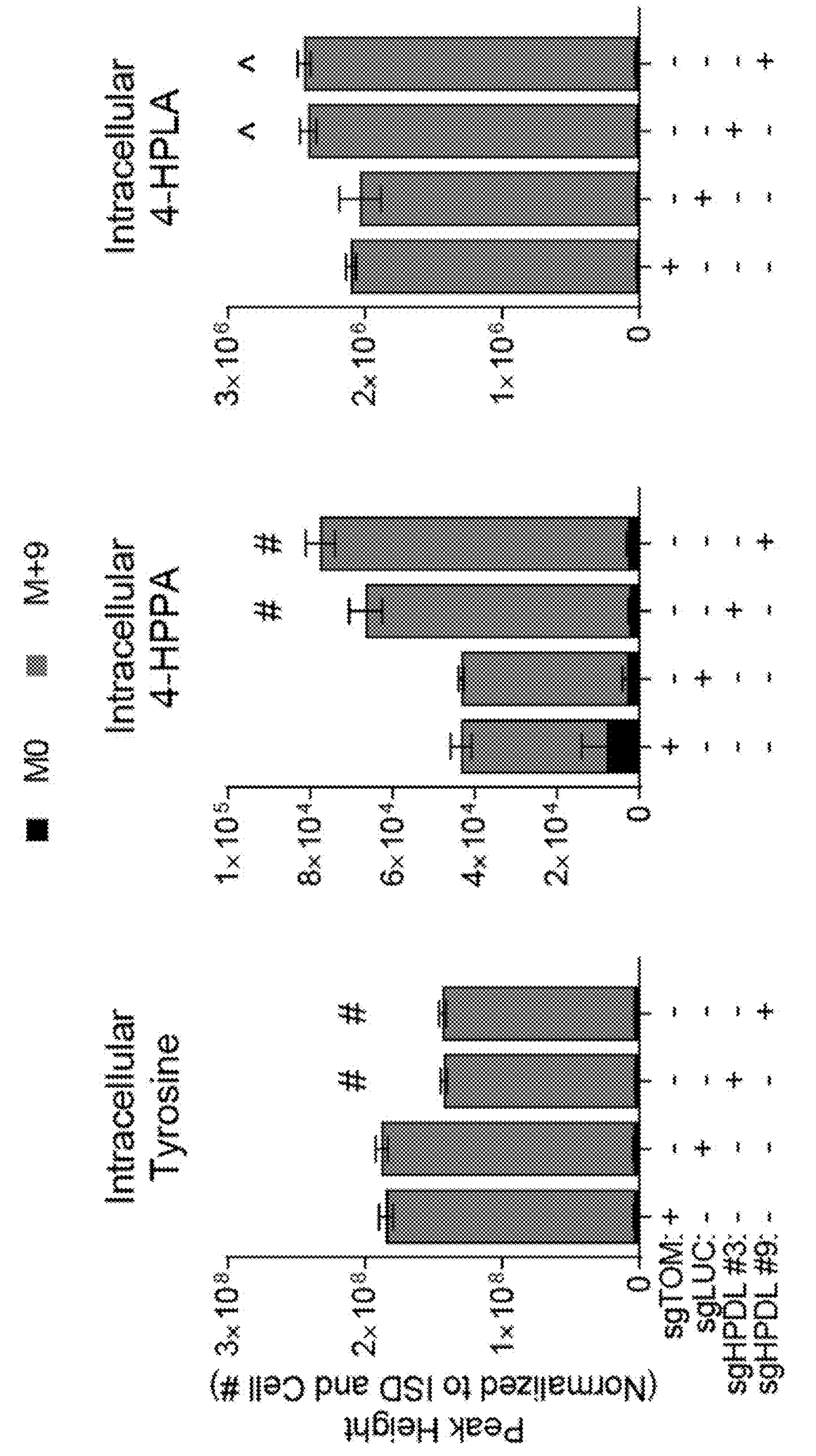
Figure 10F:
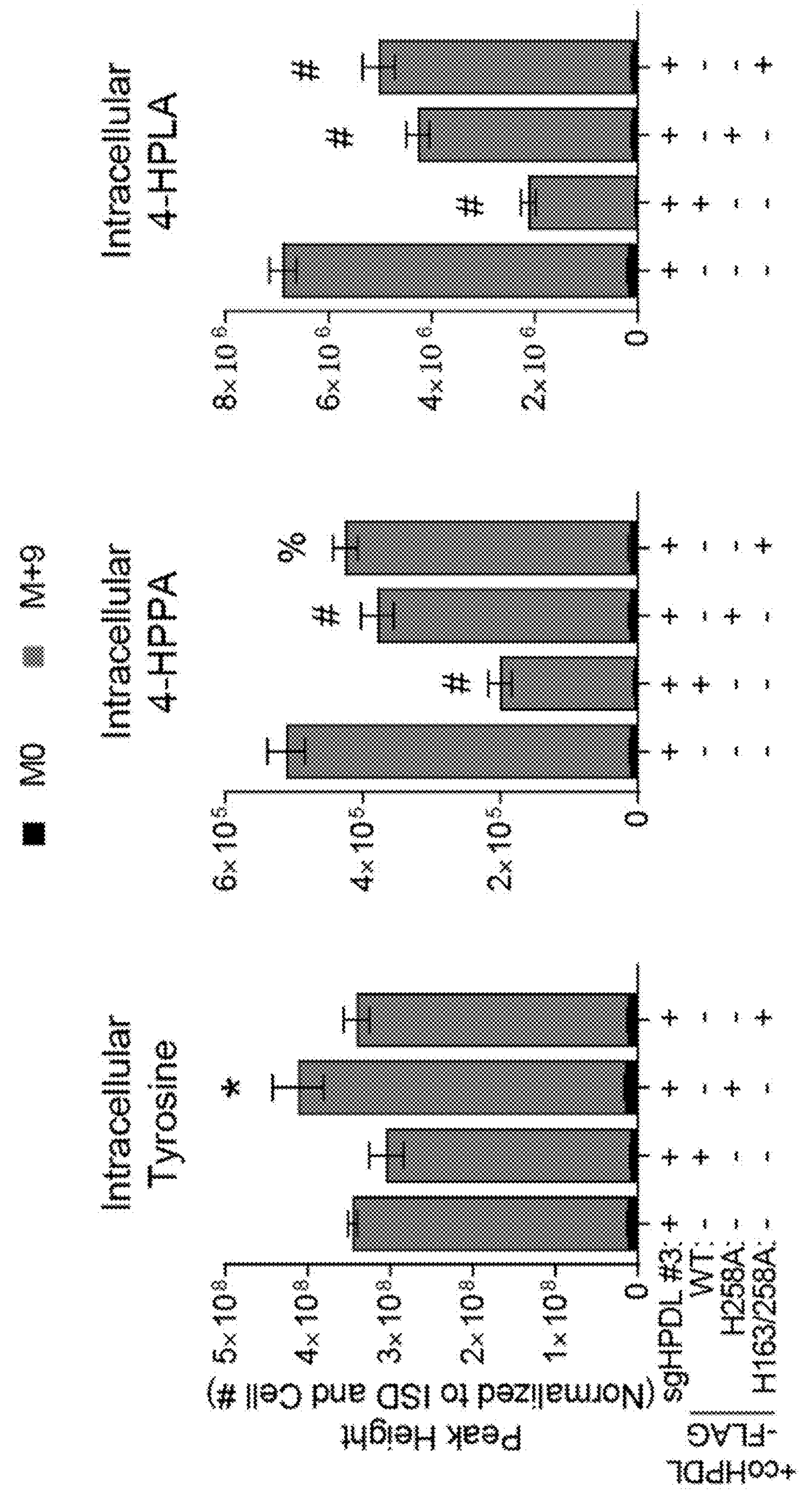
Figure 10G:
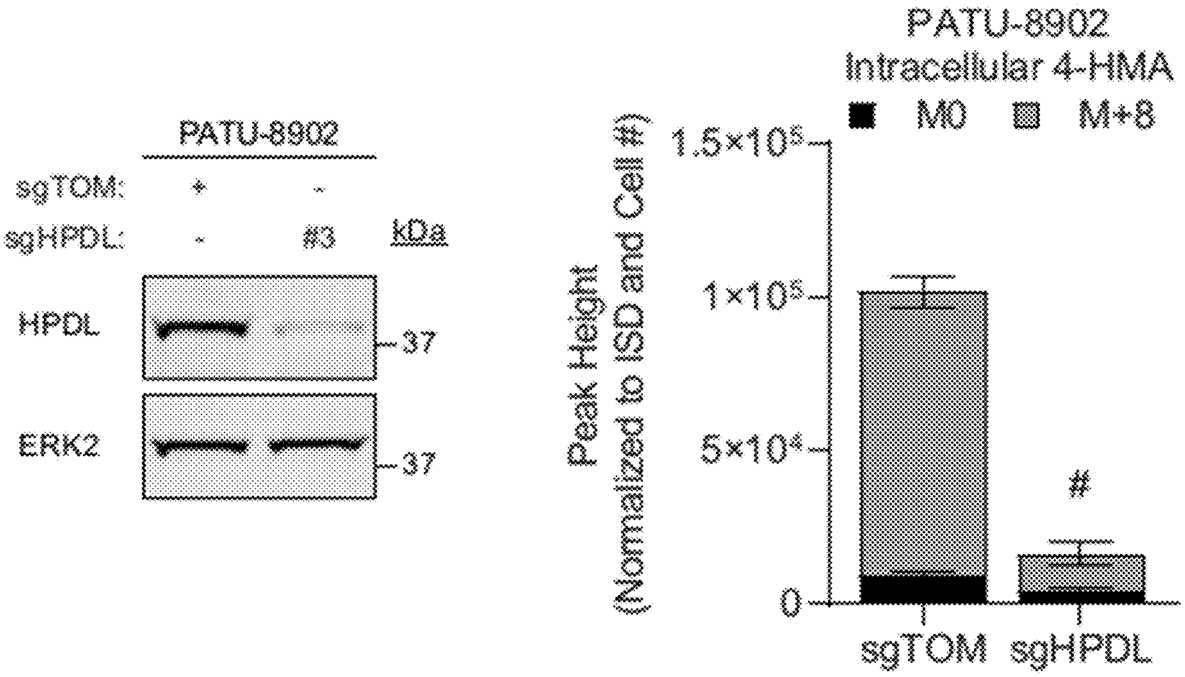

FIGS. 10A-10G show human HPDL as an ortholog of *A. orientalis* HmaS. Phylogenetic tree of HPD (4-hydroxyphenylpyruvate dioxygenase), HPDL (HPD-like), and HmaS (4-hydroxymandelate synthase) cDNA (FIG. 10A) and protein (FIG. 10B) sequences across several model organisms (FIGS. 10A-10B). Protein sequence alignment of HPD, HPDL and HmaS (FIGS. 10C). FIG. 10C discloses SEQ ID NOS 24-26, respectively, in order of appearance. Catalytic histidines involved in coordinating the iron ion needed for activity are highlighted in red. Specific residues in *Streptomyces avermitilis* and *Pseudomonas fluorescens* HPD have been mutated in other studies, and the human equivalent mutations are as indicated; hydrophobic (shade), polar (shade *) amino acids and proline (shade ^). The HPD P239T mutant decreased HGA production and generated oxopinone. The $N_2$41I/L mutation abolished HGA production by HPD. The HPD S226A mutations blocked HGA production. However, the mutation in the equivalent site in HMS (S201A) did not affect the generation of 4-HMA. The F337V/L mutation in HPD decreased HGA synthesis and allowed slight production of 4-HMA. Growth curve of MIAPACA2 cells expressing control (sgTOM and sgLUC) and sgHPDL guides for the indicated times at 21% $O_2$. (n=3 technical replicates for each cell line, performed at least twice) (FIG. 10D). Pooled deletion of sgHPDL did not decrease the proliferation of MIAPACA2 cells in standard media. Total levels of unlabelled and $^{13}C$-labelled Tyr, 4-HPPA, 4-HPLA from MIAPACA2 cells expressing control (sgTOM and sgLUC), and HPDL sgRNA guides (FIG. 10E). Cells were grown in $^{13}C_9$-Tyr at 21% $^{16}O_2$ for 24 hours (from FIG. 3D). (n=5 for each group). Total levels of unlabelled and $^{13}C$-labelled Tyr, 4-HPPA, 4-HPLA from MIAPACA2 sgHPDL #3 cells with or without expression of sgRNA-resistant HPDL-FLAG wild-type (WT) and catalytically inactive mutants (H258A, and H163/258A) (FIG. 10F). Cells were grown in $^{13}C_9$-Tyr at 21% $^{16}O_2$ for 24 hours (from FIG. 3E). (n=5 for each group). Catalytically active HPDL reduced levels of HPPA and 4-HPLA. Total levels of unlabelled and $^{13}C_8$-labelled 4-HMA from PATU-8902 cells expressing control (sgTomato; sgTOM), or HPDL sgRNA (FIG. 10G). Cells were grown in $^{13}C_9$-Tyr at 21% $^{16}O_2$ for 24 hours. (n=3 for each group). Immunoblots of HPDL levels from PATU-8902 cells expressing control and HPDL sgRNAs. ERK2 serves as a loading control. "n" represents the number of biologically independent replicates for each group and condition, unless indicated (FIG. 10D). Graphs are represented as mean±s.d. (FIG. 10D) or s.e.m. (FIGS. 10E-10F) and were compared by two-tailed Student t-test (FIG. 10G), or two-way ANOVA (FIGS. 10D-10F), followed by Tukey post-hoc test (*p<0.05, ^p<0.01, %p<0.005, #p<0.0001).

Figure 11A:
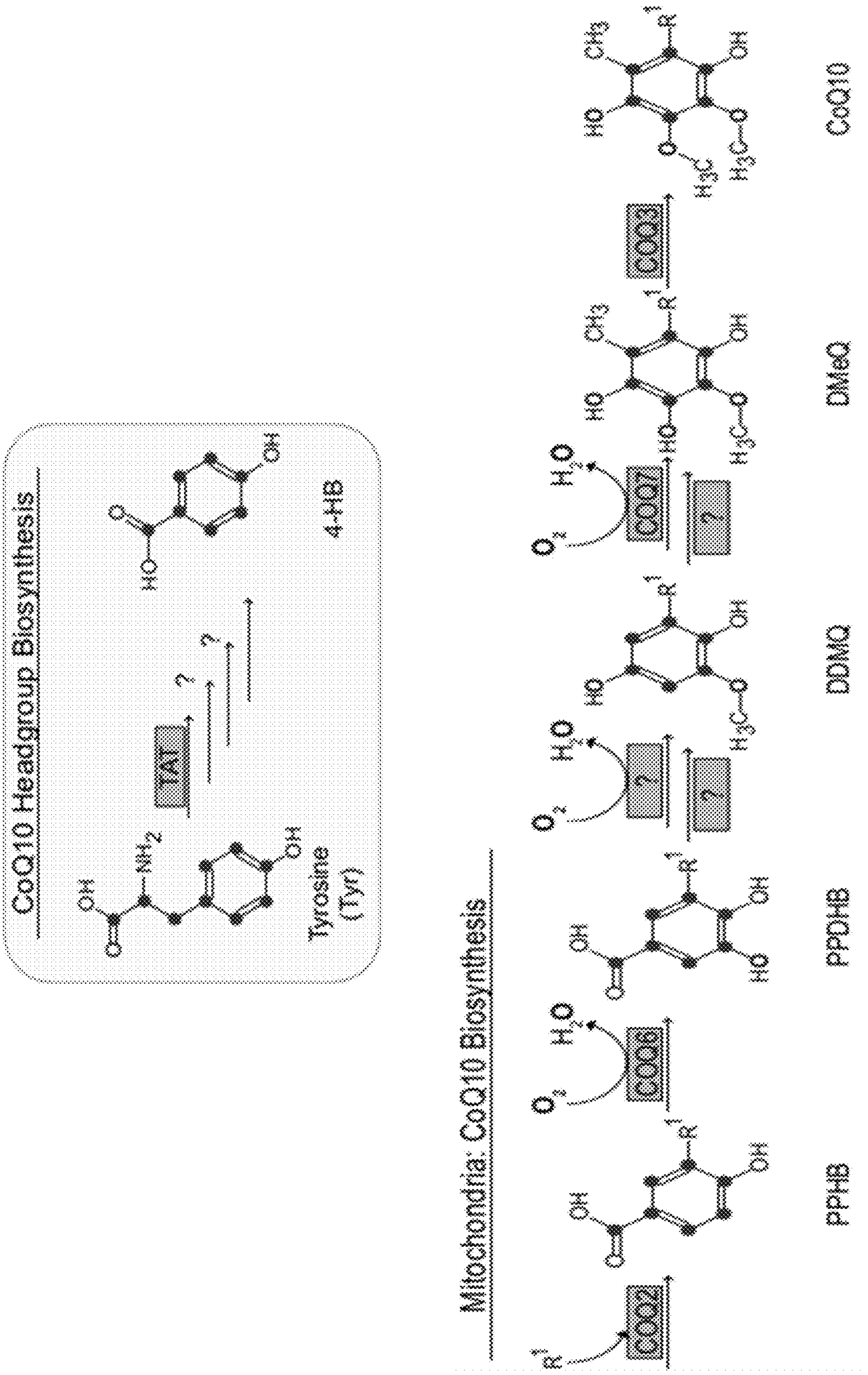
Figure 11B:
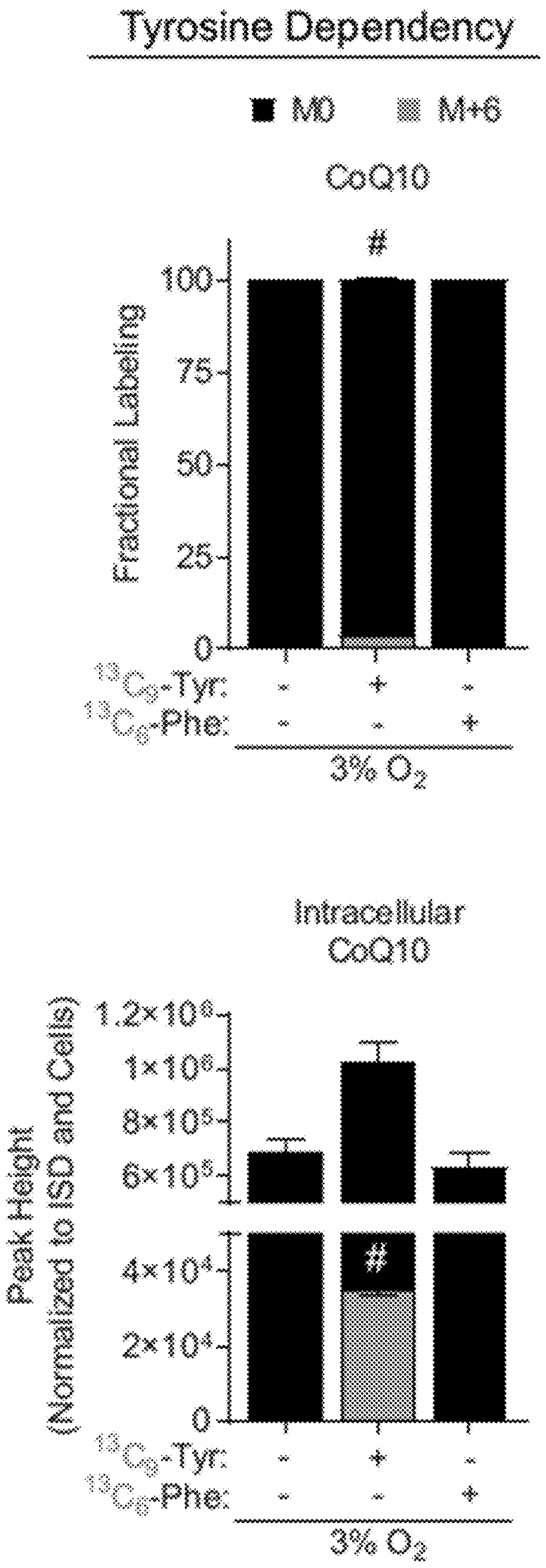
Figure 11C:
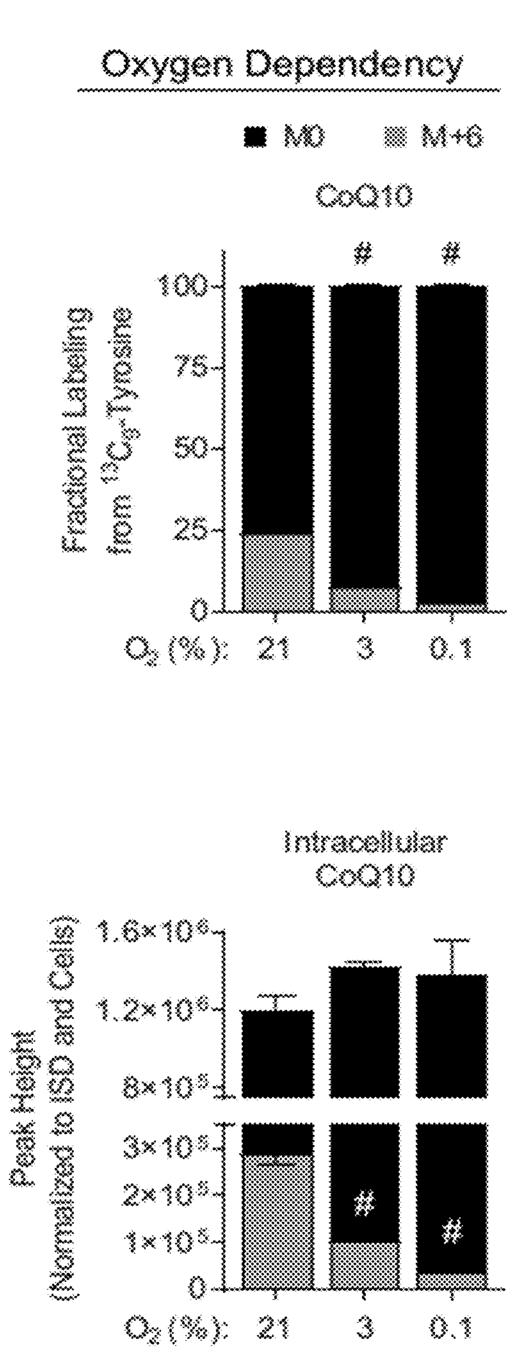
Figure 11D:
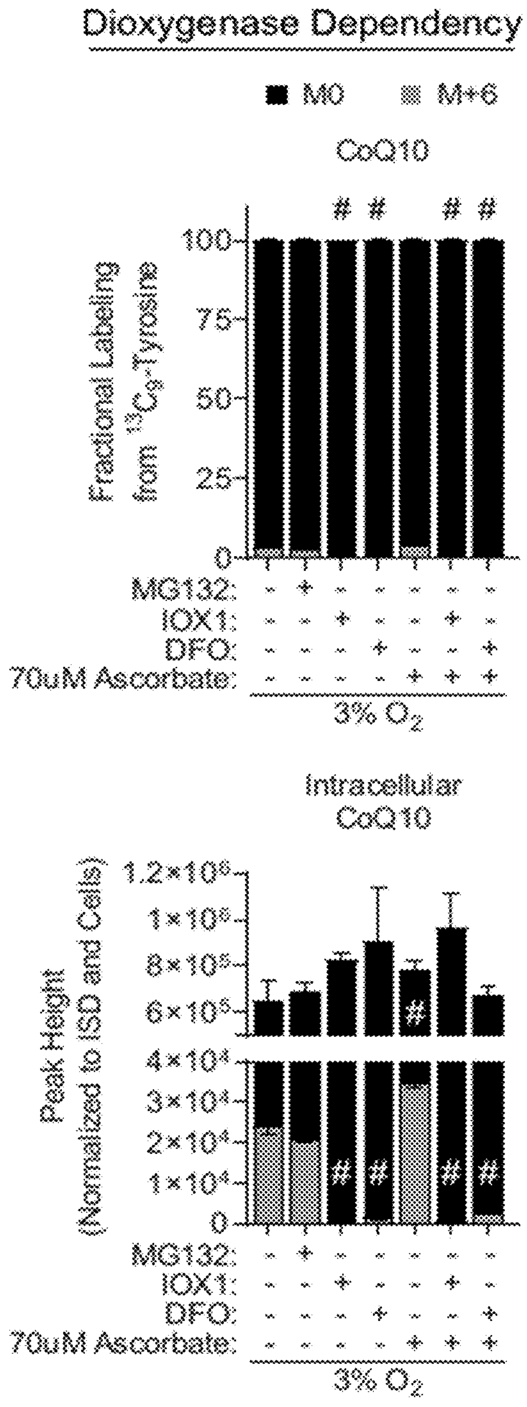
Figure 11E:
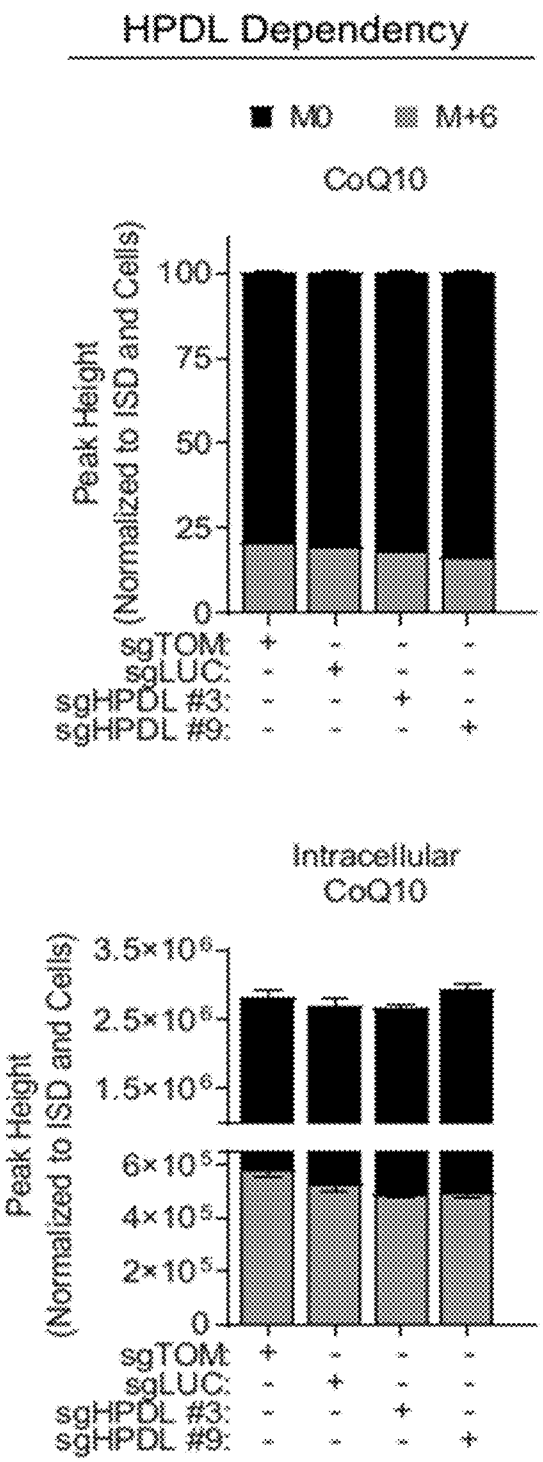
Figure 11F:
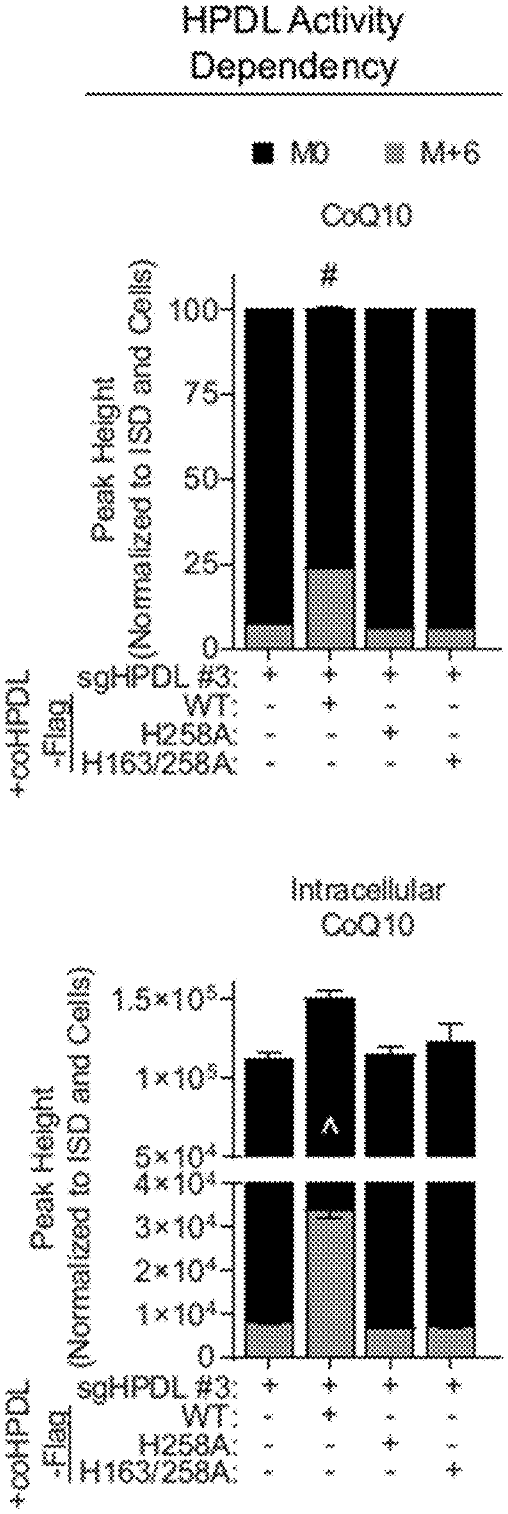
Figure 11G:
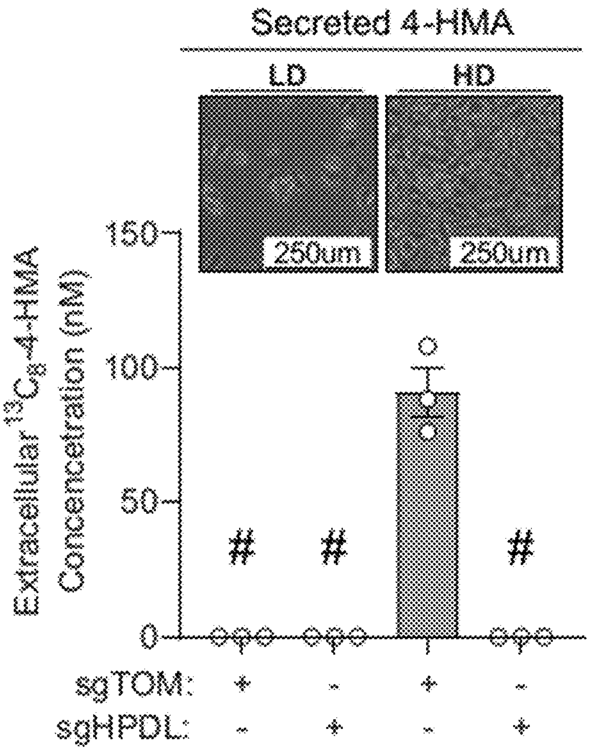
Figure 11H:
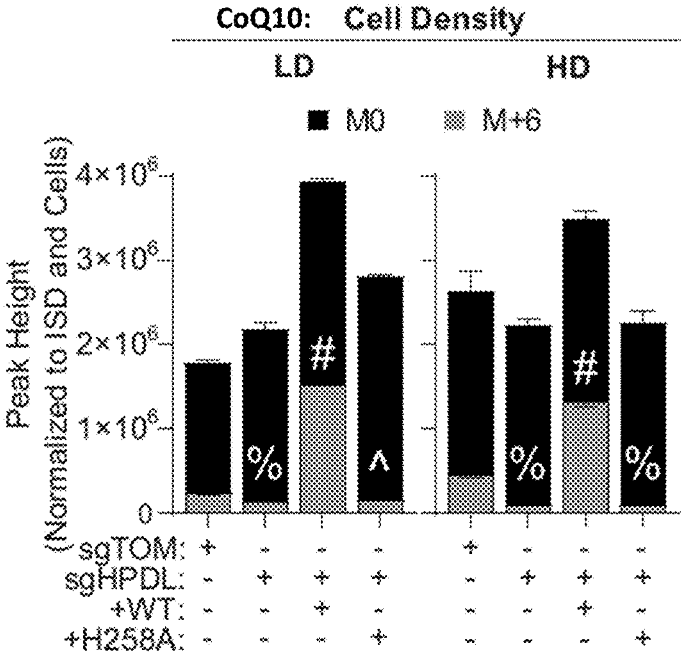
Figure 11I:
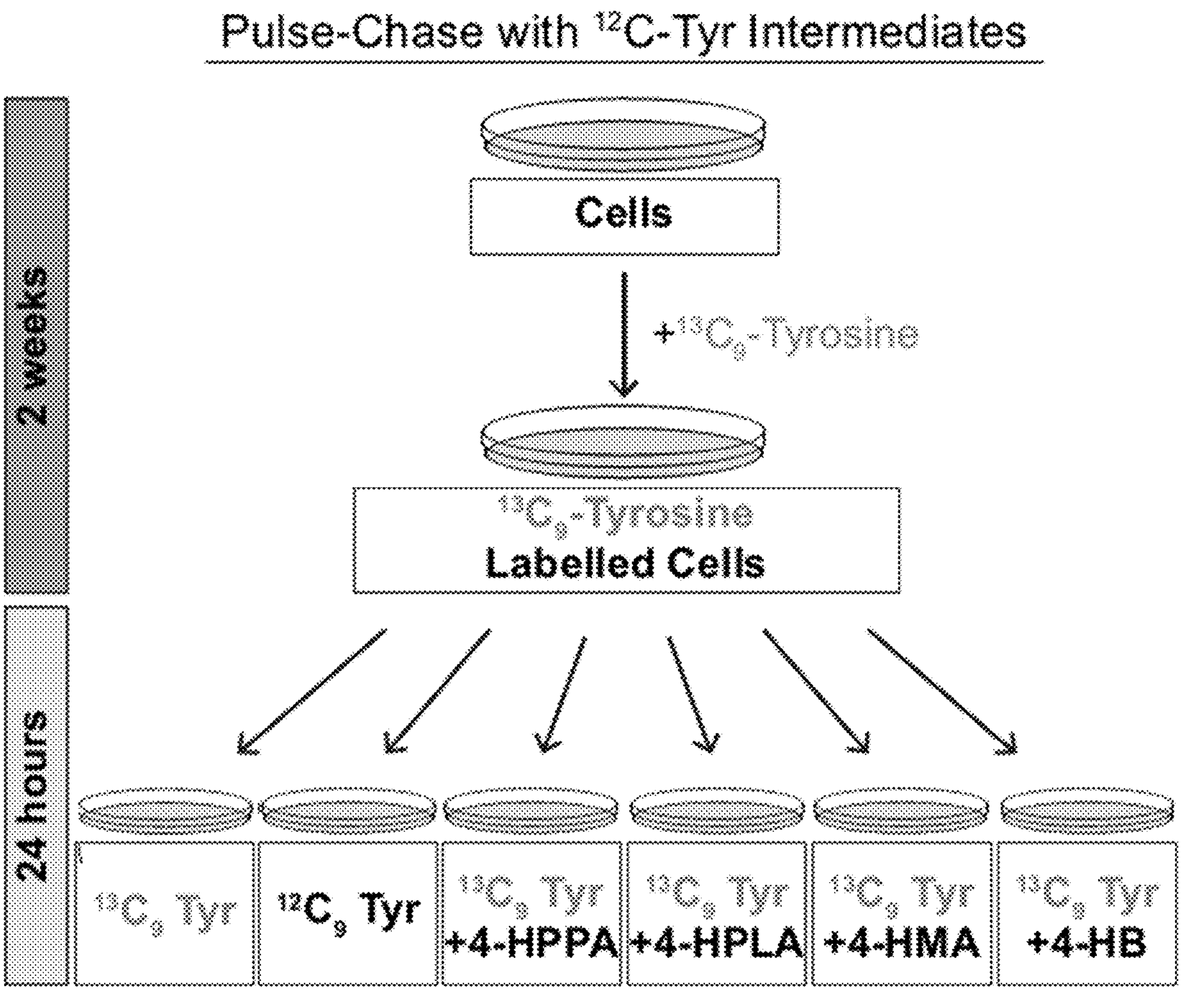
Figure 11J:
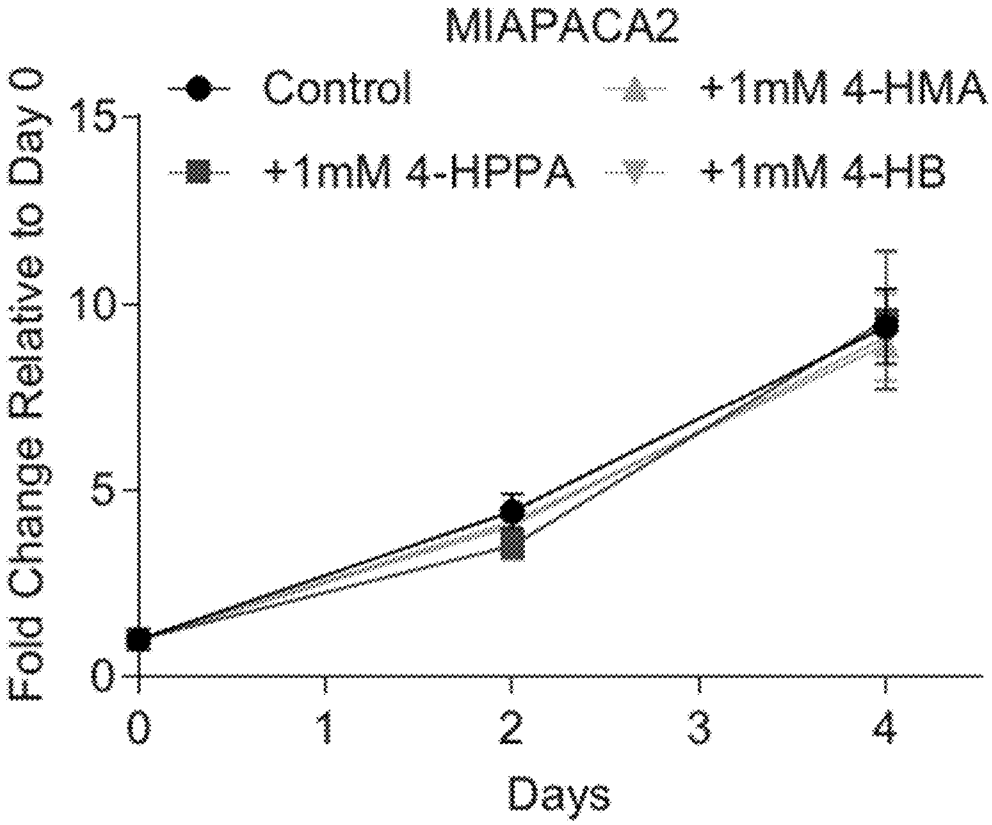
Figure 11K:
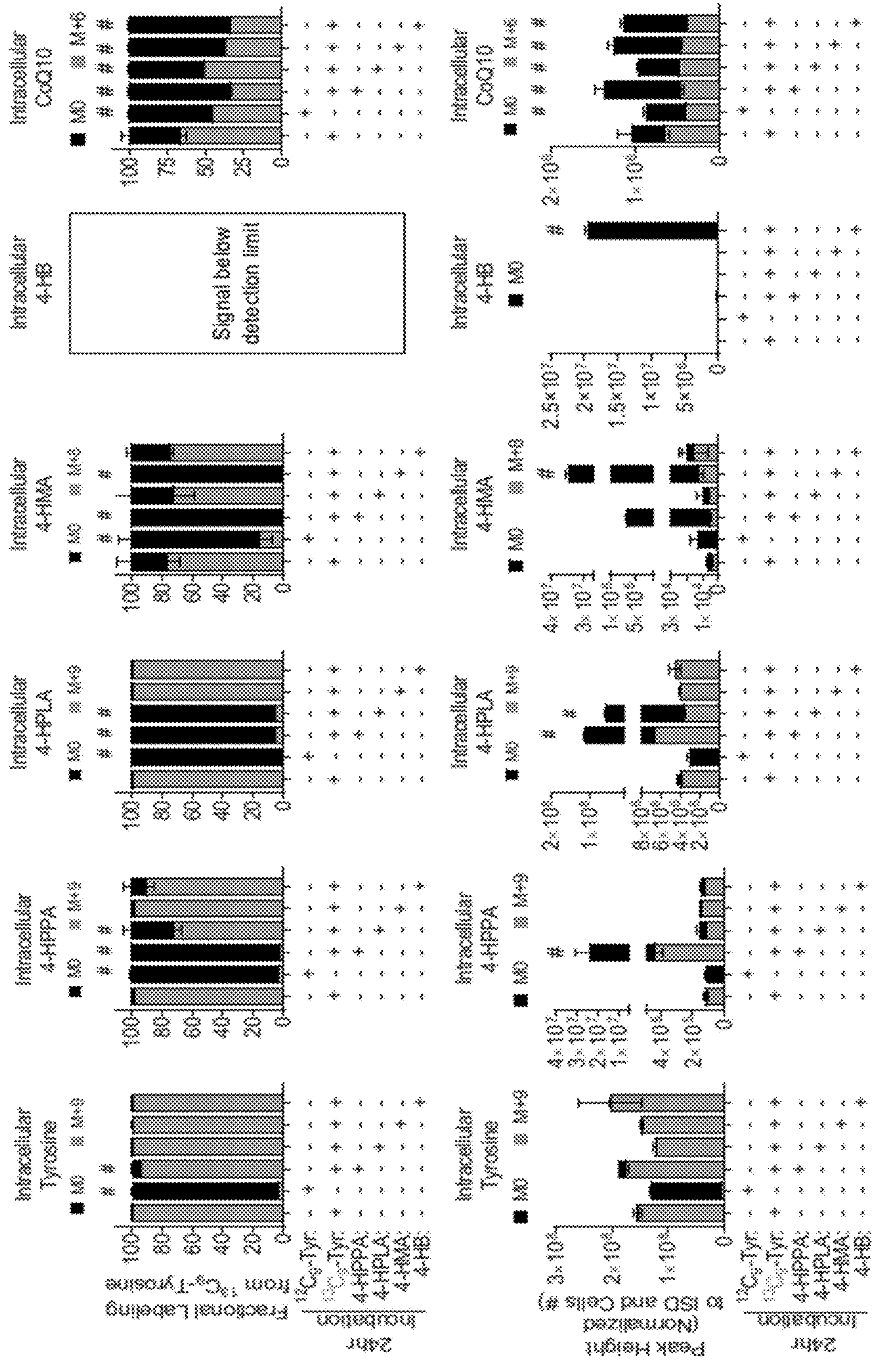
Figure 11L:
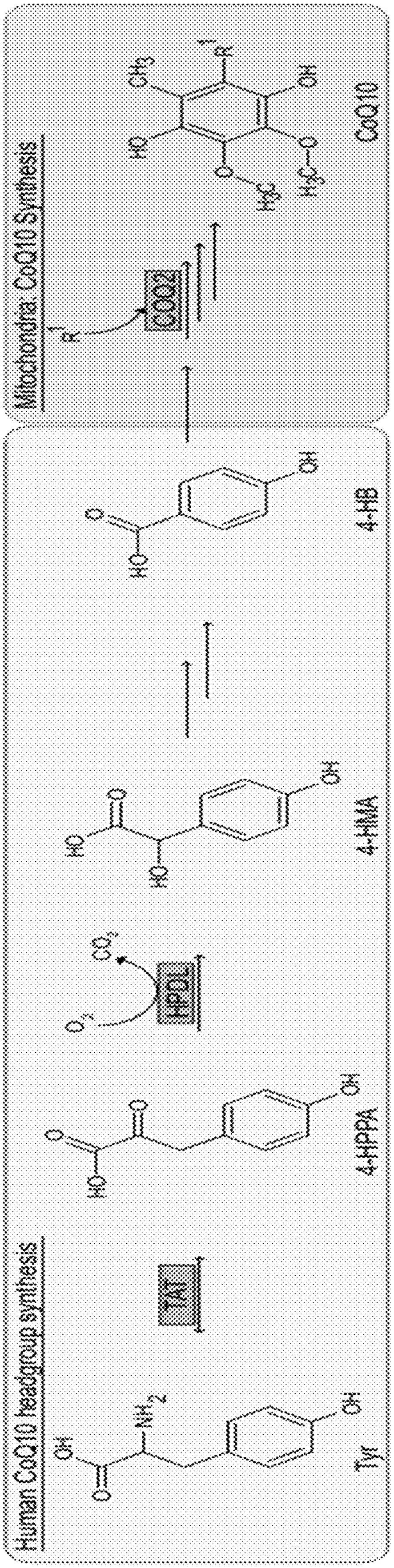

FIGS. 11A-11L show HPDL expression affects fractional labelling of CoQ10. Schematic of known and unknown components of the CoQ10 biosynthesis pathway in humans. R1 reflects the polyprenyl tail that is attached to 4-HB (FIG. 11A). PPHB: polyprenyl-hydroxbenzoate; PPDHB: polyprenyl-dihydroxybenzoate; DDMQ: demethoxy-demethyl-coenzyme Q; DmeQ: dimethyl-coenzyme Q: CoQ10: coenzyme Q10. Fractional labelling and total levels of CoQ10 from MIAPACA2 grown in unlabelled, $^{13}C_9$-Tyr-, and $^{13}C_6$-Phe-labelled media for 24 hours at 3% $^{16}O_2$ (n=5 for each group) (FIG. 11B). Labelled Tyr was incorporated into CoQ10 but labelled phenylalanine was not. Fractional labelling and total levels of CoQ10 from MIAPACA2 cells grown in $13C_9$-Tyr at 21%, 3% and 0.1% $^{16}O_2$ for 24 hours (n=5 for each group) (FIG. 11C). CoQ10 was labelled by $^{13}C_9$-Tyr in an oxygen-dependent manner. Fractional labelling and total levels of CoQ10 from MIAPACA2 cells grown in $^{13}C_9$-Tyr containing media, and treated with or without MG132 (proteasomal inhibitor), IOX1 (dioxygenase inhibitor), DFO (iron chelator), and/or physiological levels of ascorbate at 3% $^{16}O_2$ for 24 hours (n=5 for each group) (FIG. 11D). IOX1 and DFO eliminated the incorporation of tyrosine into CoQ10. Fractional labelling and total intracellular levels of unlabelled and $^{13}C_6$-labelled CoQ10 from MIAPACA2 cells expressing control (sgTOM and sgLUC) and HPDL sgRNA guides (FIG. 11E). Cells were grown in $^{13}C_9$-Tyr at 21% $^{16}O_2$ for 24 hours (n=5 for each group). Fractional labelling of CoQ10 from MIAPACA2 sgHPDL cells with or without expression of sgRNA-resistant coHPDL-FLAG wild-type (WT) and catalytically-inactive mutant coHPDL (H258A, and H163/258A) (FIG. 11F). Cells were grown in $^{13}C_9$-Tyr at 21% $^{16}O_2$ for 24 hours (n=5 for each group). Extracellular concentrations of $^{13}C_8$-labelled 4-HMA released from MIAPACA2 cells expressing control and HPDL sgRNAs (FIG. 11G). Cells were grown in $^{13}C_9$-Tyr at 21% $^{16}O_2$ for 24 hours at low (LD) and high (HD) cell densities (n=3 for each group). Representative images of LD and HD cells are shown. The effect of cell density on total intracellular levels of unlabelled and $^{13}C_6$-labelled CoQ10 from MIAPACA2 cells expressing control and HPDL sgRNAs with or without expression of coHPDL WT and catalytically-inactive mutant (FIG. 11H). Cells were grown in $^{13}C_9$-Tyr at 21% $^{16}O_2$ for 24 hours at LD and HD (n=3 for each group). HPDL is required for CoQ10 biosynthesis at high cell densities. Schematic of pulse-chase study using tyrosine-derived intermediates shown in FIG. 11K (FIG. 11I). Cells were labelled with $^{13}C_9$-Tyr for two weeks before being grown in $^{12}C_9$-Tyr or $^{13}C_9$-Tyr with or without unlabelled 4-HPPA, 4-HPLA, 4-HMA, and 4-HB for 24 hours at 21% $O_2$. Growth curve of MIAPACA2 cells treated with or without 1 mM 4-HPPA, 4-HPLA, 4-HMA, and 4-HB for the indicated times at 21% $O_2$. (n=3 technical replicates for each cell line, performed at least twice) (FIG. 11J). The CoQ10 intermediates did not affect cell growth in full media. Total levels and fractional labelling of unlabelled and $^{13}C$-labelled metabolites in the CoQ10 headgroup biosynthesis pathway in humans (FIG. 11K). Cells were treated as described in FIG. 11I, and total intracellular levels of Tyr, 4-HPPA, 4-HMA, 4-HB, and CoQ10 were measured. (n=4 for each group). Endogenous 4-HB was below the limit of detection. Each metabolite reduced labeling of the metabolites downstream in the CoQ10 headgroup synthesis pathway. Schematic of CoQ10 headgroup biosynthesis pathway in humans based on metabolite abundances and fractional labelling from FIG. 11K (FIG. 11L). "n" represents the number of biologically independent experiments for each group and condition, unless indicated (FIG. 11J). Graphs represent mean s.e.m. were compared using one- (FIGS. 11D-11H), and two- (FIGS. 11*b*-11C, 11J-11K) way ANOVA, followed by Tukey (FIGS. 11G-11H) post-hoc test (*p<0.05, ^p<0.01, %p<0.005, #p<0.0001).

Figure 12A:
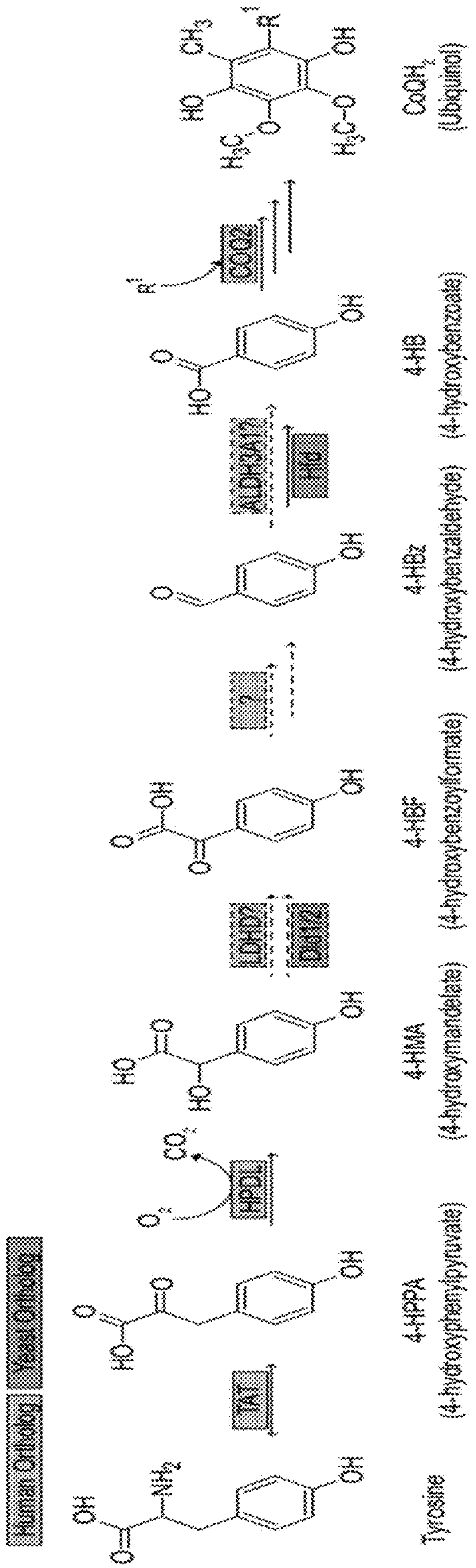
Figure 12B:
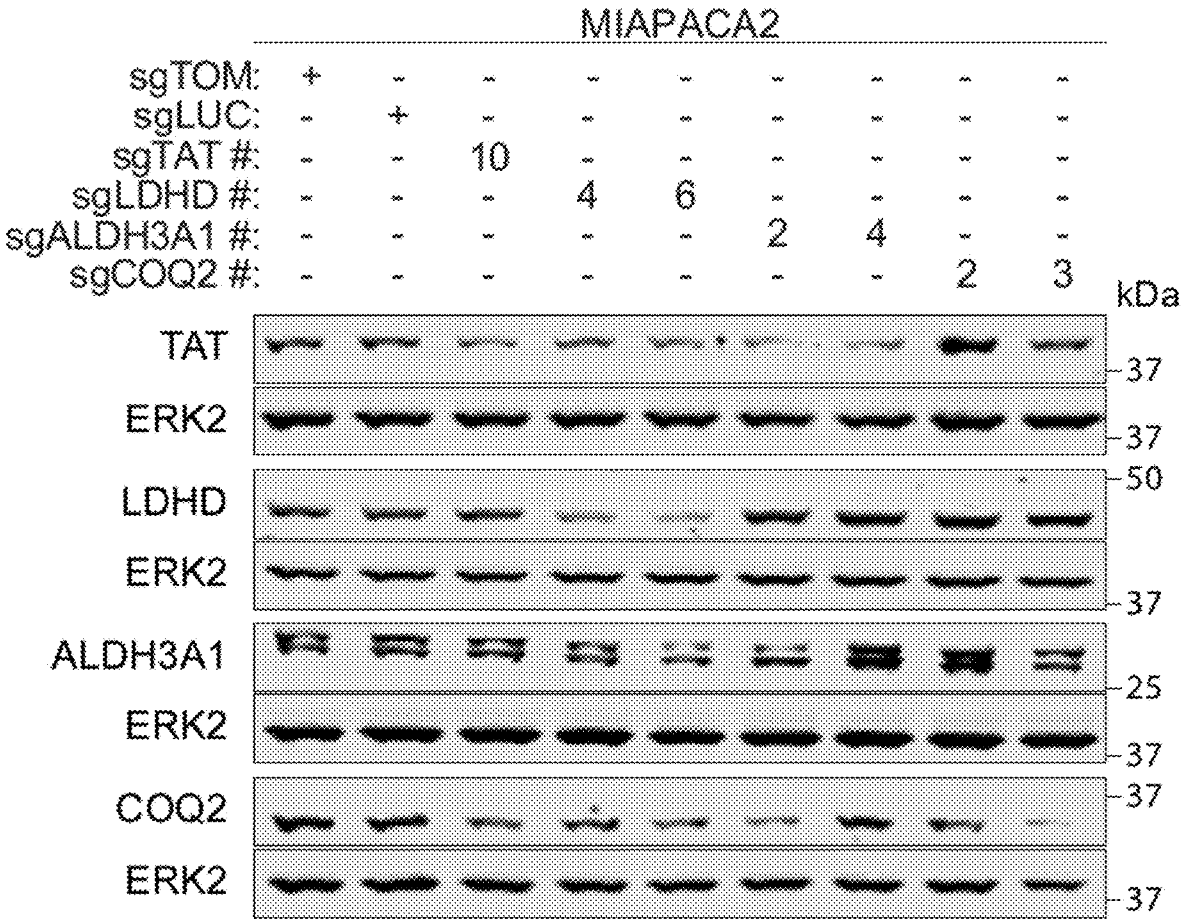
Figure 12C:
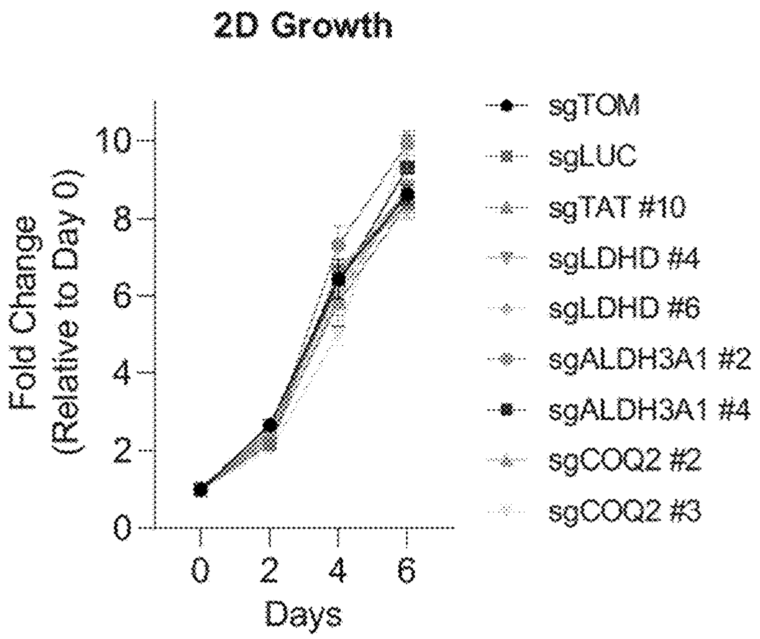
Figure 12D:
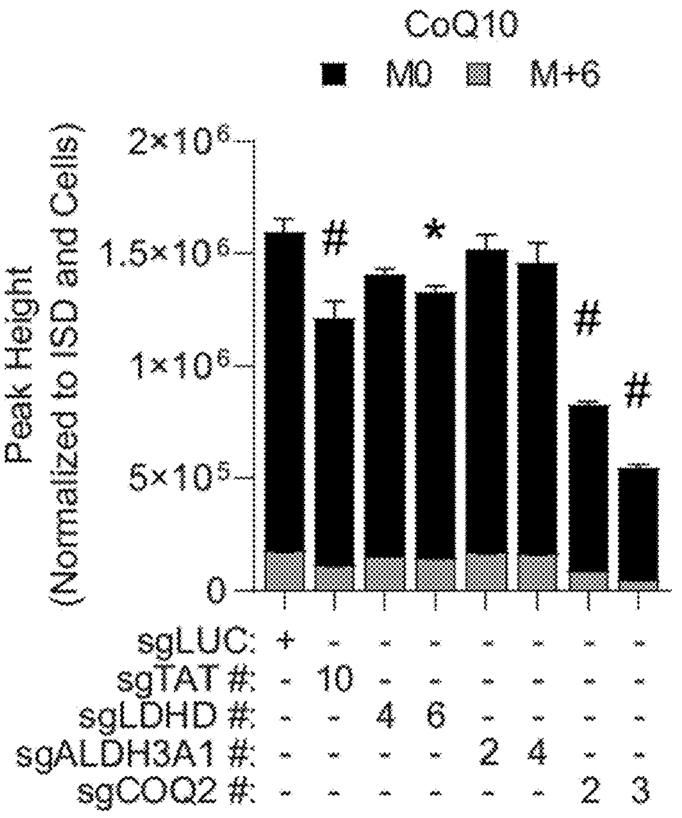
Figure 12E:
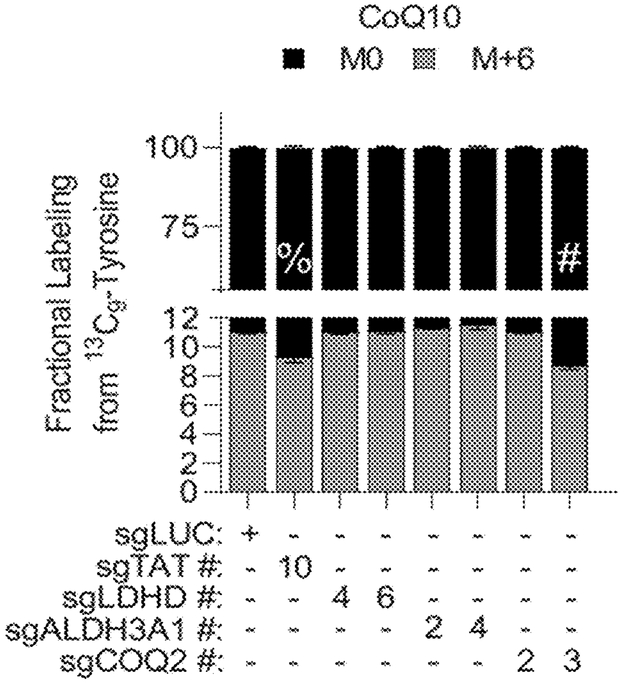
Figure 12F:
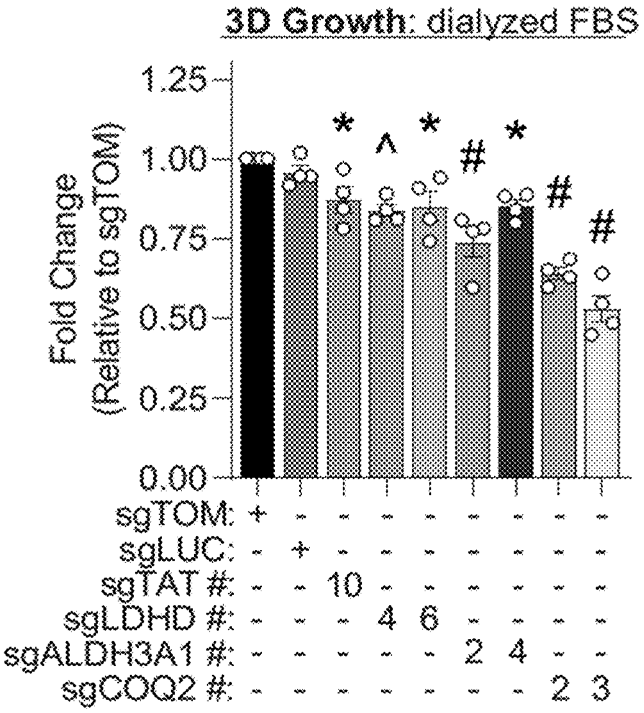
Figure 12G:
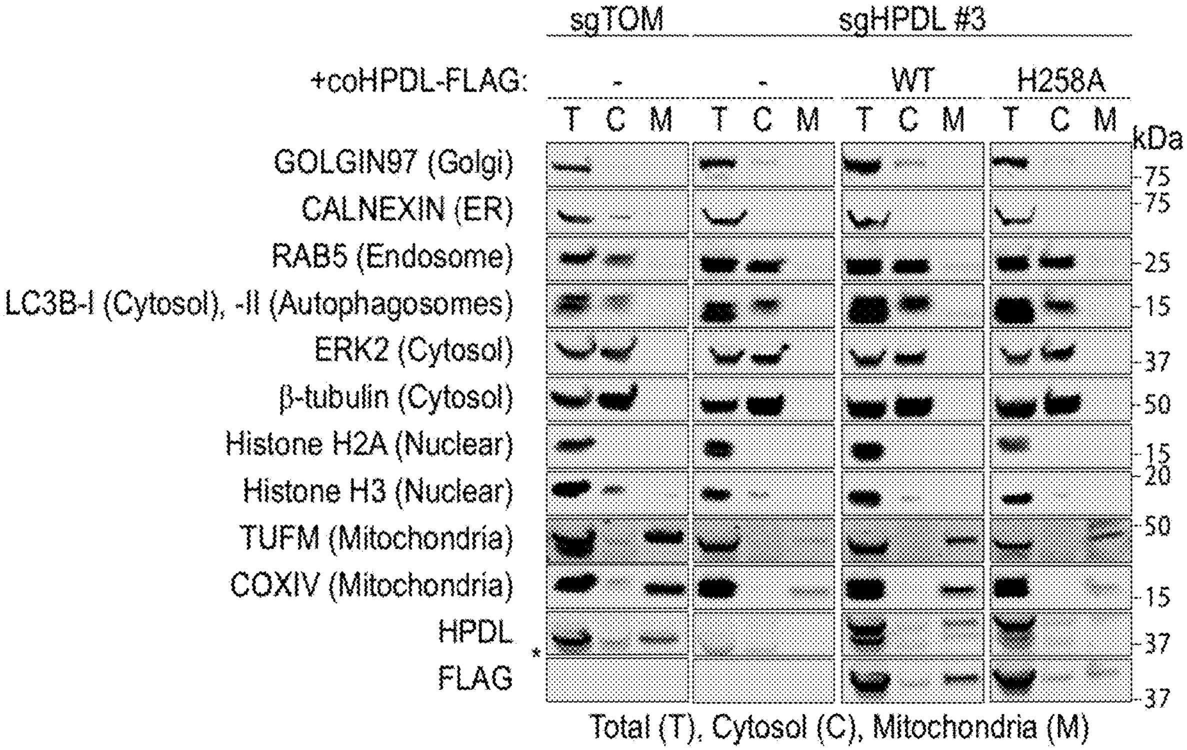
Figure 12H:
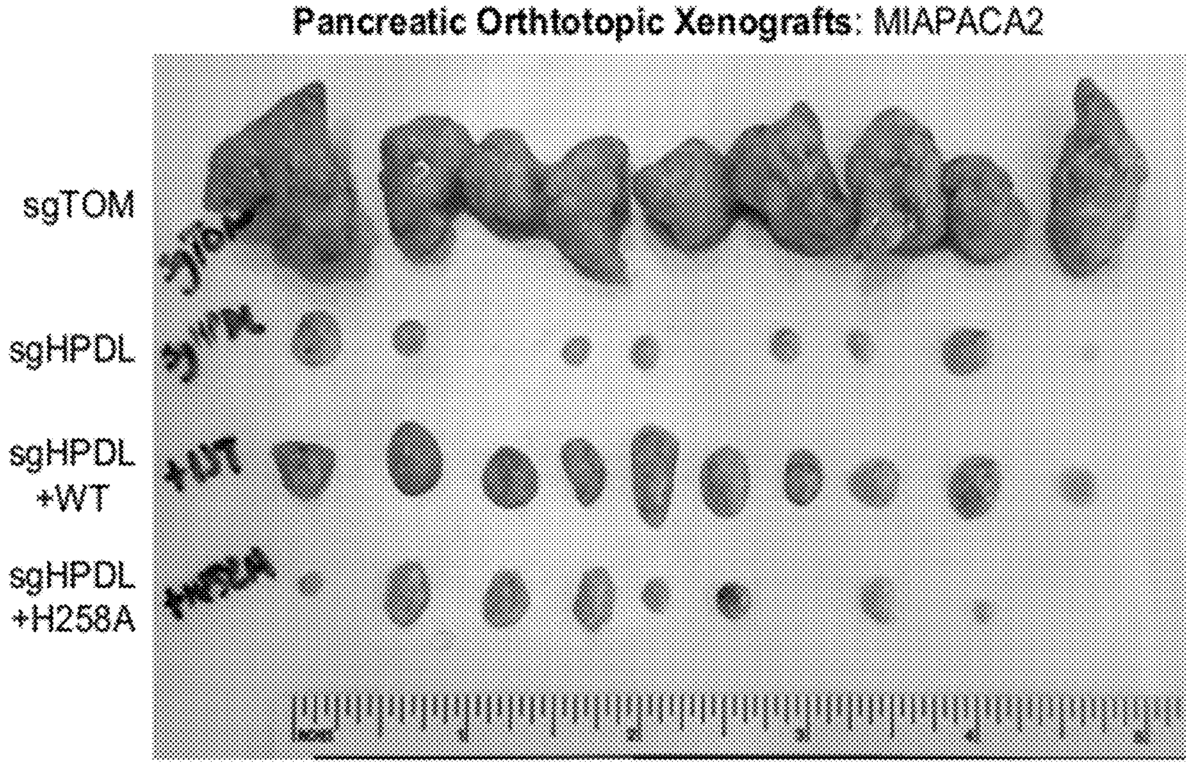
Figure 12I:
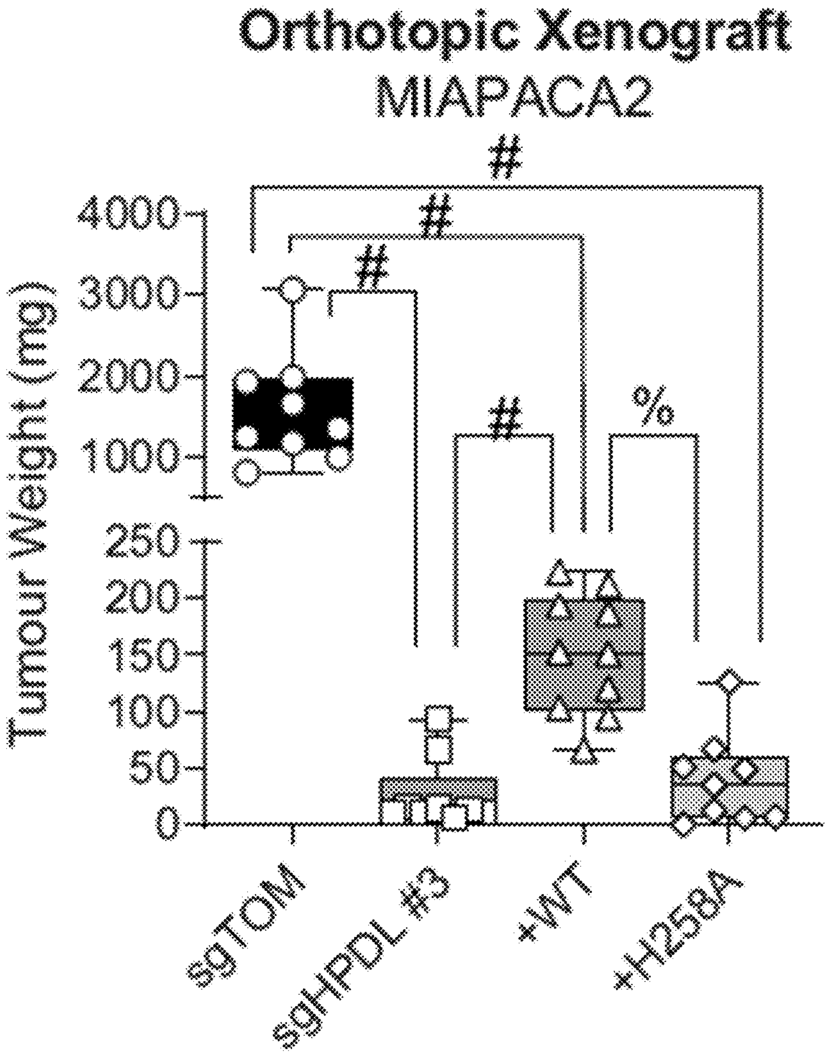
Figure 12J:
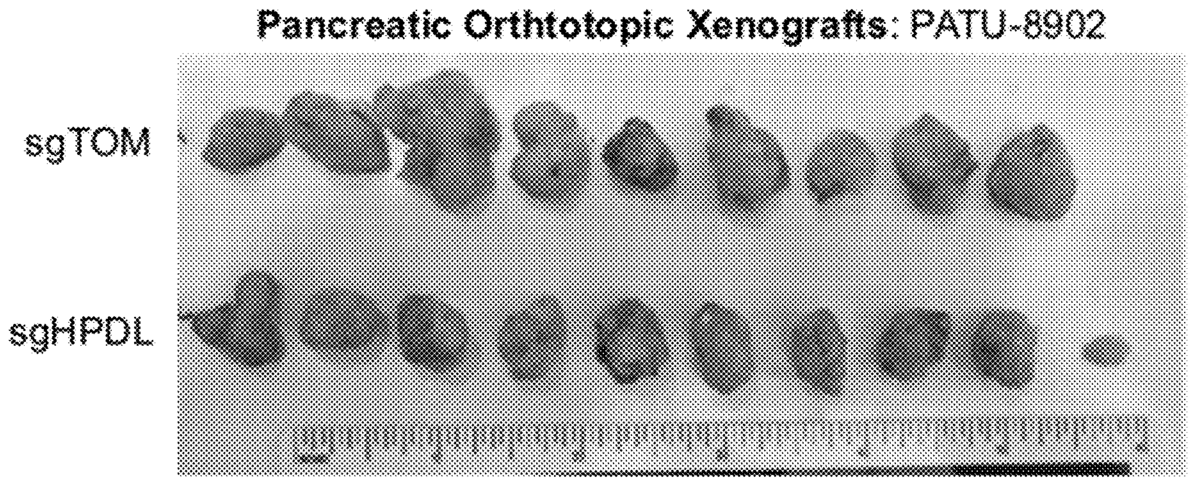
Figure 12K:
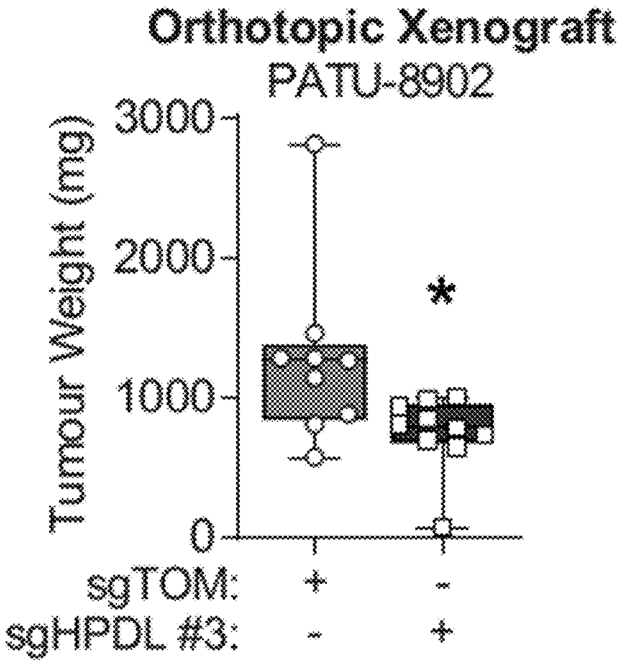
Figure 12L:
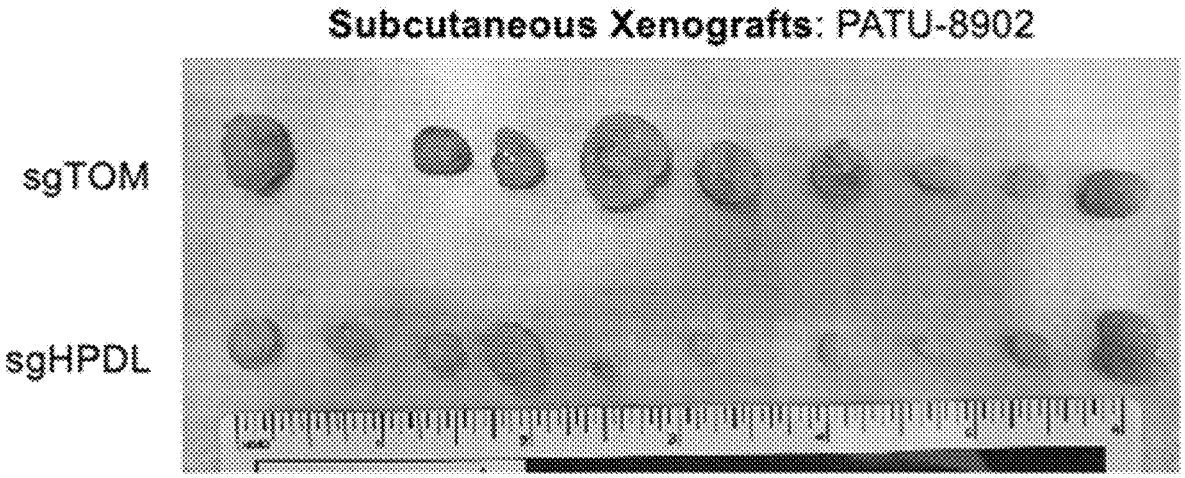
Figure 12M:
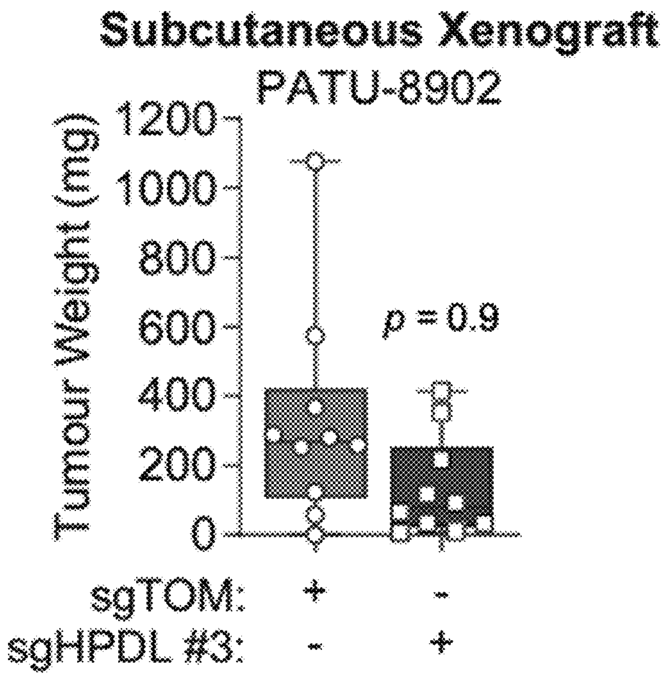
Figure 12N:
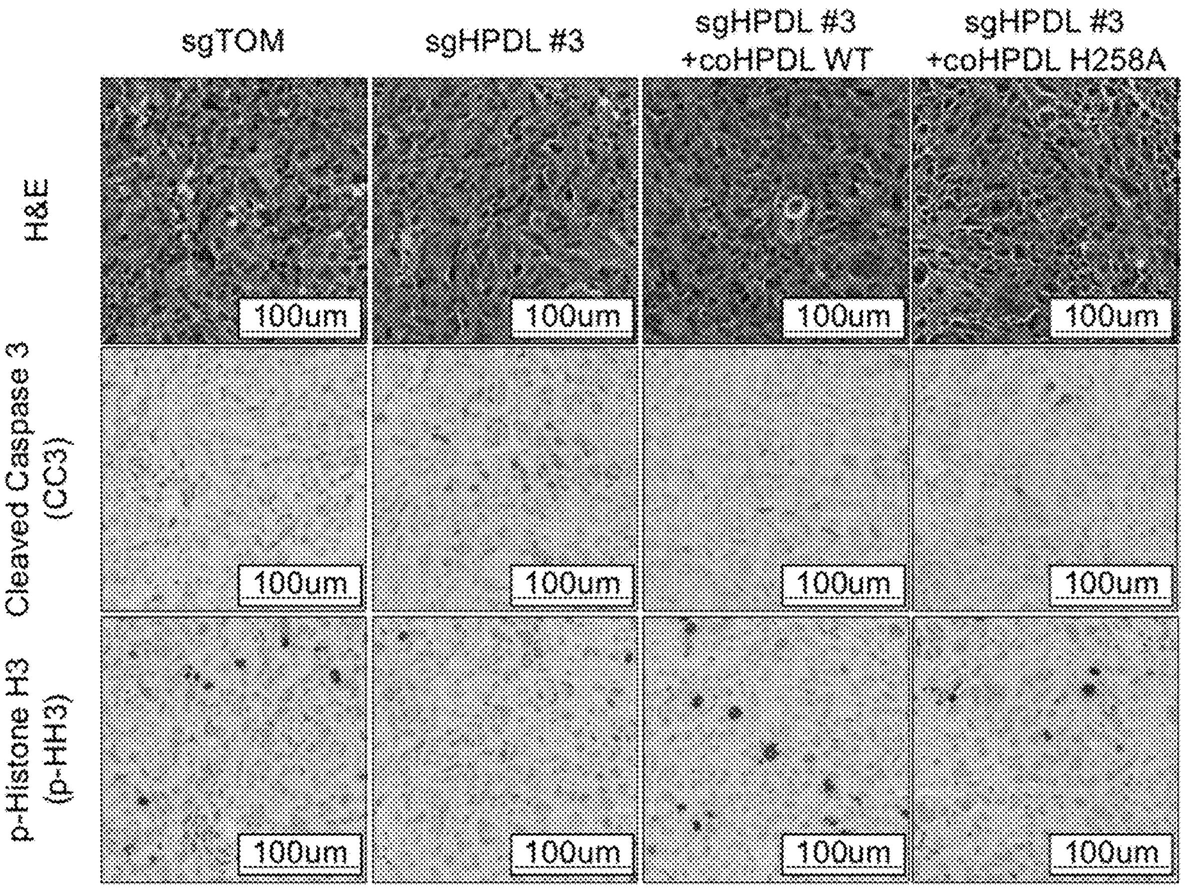
Figure 12O:
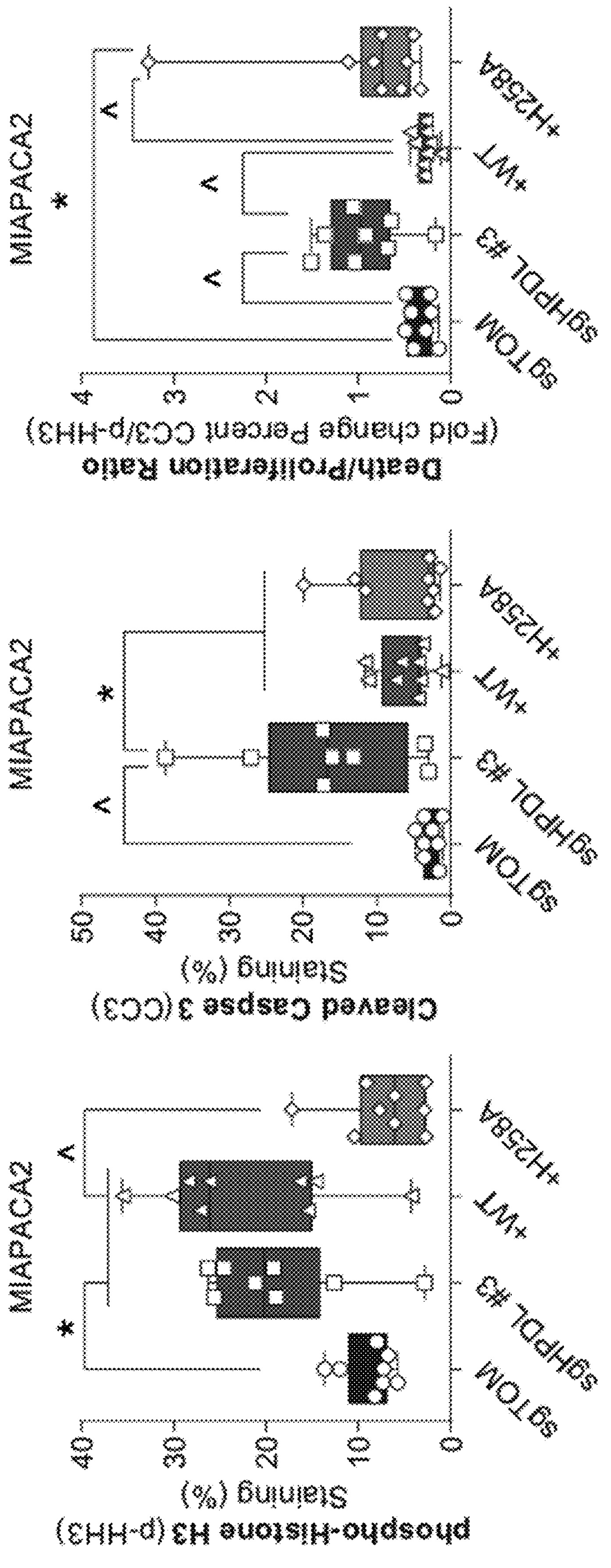
Figure 12P:
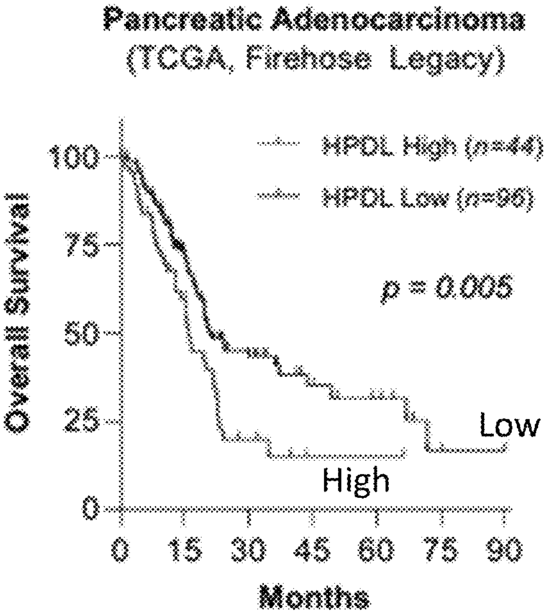

FIGS. 12A-12P show CoQ10 as important for growth in 3D, but not 2D, conditions. Schematic of known and potential intermediates in the CoQ10 headgroup biosynthesis pathway in humans and yeast (FIG. 12A). Dotted lines reflect potential pathways and enzymes. Immunoblot of MIAPACA2 cells expressing control (sgTOM or sgLUC), TAT, LDHD, ALDH3A1, and COQ2 sgRNAs. ERK2 served as a loading control (FIG. 12B). Experiment was performed twice to check for knockout efficiency. Growth in 2D culture of MIAPACA2 cells expressing control (sgTOM or sgLUC), TAT, LDHD, ALDH3A1, and COQ2 sgRNAs (n=4 for each group) (FIG. 12C). Knockout of genes had no effect on 2D growth. Total levels (FIG. 12D) and fractional labelling (FIG. 12E) of CoQ10 in MIAPACA2 cells expressing control, TAT, LDHD, ALDH3A1, and COQ2 sgRNAs. Cells were grown in $^{13}C_9$-Tyr at 21% $^{16}O_2$ for 24 hours (n=5 for each group) (FIG. 12D-12E). Growth in 3D culture of MIAPACA2 cells expressing control, TAT, LDHD, ALDH3A1, and COQ2 sgRNAs (n=4 for each group) after three days (FIG. 12F). CoQ10 biosynthesis pathway genes were important for 3D growth. Immunoblot of total, cytosolic, and mitochondrial fractions from MIAPACA2 cells expressing control and HPDL sgRNA with or without sgRNA-resistant HPDL WT or catalytically impaired mutant (FIG. 12G). Specific organelle markers are indicated next to the antibodies. HPDL was detected in purified mitochondria. Tumour images (FIG. 12H) and weights (FIG. 12I) from second experiment set of orthotopic pancreatic tumour xenografts from MIAPACA2 cells expressing control or HPDL sgRNA with coHPDL WT or catalytically inactive mutant after 6 weeks post-injection (FIG. 12H-12I). First experiment set can be found on FIG. 4I. Tumour images (FIGS. 12J, 12L) and weight (FIGS. 12K, 12M) of orthotopic (FIGS. 12J-12K) or subcutaneous (FIGS. 12L-12M) pancreatic tumour xenograft of PATU-8902 cells expressing control or HPDL sgRNA after 5 weeks post-injection (FIGS. 12J-12M). Representative images (FIG. 12N) and quantification (FIG. 12O) of H&E and immunohistochemistry for cleaved caspase 3 (CC3) and phospho-histone H3 (p-HH3) from MIAPACA2 tumours from FIG. 4I (FIGS. 12N-12O). Progression-free survival of HPDL high (n=44) and low (n=96) expressing PDAC tumours from the TCGA dataset (FIG. 12P). Survival curve was compared using the Log-rank (Mantel-Cox) test. "n" represents the number of biologically independent experiments for each group and condition. Survival curve (FIG. 12P) was compared using the two-sided Log-rank (Mantel-Cox) test. Graphs (mean±s.e.m. or median±max/min (FIG. 12I, 12K, 12M, 12O)) were compared by one- (FIGS. 12D-12F, 12I, 12O) or two-way ANOVA (FIG. 12C-12E), or two-tailed Mann Whitney test (12K, 12M), followed by Tukey (FIG. 12C-12F) or Holm-Sidak (FIG. 12I, 12M) post-hoc test (*p<0.05, ^p<0.01, %p<0.005, #p<0.0001).

Figure 13:
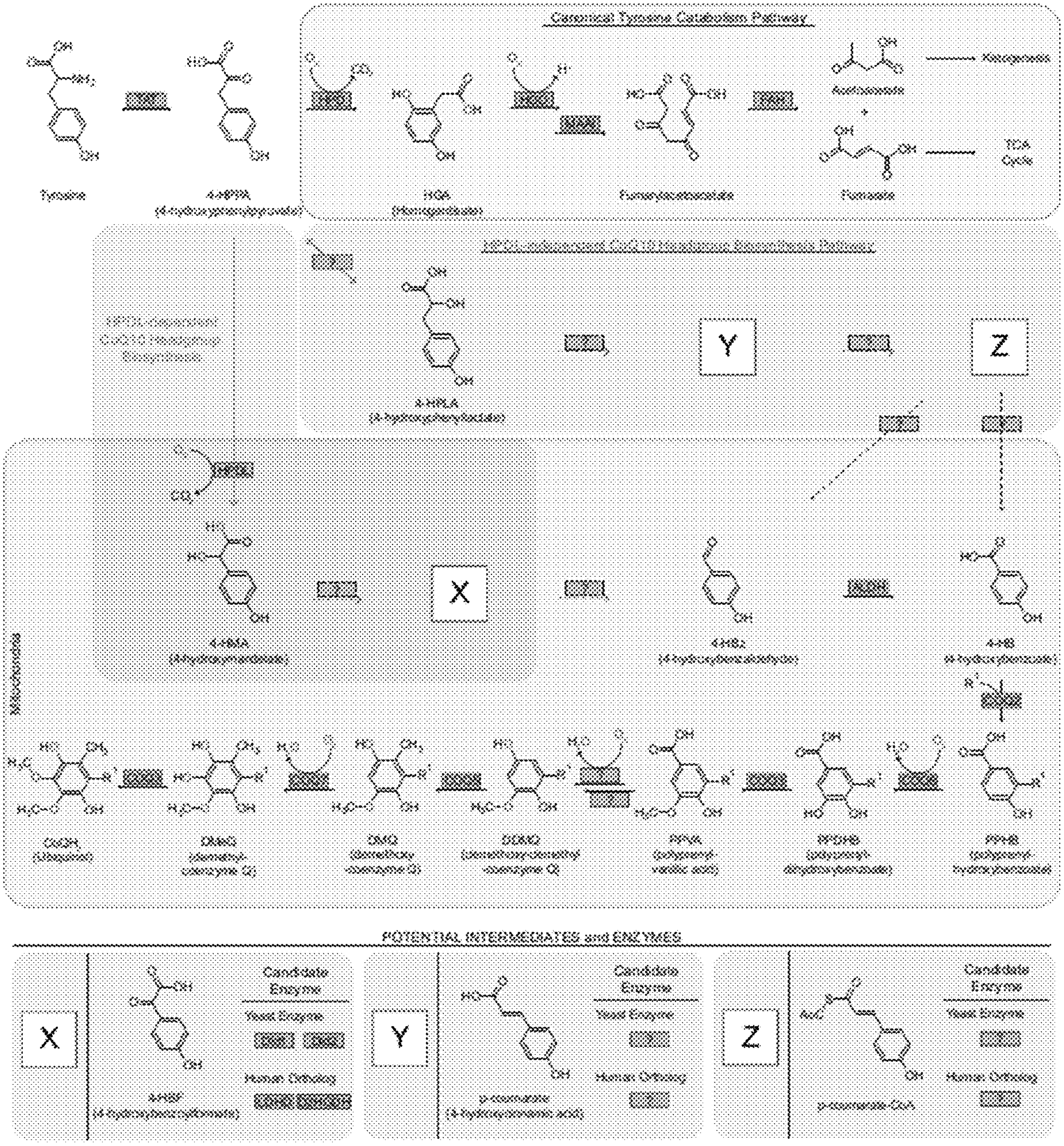

FIG. 13 shows the HPDL-dependent CoQ10 biosynthesis pathway. The canonical tyrosine catabolism, HPDL-dependent (red), and HPDL-independent (purple) CoQ10 biosynthetic pathways are shown as indicated. The HPDL-independent pathway was proposed from earlier studies in rats (Booth et al., 1960). Dotted lines represent unknown pathway or transport steps. Potential intermediates and enzymes are proposed within the 4-HMA, HPDL-dependent and -independent pathways.

Figure 14A:
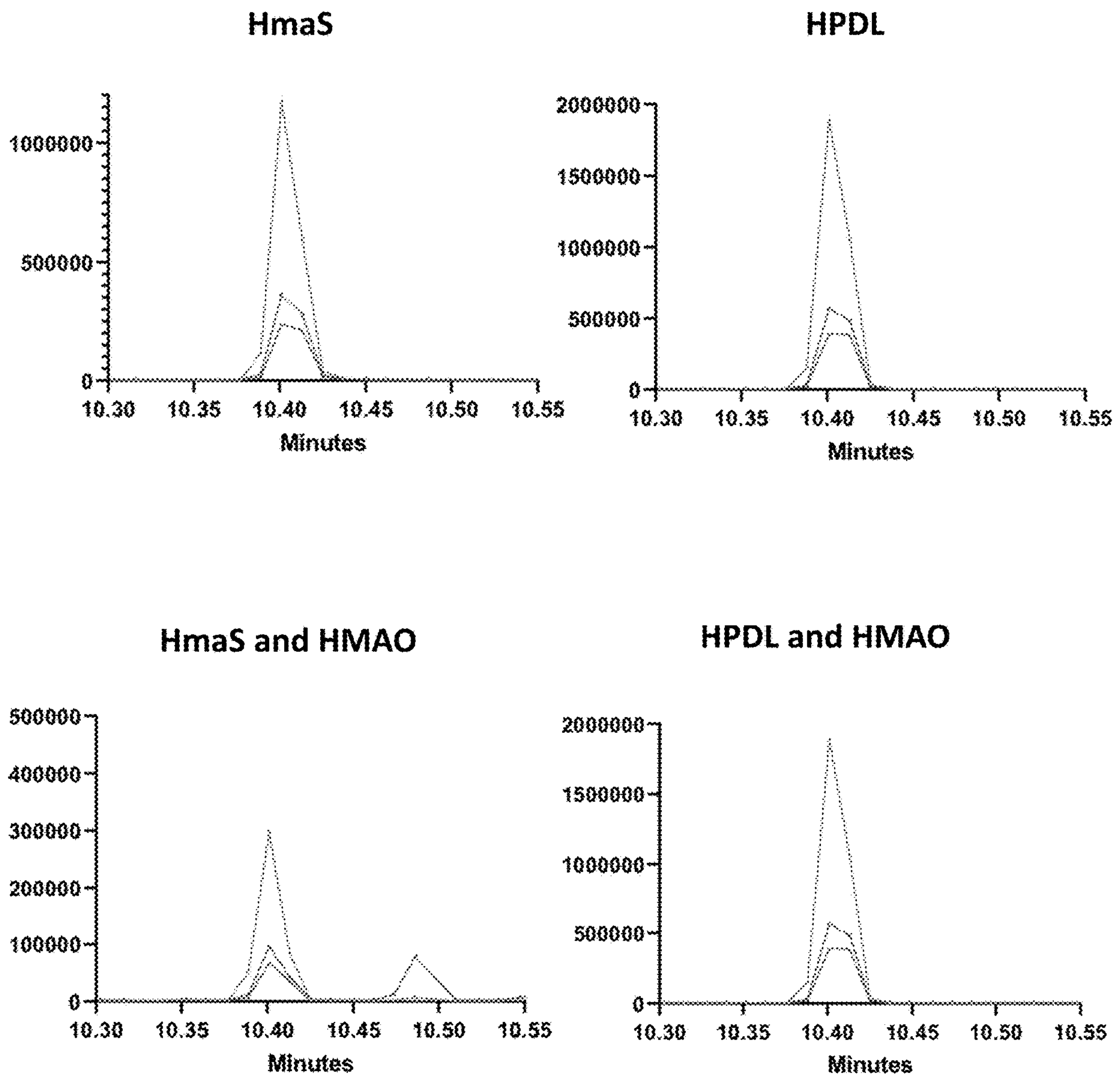
Figure 14B:
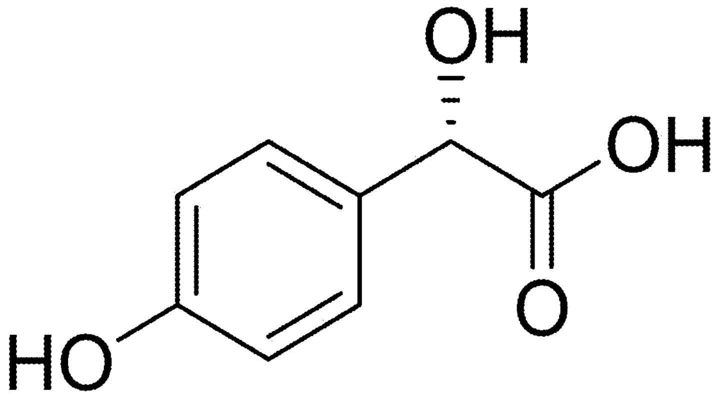
Figure 14B:
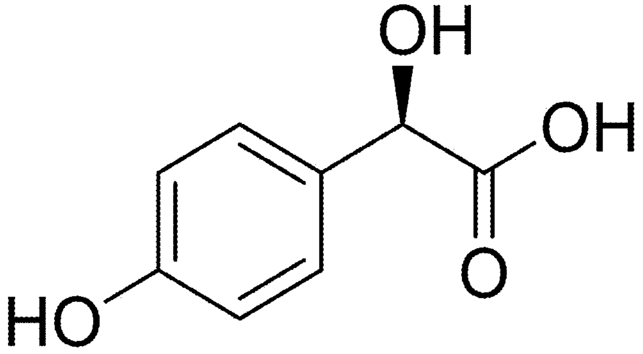

FIGS. 14A and 14B show results from coupled enzymatic assays.

Figure 15:
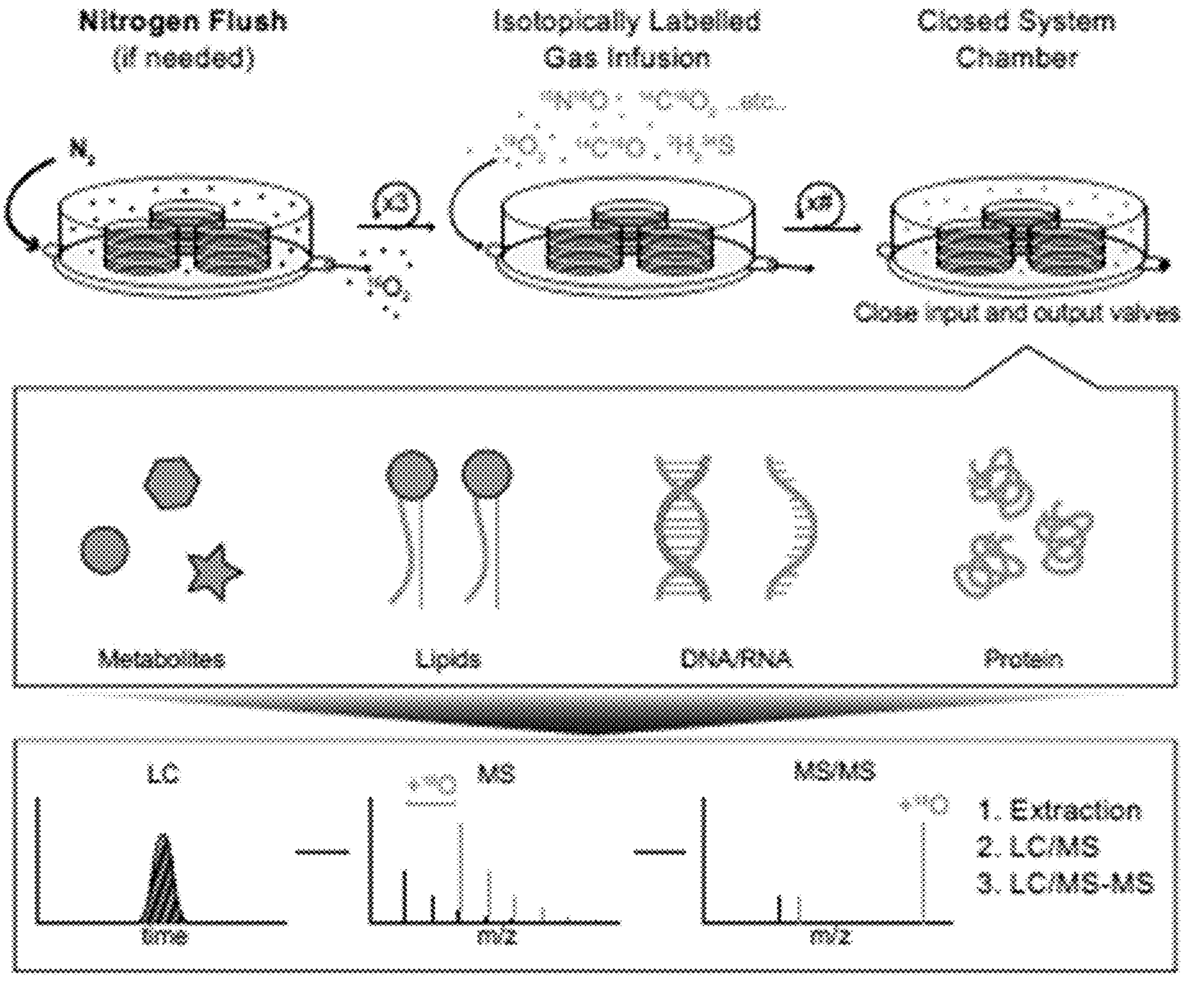

FIG. 15 shows other applications of GASSP. GASSP can be adapted to label cells with a wide range of isotopically labelled gases to study their fates in metabolites, lipids, nucleotides, and protein in cells, and to mechanistically understand the biological effects of these gases.

Figure 16:
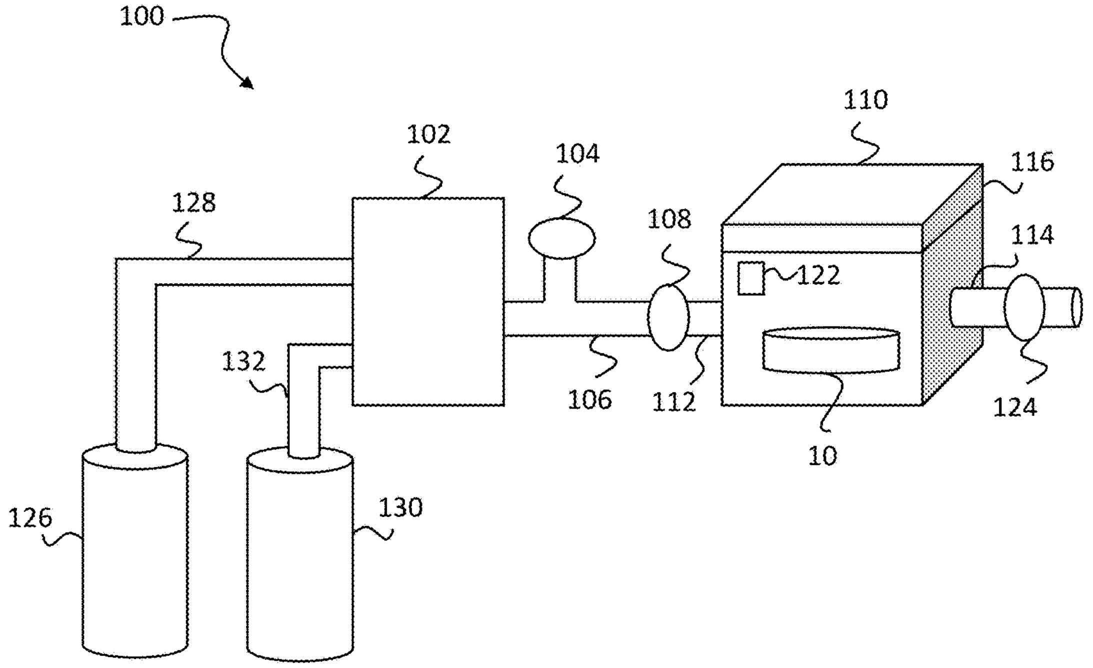

FIG. 16 is an illustration of an example controlled gas system according to aspects of the present invention.

Figure 17A:
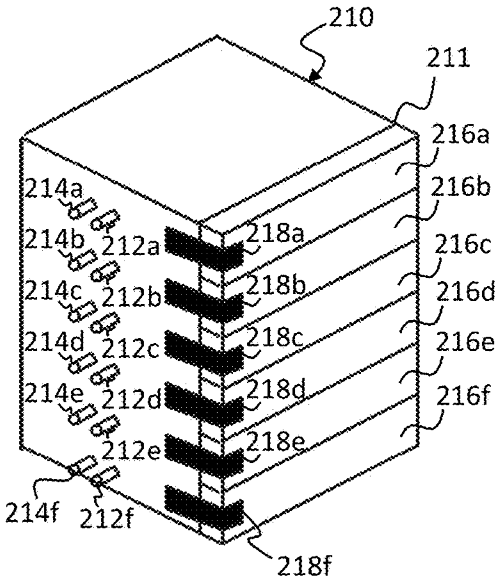
Figure 17B:
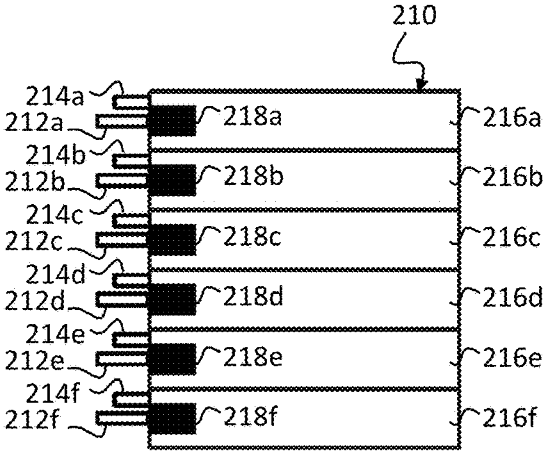
Figure 17C:
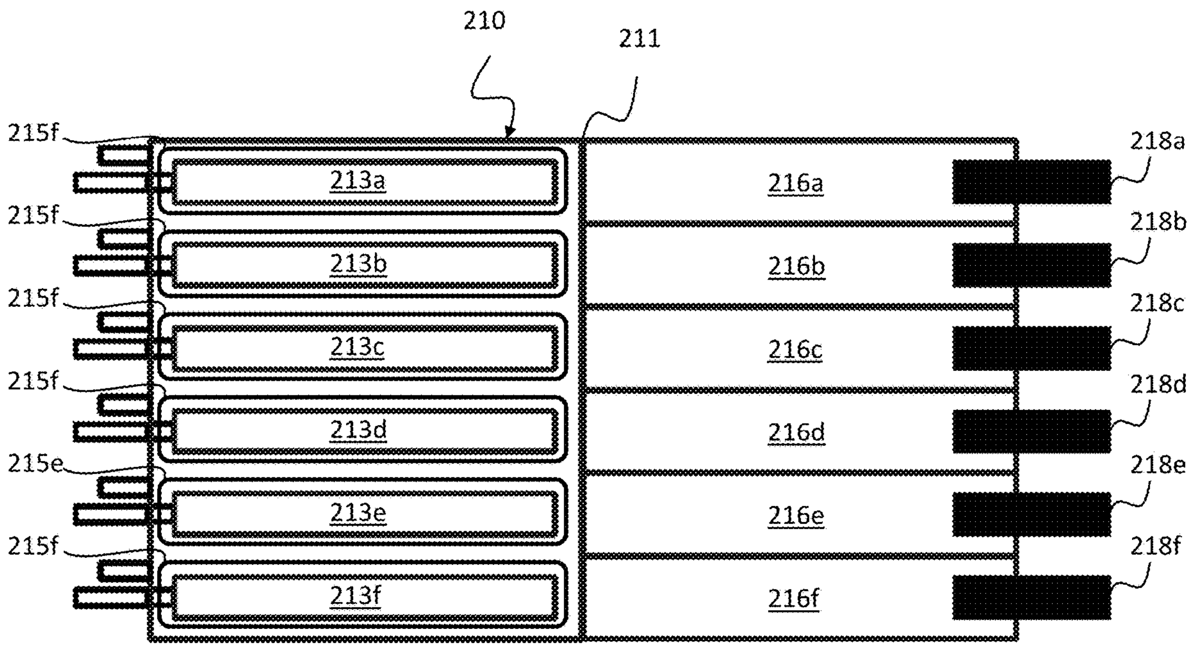

FIGS. 17A-17C are illustrations of an example chambered apparatus usable in the example controlled gas system according to aspects of the present invention.

Figure 18A:
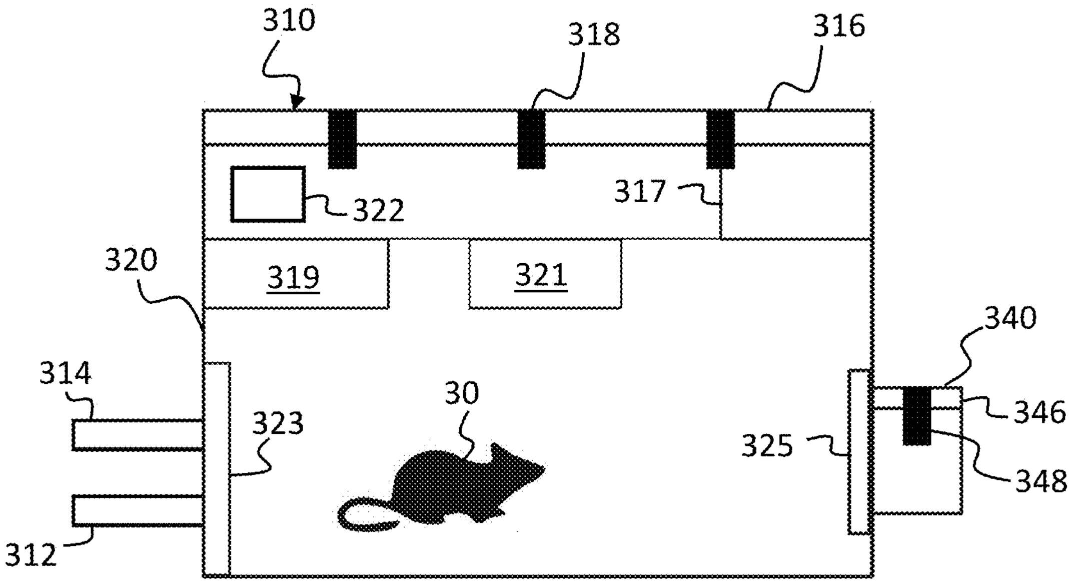
Figure 18B:
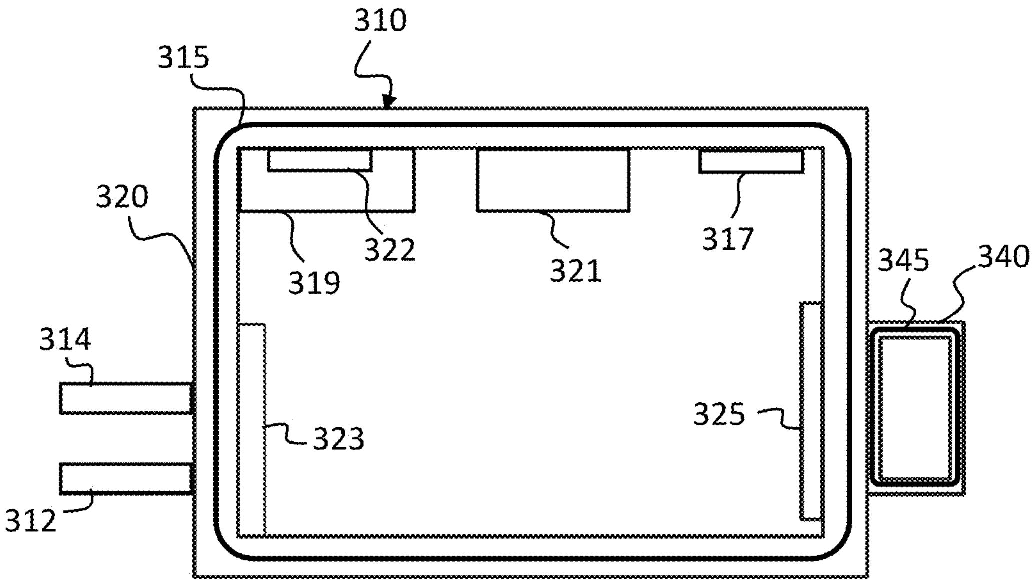

FIGS. 18A-18B are illustrations of another example chambered apparatus usable in the example controlled gas system according to aspects of the present invention.

Figure 19:
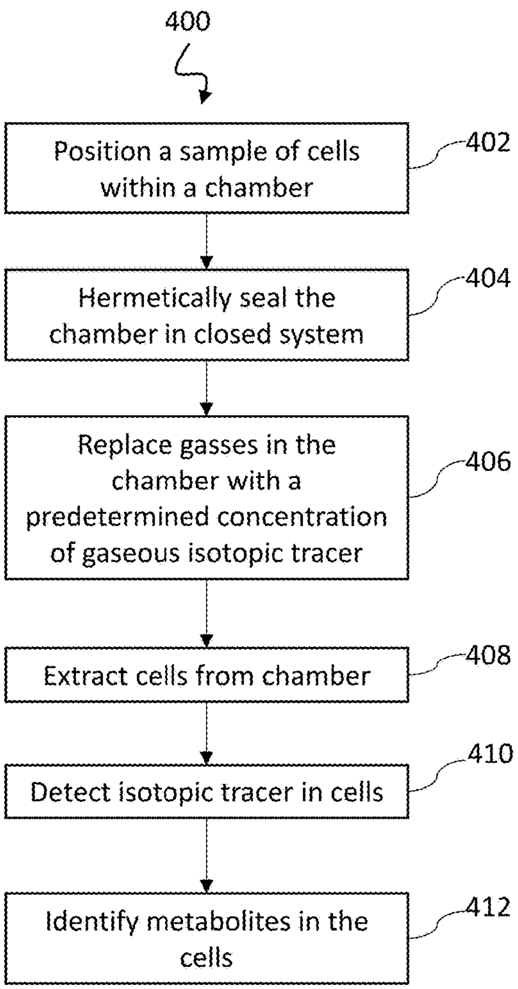

FIG. 19 is a flow diagram outlining an example method according to aspects of the present invention.

Figure 20:
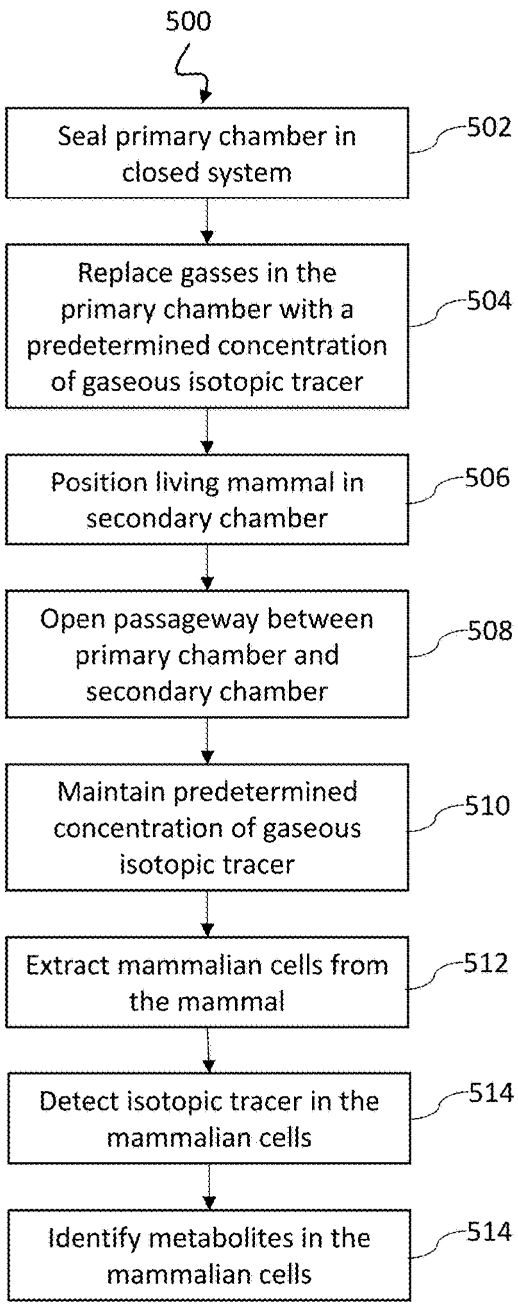

FIG. 20 is a flow diagram outlining another example method according to aspects of the present invention.

Figure 21A:
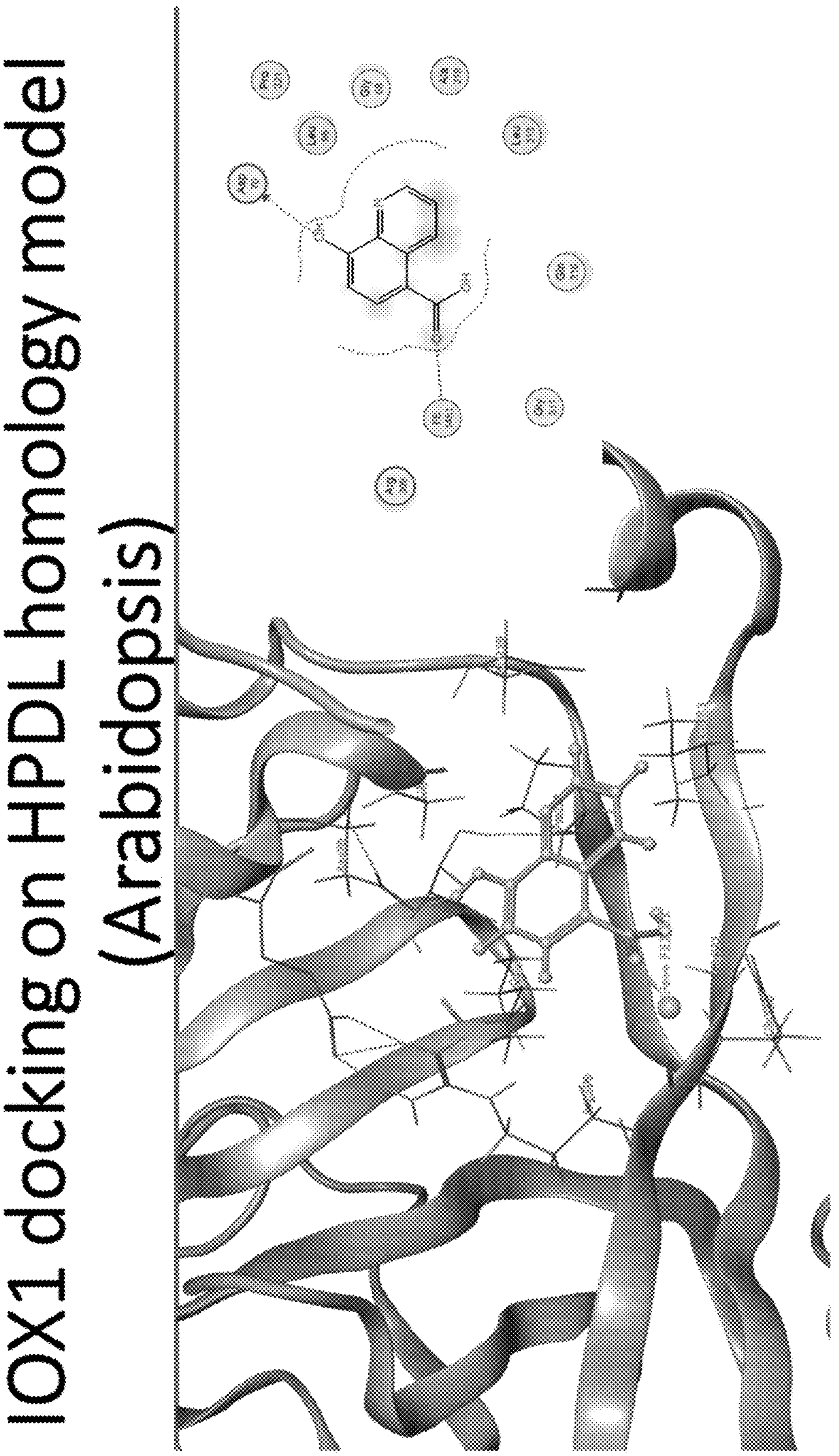
Figure 21B:
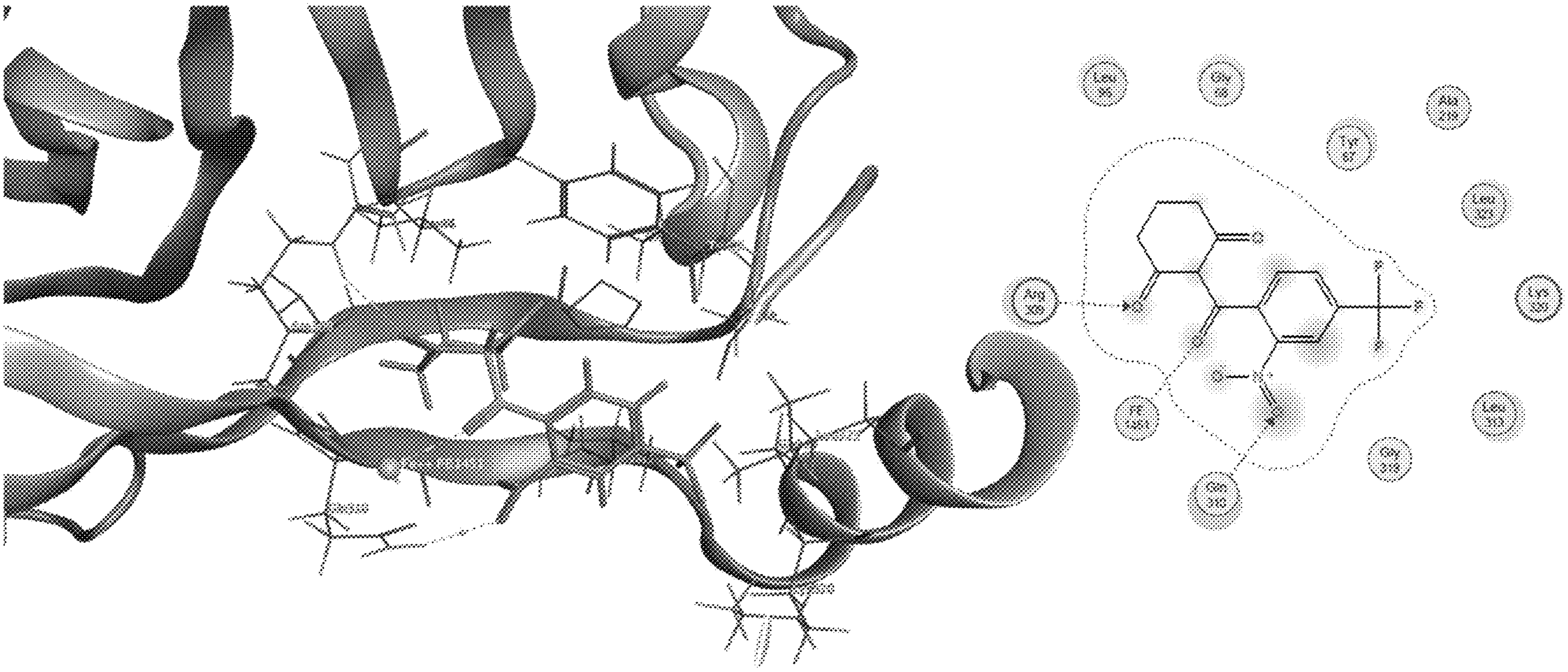
Figure 21C:
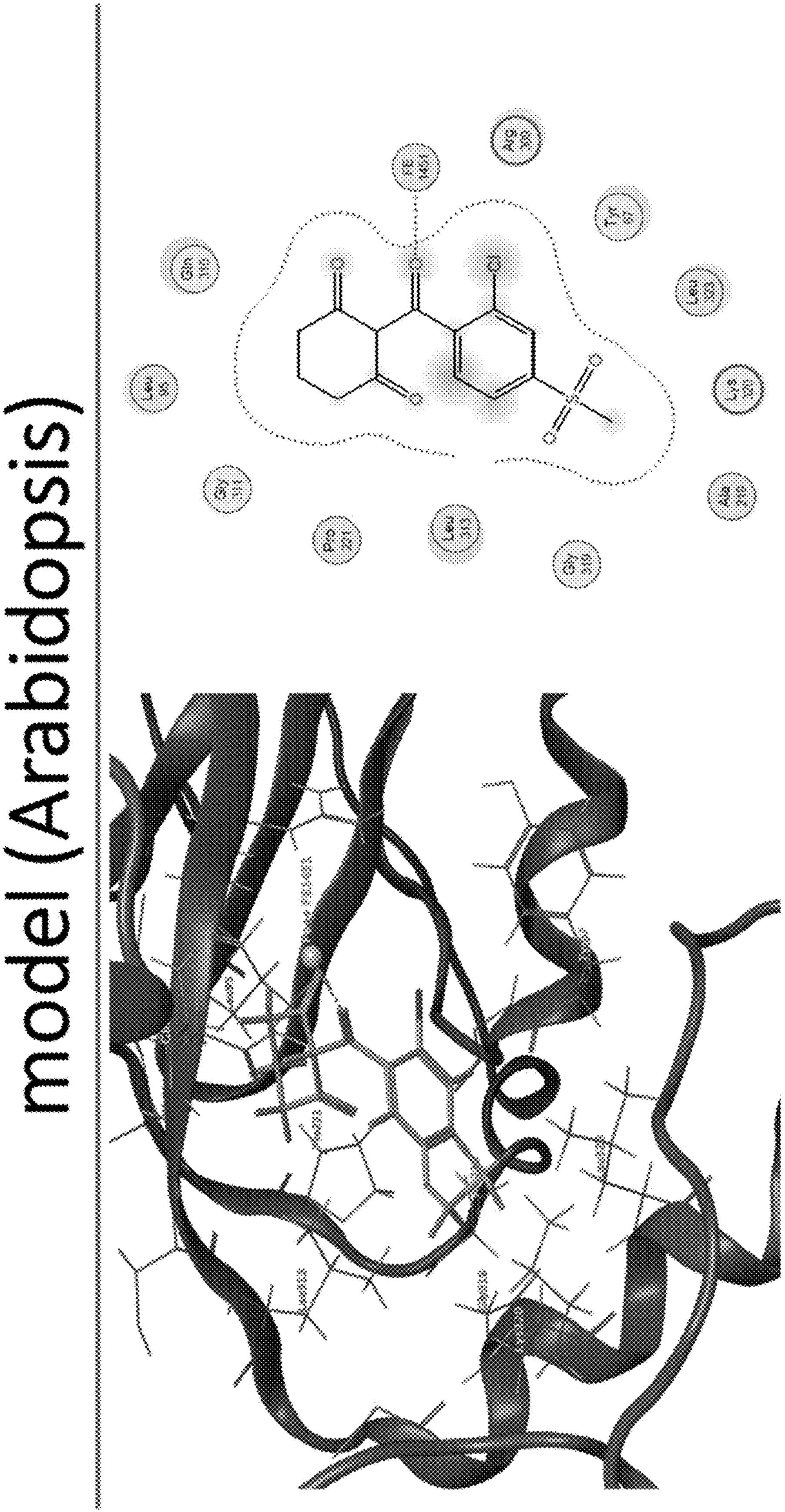

FIGS. 21A-21C show computational docking of IOX1 (FIG. 21A), Nitisinone (FIG. 21B), and Sulcotrione (FIG. 21C) on HPDL homology model from *Arabidopsis*.

Figure 22A:
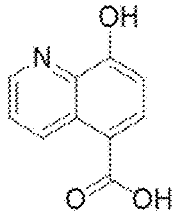
Figure 22A:
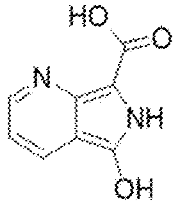
Figure 22A:
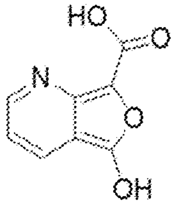
Figure 22A:
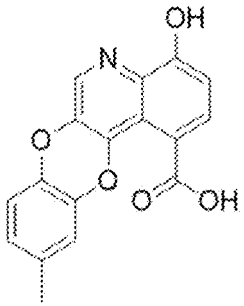
Figure 22A:
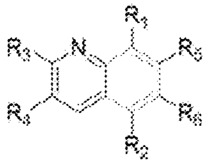
Figure 22A:
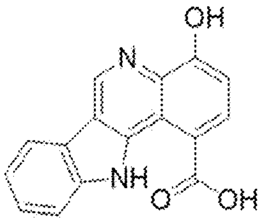
Figure 22A:
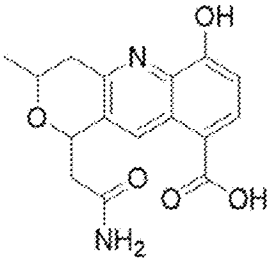
Figure 22A:
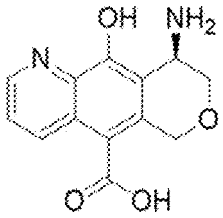

FIGS. 22A-22C show derivatives and scaffolds based on IOX1 (FIG. 22A), Nitisinone (FIG. 22B), and Sulcotrione (FIG. 22C) which may be used as potential HPDL inhibitors.

Figure 23A:
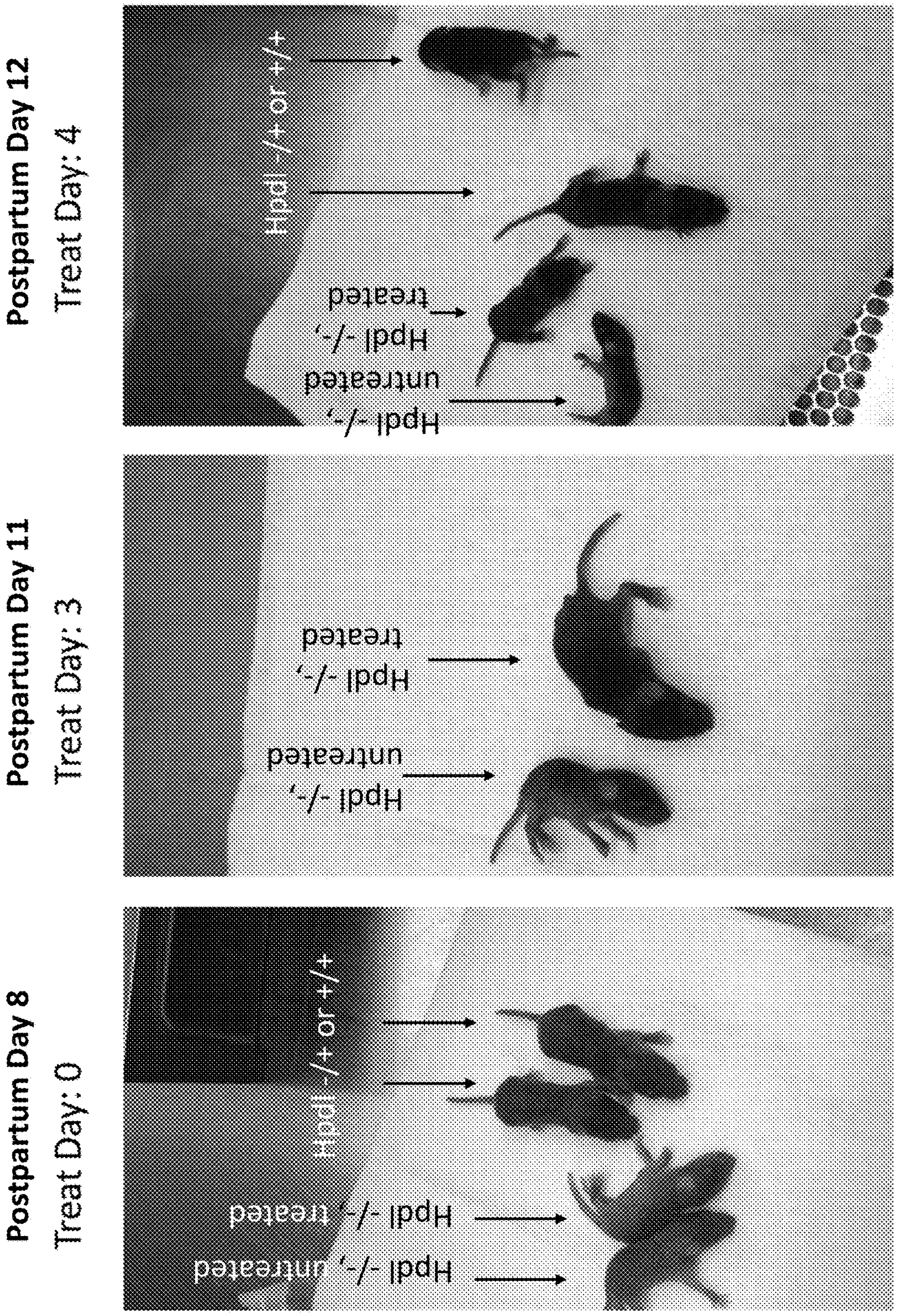
Figure 23B:
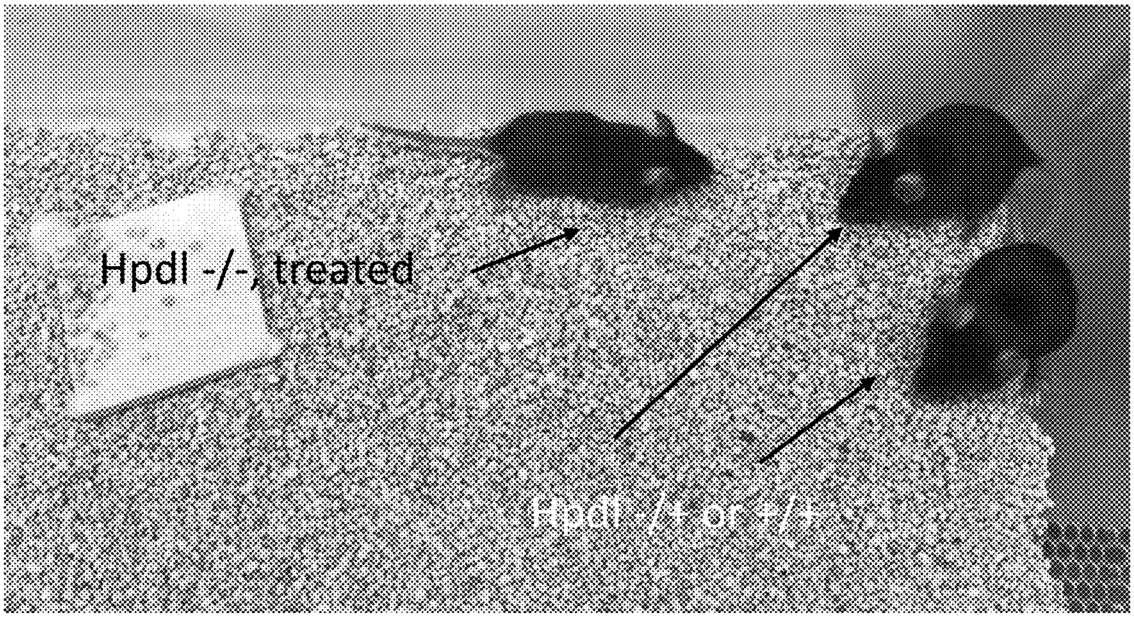

FIG. 23 shows the effect of treating a mouse with 4-HMA (10 μL of a 10 mM solution in water; 18.6 μg mouse; final dose is ~10 mg/kg) starting on postpartum day 3 or postpartum day 8.

Figure 24:
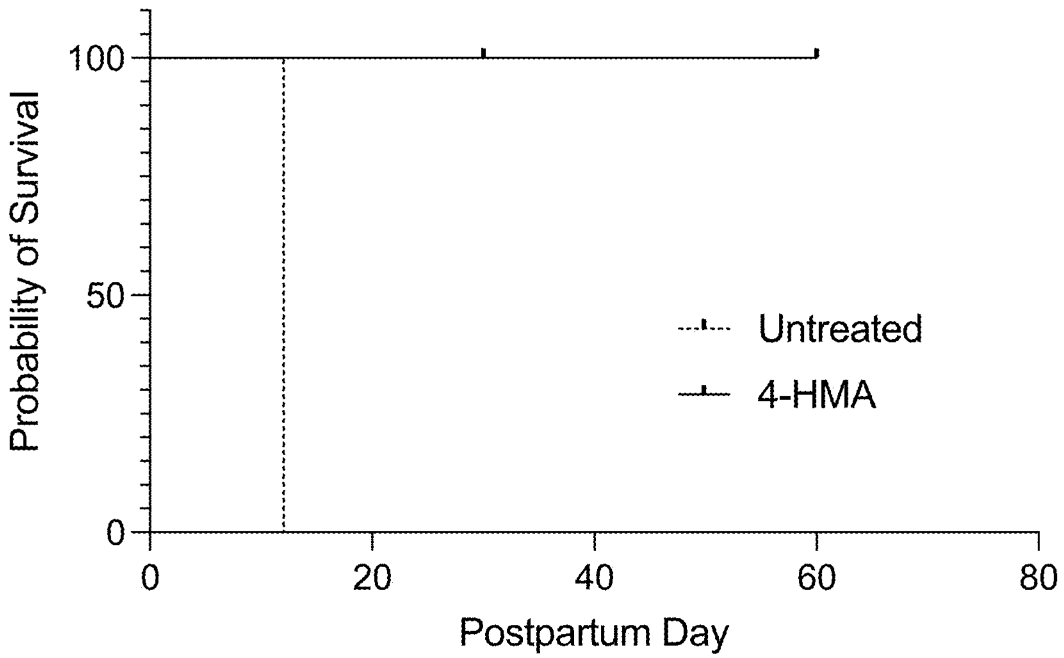

FIG. 24 shows survival data for an untreated mouse pup and mouse pups treated with 4-HMA.

Figure 25:
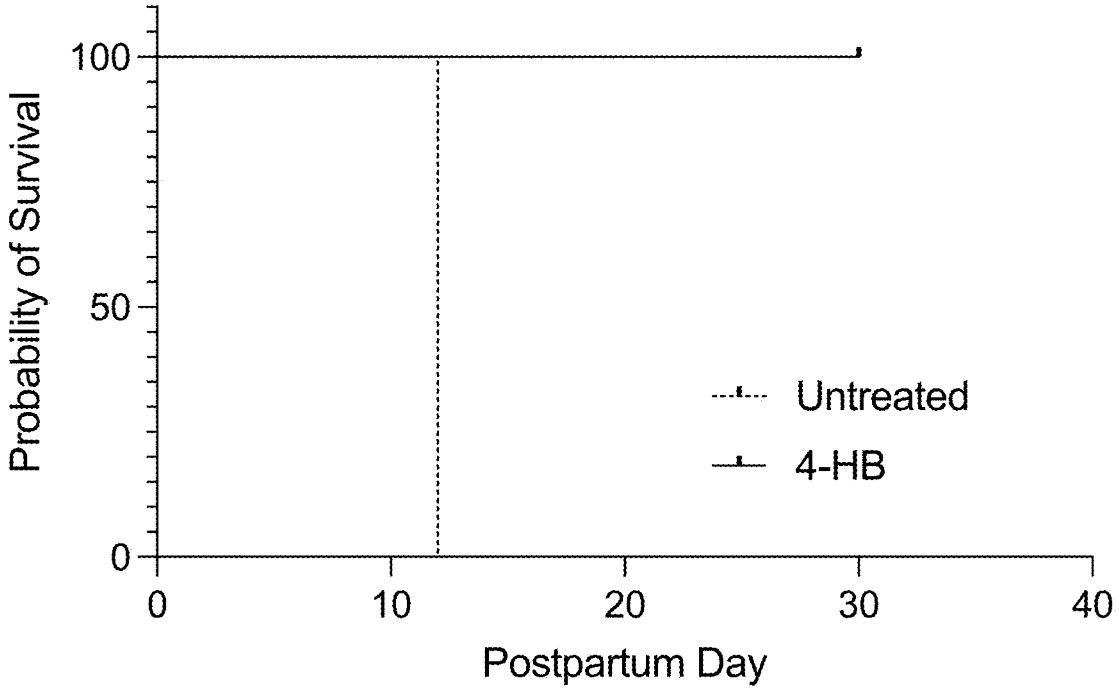

FIG. 25 shows results observed with 4-HB supplementation (10 mg/kg) in mouse pups.

DETAILED DESCRIPTION

Some aspects of the present application is based on the discovery that HPDL catalyzes a critical step in the synthesis of the headgroup of Coenzyme Q10 (CoQ10). HPDL makes R-4-hydroxymandelate ((R)-4-HMA), which is a long sought intermediate in the synthesis of the CoQ10 headgroup. R-4-HMA is converted to 4-hydroxybenzoic acid (4-HB). 4-HMA is chiral, with both (R) and (S)-enantiomers theoretically possible, and HPDL appears to produce exclusively the R-enantiomer of this molecule. The data here also show that 4-HMA is readily taken up by cells and incorporated into CoQ10.

Because the pharmacokinetics of CoQ10 are not well understood and it is not clear how much orally ingested CoQ10 is actually absorbed, and because 4-HMA is soluble, the natural product of HPDL, and is taken up by cells, supplementation with 4-HMA, 4-HB, or other intermediates (e.g., 4-hydroxybenzoylformate (4-HBF), 4-hydroxybenzaldehyde (4-HBz)) should treat patients with CP or neurodevelopmental disease induced by HPDL mutations. If CoQ10 were readily absorbed and entered the brain, it could treat this disease as well.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

As used herein, the terms "hermetically sealed" and "closed system" refer to a configuration of a system or an apparatus in which gasses are not permitted to flow but for flow through specifically designated inlet and/or outlet ports. An inlet port can be hermetically sealed by virtue of being mechanically connected with gas-impermeable materials to a controlled gas flow or by being hermetically closed (e.g. by a gas-impermeable closed valve). An outlet port can be hermetically sealed by virtue of being hermetically closed or by virtue of gas flow in only a single direction, i.e. out of the closed system.

As used herein, the term "alkyl" is given its ordinary meaning in the art and can include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_{1-20}$ for straight chain, $C_{2-20}$ for branched chain), and alternatively, about 1-10 carbon atoms, or about 1 to 6 carbon atoms. In some embodiments, a cycloalkyl ring has from about 3-10 carbon atoms in their ring structure where such rings are monocyclic or bicyclic, and alternatively about 5, 6 or 7 carbons in the ring structure. In some embodiments, a cycloalkyl group is a cyclopropyl, a cyclobutyl, a cyclopentyl, or a cyclohexyl group. In some embodiments, an alkyl group can be a lower alkyl group, wherein a lower alkyl group comprises 1-4 carbon atoms (e.g., $C_{1-4}$ for straight chain lower alkyls). When used in the context of a divalent alkyl group, it is to be understood that "alkyl" refers to an alkylene group.

As used herein, the term "alkenyl" refers to an alkyl group, as defined herein, including straight-chain alkenyl groups, branched-chain alkenyl groups, and cycloalkenyl groups having one or more double bonds. In certain embodiments, a straight chain or branched chain alkenyl has about 1-20 carbon atoms in its backbone (e.g., $C_{2-20}$ for straight chain, $C_{3-20}$ for branched chain), and alternatively, about 2-10 carbon atoms, or about 2 to 6 carbon atoms. In some embodiments, an alkenyl group has 1, 2, 3, 4, 5, or 6 double bonds. In some embodiments, a cycloalkenyl ring has from about 3-10 carbon atoms in the ring structure where such rings are monocyclic or bicyclic, and alternatively about 5, 6 or 7 carbons in the ring structure, and 1, 2, or 3 double bonds. In some embodiments, a cycloalkenyl group is a cyclopropenyl, a cyclobutenyl, a cyclobutadienyl, a cyclopentenyl, a cyclopentadienyl, a cyclohexenyl, or a cyclohexadienyl group. In some embodiments, an alkenyl group can be a lower alkenyl group, wherein a lower alkenyl group comprises 2-4 carbon atoms (e.g., $C_{2-4}$ for straight chain lower alkenyls). In one embodiment, a cycloalkenyl group has six carbon atoms and one double bond.

As used herein, the term "alkynyl" refers to an alkyl group, as defined herein, including straight-chain alkynyl groups, branched-chain alkynyl groups, and cycloalkynyl groups having one or more triple bonds. In certain embodiments, a straight chain or branched chain alkynyl has about 2-20 carbon atoms in its backbone (e.g., $C_{2-20}$ for straight chain, $C_{3-20}$ for branched chain), and alternatively, about 2-10 carbon atoms, or about 2 to 6 carbon atoms. In some embodiments, an alkynyl group has 1, 2, 3, 4, 5, or 6 triple bonds. In some embodiments, a cycloalkynyl ring has from about 6-12 carbon atoms in the ring structure where such rings are monocyclic or bicyclic, and alternatively about 8, 9, or 10 carbons in the ring structure, and 1, 2, or 3 triple bonds. In some embodiments, an alkynyl group can be a lower alkynyl group, wherein a lower alkynyl group comprises 2-4 carbon atoms (e.g., $C_{2-4}$ for straight chain lower alkynyls).

The term "heteroalkyl" is given its ordinary meaning in the art and refers to alkyl groups as described herein in which one or more carbon atoms is replaced with a heteroatom (e.g., oxygen, nitrogen, sulfur, and the like). In some embodiments, a heteroalkyl group can have one or more of methylene groups replaced with —O—, —S—, or —NH—, in which the hydrogen of —NH— is optionally substituted. Examples of heteroalkyl groups include, but are not limited to, alkoxy, poly(ethylene glycol)-, alkyl-substituted amino, tetrahydrofuranyl, piperidinyl, morpholinyl, etc.

The term "haloalkyl" is given its ordinary meaning in the art and refers to alkyl groups as described herein in which one or more hydrogen atoms is replaced by a halogen atom, i.e., F, Cl, Br, or I. In some embodiments a haloalkyl group can be a perfluoroalkyl group, i.e., a group where all hydrogen atoms are replaced with fluoride atoms. In some embodiments a haloalkyl group can be a halomethyl group, i.e., a $C_1$ group with 1, 2, or 3 halogen atoms, e.g., $—CF_3$, $—CF_2H$, $—CH_2F$, $—CH_2Cl$, $—CH_2Br$; $—CH_2I$. In some embodiments a haloalkyl group can be, e.g., $—CF_3$, $—CF_2H$, $—CH_2F$, $—CH_2Cl$, $—CH_2Br$; $—CH_2I$, $—CH_2CF_3$, $CH_2CH_2F$, $—CH_2CH_2Br$, $—CH_2CH_2Cl$, $—CH_2CH_2I$, etc.

The term "haloalkoxy" is given its ordinary meaning in the art and refers to alkoxy groups as described herein, i.e. alkyl groups bonded to an oxygen atom, in which one or more hydrogen atoms is replaced by a halogen atom, i.e., F, Cl, Br, or I. In some embodiments a haloalkoxy group can be a perfluoroalkoxy group, i.e., a group where all hydrogen atoms are replaced with fluoride atoms. In some embodiments a haloalkoxy group can be, e.g., $—OCF_3$, $—OCF_2H$, $—OCH_2F$, $—OCH_2Cl$, $—OCH_2Br$; $—OCH_2I$, $—OCH_2CF_3$, $—OCH_2CH_2F$, $—OCH_2CH_2Br$, $—OCH_2CH_2Cl$, $—OCH_2CH_2I$, etc.

The term "aryl" used alone or as part of a larger moiety as in "aralkyl," "aralkoxy," "aryloxy" or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" can be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which can bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The term "aralkyl" refers to alkyl groups as described herein in which one or more hydrogen atoms is substituted by aryl groups, where the radical or point of attachment is on the alkyl group. The alkyl part of an aralkyl group is optionally substituted as described in the term "alkyl" above. The aryl part of the aralkyl group is optionally substituted as described in the term "alkyl" above.

The term "alkylaryl" refers to aryl groups as described herein in which one or more hydrogen atoms is substituted by alkyl groups, where the radical or point of attachment is on the aryl group. The aryl part of the alkylaryl group is optionally substituted as described in the term "aryl" above. The alkyl part of an alkylaryl group is optionally substituted as described in the term "alkyl" above.

The terms "heteroaryl" and "heteroar-," used alone of as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 $\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, pyridine, quinoline, isoquinoline, quinolizine, pyrido[1,2-a]pyrazine, 1,8-naphthyridine, purine, chromene, indole, phenanthrene, benzo[H]quinoline, anthraquinone, and phenanthrol[1,2-b]furan groups. In some embodiments, a heteroaryl is a heterobiaryl group, such as bipyridyl and the like. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group can be monocyclic, bicyclic, tricyclic, tetracyclic, and/or otherwise polycyclic. The term "heteroaryl" can be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is saturated, partially unsaturated, or aromatic, and having, in addition to carbon atoms, one or more, e.g., one to four, heteroatoms, as defined above. As used herein, the term "heterocycle" encompasses heteroaryl groups, as defined above. In one embodiment, a heterocycle can be a saturated, partially unsaturated, or aromatic, 5-7 membered monocyclic moiety comprising from 1 to 3 nitrogen atoms, e.g., a pyrrole, an imidazole, a pyrazole, a pyrazole, a triazole, a piperidine, a piperazine, a pyridazine, a pyridine, 2H-pyridine, a pyridone, a pyrimidine, or a pyrazine, including monovalent or divalent radicals thereof. When used in reference to a ring atom of a heterocycle, the term "nitrogen" includes a substituted nitrogen. In one embodiment, a heterocycle can be a saturated, partially unsaturated, or aromatic, 5-7 membered monocyclic moiety comprising from 1 to 3 oxygen atoms, e.g., a tetrahydrofuran (i.e., oxolane), a furan, a dihydrofuran, a dioxolane, a tetrahydropyran (i.e., oxane), a pyran, a dihydropyran, a dioxane, a dioxine, a trioxane, an oxepane, or an oxepine, including monovalent or divalent radicals thereof. In one embodiment, a heterocycle can be thiophene, oxazole, thiazole, or morpholine, including monovalent or divalent radicals thereof.

A heterocyclic ring can be attached, e.g., to its pendant group, at any heteroatom or carbon atom that results in a stable structure. Examples of such saturated or partially unsaturated heterocyclic radicals include, without limitation, tetrahydropyranyl, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as phenyl, indolinyl, 3H-indolyl, chromanyl, phenanthridinyl, or tetrahydroquinolinyl. A heterocyclyl group can be monocyclic, bicyclic, tricyclic, tetracyclic, and/or otherwise polycyclic. The term "heterocyclylalkyl" refers to an alkyl group substituted by a heterocyclyl.

The term "heteroatom" means one or more of oxygen, sulfur, nitrogen, phosphorus, or silicon, including any oxidized form of nitrogen, sulfur, phosphorus, or silicon; the quaternized form of any basic nitrogen. In some embodiments, a heteroatom can be a substitutable nitrogen of a heterocyclic ring.

The term "unsaturated," as used herein, means that a moiety has one or more units of unsaturation.

The term "halogen" means F, Cl, Br, or I atom, and/or its radical or substituent, namely —F, —Cl, —Br, or —I.

As described herein, in certain embodiments, certain compounds of the disclosure can be indicated to comprise "optionally substituted" moieties. When indicated, in general, the term "substituted," whether preceded by the term "optionally" or not, means that one or more hydrogens of the designated moiety are replaced with a suitable substituent. Unless otherwise indicated, an "optionally substituted" group can have a suitable substituent at each substitutable position of the group, and when more than one position in any given structure can be substituted with more than one substituent selected from a specified group, the substituent can be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

As used herein, a substituent, e.g., —B, can be represented as a

where  denotes a point of attachment.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure.

The present application also includes pharmaceutically acceptable salts of the compounds described herein. The "pharmaceutically acceptable salts" include a subset of the "salts" described above which are conventional non-toxic salts of the parent compound formed, for example, from non-toxic inorganic or organic acids. Lists of suitable salts are found in Remington's Pharmaceutical Sciences, 17th ed., Mack Publishing Company, Easton, Pa., 1985, p. 1418 and Berge, S M et al, *Journal of Pharmaceutical Science,* 1977, 66, 1, 1-19. By way of an example, in an embodiment of the disclosure pharmaceutically acceptable salts can comprise a suitable anion selected from $F^-$, $Cl^-$, $Br^-$, $I^-$, $OH^-$, $^-BF_4$, $CF_3SO_3^-$, monobasic sulfate, dibasic sulfate, monobasic phosphate, dibasic phosphate, or tribasic phosphate, $NO_3^-$, $PF_6^-$, $NO_2^-$, carboxylate, $C_eF_fSO_3^-$, (where e=2-10 and f=2e+1), acetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, glycollyalarsanilate, hexanoate, hydrabamine, hydroxynaphthoate, isthionate, lactate, lactobionate, malate, maleate, mandelate, mesylate, methylbromide, methylnitrate, mucate, napsylate, octanoate, oleate, oxalate, palmitate, pamoate, pantothenate, polygalacturonate, propionate, salicylate, stearate, subacetate, succinate, tartrate, teoclate, tosylate, or triethiiodide. By way of another example, in an embodiment of the disclosure pharmaceutically acceptable salts can comprise a suitable cation selected from aluminum, arginine, benzathine, calcium, chloroprocaine, choline, diethanolamine, ethanolamine, ethylenediamine, lysine, magnesium, histidine, lithium, meglumine, potassium, procaine, sodium, triethylamince, or zinc. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "prodrug" as used herein includes a chemical which may be transformed in vivo to a pharmacologically active drug. The term "metabolite" as used herein includes a chemical that a given agent is transformed into in vivo.

The enantiomeric excess, or "ee," for a given pair of enantiomers is the percentage of the major enantiomer less the percentage of the minor enantiomer. A "racemate" or "racemic mixture" is an equal mixture of two enantiomers and therefore has 0% ee.

The term "enantiomerically enriched" or "enantioenriched" as used herein includes compounds that are mixtures with one enantiomer's being present in excess over the other (ee >0% and <100%). For example, a sample of 40% ee consists of 70% of the major enantiomer and 30% of the minor enantiomer.

The term "enantiomerically pure" or "enantiopure" as used herein includes compounds where the quantification of the minor enantiomer becomes difficult, e.g., with an ee of 99% or greater. Ideally, enantiopure compounds consist of a single enantiomer only.

The term "sample" as used herein includes any biological specimen obtained from a subject or patient. Samples that can be used in the methods of the present disclosure include, without limitation, tumor sample, whole blood, plasma, serum, red blood cells, white blood cells (e.g., peripheral blood mononuclear cells (PBMC), polymorphonuclear (PMN) cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample such as a biopsy (e.g., needle biopsy), and cellular extracts thereof. In some embodiments, when the subject is a pregnant female, the sample may be a fetal DNA sample (e.g., cell-free fetal DNA (cffDNA)).

As used herein, the term "subject" or "patient" refers to mammals and includes, without limitation, human and veterinary animals. In a preferred embodiment, the subject is human.

The terms "treat" or "treatment" of a state, disorder or condition include: (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof, or (3) relieving the disease, i.e., causing regression of the state, disorder or condition or at least one of its clinical or sub-clinical symptoms. The benefit to a subject to be treated is either statistically significant or at least perceptible to the patient or to the physician.

An "effective amount" of a compound described herein refers to an amount sufficient to elicit the desired biological response, i.e., treating the state, disorder or condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a state, disorder or condition or to delay or minimize one or more symptoms associated with the state, disorder or condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

Several technical issues make isotopic gaseous labelling of cells challenging and limit its widespread use. These include the need for a custom labelling apparatus, the large amount of costly isotopic gas required for each experiment, complete exclusion of abundant non-isotopic gas to maximize labeling, and continuous monitoring of isotopic gas concentrations during a study.

Examples presented herein generally focus on isotopic gaseous labelling of mammalian cells using $^{18}O_2$. However, other labeled gasses (also referred to herein as "isotopic tracers") can be substituted as understood by a person skilled in the pertinent art including, but not limited to $^{15}N_{18}O$, $^{15}N^{16}O$, $^{14}N^{18}O$ $^{12}C^{18}O$, $^{18}O_2$, $^{13}C^{16}O$, $^{13}C^{16}O_2$, $^{2}H_2{}^{34}S$, and/or derivatives thereof. Further, isotopic gaseous labelling can be applied to other types of cells can be substituted as understood by a person skilled in the pertinent art including, but not limited to including but not limited to plant, animal, fungi, bacteria, etc.

FIG. 16 is an illustration of an example controlled gas system 100. To perform isotopic labeling (also referred to herein as "isotopic tracing"), a sample 10 including cells are placed into a chamber 110, the chamber is sealed such that the system 100 is a closed system (meaning entry of gasses into the chamber is controlled by the system 100), the chamber 110 is purged of initial gasses (e.g. atmospheric gas ($O_2$, $CO_2$, $N_2$) by a purge gas source 126, gaseous isotopic tracer is flowed into the chamber 110 from an isotopic gas source 130, the cells metabolize in the chamber 110 in the presence of the isotopic gas, the sample 10 is extracted from the chamber 110, and isotopic tracer is detected in the cells.

The gas system 100 includes the purge gas source 126 (e.g. liquid $N_2$ dewar or the like), the isotopic gas source 130 (e.g. nitrocarbox cylinder), a control system 102 including flow meters, valves, mixers, etc., respective gas lines 128, 132 from the purge gas source 126 and isotopic gas source 130 to the control system 102, the sample chamber 110, and a gas line 106 from the control system 102 to an inlet port 112 of the sample chamber 110. The gas system 100 can further include valves including a pressure relief valve 104 (e.g. 2 psi popoff valve), an inlet valve 108, an outlet valve 124, and/or alternative valve configurations as understood by a person skilled in the pertinent art.

The control system 102 can further include electronics to facilitate automated air flow control into the inlet port 112 of the sample chamber 110. The electronics can include a processor and non-transitory computer readable medium with software instructions stored thereon executable by the processor to cause the control system 102 to perform automated air flow control including air flow control processes described elsewhere herein. The electronics can further include associated hardware to perform various functions such as closing and/or opening valves, closing and/or opening passageways for samples, receiving data from sensors (e.g. wireless and/or wired receivers, transmitters, and/or transceivers), and other such functions as understood by a person skilled in the pertinent art, including those functions described elsewhere herein.

The system 100 can include a gas sensor 122 configured to detect concentration of isotopic gas in the chamber 110. Flow of isotopic gas to the chamber 110 can be controlled based on a detected concentration of isotopic gas in the chamber detected by the gas sensor 122. In some examples, the control system 102 can receive sensor data from the gas sensor 122 and control the flow of isotopic gas into the chamber 110 based on the sensor data.

The control system 100 can include additional gas sources not illustrated which feed into the control system 102 to achieve a desired mixture of gas within the chamber 110.

The system 100 can further include additional features within the chamber 110 to achieve a desired gas mixture within the chamber 110, and/or stabilize the sample 100. For instance, a 15 centimeter dish of water can be placed in the chamber to provide humidity.

In one example process of labeling cells of the sample 10 using the system 100, while atmospheric gas ($O_2$, $CO_2$, $N_2$) is expelled from the chamber, both the inlet valve 108 and outlet valve 124 of the chamber 110 are opened, and $N_2$ is flushed into the chamber 110 at a rate of 40 liters/min for 2 minutes, after which both valves 108, 124 are quickly closed to allow the chamber 110 gasses to equilibrate for 10 minutes. $N_2$ flushing is repeated for a total of three times, and/or until the sensor 122 in the chamber stabilizes at approximately 0% $O_2$.

Next in the example process, the inlet valve 108 is opened and an isotopic gaseous mixture, such as $^{18}O_2$:5% $CO_2$:$N_2$, is flushed into the system at a rate of 2.5 liters/min. Subsequently, the outlet valve 124 is immediately opened to allow gas flow out of the chamber 110, and to release the pressure in the chamber 110. The chamber 110 is injected with the isotopic gaseous mixture for 1 minute before closing the inlet valve 108 and outlet valve 124. The chamber 110 is allowed to equilibrate for 5 minutes. This process is repeated seven times, and/or until the desired oxygen concentration is reached. Different isotopic gaseous mixtures can be used. For 3%, 1%, and 0.2% $^{18}O_2$ labelling studies, the chamber 110 can be infused with approximately 5%:5%:90%, approximately 1.5%:5%:93.5%, and approximately 0.5%:5%:94.5% $^{18}O_2$:$CO_2$:$N_2$, respectively. The isotopic gaseous-infused chamber 110 is then placed in a 37° C., 5% $CO_2$ tissue culture incubator for 24 hours. The gaseous concentration in the chamber 110 is monitored regularly. At the end of the 24 incubation cycle, the chamber 110 is opened inside a chemical fume hood and cells are extracted to identify metabolites as described elsewhere herein.

For the example process, preferably a cylinder of each gas is be connected to a manifold (part of control system 102 not specifically illustrated) that is linked to the gas sensor 122 in the chamber 110. This manifold can be programmed to purge the chamber 110 with nitrogen and refill it with 5% $CO_2$ and labeled $^{18}O$ or another gas to a specified concentration automatically.

Using a typical known incubation chamber as the illustrated chamber 110 may present some challenges. For instance, (~5 L) a Billups-Rothenberg modulator incubator chamber (MIC-101) has a volume of approximately 5 liters which may therefore present significant expense of isotopic gasses, and the configuration of the MIC-101 requires that the closed environment of the system 100 is broken when samples are removed which hampers the ability to assess labelling with time (kinetic labelling/tracing experiments). Further, the MIC-101 is not configured for live animal testing.

FIGS. 17A-17C are illustrations of an example chambered apparatus 210 usable in the example controlled gas system 100 in place of the chamber 110 illustrated in FIG. 16. The chambered apparatus 210 can include smaller volume chambers to reduce the volume of isotopic gas needed and individually accessible samples to facilitate kinetic labelling. The chambered apparatus 210 includes several separately sealable chambers 213*a-f*, respective inlet ports 212*a-f* for each chamber 213*a-f*, respective outlet ports 214*a-f* for each chamber 210*a-f*, and respective doors 216*a-f* with respective latches 218*a-f* for each chamber 218. Each chamber preferably has an internal volume of about 0.25 liters to about 5 liters.

The doors 216*a-f* can be hinged to the apparatus 210 at a hinged edge 211. The doors 216*a-f* can hermetically seal to a hermetically sealable openings to each respective chamber 213*a-f*. Each opening can include a respective seal 215*a-f* that presses into the respective door 216*a-f* when the door 216*a-f* is closed to thereby hermetically seal the chambers 213*a-f* individually. When the door 216*a-f* is open, a sample 10 can pass through the respective opening into the respective chamber 213*a-f*.

Configuring the apparatus 210 with the closed system 100 illustrated in FIG. 16 may require additional tubing, valves, gas sensors, etc. as understood by a person skilled in the pertinent art to connect to the increased number of input ports 212*a-f* and outlet ports 214*a-f*. The gas flow control system 102 can be configured to provide a predetermined concentration of gaseous isotopic tracer within some or all of the chambers 213*a-f*. The closed system 100 and the gas flow control system 102 can be configured to provide the same predetermined concentration of gaseous isotopic tracer to all of the chambers 213*a-f* or the closed system 100 and the gas flow control system 102 can be configured to provide various predetermine concentration of gasses so that different chambers 213*a-f* can receive different predetermined concentrations of gases. The gas flow control system 102 may also be configurable to vary predetermined concentration of isotopic tracer over time. Additionally, or alternative, the system 100 can include an accessory to adapt the gas flow control system 102 configured as illustrated and described in relation to FIG. 16 to the apparatus 210 illustrated in FIGS. 17A-17C. The accessory can include appropriate fluidic control hardware to facilitate mechanical connection of the gas flow control system 102 to the chambered apparatus 210. The accessory can further include electronic hardware and software (e.g. processor and memory with instructions) to automate processes described herein such as flow control and valve control.

The apparatus 210 preferably is constructed primarily of clear or transparent materials such as gas-impermeable plastic so that samples placed therein can be visually monitored when the system 100 is closed. Inlet ports 212*a-f* and outlet ports 214*a-f* for each chamber 213*a-f* are gas impermeable and are preferably flexible to facilitate changing of valves. Inlet ports 212*a-f* and outlet ports 214*a-f* are preferably of sufficient length so that clamps over the ports 212*a-f*, 214*a-f* can hermetically seal.

The apparatus 210 can be constructed to have a singular housing that structurally supports every chamber 213*a-f* and associated components. Additionally, or alternatively, the chambers 213*a-f* can be modular, e.g. stackable and/or able to interlock. For instance, the apparatus 210 as illustrated can be configured to stack and/or interlock with similar compatible apparatuses. Alternatively, the apparatus 210 as illustrated can be modified such that each chamber 213*a-f* and its associated components can be individually separated from the apparatus 210.

FIGS. 18A-18B are illustrations of another example chambered apparatus 310 usable in the example controlled gas system 100 in place of the chamber 110 illustrated in FIG. 16. The example chambered apparatus 310 is configured to facilitate controlled gaseous environment testing with a living experimental animal 30 such as a small mammal or other suitable animal. In some examples, the chambered apparatus 310 can be configured to facilitate controlled gaseous environment testing with a mouse, rat, *C. elegan* (nematode, D. melangaster (fruit fly), plants (*A. thaliana* or others), algae, and/or unicellar animals, etc. A challenge with performing gaseous isotopic tracing on living animal cells using above-described processes is that when the chamber 110 is purged of atmosphere, a living animal in the chamber may suffocate. To address the issue, the chambered apparatus 310 includes a primary chamber 320 in which the majority of the experiment is conducted, a secondary chamber 340 to temporarily house the animal as the gas mixture in the primary chamber 320 stabilizes at the beginning of the experiment, and a passageway with a door 325 between the primary chamber 320 and secondary chamber 340 to allow the animal 30 to cross over into the primary chamber 320 once the gas mixture in the primary chamber 320 is stabilized. The illustrated example in FIGS. 18A-18B can be modified to include modular capability for the animal portion. The illustrated example in FIGS. 18A-18B can be modified to include a glove box portion and small airlock so samples can be taken out over time, put in the airlock and removed while the animal is still exposed without breaking the larger seal of the closed system. In such examples, the animal small box 340 may double as the airlock in which case, the passthrough door 325 can be left open until the atmosphere balances and then samples can be passed back out. The animal small box 340 may also include an atmosphere feed to purge for sampling.

The apparatus 310 can be configured to prevent gasses from the secondary chamber 340 from disturbing the controlled gas mixture in the primary chamber 320 when the door 325 is opened to allow the animal 30 to pass into the primary chamber 320. The secondary chamber 340 can be of significantly smaller volume than the primary chamber 320 to minimize effect of gas mixture from the secondary chamber. The primary chamber preferably has a volume of about 3 liters to about 10 liters. The secondary chamber preferably has a volume of about 0.1 liters to about 0.5 liters. These dimensions may be suitable for a small mammal such as a mouse. The dimensions of the primary chamber and the secondary chamber can be scaled to accommodate a range of animal sizes. Other strategies can be incorporated to prevent gas mixture between the primary chamber 320 and secondary chamber 340 including turning off air flow to have still air during cross-over of the animal 30, putting the door 325 on a timer so that the door is not open for a prolonged time, a motivator to encourage the animal 30 to cross over quickly, prolonged experiment time so that even if $^{16}O_2$ comes into the primary chamber 320, the concentration goes down as experiment progresses and more $^{18}O_2$ is put into the primary chamber 320. An alternative strategy can be used to account for gas mixture in the primary chamber 320 with the secondary chamber 340 in which air from both chambers 320, 340 is allowed to completely mix and final concentration of isotopic tracer can be calculated based on known volumes of the primary chamber 320 and secondary chamber 340.

The chambered apparatus 310 includes a lid 340 that can be opened to place the living animal 30 into the secondary chamber 340. The lid 340 can press into a seal 345 to hermetically seal the secondary chamber 340. The door 325 can also mate with a seal to seal the passageway between the primary chamber 320 and the secondary chamber 340.

The chambered apparatus 310 includes a gas inlet port 312 and a gas outlet port 314 to the primary chamber 320. The inlet port 312 can be connected to tubing 106 of the closed system 100 illustrated in FIG. 16. The apparatus 310 includes a gas sensor 322 which can function similar to the gas sensor 122 illustrated in FIG. 16.

The apparatus 310 can further include features specific to the care of the living animal 30 such as a water container 319 and a food container 321. The apparatus 310 can include a $CO_2$ absorber 317 within the primary chamber 320 to absorb $CO_2$ exhaled by the living animal 30 during the experiment to help maintain a desired gas mixture within the primary chamber 320. The apparatus 310 can further include a protective wire cage 323 over the inlet port 312 and outlet port 314 to prevent the living animal from damaging those ports.

The apparatus 310 can include a lid 316 with latches 318 that can be opened to remove the animal 30 from the chamber 310 and/or extract cells from the animal 30. The apparatus 310 can include a seal 315 to which the lid 316 of the primary chamber 320 can mate to hermetically seal the primary chamber 320.

The system 100 can be configured to provide flow of isotopic gas into the primary chamber while the living animal breathes to maintain a predetermined concentration of isotopic gas in the primary chamber. The flow can be automatically controlled by the gas flow control system 102 illustrated in FIG. 16, or other suitable system as understood by a person skilled in the pertinent art. The flow can be controlled based at least in part on signals from the gas sensor 322. The system 100 can be configured to maintain a predetermined concentration of $^{18}O_2$ assuming an oxygen consumption rate of the animal of between about 30 milliliters/hour and about 100 milliliters/hour.

The door 325 between the primary chamber 320 and the secondary chamber 340 can be automatically controlled to open and close based on gas mixture in the primary chamber 320. The door 325 can preferably be wirelessly controlled.

The apparatus 310 is preferably constructed primarily of clear or transparent material so that the animal 30 can be monitored visually. The apparatus 310 is preferably constructed of gas-impermeable plastic for an air-tight seal. Inlet port 312 and outlet ports 314 are gas impermeable and are preferably flexible to facilitate changing of valves. The inlet port 312 and outlet port 314 are preferably of sufficient length so that clamps over the ports 312, 314 can hermetically seal.

FIG. 19 is a flow diagram outlining an example method 400. At step 402 a sample is positioned within a chamber. The sample and chamber can be configured similar to the sample 10, and chamber 110 illustrated in FIG. 16 or chamber 213*a-f* of the apparatus 210 illustrated in FIGS. 17A-17C, variations thereof, or alternatives thereto as understood by a person skilled in the pertinent art according to the teachings herein.

At step 404, the chamber can be hermetically sealed in a closed system. The closed system can be configured similar to the closed system 100 illustrated in FIG. 16, a variation thereof, or an alternative thereto as understood by a person skilled in the pertinent art according to the teachings herein.

At step 406, gasses in the chamber can be replaced with a predetermined concentration of gaseous isotopic tracer. The gasses can be replaced according to processes described elsewhere herein, variations thereof, or alternatives thereto as understood by a person skilled in the pertinent art according to the teachings herein. For instance, the gasses can be purged before injection of gaseous isotopic tracer. The sample can remain in the predetermined concentration of gaseous isotopic tracer for a predetermined amount of time.

At step 408, cells can be extracted from the chamber.

At step 410, isotopic tracer can be detected in the cells. The isotopic tracer can be detected using mass spectroscopy and/or alternative suitable technique as understood by a person skilled in the pertinent art according to the teachings herein.

At step 412, metabolites can be identified in the cells. The metabolites can be identified using various techniques including those described elsewhere herein and/or alternative suitable technique as understood by a person skilled in the pertinent art according to the teachings herein.

FIG. 20 is a flow diagram outlining another example method 500. At step 502, a primary chamber can be sealed in a closed system. The primary chamber can be configured similar to the primary chamber 320 of the apparatus 310 illustrated in FIGS. 18A-18B, variations thereof, or alternatives thereto as understood by a person skilled in the pertinent art according to the teachings herein. The closed system can be configured similar to the closed system 100 illustrated in FIG. 16, variations thereof, or alternatives thereto as understood by a person skilled in the pertinent art according to the teachings herein.

At step 504, gasses in the primary chamber can be replaced with a predetermined concentration of gaseous isotopic tracer. The gasses can be replaced according to processes described elsewhere herein, variations thereof, or alternatives thereto as understood by a person skilled in the pertinent art according to the teachings herein. For instance, the gasses can be purged before injection of gaseous isotopic tracer. While purging, oxygen concentration can be reduced to about 0%.

At step 506, a living mammal can be positioned in a secondary chamber. The secondary chamber can be configured similarly to the secondary chamber 340 illustrated in FIGS. 18A-18B, variations thereof, or alternatives thereto as understood by a person skilled in the pertinent art according to the teachings herein.

At step 508, a passageway between the primary chamber and the secondary chamber can be opened. The passageway can be closed by a door configured similarly to the door 325 illustrated in FIGS. 18A-18B, variations thereof, or alternatives thereto as understood by a person skilled in the pertinent art according to the teachings herein. While the passageway is open, the living mammal can travel from the secondary chamber into the primary chamber.

At step 510, the predetermined concentration of gaseous isotopic tracer can be maintained in the primary chamber. The mammal can be living in the primary chamber during step 510. The concentration of gaseous isotopic tracer can be maintained according to processes described elsewhere herein, variations thereof, or alternatives thereto as understood by a person skilled in the pertinent art according to the teachings herein.

At step 512, mammalian cells can be extracted from the mammal. The cells can be extracted while the mammal is alive or dead. For instance, non-endpoint samples (e.g. blood draw) may be taken while the mammal is alive and exposed to the predetermined concentration of gaseous isotopic tracer.

At step 514, isotopic tracer is detected in the mammalian cells. The isotopic tracer can be detected using mass spectroscopy and/or alternative suitable technique as understood by a person skilled in the pertinent art according to the teachings herein.

At step 516, metabolites can be identified in the cells. The metabolites can be identified using various techniques including those described elsewhere herein and/or alternative suitable technique as understood by a person skilled in the pertinent art according to the teachings herein.

Certain examples and implementations of the disclosed technology are described above with reference to block and flow diagrams of systems and methods and/or computer program products according to example embodiments or implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, may be repeated, or may not necessarily need to be performed at all, according to some embodiments or implementations of the disclosed technology.

These computer-executable program instructions may be loaded onto a computing system such as a general-purpose computer, a special-purpose computer, a processor, or other programmable data processing apparatus to produce a machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a manner, such that the instructions stored in the computer-readable memory produce an article of manufacture including instruction means that implement one or more functions specified in the flow diagram block or blocks.

Certain examples or implementations of the disclosed technology may provide for a computer program product, including a computer-usable medium having a computer-readable program code or program instructions embodied therein, said computer-readable program code adapted to be executed to implement one or more functions specified in the flow diagram block or blocks. Likewise, the computer program instructions may be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Processors described herein may include one or more processing units (e.g., in a multi-core configuration). Further, processors described herein may be implemented using one or more heterogeneous processor systems in which a main processor is present with secondary processors on a single chip. As another illustrative example, the processors may be a symmetric multi-processor system containing multiple processors of the same type. Further, the processors may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein. Additionally, the processors may perform partial processing and receive partial processing by a processor and/or computing device communicatively coupled to the processors.

In one aspect, the present disclosure provides a method of treating a pancreatic cancer in a subject in need thereof, comprising the following steps:

a) determining expression level of 4-hydroxyphenylpyruvate dioxygenase-like (HPDL) in a sample obtained from the subject;
b) comparing the HPDL expression level determined in step (a) with a control level of HPDL expression; and
c) administering an effective amount of an HPDL inhibitor to the subject exhibiting a higher level of HPDL expression as compared to the control level.

It is contemplated that patients who have high expression level of HPDL can be candidates for treatment with an HPDL inhibitor described herein. HPDL expression level can be determined via suitable methods for determining protein expression at a mRNA level and/or at protein level. In some embodiments, HPDL expression level is determined at mRNA level via RNA-seq, or reverse transcription polymerase chain reaction (rt-PCR), or fluorescence in situ hybridization (FISH). In some embodiments, the HPDL expression level is determined at protein level via immunohistochemistry (IHC) staining or immunofluorescence.

As a non-limiting example, HPDL levels may be determined by chromogenic immunohistochemistry using an anti-HPDL antibody as the primary antibody and an HRP-linked secondary antibody followed by DAB staining. Grading would be accomplished by a score of 0, 1, 2, or 3+, with 0-1+ considered low and 2-3+ considered high. 0=no staining, 1=weak staining, 2=moderate staining, 3=strong staining.

Patients with high HPDL may be more sensitive to the addition of an electron transport chain (ETC) inhibitor such as metformin to platinum-based chemotherapy as these tumors might have higher capacity for nucleotide synthesis driven by ETC activity.

Patients who are unresectable and have high HPDL may be managed with single-agent chemotherapy as they are likely to have a poor survival even following downstaging. Patients with low HPDL may be managed with multiagent chemotherapy (e.g., FOLFIRINOX), ideally with chemoradiotherapy, to maximize the possibility of downstaging to consider resection, as these patients likely will have improved outcomes.

Patients who are borderline resectable and have high HPDL may be treated with single-agent chemotherapy alone or best supportive care as they are likely to have a poor prognosis. Patients who are borderline resectable and have low HPDL may be treated with neoadjuvant chemo-RT to maximize chance of resection followed by surgery. Overall and progression-free survival can be better for borderline resectable low HPDL patients. These patients also likely have lower burden of micrometastatic disease and are more likely to respond to multiagent chemotherapy.

COMPOUNDS OF THE DISCLOSURE

In one aspect, provided herein is a compound having the structure of Formula (I):

(I)

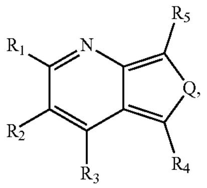

or a pharmaceutically acceptable salt thereof, wherein:

Q is selected from —O—, —NH—, and

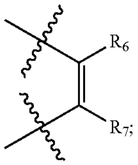

$R_1$, $R_2$, and $R_3$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of which optionally contains 1-8 heteroatoms selected from halogen, O, N, and S; —OH, =O, —$CO_2$H, —$NO_2$, —$NH_2$, —NHR*, —$NR^*_2$, —N—OH, —$HSO_3$, —$H_2PO_3$, —OR*, —(C=O)—R*, —$CO_2$R*, —CO—$NH_2$, —CO—NHR*, —$SO_2$—NHR*, or adjacent two moieties combine to form a fused ring which may optionally contain 1-3 heteroatoms selected from halogen, O, N, and S and which may be further substituted by one or more R*, wherein when Q is

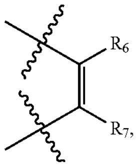

at least one of $R_1$, $R_2$, and $R_3$ is not H;

$R_4$ and $R_5$ are independently selected from —OH and —$CO_2$H;

$R_6$ and $R_7$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of which optionally contains 1-8 heteroatoms selected from halogen, O, N, and S; —OH, =O, —$CO_2$H, —$NO_2$, —$NH_2$, —NHR*, —$NR^*_2$, —N—OH, —$HSO_3$, —$H_2PO_3$, —OR*, —(C=O)—R*, —$CO_2$R*, —CO—$NH_2$, —CO—NHR*, —$SO_2$—NHR*, or $R_6$ and $R_7$ combine to form a fused ring, and R* is independently selected at each occurrence from hydrogen or $C_1$-$C_{12}$ hydrocarbons each of which optionally contains 1-8 heteroatoms selected from halogen, O, N, and S and combinations thereof.

In one embodiment, when Q is

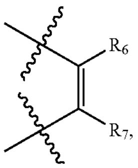

at least one of $R_1$, $R_2$, and $R_3$ is not H.

In one embodiment, Q is —O—.

In one such embodiment, the compound has the structure of Formula (IA):

(IA)

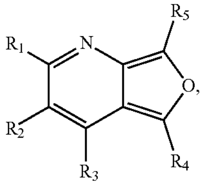

or a pharmaceutically acceptable salt thereof.

In one embodiment, Q is —NH—.

In one such embodiment, the compound has the structure of Formula (IB):

(IB)

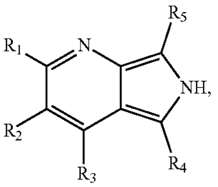

or a pharmaceutically acceptable salt thereof.

In one embodiment, Q is

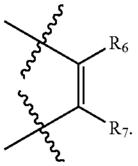

In one such embodiment, the compound has the structure of Formula (IC):

(IC)

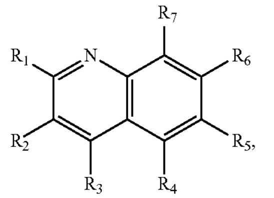

or a pharmaceutically acceptable salt thereof.

In one such embodiment, the compound has the structure of Formula (ID):

(ID)

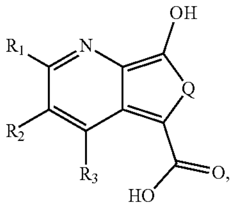

or a pharmaceutically acceptable salt thereof, wherein Q is —O— or —NH— and $R_1$, $R_2$, and $R_3$ are as defined above.

In one such embodiment, the compound has the structure of Formula (IE):

(IE)

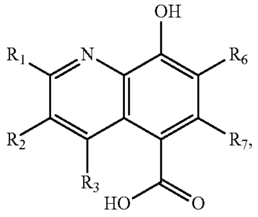

or a pharmaceutically acceptable salt thereof, wherein $R_1$, $R_2$, $R_3$, $R_6$, and $R_7$ are as defined above.

In one aspect, the present invention provides 2-hydroxy-2-(4-hydroxyphenyl)acetic acid (also known as 4-hydroxymandelic acid (4-HMA)), or a pharmaceutically acceptable salt, solvate, hydrate, polymorph, co-crystal, tautomer, stereoisomer, isotopically labeled derivative, or prodrug thereof.

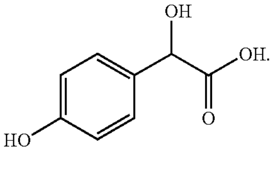

(4-HMA)

In one embodiment, 4-HMA is provided as a racemic mixture of the R- and the S-enantiomers of 4-HMA, depicted below:

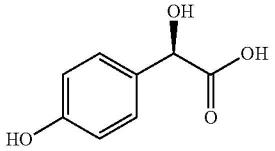

and (R)-4-HMA

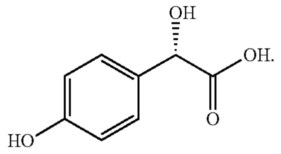

(S)-4-HMA

In another embodiment, 4-HMA is provided as an enantioenriched mixture of the R-enantiomer, i.e., (R)-4-HMA. In one embodiment, the (R)-4-HMA is present with an enantiomeric excess (ee) of about 20% or greater, or about 30% or greater, or about 40% or greater, or about 50% or greater, or about 60% or greater, or about 70% or greater, or about 80% or greater, or about 85% or greater, or about 90% or greater, or about 95% or greater, or about 96% or greater, or about 97% or greater, or about 98% or greater, or about 99% or greater, or about 99.5% or greater, or about 99.9% or greater.

In one embodiment, the (R)-4-HMA is present with an enantiomeric excess (ee) of at least about 20%, or at least about 30%, or at least about 40%, or at least about 50%, or at least about 60%, or at least about 70%, or at least about 80%, or at least about 85%, or at least about 90%, or at least about 95%, or at least about 98%, or at least about 99%.

In another embodiment, 4-HMA is provided as the enantiopure R-enantiomer (R)-4-HMA.

In another embodiment, 4-HMA is provided as an enantioenriched mixture of the S-enantiomer, i.e., (S)-4-HMA. In one embodiment, the (S)-4-HMA is present with an enantiomeric excess (ee) of about 20% or greater, or about 30% or greater, or about 40% or greater, or about 50% or greater, or about 60% or greater, or about 70% or greater, or about 80% or greater, or about 85% or greater, or about 90% or greater, or about 95% or greater, or about 96% or greater, or about 97% or greater, or about 98% or greater, or about 99% or greater, or about 99.5% or greater, or about 99.9% or greater.

In one embodiment, the (S)-4-HMA is present with an enantiomeric excess (ee) of at least about 20%, or at least about 30%, or at least about 40%, or at least about 50%, or at least about 60%, or at least about 70%, or at least about 80%, or at least about 85%, or at least about 90%, or at least about 95%, or at least about 98%, or at least about 99%.

In another embodiment, 4-HMA is provided as the enantiopure S-enantiomer (S)-4-HMA.

In another aspect, the present invention provides metabolites of 4-hydroxymandelic acid (4-HMA), or a pharmaceutically acceptable salt, solvate, hydrate, polymorph, co-crystal, tautomer, stereoisomer, isotopically labeled derivative, or prodrug thereof. For example, a metabolite of 4-hydroxymandelic acid (4-HMA) may be a reaction intermediate or metabolic pathway intermediate involved in the CoQ10 biosynthesis pathway, such as those described in FIG. 13, e.g., 4-hydroxybenzoylformate (4-HBF), 4-hydroxybenzaldehyde (4-HBz), and 4-hydroxybenzoate (4-HB).

In another aspect, the present invention provides 4-hydroxybenzoic acid (4-HB), or a pharmaceutically acceptable salt, solvate, hydrate, polymorph, co-crystal, tautomer, stereoisomer, isotopically labeled derivative, or prodrug thereof.

In another aspect, the present invention provides 4-hydroxybenzoylformate (4-HBF), or a pharmaceutically acceptable salt, solvate, hydrate, polymorph, co-crystal, tautomer, stereoisomer, isotopically labeled derivative, or prodrug thereof.

In another aspect, the present invention provides 4-hydroxybenzaldehyde (4-HBz), or a pharmaceutically acceptable salt, solvate, hydrate, polymorph, co-crystal, tautomer, stereoisomer, isotopically labeled derivative, or prodrug thereof.

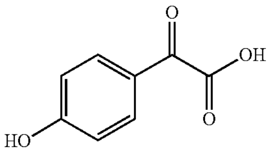

4-HBF

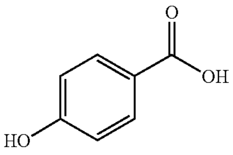

4-HB

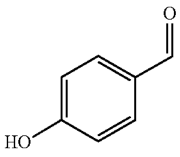

4-HBz

Pharmaceutical Compositions and Administration

The present invention also provides pharmaceutical compositions comprising a compound described herein, or a pharmaceutically acceptable salt, solvate, hydrate, polymorph, co-crystals, tautomer, stereoisomer, isotopically labeled derivative, or prodrug thereof, wherein $R_1$, $R_2$, $R_3$, $R_6$, and $R_7$ are as defined above.

In one embodiment, $R_1$ and $R_2$ combine to make a fused ring.

In one embodiment, $R_2$ and $R_3$ combine to make a fused ring.

In one embodiment, $R_6$ and $R_7$ combine to make a fused ring.

In some embodiments, the compound having the structure of Formula (I) is selected from the group consisting of:

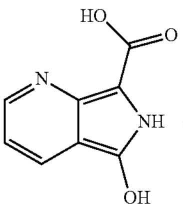

,

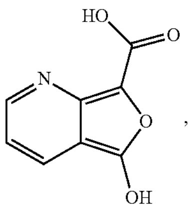

,

-continued

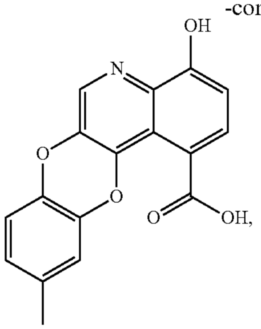

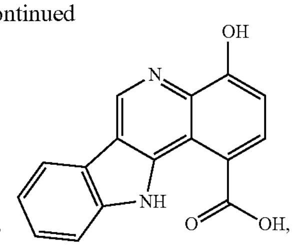

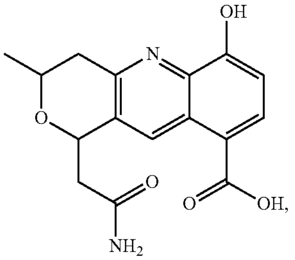

and

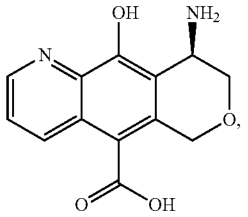

or a pharmaceutically acceptable salt thereof.

In another aspect, provided herein is a compound having the structure of Formula (II):

(II)

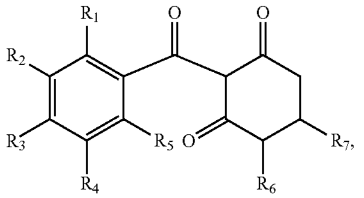

or a pharmaceutically acceptable salt thereof, wherein:

$R_1$ is selected from —$NO_2$, —Cl, and a $C_{1-12}$ alkyl which may be optionally substituted with one or more of —OH, =O, —$CO_2H$, —$NO_2$, —$NH_2$, —NHR*, —$NR^*_2$, —N—OH, —$HSO_3$, —$H_2PO_3$, —OR*, —(C=O)—R*, —$CO_2R^*$, —CO—$NH_2$, —CO—NHR*, and —$SO_2$—NHR*;

$R_2$, $R_3$, $R_4$, $R_5$, $R_6$ and $R_7$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of which optionally contains 1-8 heteroatoms selected from halogen, O, N, and S; —OH, =O, —$CO_2H$, —$NO_2$, —$NH_2$, —NHR*, —$NR^*_2$, —N—OH, —$HSO_3$, —$H_2PO_3$, —OR*, —(C=O)—R*, —$CO_2R^*$, —CO—$NH_2$, —CO—NHR*, —$SO_2R^*$, —$SO_2$—NHR*, or adjacent two moieties combine to form a fused ring which may optionally contain 1-3 heteroatoms selected from halogen, O, N, and S and which may be further substituted by one or more R*, and R* is independently selected at each occurrence from hydrogen or $C_1$-$C_{12}$ hydrocarbons each of which optionally contains 1-8 heteroatoms selected from halogen, O, N, and S and combinations thereof, with a proviso that the compound of Formula (II) does not have the structure selected from

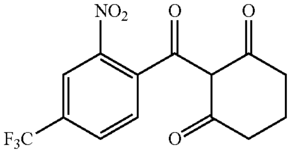

and (nitisinone)

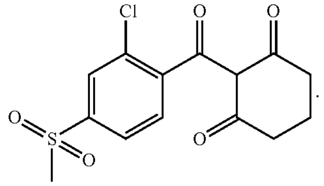

(sulcotrione)

In one embodiment, the compound of Formula (II) does not have the structure selected from

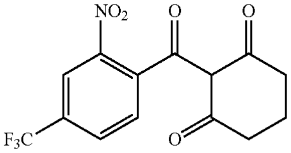

and (nitisinone)

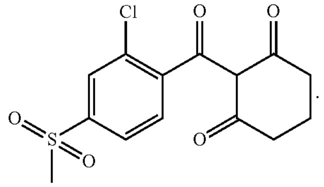

(sulcotrione)

In one embodiment, $R_1$ is —$NO_2$.

In one such embodiment, the compound has the structure of Formula (IIA):

(IIA)

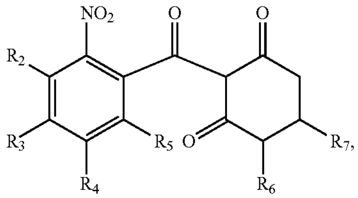

or a pharmaceutically acceptable salt thereof.

In one embodiment, $R_1$ is —Cl.

In one such embodiment, the compound has the structure of Formula (IIB):

(IIB)

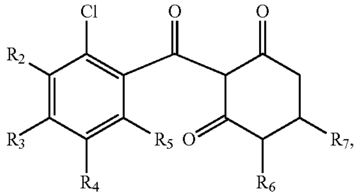

or a pharmaceutically acceptable salt thereof.

In one embodiment, $R_1$ is a $C_{1-12}$ alkyl substituted with one or more of —OH, ═O, —$CO_2H$, —$NO_2$, —$NH_2$, —NHR*, —$NR*_2$, —N—OH, —$HSO_3$, —$H_2PO_3$, —OR*, —(C═O)—R*, —$CO_2R*$, —CO—$NH_2$, —CO—NHR*, and —$SO_2$—NHR*.

In one embodiment, $R_1$ is a $C_{1-6}$ alkyl substituted with one or more of —OH, ═O, —$CO_2H$, —$NO_2$, —$NH_2$, —NHR*, —$NR*_2$, —N—OH, —$HSO_3$, —$H_2PO_3$, —OR*, —(C═O)—R*, —$CO_2R*$, —CO—$NH_2$, —CO—NHR*, and —$SO_2$—NHR*.

In one embodiment, $R_1$ is

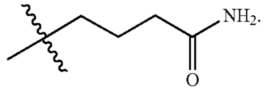 [SMILES: *CCCC(N)=O]

In one embodiment, $R_2$ is hydrogen.

In one embodiment, $R_2$ is a $C_{1-12}$ alkyl. In one embodiment, $R_2$ is a $C_{1-6}$ alkyl. In one embodiment, $R_2$ is a $C_{1-4}$ alkyl.

In one embodiment, $R_2$ and $R_3$ combine to make a fused ring.

In one embodiment, $R_3$ and $R_4$ combine to make a fused ring.

In one embodiment, $R_4$ and $R_5$ combine to make a fused ring.

In one embodiment, $R_6$ and $R_7$ combine to make a fused ring.

In one embodiment, $R_3$ is selected from hydrogen, $C_{1-4}$ haloalkyl, and $SO_2R*$, wherein R* is a $C_{1-4}$ alkyl. In one embodiment, $R_3$ is $CF_3$. In one embodiment, $R_3$ is $SO_2CH_3$.

In some embodiments, the compound having the structure of Formula (II) is selected from the group consisting of:

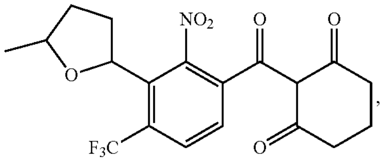

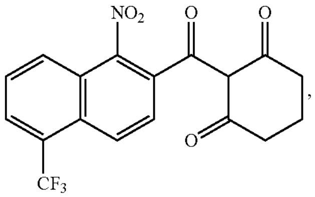

-continued

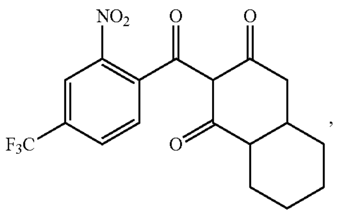

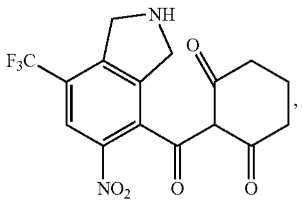

, and

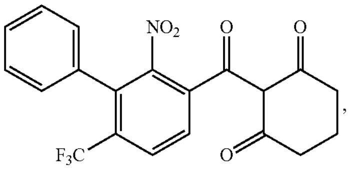

or a pharmaceutically acceptable salt thereof.

In some embodiments, the compound having the structure of Formula (II) is selected from the group consisting of:

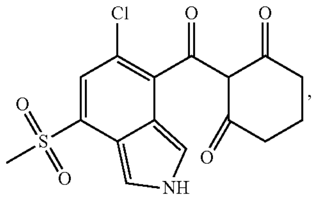

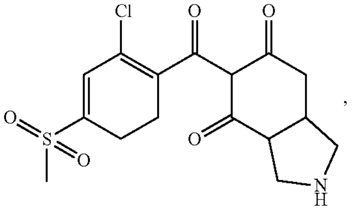

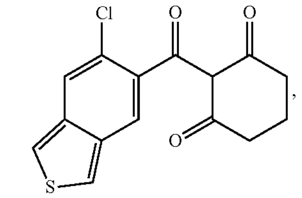

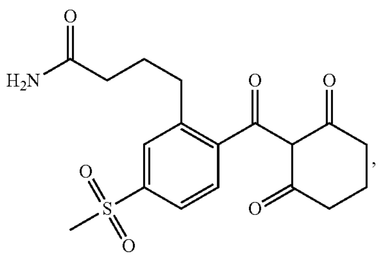

, and

-continued

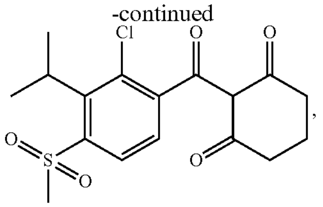

or a pharmaceutically acceptable salt thereof.

In one aspect, provided herein is a method of treating a pancreatic cancer in a subject in need thereof comprising administering to the subject a compound having the structure of Formula (I):

(I)

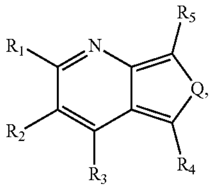

or a pharmaceutically acceptable salt thereof, wherein:

Q is selected from —O—, —NH—, and

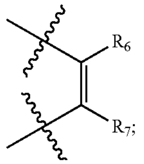

$R_1$, $R_2$, and $R_3$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of a which optionally contains 1-8 heteroatoms selected from halogen, O, N, and S; —OH, ═O, —$CO_2$H, —$NO_2$, —$NH_2$, —NHR*, —NHR*$_2$, —N—OH, —$HSO_3$, —$H_2PO_3$, —OR*, —(C═O)—R*, —$CO_2$R*, —CO—$NH_2$, —CO—NHR*, —$SO_2$—NHR*, or adjacent two moieties combine to form a fused ring which may optionally contain 1-3 heteroatoms selected from halogen, O, N, and S and which may be further substituted by one or more R*;

$R_4$ and $R_5$ are independently selected from —OH and —$CO_2$H;

$R_6$ and $R_7$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of which optionally contains 1-8 heteroatoms selected from halogen, O, N, and S; —OH, ═O, —$CO_2$H, —$NO_2$, —$NH_2$, —NHR*, —NR*$_2$, —N—OH, —$HSO_3$, —$H_2PO_3$, —OR*, —(C═O)—R*, —$CO_2$R*, —CO—$NH_2$, —CO—NHR*, —$SO_2$—NHR*, or $R_6$ and $R_7$ combine to form a fused ring, and R* is independently selected at each occurrence from hydrogen or $C_1$-$C_{12}$ hydrocarbons each of which optionally contains 1-8 heteroatoms selected from halogen, O, N, and S and combinations thereof.

In one embodiment, when Q is

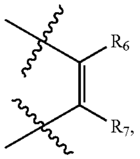

at least one of $R_1$, $R_2$, and $R_3$ is not H.

In one embodiment, Q is —O—.

In one such embodiment, the compound has the structure of Formula (IA):

(IA)

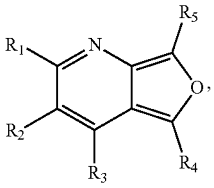

or a pharmaceutically acceptable salt thereof.

In one embodiment, Q is —NH—.

In one such embodiment, the compound has the structure of Formula (IB):

(IB)

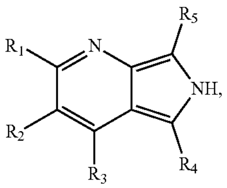

or a pharmaceutically acceptable salt thereof.

In one embodiment, Q is

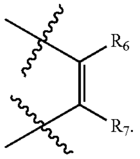

In one such embodiment, the compound has the structure of Formula (IC):

(IC)

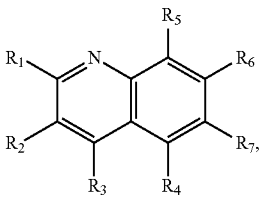

or a pharmaceutically acceptable salt thereof.

In one such embodiment, the compound has the structure of Formula (ID):

(ID)

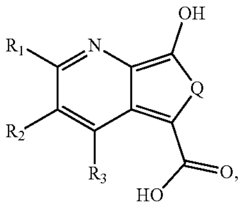

or a pharmaceutically acceptable salt thereof, wherein Q is —O— or —NH— and $R_1$, $R_2$, and $R_3$ are as defined above.

In one such embodiment, the compound has the structure of Formula (IE):

(IE)

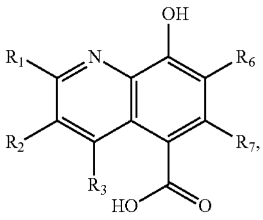

or a pharmaceutically acceptable salt thereof, wherein $R_1$, $R_2$, $R_3$, $R_6$, and $R_7$ are as defined above.

In one embodiment, $R_1$ and $R_2$ combine to make a fused ring.

In one embodiment, $R_2$ and $R_3$ combine to make a fused ring.

In one embodiment, $R_6$ and $R_7$ combine to make a fused ring.

In some embodiments, the compound having the structure of Formula (I) is selected from the group consisting of:

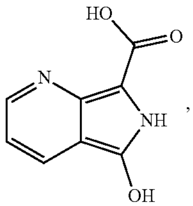

,

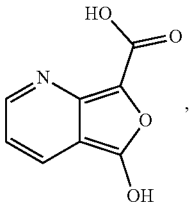

,

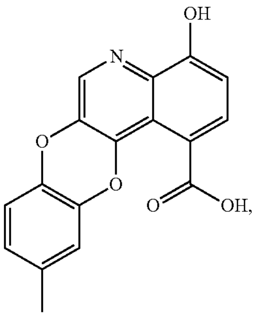

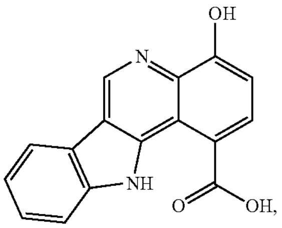

-continued

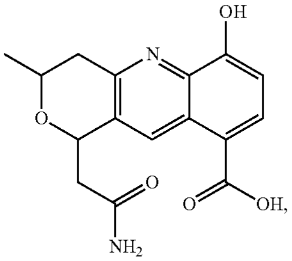

and

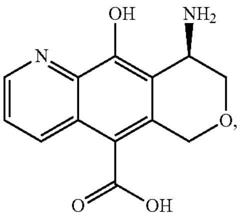

or a pharmaceutically acceptable salt thereof.

In another aspect, provided herein is a method of treating a pancreatic cancer in a subject in need thereof comprising administering to the subject a compound having the structure of Formula (II):

(II)

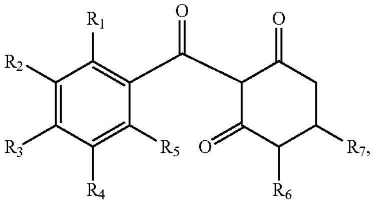

or a pharmaceutically acceptable salt thereof, wherein:

$R_1$ is selected from —$NO_2$, —Cl, and a $C_{1-12}$ alkyl which may be optionally substituted with one or more of —OH, ═O, —$CO_2H$, —$NO_2$, —$NH_2$, —NHR*, —$NHR^*_2$, —N—OH, —$HSO_3$, —$H_2PO_3$, —OR*, —(C═O)—R*, —$CO_2R^*$, —CO—$NH_2$, —CO—NHR*, and —$SO_2$—NHR*;

$R_2$, $R_3$, $R_4$, $R_5$, Res and $R_7$ are independently selected from hydrogen, $C_{1-12}$ alkyl, $C_{1-12}$ alkenyl, $C_{6-12}$ aryl, $C_{1-12}$ aralkyl, $C_{1-4}$ haloalkyl, or a combination thereof, each of which optionally contains 1-8 heteroatoms selected from halogen, O, N, and S; —OH, ═O, —$CO_2H$, —$NO_2$, —$NH_2$, —NHR*, —$NR^*_2$, —N—OH, —$HSO_3$, —$H_2PO_3$, —OR*, —(C═O)—R*, —$CO_2R^*$, —CO—$NH_2$, —CO—NHR*, —$SO_2R^*$, —$SO_2$—NHR*, or adjacent two moieties combine to form a fused ring which may optionally contain 1-3 heteroatoms selected from halogen, O, N, and S and which may be further substituted by one or more R*, and R* is independently selected at each occurrence from hydrogen or $C_1$-$C_{12}$ hydrocarbons each of which optionally contains 1-8 heteroatoms selected from halogen, O, N, and S and combinations thereof.

In one embodiment, the compound of Formula (II) does not have the structure selected from

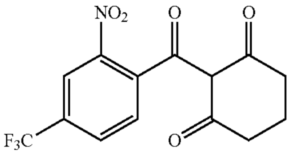

and (nitisinone)

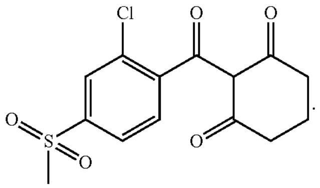

(sulcotrione)

In one embodiment, $R_1$ is —$NO_2$.

In one such embodiment, the compound has the structure of Formula (IIA):

(IIA)

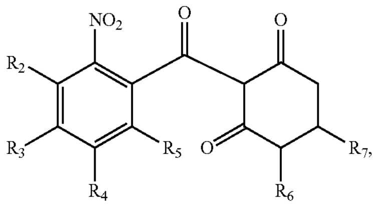

or a pharmaceutically acceptable salt thereof.

In one embodiment, $R_1$ is —Cl.

In one such embodiment, the compound has the structure of Formula (IIB):

(IIB)

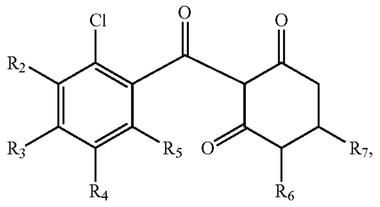

or a pharmaceutically acceptable salt thereof.

In one embodiment, $R_1$ is a $C_{1-12}$ alkyl substituted with one or more of —OH, ═O, —$CO_2H$, —$NO_2$, —$NH_2$, —NHR*, —$NR^*_2$, —N—OH, —$HSO_3$, —$H_2PO_3$, —OR*, —(C═O)—R*, —$CO_2R^*$, —CO—$NH_2$, —CO—NHR*, and —$SO_2$—NHR*.

In one embodiment, $R_1$ is a $C_{1-6}$ alkyl substituted with one or more of —OH, ═O, —$CO_2H$, —$NO_2$, —$NH_2$, —NHR*, —$NR^*_2$, —N—OH, —$HSO_3$, —$H_2PO_3$, —OR*, —(C═O)—R*, —$CO_2R^*$, —CO—$NH_2$, —CO—NHR*, and —$SO_2$—NHR*.

In one embodiment, $R_1$ is

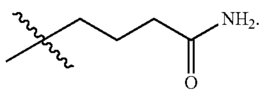 [SMILES: *CCCC(N)=O]

In one embodiment, $R_2$ is hydrogen.

In one embodiment, $R_2$ is a $C_{1-12}$ alkyl. In one embodiment, $R_2$ is a $C_{1-6}$ alkyl. In one embodiment, $R_2$ is a $C_{1-4}$ alkyl.

In one embodiment, $R_2$ and $R_3$ combine to make a fused ring.

In one embodiment, $R_3$ and $R_4$ combine to make a fused ring.

In one embodiment, $R_4$ and $R_5$ combine to make a fused ring.

In one embodiment, $R_6$ and $R_7$ combine to make a fused ring.

In one embodiment, $R_3$ is selected from hydrogen, $C_{1-4}$ haloalkyl, and $SO_2R^*$, wherein $R^*$ is a $C_{1-4}$ alkyl. In one embodiment, $R_3$ is $CF_3$. In one embodiment, $R_3$ is $SO_2CH_3$.

In some embodiments, the compound having the structure of Formula (II) is selected from the group consisting of:

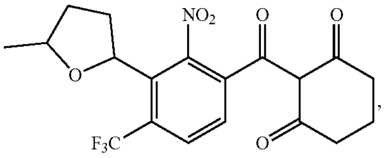

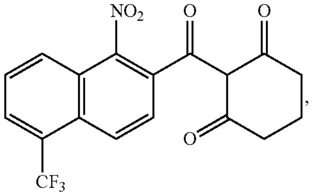

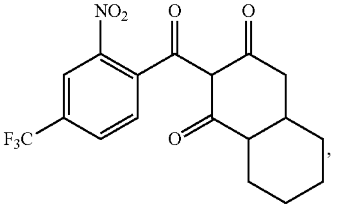

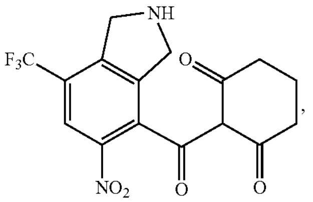

and

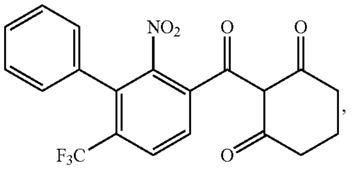

or a pharmaceutically acceptable salt thereof.

In some embodiments, the compound having the structure of Formula (II) is selected from the group consisting of:

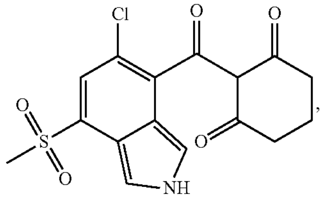

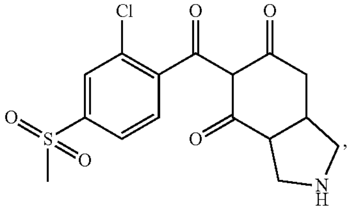

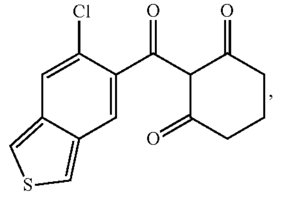

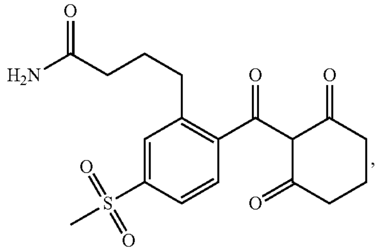

and

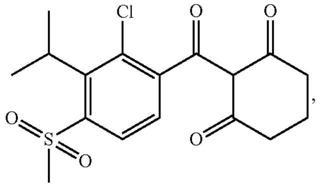

or a pharmaceutically acceptable salt thereof.

In some embodiments, the methods of the present disclosure comprises administering to the subject one or more treatments selected from a chemotherapy, a chemoradiotherapy, a neoadjuvant chemoradiotherapy, a radiotherapy, a surgery, and any combination thereof. Non-limiting examples of chemotherapies suitable for use in the methods of the present disclosure include FOLFIRINOX (Leucovorin calcium/Folinic acid, 5-fluorouracil, Irinotecan, Oxaliplatin); gemcitabine, albumin-bound paclitaxel (Abraxane), capecitabine, cisplatin, docetaxel, mitomycin C. Non-limiting examples of radiation therapies include external beam radiation therapy. Doses and fractionation of the external beam radiation therapy may vary, but typically 20 Gy/10 fractions (treatments)+20 Gy/10 fractions or up to 60 Gy in 30 fractions, given alone or in combination with 5-fluorouracil.

In one aspect, provided herein is a method of predicting prognosis of pancreatic cancer in a subject having pancreatic cancer, comprising the following steps.

a) determining expression level of 4-hydroxyphenylpyruvate dioxygenase-like (HPDL) protein in a sample obtained from the subject;
b) comparing the HPDL expression level determined in step (a) with a control level of HPDL expression; and c) determining the subject (i) as having poor prognosis if the HPDL expression level is higher than the control level, or (ii) as having good prognosis if the HPDL expression level is lower than or equal to the control level.

Although not wishing to be bound by theory, a "poor prognosis" in pancreatic cancer usually refers to an expected survival of about 1 year while a "good prognosis" refers to an expected survival of 3-3.5 years. However, only up to 10% of patients who are diagnosed early have long-term survival after treatment. The survival statistics for in pancreatic cancer can be found in, e.g., Carrato et al., J Gastrointest Cancer. 2015 September; 46(3):201-11 doi: 10.1007/s12029-015-9724-1, which is herein incorporated by reference in its entirety.

The present invention also provides pharmaceutical compositions comprising a compound described herein, or a pharmaceutically acceptable salt, solvate, hydrate, polymorph, co-crystals, tautomer, stereoisomer, isotopically labeled derivative, or prodrug thereof, and optionally a pharmaceutically acceptable excipient.

The effective amount of the compound in the composition may be useful for treating or preventing (or both) a disease or disorder associated with aberrant activity (e.g., reduced or abolished activity) of HPDL, treating or preventing (or both) a disease associated with abnormal production of CoQ10 (e.g., insufficient CoQ10 production), modulating HPDL expression and/or activity, and/or modulating (e.g., increasing) CoQ10 production as a single agent, a mixture, or in combination with one or more additional pharmaceutical agents.

The effective amount of the compound in the composition may be useful for treating or preventing (or both) a disease or disorder associated with upregulated activity of HPDL, and/or inhibiting HPDL expression and/or activity as a single agent, a mixture, or in combination with one or more additional pharmaceutical agents.

An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

Pharmaceutical compositions described herein can be prepared by any method known in the art of pharmacology. In general, such preparatory methods include the steps of bringing the compound(s) described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™) polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *Litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (I) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity in treating or preventing (or both) a disease or disorder associated with aberrant activity (e.g., reduced or abolished activity) of HPDL, treating or preventing (or both) a disease associated with abnormal production of CoQ10 (e.g., insufficient CoQ10 production), modulating HPDL expression and/or activity, and/or modulating (e.g., increasing) CoQ10 production), bioavailability, reduce and/or modify their metabolism, inhibit their excretion, and/or modify their distribution within the body of a subject. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agent(s) and/or the desired therapeutic and/or prophylactic effect to be achieved. In general, it is expected that the additional pharmaceutical agent(s) utilized in combination be utilized at levels that do not exceed the levels at which they are utilized individually. In some embodiments, the levels utilized in combination will be lower than those utilized individually.

Methods of the Treatment and Uses

The present invention also provides methods of using the compound(s) or pharmaceutical compositions comprising the compound(s) described herein, such as 4-HMA (e.g., (R)-4-HMA), 4-HB, 4-HBF, 4-HBz or CoQ10, for treating or preventing a disease or disorder.

In various embodiments, the disease or disorder is related to or caused by one or more mutations in the HPDL gene. Such mutations may be present in one or both alleles in the HPDL gene. In some embodiments, the disease or disorder is related to or caused by one or more mutations in other gene(s) involved in CoQ10 headgroup synthesis. Such mutations may be present in one or both alleles in the target gene.

The other gene(s) involved in CoQ10 headgroup synthesis may include, but are not limited to, Tyrosine Aminotransferase (TAT), Lactate Dehydrogenase D (LDHD), D-2-Hydroxyglutarate Dehydrogenase (D2HGDH), Aldehyde Dehydrogenase 3 Family Member A1 (ALDH3A1), 4-hydroxybenzoate polyprenyltransferase, mitochondrial, (COQ2), Ubiquinone biosynthesis monooxygenase COQ6, mitochondrial (COQ6), Ubiquinone biosynthesis O-methyltransferase, mitochondrial (COQ3), 2-methoxy-6-polyprenyl-1,4-benzoquinol methylase, mitochondrial (COQ5), 5-demethoxyubiquinone hydroxylase, mitochondrial (COQ7), and/or Ubiquinone biosynthesis O-methyltransferase, mitochondrial (COQ3). Non-limiting examples of mutations in such genes include, but are not limited to, LDHD mutations Arg370Trp, Thr463Met, Trp376Cys; D2HGDH mutations Val444Ala, Ile147Ser, c.293-23A>G (IVS1AS, A-G, -23), c.685-2A>G (IVS4AS, A-G, -2), Asn439Asp, 326dupTC, Asp375Tyr; COQ2 mutations Tyr297Cys, Arg197His, Asn228Ser, Ser146Asn, Met128Val, Val393Ala, Arg387Ter, Arg387Gln, 1198delT; COQ5 mutation 9.6-kb Dup; and COQ7 mutation Val141Glu.

In some embodiments, the compound(s) or pharmaceutical compositions of the present disclosure may be useful in treating a neurodegenerative or psychiatric disease.

In some embodiments, the compound(s) or pharmaceutical compositions of the present disclosure may be useful in treating a childhood neurodegenerative disease. Non-limiting examples of childhood neurodegenerative diseases include cerebral palsy including autosomal recessive spastic cerebral palsy, mitochondrial diseases, neonatal encephalopathy, adolescent-onset spastic paraplegia, pure and complicated hereditary spastic paraplegia. Mutations in the HPDL gene that may be associated with a childhood neurodegenerative disease have been described[37-40]. Such mutations include, but are not limited to, p. Leu176Pro (c.527 T>C; rs773333490), p.Ala78Thr, p.Gly126Ser, p.Leu164Pro, p.Gly301Val, p.Gly50Asp (c.149G>A), p.Trp157Arg (c.469T>C), p.Cys168Tyr (c.503G>A), p.Trp179Cys (c.537G>C), p.Leu217Pro (c.650T>C), p.Leu234Pro (c.701T>C), p.Leu248Pro (c.743T>C), p.His251Gln (c.753C>A), p.Gly260Glu (c.779G>A), p.Ile266Thr (c.797T>C), p.Tyr287His (c.859T>C), p.His163Ala, p.His258Ala, p.Gly319Argfs*15, p.Gln32*, p.Glu94Serfs*37 (c.280del). p.Ala115Cysfs*82 (c.342_343insTGCC), p.Leu234Glyfs*94 (c.698_699insTGGGCCAGCATTGTCCCCACTCTTGTTCT-GGCTGAGTC (SEQ ID NO: 23)), p.Gln241* (c.721C>T), and p.Gln342* (c.1024C>T).

In some embodiments, the compound(s) or pharmaceutical compositions of the present disclosure may be useful in treating cerebral palsy.

In some embodiments, when the subject being treated is a child, the child may be treated with the compound(s) or pharmaceutical compositions comprising the compound(s)

described herein, such as 4-HMA (e.g., (R)-4-HMA), 4-HB, 4-HBF, 4-HBz or CoQ10, in utero, immediately after birth, or in postpartum days.

In some embodiments, the method may involve treating a newborn or infant by administering the compound(s) or pharmaceutical compositions comprising the compound(s) described herein, such as 4-HMA (e.g., (R)-4-HMA), 4-HB, 4-HBF, 4-HBz or CoQ10, to the newborn or infant.

In some embodiments, the method may involve treating an unborn fetus by administering the compound(s) or pharmaceutical compositions comprising the compound(s) described herein, such as 4-HMA (e.g., (R)-4-HMA), 4-HB, 4-HBF, 4-HBz or CoQ10, to the pregnant female.

In some embodiments, the compound(s) or pharmaceutical compositions of the present disclosure may be useful in treating an adult neurodegenerative disease. Non-limiting examples of adult neurodegenerative diseases include Alzheimer's disease and Parkinson's disease. For Alzheimer's disease, genome-wide association study (GWAS) data are available showing an association between Alzheimer's disease and HPDL (see, e.g., ebi.ac.uk/gwas/genes/HPDL).

In some embodiments, the compound(s) or pharmaceutical compositions of the present disclosure may be useful in treating a psychiatric diseases. Non-limiting examples of psychiatric diseases include schizophrenia, major depressive disorder, and bipolar disorders.

In some embodiments, the compound(s) or pharmaceutical compositions of the present disclosure may be useful in treating aging, obesity, or metabolic syndrome, in which mitochondrial function declines.

In some embodiments, the compound(s) or pharmaceutical compositions of the present disclosure may be useful in treating cachexia or chronic fatigue syndrome.

In some embodiments, the compound(s) or pharmaceutical compositions of the present disclosure may be useful in treating a cardiac disease. Non-limiting examples of cardiac diseases include myocardial infarction and heart failure.

In some embodiments, the compound(s) or pharmaceutical compositions of the present disclosure may be useful in treating an immune deficiency or vitamin deficiencies (e.g. scurvy, which has low vitamin C).

Additional diseases that may be treated with the compound(s) or pharmaceutical compositions of the present disclosure include but, are not limited to, a kidney disease, inflammation, and/or those described in, for example, Hernández-Camacho et al., Front Physiol. 2018 Feb. 5; 9:44 and Doimo M et al., Mol Syndromol. 2014 July; 5(3-4): 156-62[41-42].

Figure 2A:
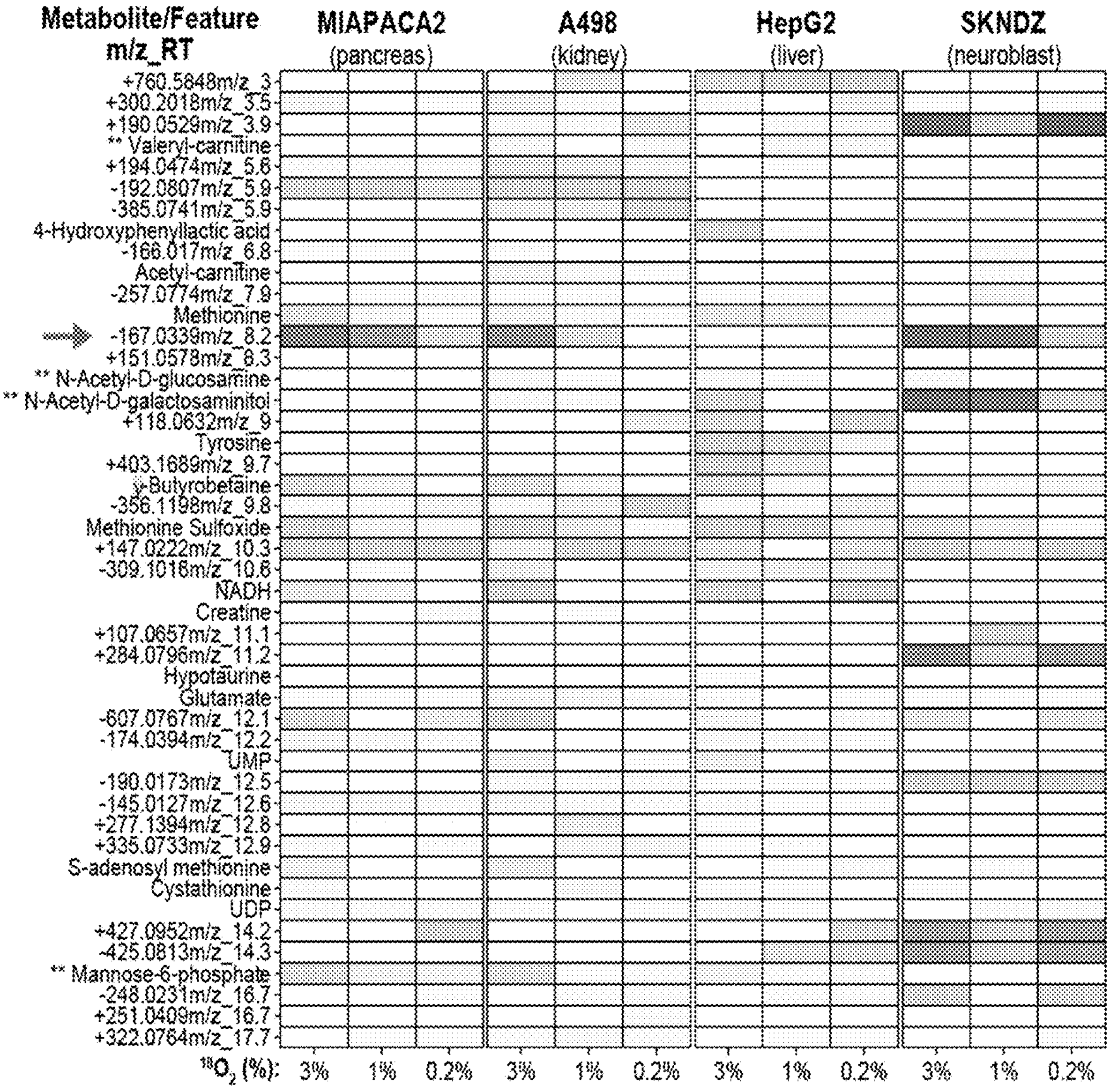
FIGS. 2A-2G show analysis of the $^{18}O_2$ labelled oxy-metabolome to identify a highly labelled metabolite, 4-hydroxymandelate, in human cells. Heatmap representing the median fractional $^{18}O$ labelling of the 49 metabolites across the indicated cell lines and oxygen tensions (FIG. 2A).  represents metabolites that had matching MS2 spectra, but needed to be validated due to multiple metabolite isomers. The arrow indicates a highly labelled unknown metabolite observed in three out of four cell lines. Correlation matrixes demonstrating the Spearman rs value based on the fractional $^{18}O$ labelling of the 46 metabolites and features across the indicated cell lines and oxygen tensions (FIG. 2B). There was good correlation of $^{18}O$ metabolite labeling within each cell line but not between cell lines. Fractional $^{18}O$ labelling of an unknown feature (167.0339 in negative ion mode, elution time of 8.2 minutes) in MIAPACA2, A498, and SKNDZ cells grown in 3%, 1%, and 0.2% $^{18}O_2$, and treated with vehicle or IOX1 (dioxygenase inhibitor) for 24 hours (n=3) (FIG. 2C). Mass spectra (MS1) of unlabelled (−167.0344 m/z) and $^{18}O$-labelled features (−169.0387 m/z and −171.0426 m/z) from MIAPACA2 cells grown in 3% $^{16}O_2$ or $^{18}O_2$ for 24 hours (FIG. 2**D). The mass shifts of one ($\Delta$2.0043) and two ($\Delta$4.0082) $^{18}O$ atoms are shown. Liquid chromatography traces showing retention times of metabolite precursors of homogentisate (HGA) and 4-hydroxymandelate (4-HMA) standards, and a highly $^{18}O$-labelled feature (−167.0344 m/z) from MIAPACA2 cells grown in 3% $^{18}O_2$ for 24 hours (FIG. 2E). The unknown $^{18}O_2$-labelled metabolite was deorphaned as 4-HMA. Unlabelled and $^{18}O$ labelled 4-HMA levels in MIAPACA2 cells grown in 3%, 1%, and 0.2% $^{18}O_2$, and treated with MG132 (proteasome inhibitor), IOX1 (dioxygenase inhibitor), DFO (iron chelator), and/or physiological levels of ascorbate for 24 hours (FIG. 2F). (n=3 in biologically independent replicates for each group and condition). 4-HMA was >70% labelled at high oxygen tensions, exhibited decreased labeling at lower oxygen tensions, and its $^{18}O$ labeling was sensitive to IOX1 and DFO. Schematic of $^{18}O$-labelling of 4-HMA by an unknown iron-dependent dioxygenase and substrate in human cells (FIG. 2G). Graphs represent mean±standard error of the mean (s.e.m.) and were compared by two-way ANOVA (FIG. 2C and FIG. 2F), followed by Bonferroni (FIG. 2C) or Tukey (FIG. 2F) post-hoc test (*p<0.05, ^p<0.01, %p<0.005, #p<0.0001).
Figure 2B:
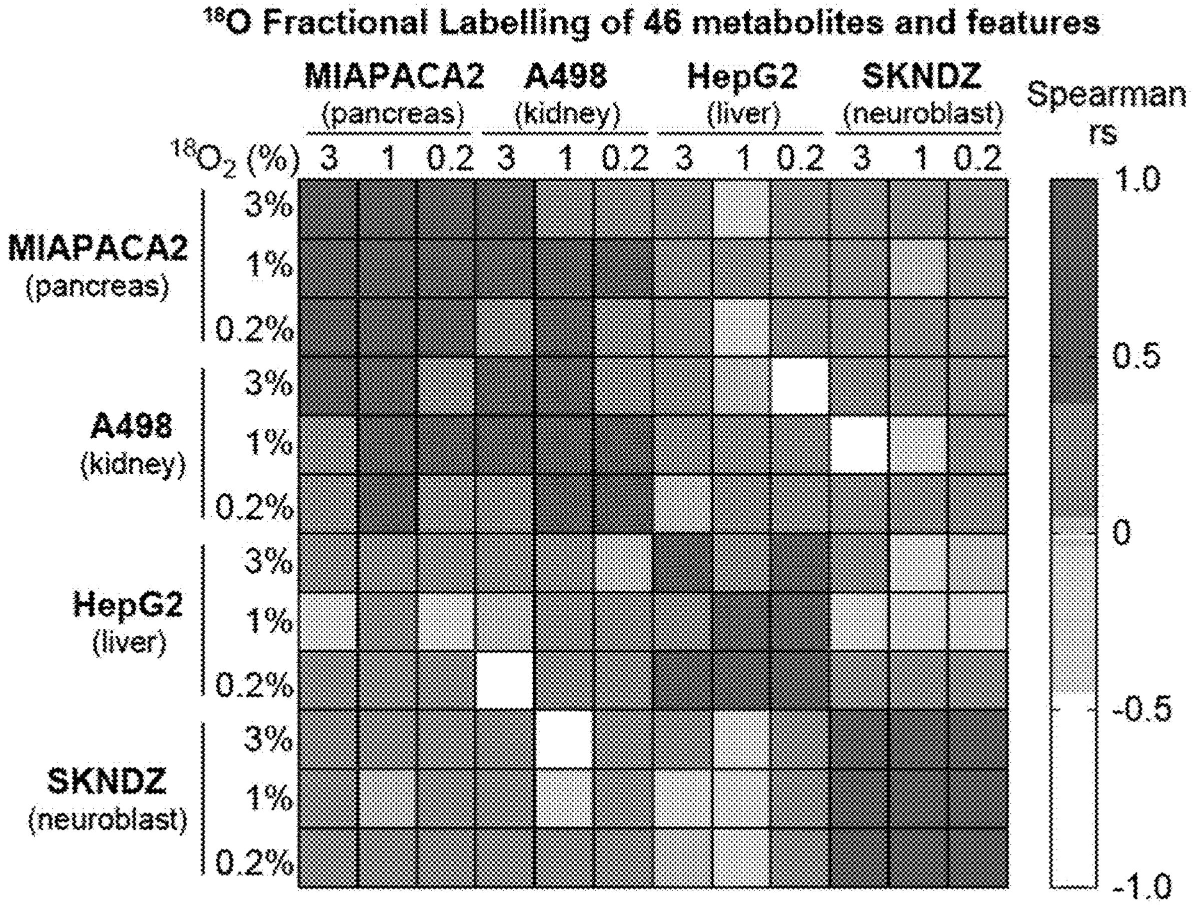
Figure 2C:
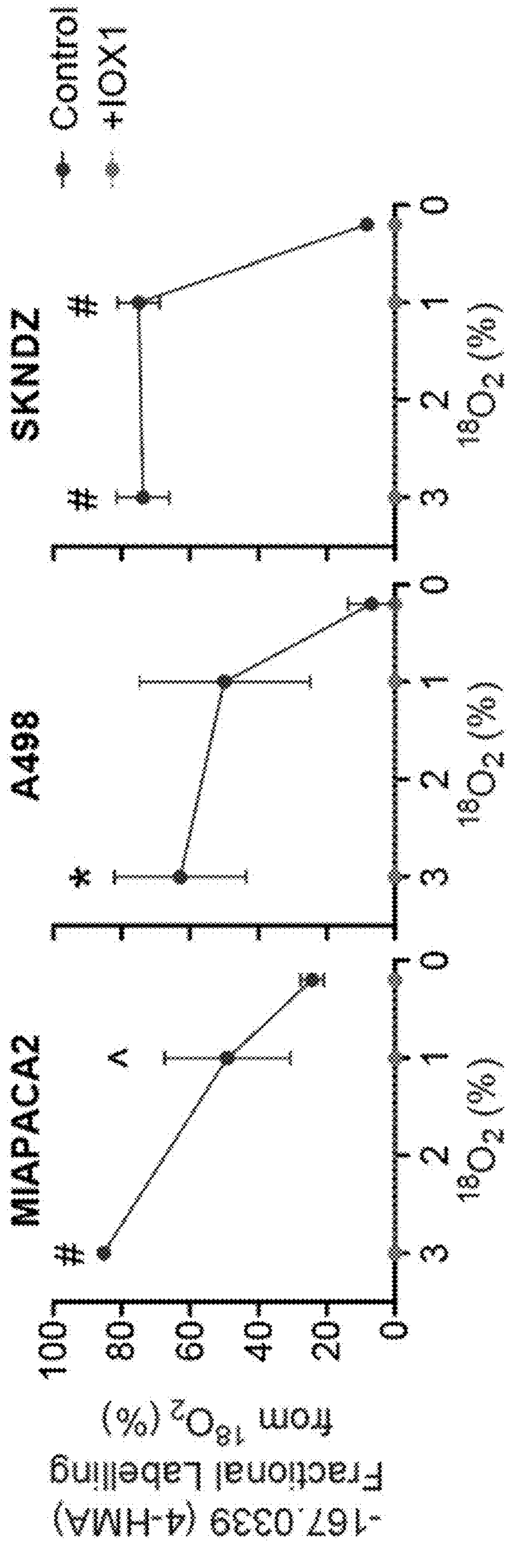
Figure 2D:
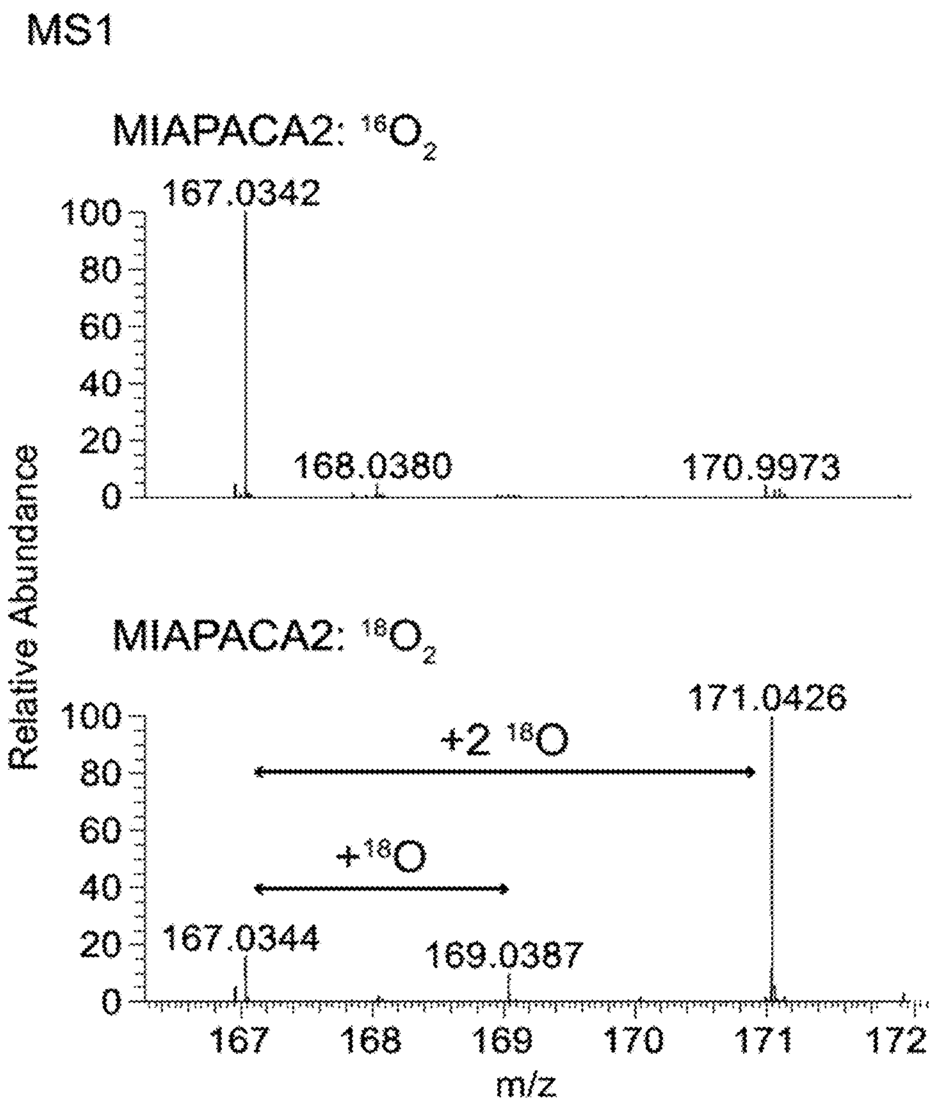
Figure 2E:
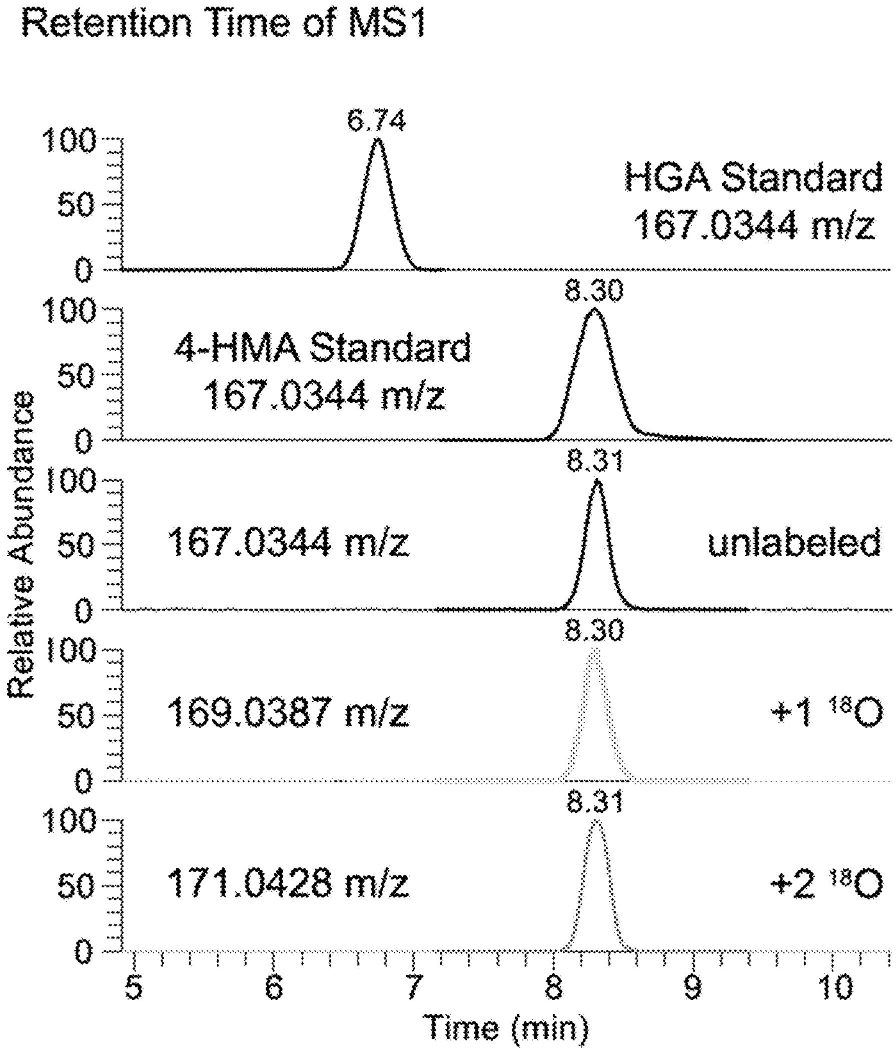
Figure 2F:
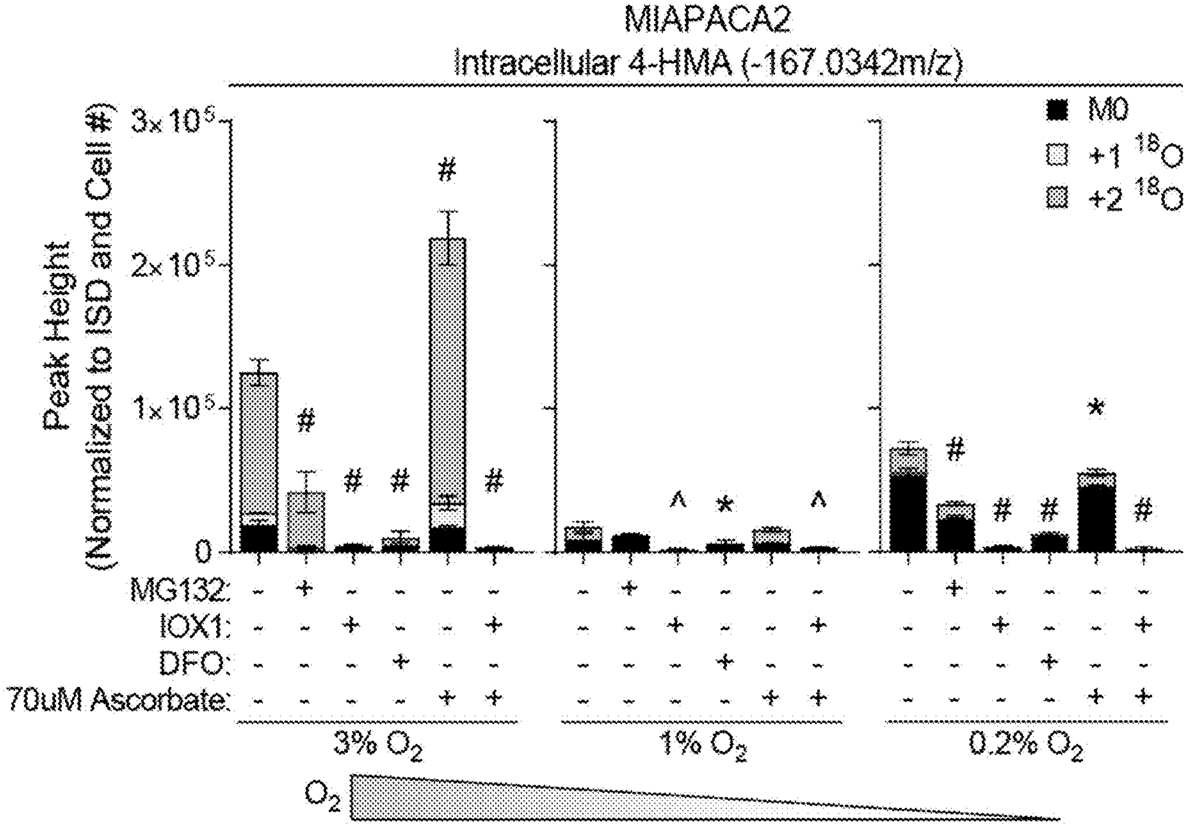

In some embodiments, the methods of the present disclosure may include administering to the subject a therapeutically effective amount of an activator of HPDL. In one embodiment, activator of HPDL is the vitamin C. Vitamin C may activate dioxygenases including HPDL. Treatment with vitamin C may activate HPDL and stimulate it to generate enough 4-HMA to compensate low 4-HMA levels due to inactive HPDL. FIG. 2F shows that treatment with physiological ascorbate (vitamin C) raises 4-HMA.

In another aspect, the present invention also provides methods of using the compound(s) or pharmaceutical compositions comprising the compound(s) described herein, such as 4-HMA (e.g., R-4-HMA), 4-HB, 4-HBF, or 4-HBz, for increasing CoQ10 biosynthesis.

In another aspect, the present invention also provides methods of determining whether a subject will respond and/or benefit from a treatment with the compound(s) or pharmaceutical compositions comprising the compound(s) described herein, such as 4-HMA (e.g., R-4-HMA), 4-HB, 4-HBF, 4-HBz, and/or CoQ10, by sequencing of the genes involved in CoQ10 headgroup synthesis (e.g., HPDL, TAT, LDHD, D2HGDH, ALDH3A1, COQ2, COQ6, COQ3, COQ5, COQ7, and COQ3) or immunohistochemistry (IHC) of the protein(s) produced by such gene(s). Low or mutant HPDL or other CoQ10 synthesis genes could predict response to the treatment.

In another aspect, methods of the present invention also include inhibiting expression of HPDL in a subject in need thereof, comprising administering to the subject a therapeutically effective amount of (S)-4-HMA, or a metabolite, pharmaceutically acceptable salt, prodrug, solvate, hydrate, or combinations thereof. The S-enantiomer at sufficient concentrations may serve as a competitive inhibitor of HPDL. It or its metabolites may also be sensed by the cell, reducing HPDL protein levels. Addition of racemic 4-HMA and 4-HB, which are the immediate and downstream products of HPDL, appear to reduce HPDL levels in the cell.

Upregulation of HPDL has been described in various diseases, including but not limited to cancers (e.g., pancreatic cancer), premalignant lesions (Barrett's esophagus), psoriasis, lupus (and presumably other autoimmune diseases), and fibrotic diseases (see, e.g., ebi.ac.uk/gxa/genes/ensg00000186603). Inhibition of HPDL using (S)-4-HMA, or a metabolite, pharmaceutically acceptable salt, prodrug, solvate, hydrate, or combinations thereof, may be useful in treating these diseases.

EXAMPLES

The following examples are provided to further describe some of the embodiments disclosed herein. The examples are intended to illustrate, not to limit, the disclosed embodiments.

Figure 1A:
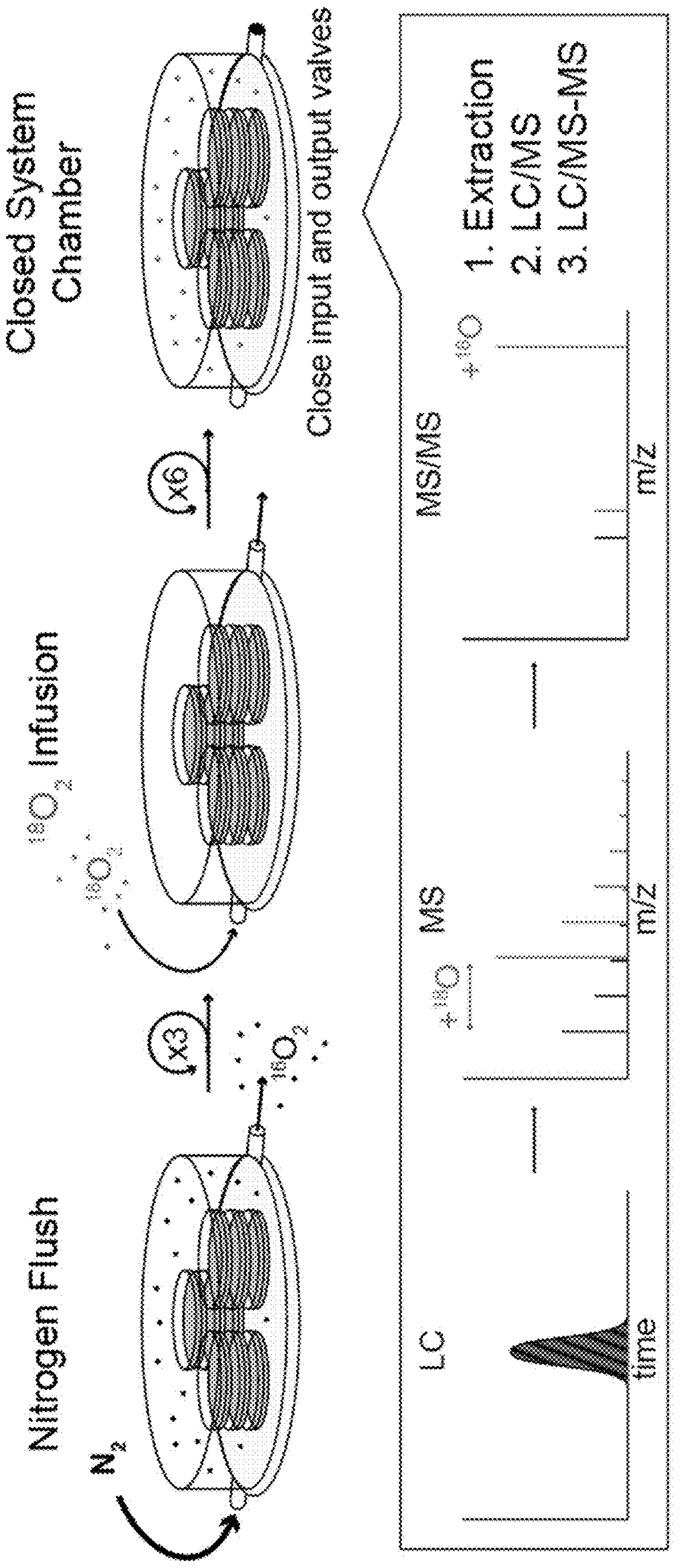
FIGS. 1A-1E show $^{18}O_2$-GASSP (GAseous-labelling in a Sealed SPace) of human cells to reveal the oxy-metabolome. Schematic of GASSP (FIG. 1A). A closed system chamber was flushed multiple times with $N_2$ to remove $^{16}O_2$. A gas mixture containing $^{18}O_2$ and $CO_2$ was pulsed several times into the closed chamber to reach the desired oxygen concentration. At the assay endpoint, the chamber was opened, cells were extracted, and metabolites separated and identified by liquid chromatography (LC) tandem mass spectrometry (LC-MS/MS). Schematic of the approach used to identify features and metabolites that were labelled by $^{18}O$ (FIG. 1B). "n" represents the number of features or metabolites identified in MIAPACA2 cells grown at 3% $^{18}O_2$. See FIG. 5G for detailed numbers. Total number of unique dioxygenase-dependent, $^{18}O$-labelled metabolites and features identified in each cell line and condition (FIG. 1C). Features were further categorized into predicted or not predicted/unknown $^{18}O$ labelled metabolites, based on known oxygen-dependent metabolic pathways, and sensitivity or insensitivity to IOX1 treatment (dioxygenase inhibitor). About half of the metabolites were predicted to be labelled by $^{18}O$ in each cell line and oxygen condition; the remainder were novel, of which at least half were sensitive to IOX1 and were likely products of iron-dependent dioxygenases. Venn diagram representing the distribution of common and unique $^{18}O$ labelled metabolites identified in each cell line (FIG. 1D). Most $^{18}O$ labelled metabolites were unique to each cell line. List of the 46 unique $^{18}O$ labelled metabolites that were identified in FIG. 1D and categorized into known oxygen-dependent metabolic pathways (FIG. 1E). ** represents metabolites that had matching MS2 spectra, but needed to be validated due to multiple metabolite isomers.

Example 1. $^{18}O_2$-GASSP (Gaseous-Labelling in a Sealed SPace) of Human Cells Reveals the Oxy-Metabolome Several technical issues make gaseous labelling of mammalian cells challenging and limit its widespread use. These include the need for a custom labelling apparatus, the large amount of costly $^{18}O_2$ required for each experiment, complete exclusion of abundant $^{16}O_2$ to maximize labeling, and continuous monitoring of $^{18}O_2$ concentrations during the study[6]. In the present experiments, these issues were overcome with a small (~5 L) closed-system chamber to label mammalian cells with $^{18}O_2$ or any other isotopically labelled gas in a robust and cost-effective manner (FIG. 1A). The chamber was flushed with multiple rounds of nitrogen ($N_2$) to remove naturally abundant, unlabelled $O_2$ ($^{16}O_2$), followed by several flushes of $^{18}O_2$:$CO_2$:$N_2$ mixes to reach the desired concentration of $^{18}O_2$. The entire process took approximately one hour, and was continuously monitored with an oxygen sensor in the chamber (FIG. 5A). Oxygen concentrations in the closed chamber remained stable at all tested oxygen tensions for at least 20 hours (FIGS. 5B-5D). This indicated that during the duration of the gaseous labelling studies, the total $^{18}O_2$ abundance in the chamber was not limiting nor was there excess atmospheric oxygen adsorbed to the plates or dissolved in the media. This gaseous labeling technique was named GAseous labelling in a Sealed SPace (GASSP).

To map the molecular fate of $O_2$ in metabolic pathways in living cells, GASSP was used to carry out $^{18}O_2$ labelling in cell lines of different tissue origins at $^{18}O_2$ concentrations that represented physiological (3%), hypoxic (1%), and severely hypoxic (0.2%) oxygen tensions found in tissues and tumours[7]. At the end of each run, polar metabolites were extracted and untargeted polar metabolomics using liquid chromatography-high resolution mass spectrometry (LC-MS) were carried out to identify metabolites labeled with $^{18}O$.

Figure 1B:
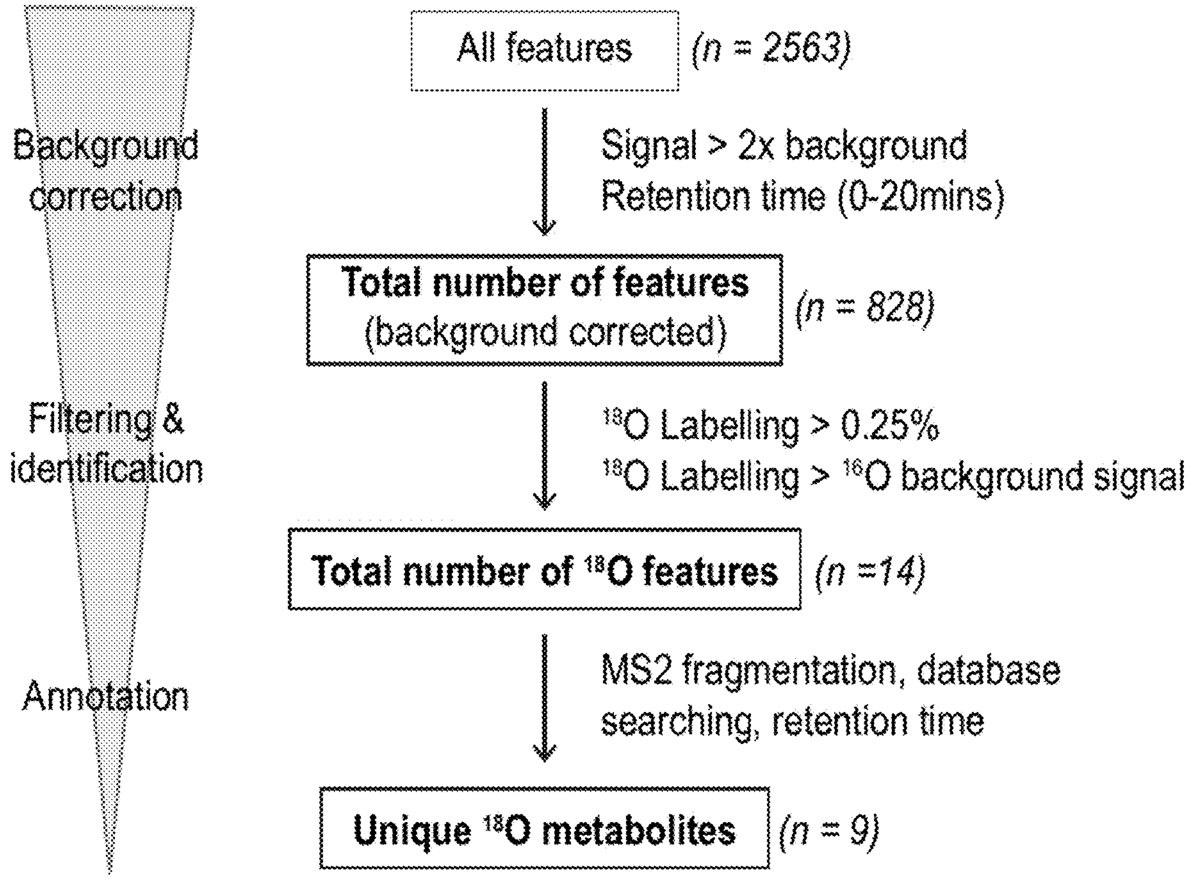

A list of unique features identified by untargeted metabolomics that were >0.25% (natural abundance of $^{18}O$ is 0.2%) labelled by $^{18}O$ atoms in each cell line at each oxygen tension was generated. In addition, background signal was controlled by requiring that $^{18}O$ labeled peaks had to have a signal that was two-fold greater than naturally occurring isotopes found in non-labelled ($^{16}O$) metabolite cell extracts. To determine the proportion of unique $^{18}O$ labelled features that were due to dioxygenase activity, cells were treated with a pan-dioxygenase inhibitor (IOX1) at concentrations that inhibit iron-dependent dioxygenases, such as the HIF1α prolyl hydroxylases (FIGS. 5E-5F) and identified $^{18}O$ labelled polar metabolites. This list of $^{18}O$ metabolites was generated by identifying all features in the unlabelled samples, filtering these features against blank samples to remove background peaks, and calculating the fractional $^{18}O$ labelling with the assumption that a metabolite would have no more than three oxygen atoms labelled, followed by manual curation of labelled features (FIG. 1B and FIG. 5G). Findings showed that the total number of $^{18}O$ labelled features varied from 4-35 depending on the cell line and oxygen tension. This accounted for 0.2-2% of small molecule features (FIG. 5G). These $^{18}O$-labelled features were termed the oxy-metabolome.

Figure 1C:
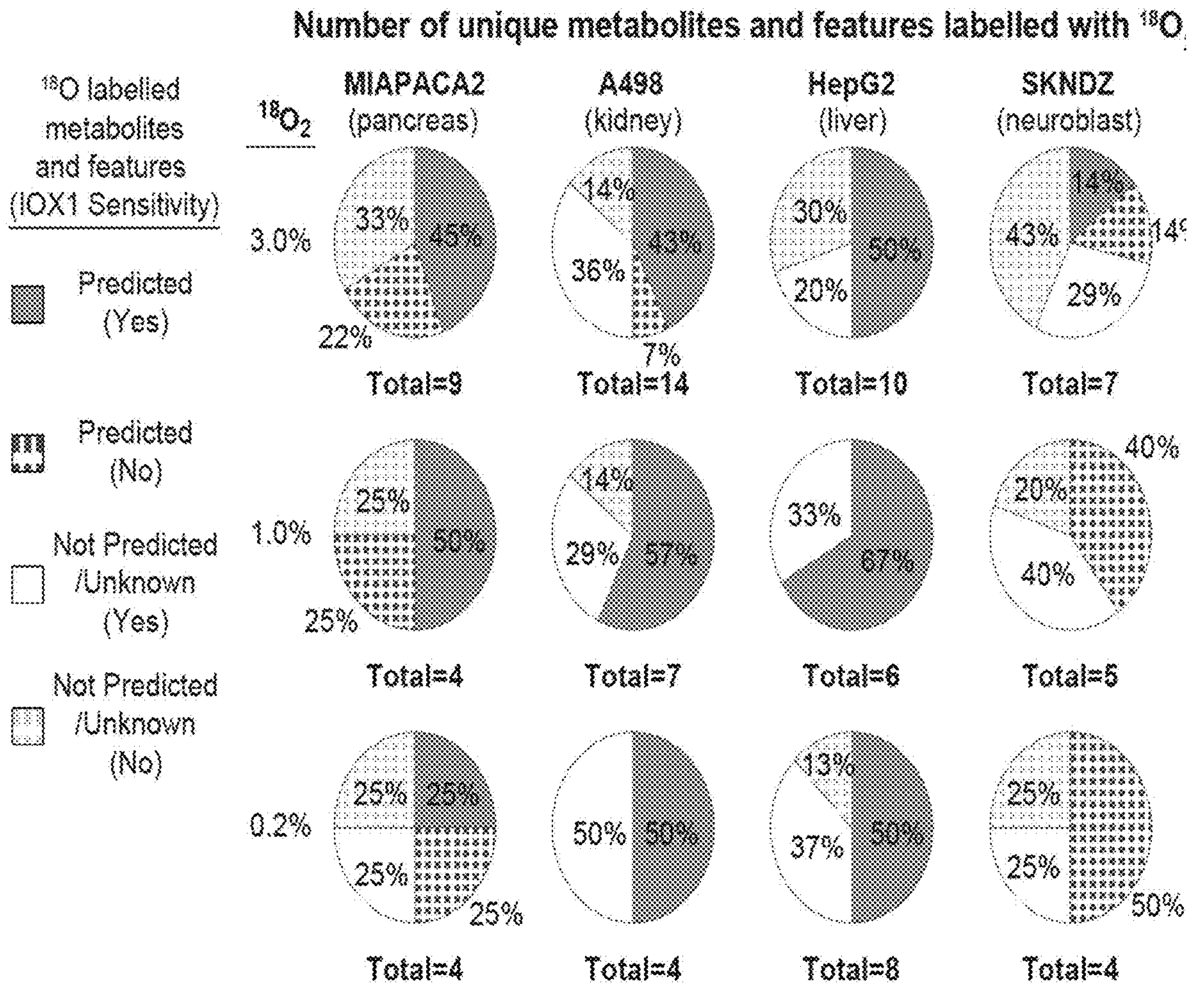
Figure 1D:
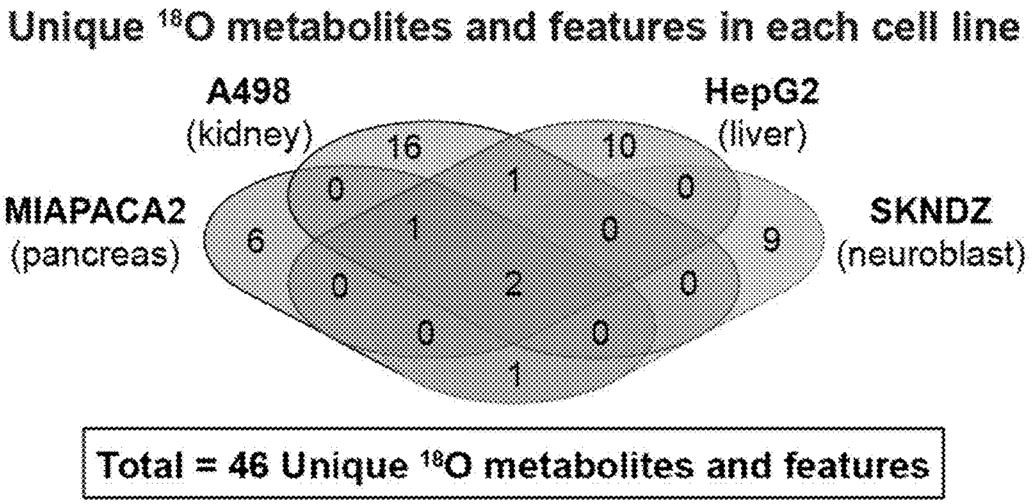
Figure 1E:
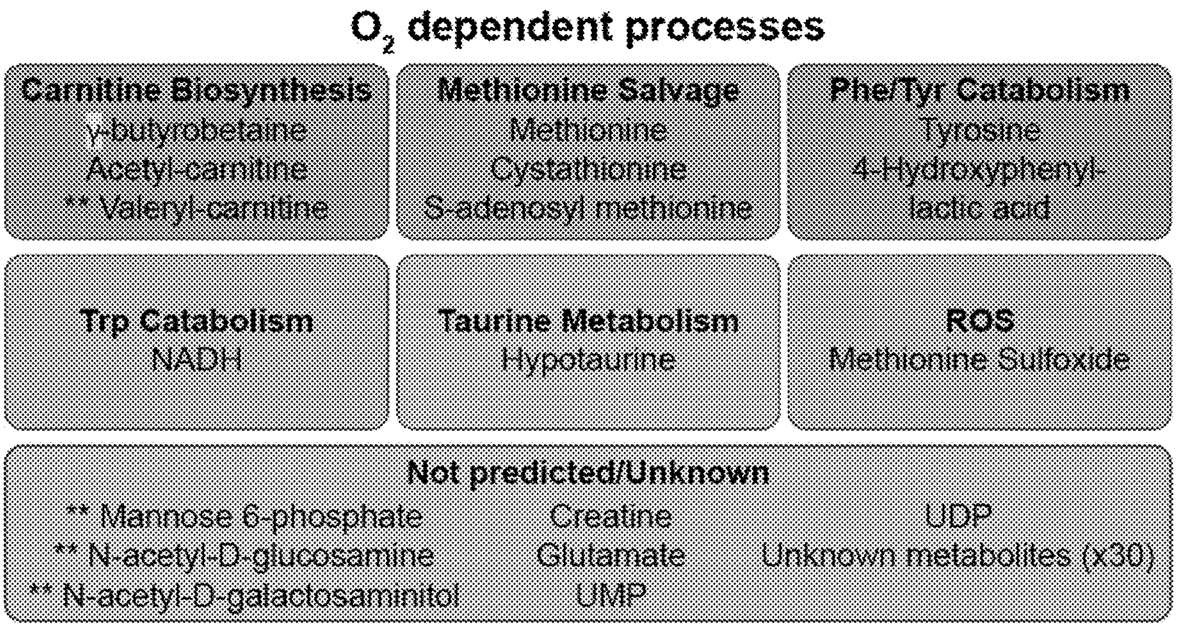

To determine the identities of the labeled metabolites, the list of $^{18}O$ labelled features was annotated to their corresponding unlabelled metabolites using retention time matching, tandem mass spectrometry (MS2) fragmentation patterns, and database searching. Labeling of metabolites such as methionine, methionine sulfoxide, and γ-butyrobetaine predicted to be directly or indirectly labelled by $^{18}O$ via known oxygen-dependent pathways was detected. Metabolites were also detected that were not predicted to be labelled by gaseous $^{18}O$, such as N-acetyl-D-glucosamine and uridine diphosphate. Multiple unknown metabolites across the different cell lines and oxygen tensions were identified (FIG. 1C). $^{18}O$ labeling of some of the metabolites was sensitive to IOX1, reflecting a dependence on dioxygenase activity. IOX1-insensitive metabolites may be made by ROS or by heme-dependent oxygenases. Across the different cell lines and oxygen tensions a non-redundant list of 49 $^{18}O$ labelled metabolites was obtained (FIGS. 1D-1E and FIG. 5H) for further analysis. Of the 49 metabolites, 46 (94%) unique $^{18}O$-labelled features were reproduced (except Metabolites 12, 24 and 26). These high confidence hits were used in subsequent analyses (FIGS. 1D-1E, FIG. 5I). Findings showed that the fractional labelling of most of the 46 $^{18}O$ labelled metabolites was increased at higher oxygen tensions across the different cell lines (FIG. 2A and FIG. 6, and Table 1).

Of the original 49 $^{18}O$ labelled metabolites, 13 metabolites (26.53%) were known, and 36 metabolites (73.47%) were unknown (unk). Metabolite 14 (Unknown_−_167.0339_8.2) was characterized as 4-Hydroxymandelate. Based on ±0.1 minute (min) retention time (RT), several metabolite pairs were identified as potentially the same metabolite; these metabolite pairs were: Metabolite 19 (Tyrosine) and Metabolite 20 (Unknown_+_403.16899.7); Metabolite 21 (γ-Butyrobetaine) and Metabolite 22 (Unknown_−_356.1198(9.8); Metabolite 25 (Unknown_+_147.0222_10.3) and Metabolite 26 (Unknown_+_181.0371_10.4); Metabolite 27 (Unknown_−_309.1016_10.6) and Metabolite 28 (NADH); Metabolite 34 (Unknown_−_607.0767_12.1) and Metabolite 35 (Unknown_−_174.0394_12.2); Metabolite 40 (Unknown_+_335.0733_12.9) and Metabolite (S-adenosyl methionine); Metabolite 44 (Unknown_+_427.0952_14.2) and Metabolite 45 (Unknown_−_425.0813_14.3); and, Metabolite 47 (Unknown_−_248.0231_16.7) and Metabolite 48 (Unknown_+_251.0409_16.7). A description of the 49 $^{18}O$ labelled metabolites is provided in the below Table 1.

TABLE 1

List of Oxygen Labelled Metabolites

| Metabolite ID | Description | Peak | Polarity | Mass by charge (m/z) | RT (min) | Unk (Yes/No) | IOX1 Sensitive (Yes/No) |
|---|---|---|---|---|---|---|---|
| Metabolite 1 | Unknown_+_760.5848_3.0 | 760.5848 | Pos mode | 760.5848 | 3 | Yes | Yes |
| Metabolite 2 | Unknown_+_300.2018_3.5 | 300.2018 | Pos mode | 300.2018 | 3.5 | Yes | Yes |
| Metabolite 3 | Unknown_+_190.0529_3.9 | 190.0529 | Pos mode | 190.0529 | 3.9 | Yes | Yes |
| Metabolite 4 | ** Valerylcarnitine | 246.1699 | Pos mode | 246.1699 | 5.2 | No | Yes |
| Metabolite 5 | Unknown_+_194.0474_5.6 | 194.0474 | Pos mode | 194.0474 | 5.6 | Yes | Yes |
| Metabolite 6 | Unknown_−_192.0807_5.9 | −192.0807 | Neg mode | 192.0807 | 5.9 | Yes | No |
| Metabolite 7 | Unknown_−_385.0741_5.9 | −385.0741 | Neg mode | 385.0741 | 5.9 | Yes | Yes |
| Metabolite 8 | 4-Hydroxyphenyll actic acid | −181.0498 | Neg mode | 181.0498 | 6.8 | No | Yes |
| Metabolite 9 | Unknown_−_166.0170_6.8 | −166.017 | Neg mode | 166.017 | 6.8 | Yes | Yes |
| Metabolite 10 | Acetyl-carnitine | 204.1228 | Pos mode | 204.1228 | 7.7 | No | No |
| Metabolite 11 | Unknown_−_257.0774_7.9 | −257.0774 | Neg mode | 257.0774 | 7.9 | Yes | Yes |
| Metabolite 12 | Unknown_+_235.1635_8.0 | 235.1635 | Pos mode | 235.1635 | 8 | Yes | No |
| Metabolite 13 | Methionine | 150.0583 | Pos mode | 150.0583 | 8.2 | No | Yes |
| Metabolite 14 | Unknown_−_167.0339_8.2 | −167.0336 | Neg mode | 167.0336 | 8.2 | Yes | Yes |
| Metabolite 15 | Unknown_+_151.0578_8.3 | 151.0578 | Pos mode | 151.0578 | 8.3 | Yes | No |

TABLE 1-continued

| List of Oxygen Labelled Metabolites | | | | | | | |
|---|---|---|---|---|---|---|---|
| Metabolite ID | Description | Peak | Polarity | Mass by charge (m/z) | RT (min) | Unk (Yes/No) | IOX1 Sensitive (Yes/No) |
| Metabolite 16 | ** N-Acetyl-D-glucosamine | 204.0868 | Pos mode | 204.0868 | 8.5 | Yes | No |
| Metabolite 17 | ** N-Acetyl-D-galactosaminitol | 224.1125 | Pos mode | 224.1125 | 8.6 | Yes | Yes |
| Metabolite 18 | Unknown_+_118.0632_9.0 | 118.0632 | Pos mode | 118.0632 | 9 | Yes | No |
| Metabolite 19 | Tyrosine | 182.0812 | Pos mode | 182.0812 | 9.6 | No | Yes |
| Metabolite 20 | Unknown_+_403.1689_9.7 | 403.1689 | Pos mode | 403.1689 | 9.7 | Yes | Yes |
| Metabolite 21 | g-Butyrobetaine | 146.1174 | Pos mode | 146.1174 | 9.8 | No | Yes |
| Metabolite 22 | Unknown_−_356.1198_9.8 | −356.1198 | Neg mode | 356.1198 | 9.8 | Yes | Yes |
| Metabolite 23 | Methionine Sulfoxide | 166.0532 | Pos mode | 166.0532 | 10.1 | No | Yes |
| Metabolite 24 | Hydroxyproline | 132.0656 | Pos mode | 132.0656 | 10.3 | No | Yes |
| Metabolite 25 | Unknown_+_147.0222_10.3 | 147.0222 | Pos mode | 147.0222 | 10.3 | Yes | No |
| Metabolite 26 | Unknown_+_181.0371_10.4 | 181.0371 | Pos mode | 181.0371 | 10.4 | Yes | No |
| Metabolite 27 | Unknown_−_309.1016_10.6 | −309.1016 | Neg mode | 309.1016 | 10.6 | Yes | Yes |
| Metabolite 28 | NADH | −664.1188 | Neg mode | 664.1188 | 10.7 | No | Yes |
| Metabolite 29 | Creatine | 263.1458 | Pos mode | 263.1458 | 11 | Yes | Yes |
| Metabolite 30 | Unknown_+_107.0657_11.1 | 107.0657 | Pos mode | 107.0657 | 11.1 | Yes | Yes |
| Metabolite 31 | Unknown_+_284.0796_11.2 | 284.0796 | Pos mode | 284.0796 | 11.2 | Yes | No |
| Metabolite 32 | Hypotaurine | 110.0273 | Pos mode | 110.0273 | 11.4 | No | Yes |
| Metabolite 33 | Glutamate | 148.0604 | Pos mode | 149.0635 | 11.8 | Yes | Yes |
| Metabolite 34 | Unknown_−_607.0767_12.1 | −607.0767 | Neg mode | 607.0767 | 12.1 | Yes | No |
| Metabolite 35 | Unknown_−_174.0394_12.2 | −174.0394 | Neg mode | 174.0394 | 12.2 | Yes | No |
| Metabolite 36 | UMP | −323.0281 | Neg mode | 323.0281 | 12.4 | Yes | Yes |
| Metabolite 37 | Unknown_−_190.0173_12.5 | −190.0173 | Neg mode | 190.0173 | 12.5 | Yes | Yes |
| Metabolite 38 | Unknown_−_145.0127_12.6 | −145.0127 | Neg mode | 145.0127 | 12.6 | Yes | No |
| Metabolite 39 | Unknown_+_277.1394_12.8 | 277.1394 | Pos mode | 277.1394 | 12.8 | Yes | No |
| Metabolite 40 | Unknown_+_335.0733_12.9 | 335.0733 | Pos mode | 335.0733 | 12.9 | Yes | Yes |
| Metabolite 41 | S-adenosyl methionine | 399.1444 | Pos mode | 399.1444 | 12.9 | No | Yes |
| Metabolite 42 | Cystathionine | −221.0589 | Neg mode | 221.0589 | 13.3 | No | Yes |
| Metabolite 43 | Unknown_−_402.9947_14.0 | −402.9947 | Neg mode | 402.9947 | 14 | Yes | Yes |
| Metabolite 44 | Unknown_+_427.0952_14.2 | 427.0952 | Pos mode | 427.0952 | 14.2 | Yes | Yes |
| Metabolite 45 | Unknown_−_425.0813_14.3 | −425.0813 | Neg mode | 425.0813 | 14.3 | Yes | Yes |
| Metabolite 46 | ** D-Mannose 6-phosphate | −168.9802 | Neg mode | 168.9802 | 14.7 | No | Yes |
| Metabolite 47 | Unknown_−_248.0231_16.7 | −248.0231 | Neg mode | 248.0231 | 16.7 | Yes | Yes |
| Metabolite 48 | Unknown_+_251.0409_16.7 | 251.0409 | Pos mode | 251.0409 | 16.7 | Yes | Yes |
| Metabolite 49 | Unknown_+_322.0764_17.7 | 322.0764 | Pos mode | 322.0764 | 17.7 | Yes | Yes |

Of the identified metabolites, only $^{18}O$ labelling of methionine sulfoxide and γ-butyrobetaine were common to all evaluated cell lines. Labeling of methionine sulfoxide in the tested cell lines was expected as ROS is produced by all cell types. Surprisingly, all cell lines made $^{18}O$ γ-butyrobetaine, which is an intermediate in carnitine biosynthesis, a metabolic process that is normally limited to the liver and kidneys[8]. Cancer cell synthesis of γ-butyrobetaine may reflect an important role of this metabolite or the need to metabolize trimethyllysine.

Unexpectedly, the majority of $^{18}O$-labelled metabolites were unique to cell lines of different tissue origins (FIG. 1D, FIG. 2B and FIGS. 6A-6H). In addition, about half of the $^{18}O$ labelled metabolites were unknown, and were not predicted targets of known oxygen-dependent metabolic pathways (FIG. 6I-6L). These data suggested that many oxygen-dependent pathways remain undescribed in mammalian cell biology.

Figure 6K:
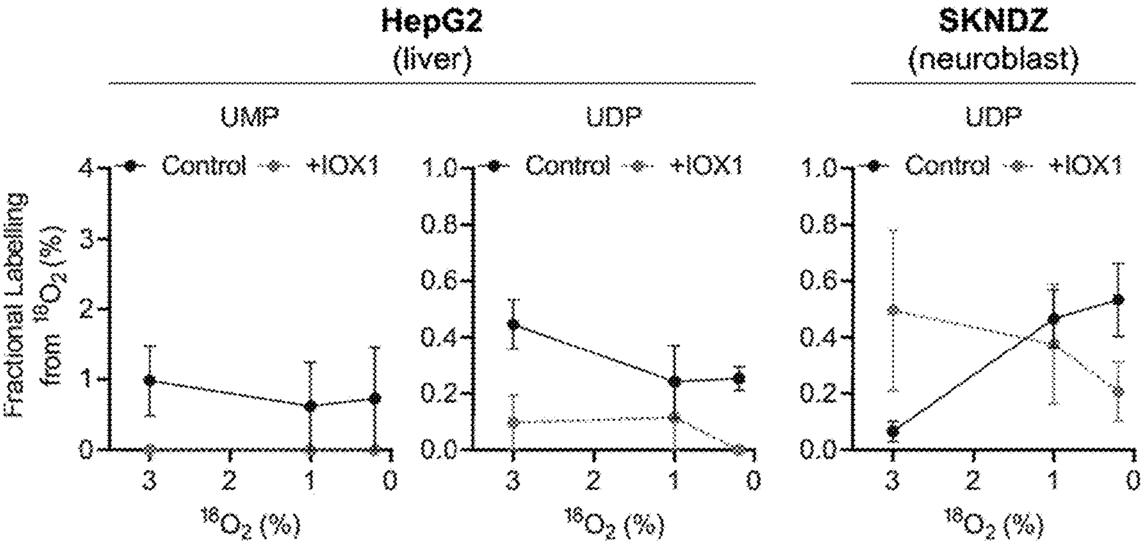
Figure 6L:
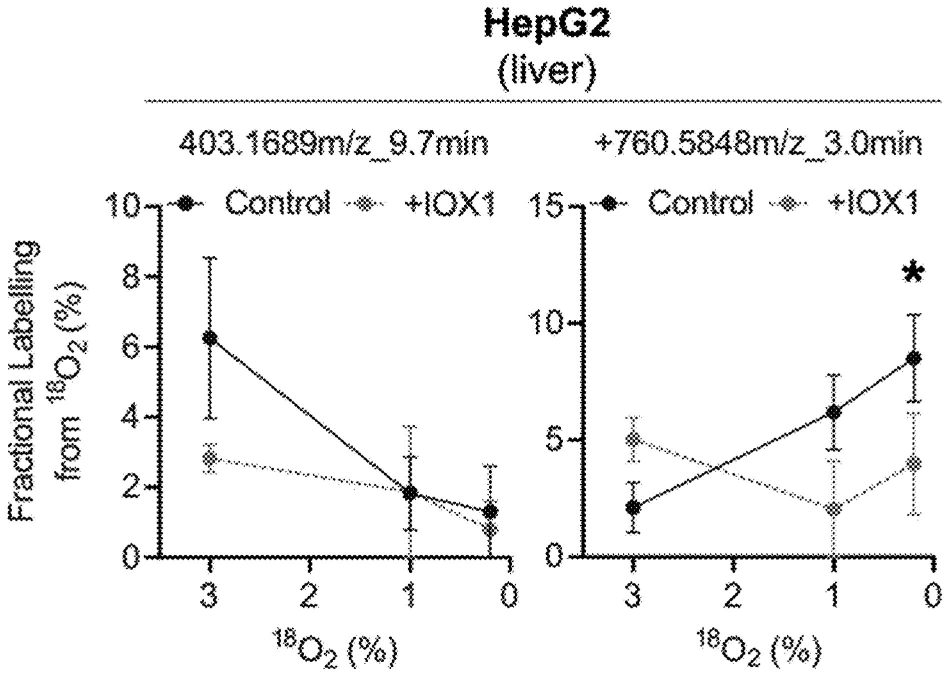
Figure 6M:
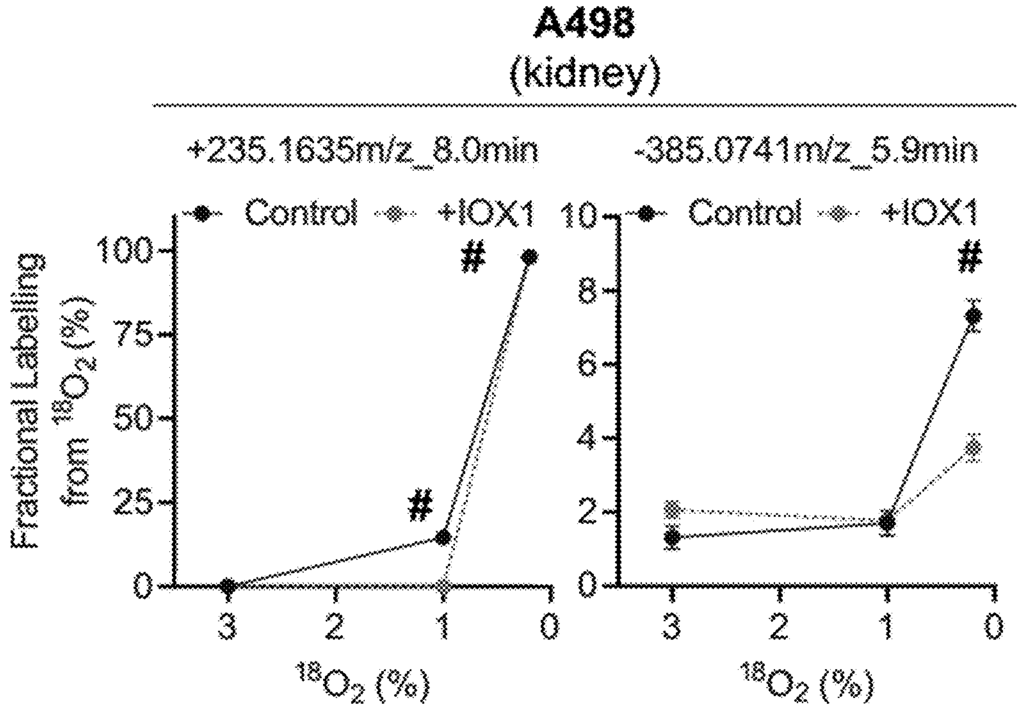

A few unidentified metabolites surprisingly exhibited higher labeling at lower oxygen tensions (FIGS. 6K-6M). Additionally, the fractional $^{18}O$ labelling response in hypoxia differed by cell line and metabolite. Some metabolites exhibited a linear change with hypoxia, whereas others responded exponentially (FIG. 2C and FIG. 6). Thus, oxygen utilization appeared heterogeneous and unique for each cell line or metabolic pathway at different physiological and hypoxic oxygen tensions.

As additional controls, MIAPACA2 cells were treated with an iron chelator (DFO, FIG. 5E-5F), a proteasome inhibitor (MG132) to induce proteotoxic stress, and physiological levels of ascorbate, an antioxidant, to determine the effects of ROS on $^{18}O$-labelling. Labelling of $^{18}O$ γ-butyrobetaine was blocked by IOX1 and DFO, consistent with the fact that trimethyllysine hydroxylase (TMLH) is an iron-dependent dioxygenase (FIGS. 7A-7D). Similarly, $^{18}O$ labeling of methionine was blocked by IOX1, but only partially blocked by DFO (FIGS. 7E-7H). This was consistent with data demonstrating that mammalian acireductone dioxygenase 1 (ADI1) may utilize different metal ions, including iron, nickel, and cobalt, to maintain catalytic activity[9]. Total levels of $^{18}O$ labelled methionine sulfoxide increased upon MG132 treatment and decreased following ascorbate treatment (FIGS. 7I-7M)[10]. Together, these results indicated that ROS-mediated damage and oxygen-dependent reactions were detectable by $^{18}O_2$-GASSP.

Example 2. Analysis of the $^{18}O_2$ Labelled Oxy-Metabolome Identifies a Highly Labelled Metabolite, 4-Hydroxymandelate, in Human Cells Many oxygen-dependent metabolites such as methionine, γ-butyrobetaine, and methionine sulfoxide, were <10% labelled by $^{18}O_2$. However, an unknown metabolite (167.0339 m/z; negative ion mode; elution at 8.2 min) was identified that was ~80-90% labelled at 3% $^{18}O_2$ in MIAPACA2 cells, confirming that high degrees of $^{18}O$ labeling were possible under the present experimental conditions (FIG. 2A and FIG. 2C). This unknown metabolite (167.0339 m/z; negative ion mode; elution at 8.2 min) had the highest fractional oxygen labeling of any metabolite, and was labeled with two $^{18}O$ atoms (>60%) at 3% $^{18}O_2$ in three out of the four human cell lines tested. Therefore, the low fractional labelling of other intracellular metabolites in the cells was likely due to low production, uptake, or turnover of these metabolites at the indicated oxygen tensions.

Figure 2G:
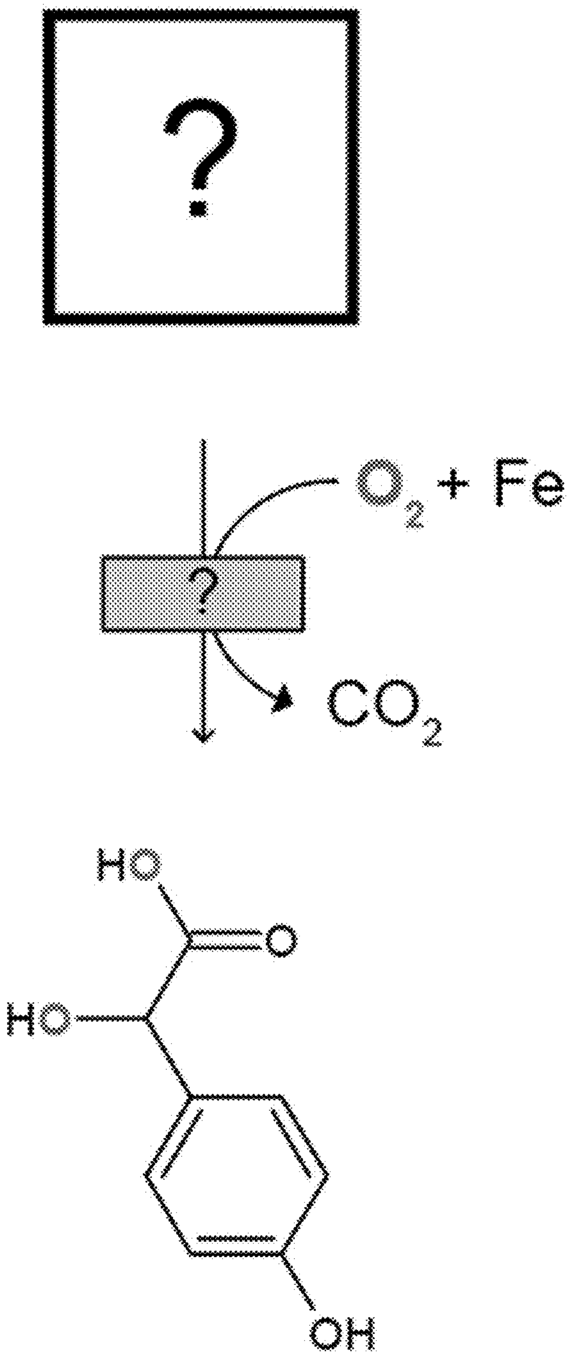

Because this unknown metabolite did not correspond to any annotated human metabolite in the panel (FIG. 2D), the retention time and MS2 fragmentation patterns of its unlabelled precursor ion were compared to several authentic standards from various databases and literature searches. The metabolite was ultimately identified as 4-hydroxymandelate (4-HMA; FIG. 2E and FIG. 8A). One atom of $^{18}O$ was incorporated in the carboxylic acid moiety and another into the Ca-hydroxyl group of 4-HMA (FIG. 8B) as confirmed by $^{18}O$-specific isotopic shifts in the tandem MS spectral fragments. 4-HMA levels and $^{18}O$ labelling were significantly attenuated by hypoxia (<1% $O_2$) and treatment with IOX1 or DFO (FIG. 2C, FIG. 2F and FIGS. 8C-8D). In addition, physiological ascorbate increased the levels of 4-HMA (FIG. 2F). Together, these data suggested that an iron-dependent dioxygenase was involved in the generation of 4-HMA in human cells. Labelling of 4-HMA was also observed at 0.2% $^{18}O_2$, which suggested that the dioxygenase involved in synthesizing 4-HMA was active at extreme hypoxia, and thus has high affinity for $O_2$ (FIG. 2C, FIG. 2F and FIGS. 8C-8D). However, the enzyme involved in 4-HMA synthesis in humans was unknown (FIG. 2G). Therefore, metabolic pathways containing 4-HMA in other organisms were searched with the goal of identifying homologous pathways and enzymes in humans.

Figure 3A:
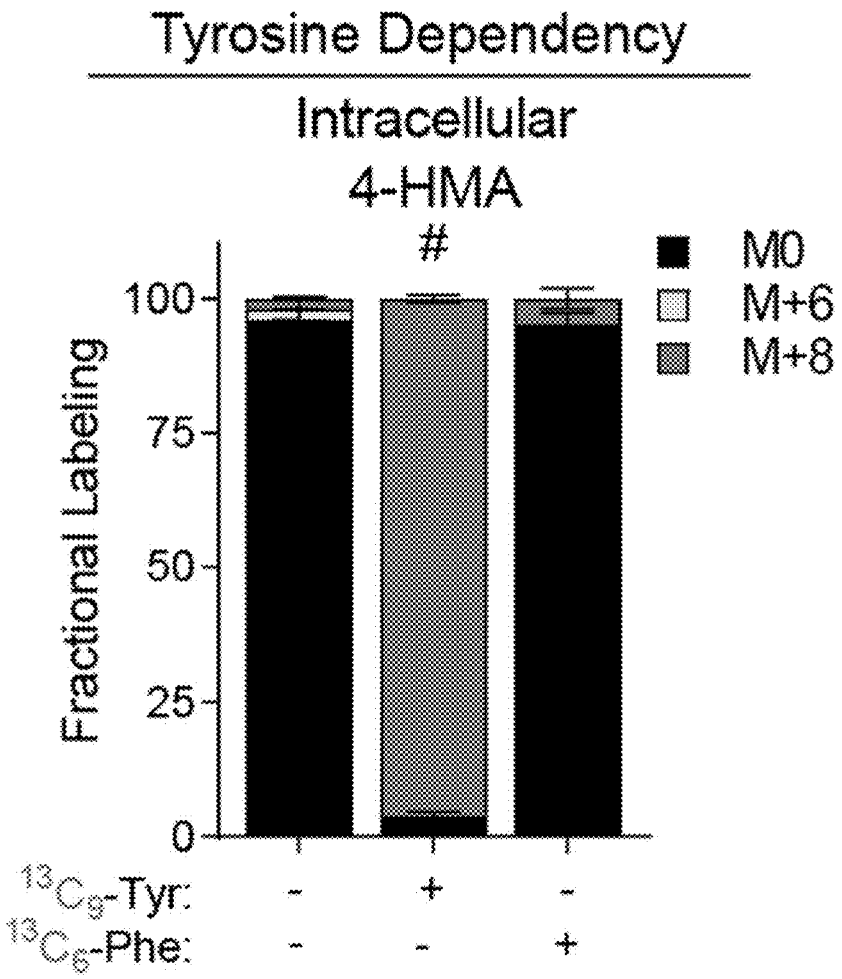
FIGS. 3A-3H show 4-HMA derivation from tyrosine and directly produced by HPDL (4-hydroxyphenylpyruvate dioxygenase-like) in human cells. Fractional labelling of intracellular 4-HMA from MIAPACA2 cells grown in unlabelled, $^{13}C_9$-Tyr-, and $^{13}C_6$-Phe-labelled media for 24 hours at 3% $^{16}O_2$ (n=5 for each group) (FIG. 3A). 4-HMA was derived from tyrosine and not phenylalanine. Total intracellular levels of unlabelled and $^{13}C_8$-labelled 4-HMA from MIAPACA2 cells grown in $^{13}C_9$-Tyr at 21%, 3% and 0.1% $^{16}O_2$ for 24 hours (n=5 for each group) (FIG. 3B). Maximal amounts of 4-HMA were found at 3% $^{16}O_2$. Total intracellular levels of unlabelled and $^{13}C_8$-labelled 4-HMA from MIAPACA2 cells grown in $^{13}C_9$-Tyr with or without the indicated reagents at 3% $^{16}O_2$ for 24 hours (n=5 for each group) (FIG. 3C). The dioxygenase inhibitors IOX1 and DFO attenuated or ablated $^{18}O$ labeling of 4-HMA. Total levels of unlabelled and $^{13}C_8$-labelled 4-HMA from MIAPACA2 cells expressing control (sgTomato; sgTOM and sgLuciferase; sgLUC), and HPDL sgRNAs (FIG. 3D). Cells were grown in $^{13}C_9$-Tyr at 21% $^{16}O_2$ for 24 hours. (n=5 for each group). Immunoblots of HPDL levels from MIAPACA2 cells expressing control and HPDL sgRNAs. S6K served as a loading control. Deletion of HPDL eliminated $^{13}C_9$-Tyr incorporation into 4-HMA. Total levels of unlabelled and $^{13}C_8$-labelled 4-HMA from MIAPACA2 sgHPDL #3 cells with or without expression of sgRNA-resistant HPDL-FLAG wild-type (WT) and catalytically inactive HPDL mutants (H258A, and H163/258A) (FIG. 3E). Cells were grown in $^{13}C_9$-Tyr at 21% $^{16}O_2$ for 24 hours. (n=5 for each group). Immunoblots of HPDL and HPDL-FLAG levels from MIAPACA2 sgHPDL #3 cells. S6K served as a loading control. Catalytically active HPDL rescued $^{13}C_9$-Tyr labeling of 4-HMA while the catalytically inactive mutants failed to do so. Total levels of 4-HMA generated from enzymatic assays using HPDL-FLAG immunoprecipitated from MIAPACA2 sgHPDL #3 cells with or without expression of sgRNA-resistant HPDL-FLAG WT (FIG. 3F). Assays were performed using the indicated substrates at 37° C. at 21% $^{16}O_2$ for 1 hour (n=3 for each condition). Immunoblots of HPDL and HPDL-FLAG levels from FLAG-immunoprecipitations. Only the combination of HPDL WT and 4-HPPA as a substrate resulted in the generation of 4-HMA. Total levels of 4-HMA generated from enzymatic assays using HPDL-FLAG immunoprecipitated from MIAPACA2 sgHPDL #3 cells with or without expression of sgRNA-resistant HPDL-FLAG WT, or catalytically inactive mutants (H258A, and H163/258A) (FIG. 3G). Assays were performed with 4-HPPA at 37° C. at 21% $^{16}O_2$ for 1 hour (n=3 for each condition). Immunoblots of HPDL and HPDL-FLAG levels from FLAG-immunoprecipitations. Only catalytically active HPDL produced 4-HMA in vitro. Schematic of the canonical tyrosine catabolism pathway and proposed non-canonical tyrosine pathway (FIG. 3H). "n" represents the number of biologically independent replicates for each group and condition. Graphs are represented as mean±s.e.m. and were compared by one- (FIG. 3G) or two-way ANOVA (FIGS. 3A-3F), followed by Tukey post-hoc test (#p<0.0001).
Figure 3B:
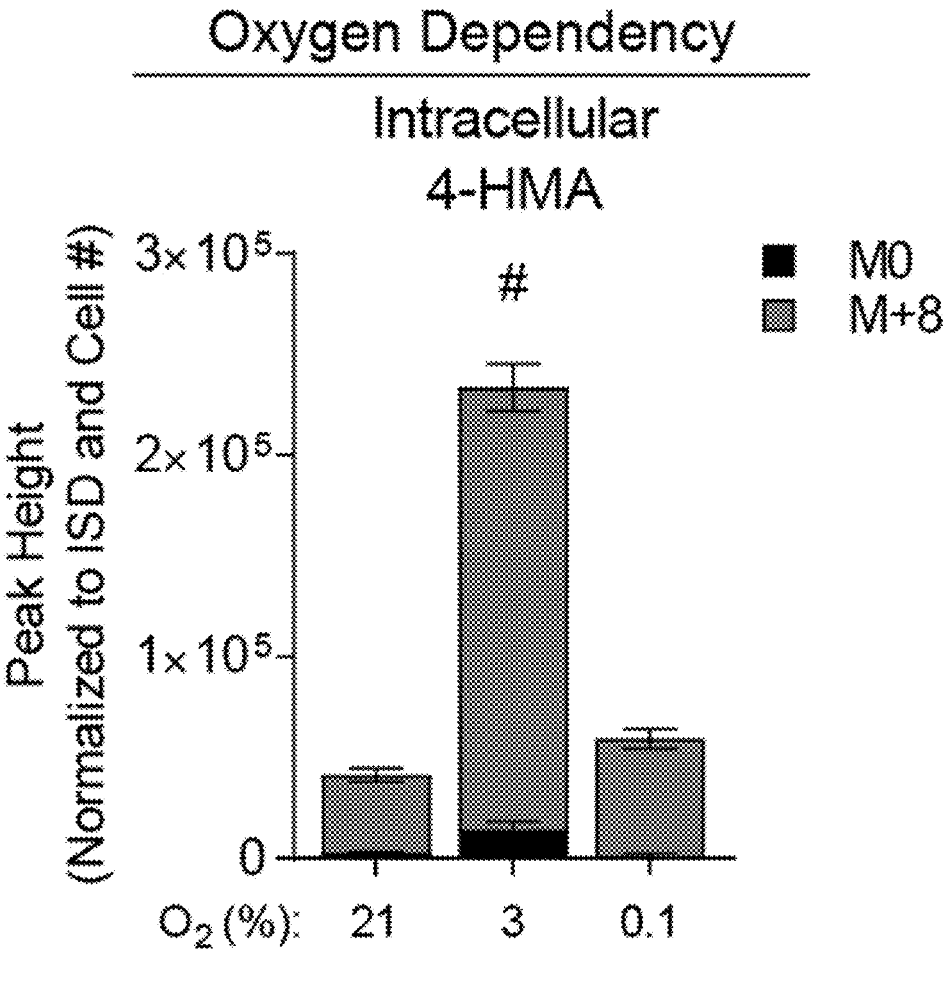
Figure 3C:
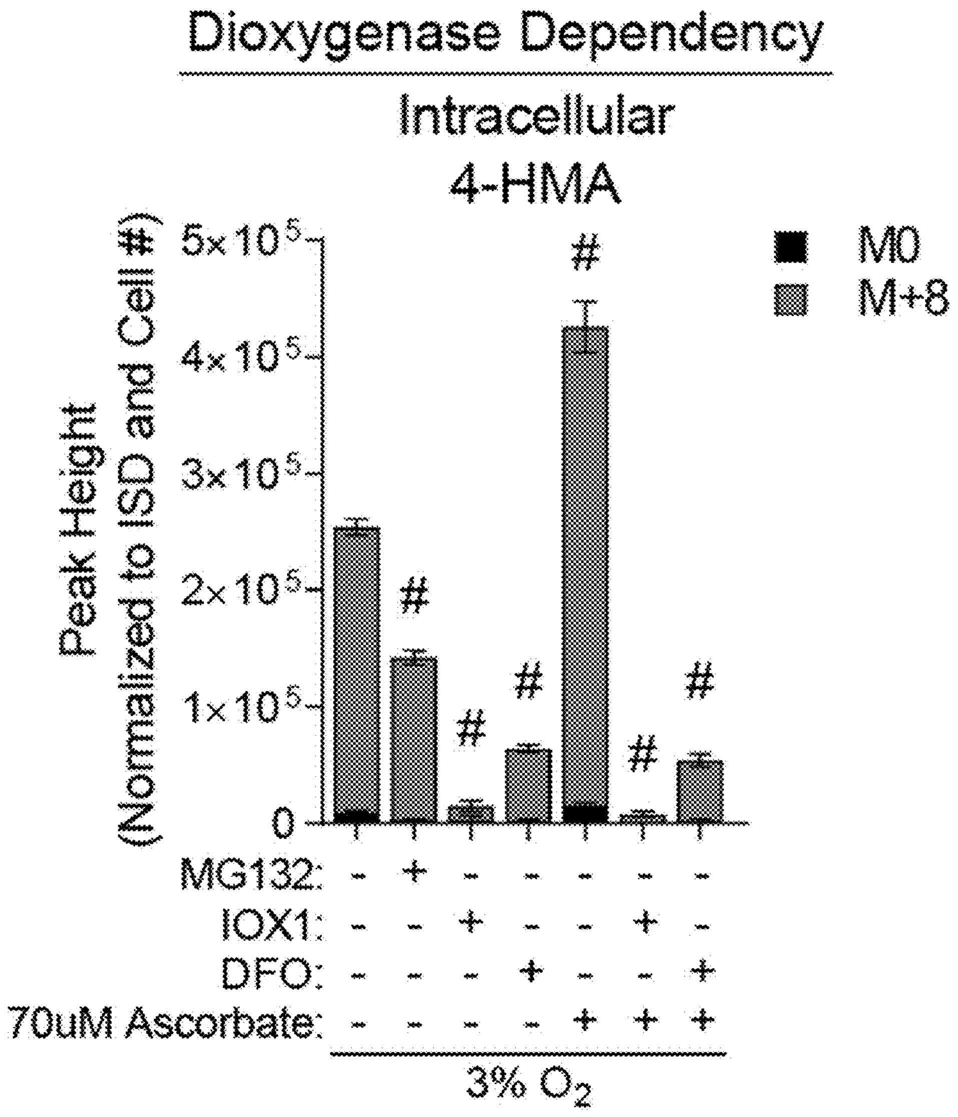
Figure 3D:
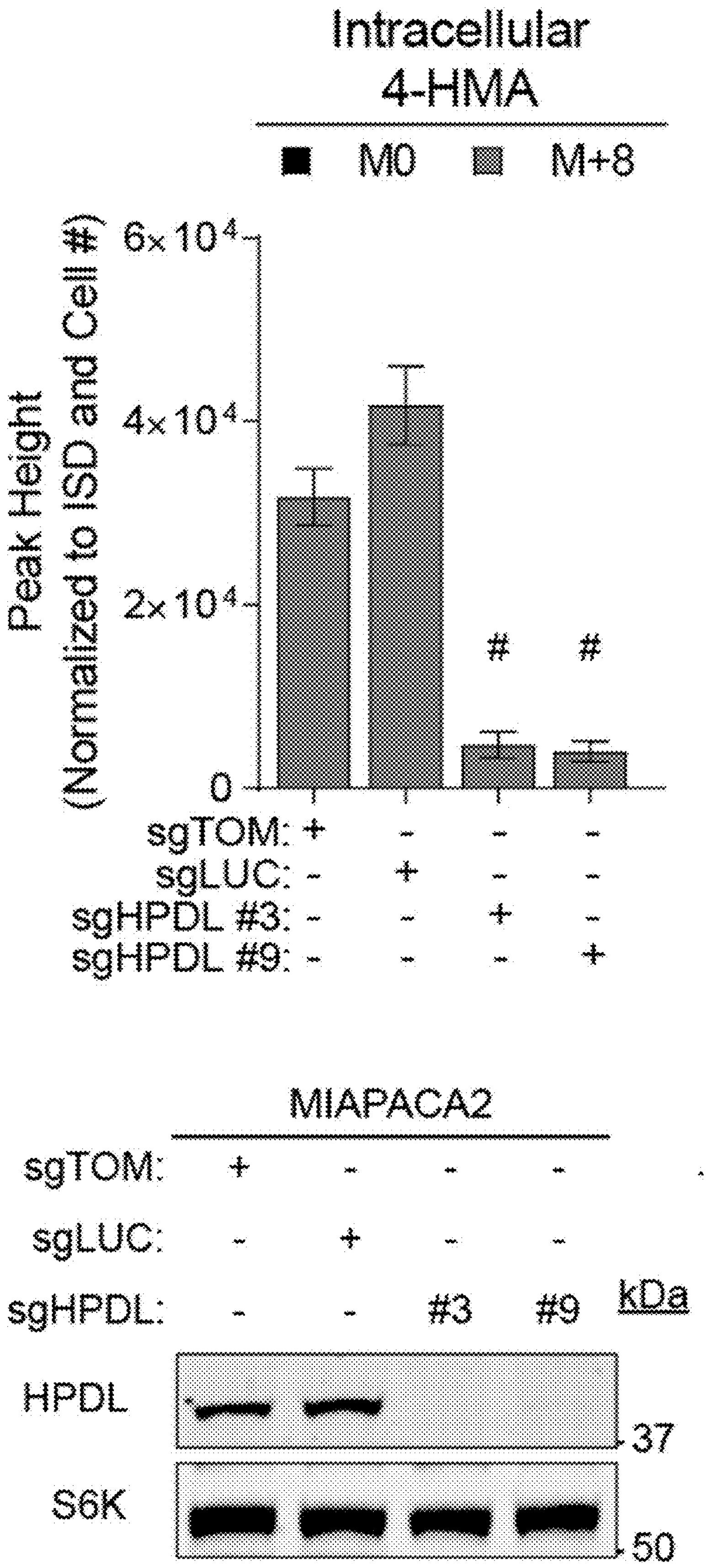

Example 3. 4-HMA is Derived from Tyrosine and Directly Produced by HPDL (4-Hydroxyphenylpyruvate Dioxygenase-Like) in Human Cells 4-HMA biosynthesis has only been described in some bacteria and in rabbits. The bacterium *A. orientalis* expresses hydroxymandelate synthase (HmaS), an iron-dependent dioxygenase that converts 4-hydroxyphenylpyruvate (4-HPPA) to 4-HMA[11-12]. The production of 4-HPPA occurs in the first step of tyrosine (Tyr) catabolism via tyrosine transaminase (TAT). In rabbits, 4-HMA was proposed to be synthesized from the degradation of tyramine and octopamine by dopamine β-hydroxylase (Dbh) and monoamine oxidase (Mao) (FIG. 9A)[13]. Tyramine is also a Tyr-derived metabolite. Therefore, all known substrates required to generate 4-HMA are derived from Tyr. In addition, Tyr can also be made from phenylalanine (Phe) by Phe hydroxylase (PAH) in mammalian liver cells[14]. To elucidate the human 4-HMA biosynthetic pathway, the fates of $^{13}C_9$-Tyr and $^{13}C_6$-Phe were traced in human cells. Consistent with the lack of $^{18}O$ labelling of Tyr in non-liver cells, which lack phenylalanine hydroxylase, 4-HMA and metabolites in the canonical Tyr catabolism pathway (4-HPPA and 4-hydroxyphenyllactate; 4-HPLA) were completely labelled by $^{13}C$-Tyr, but not by Phe (FIG. 3A and FIG. 9B). In addition, octopamine and tyramine were not detected in the human cells examined, which suggested that 4-HMA was not produced from tyramine. Additionally, the generation of 4-HMA by tyramine would result in the incorporation of a single $^{18}O$ at the Ca position of the carboxylic acid of 4-HMA (FIG. 9A). However, this was not observed by $^{18}O$ labelling (FIG. 8B). Therefore, it was unlikely that 4-HMA biosynthesis from octopamine and tyramine catabolism occurred in the present system.

Consistent with $^{18}O$ labelling, $^{13}C_9$-Tyr-derived 4-HMA also was severely inhibited by IOX1 and DFO, increased with ascorbate, and was sensitive to hypoxia (FIGS. 3B-3C and FIGS. 9C-9D). Unexpectedly, 4-HMA levels also were lower in hyperoxic (21%) conditions compared to 3% $O_2$, reflecting either decreased production or increased consumption of this metabolite at 21% $O_2$. Nonetheless, these data indicate that 4-HMA is derived from Tyr, and that 4-HMA synthesis requires an iron-dependent dioxygenase in human cells. As Tyr-derived metabolites were decreased under hypoxic and IOX1- and DFO-treated conditions (FIGS. 9C-9D), humans may possess an enzyme with similar activity to bacterial HmaS.

Although the human genome does not encode any known enzyme with HmaS-like activity, sequence alignment revealed two human homologs, hydroxyphenylpyruvate dioxygenase (HPD) and HPD-like (HPDL) with >80% homology to HmaS at the protein and cDNA level (FIGS. 10A-10C). HPD is a dioxygenase that synthesizes homogentisate (HGA), from 4-HPPA during Tyr catabolism[5]. Unlike HmaS, HPD is not able to synthesize 4-HMA[15,16]. Because of the homology and substrate preference between HPD and HmaS, several studies have compared the active sites of these enzymes to determine the catalytic mechanism of generating homogentisate (HGA) or 4-HMA, respectively. It has been reported that a single F337 to valine or isoleucine mutation in HPD, which mimics the sequence of HmaS, decreases HGA synthesis, and allows slight production of 4-HMA[15,16]. In contrast with HPD, little is known about the function and activity of HPDL.

Sequence alignment and distance mapping at the gene and protein level revealed that HPDL was more similar to HmaS than to HPD (FIGS. 10A-10B). Protein sequence alignment of HPD, HmaS, and HPDL revealed that HPDL has an isoleucine at the F337 equivalent observed in HPD, suggesting that it may generate 4-HMA (FIG. 10C). In addition, the vicinal oxygen chelate (VOC) domains of HPD, HDPL and HmaS all contained conserved histidine residues required for iron coordination and enzymatic activity (FIG. 10C)[15,16]. As this implied that HPDL could have functional dioxygenase activity, the uncharacterized protein HPDL and its potential role in 4-HMA synthesis became a focal point of the present work.

Figure 3E:
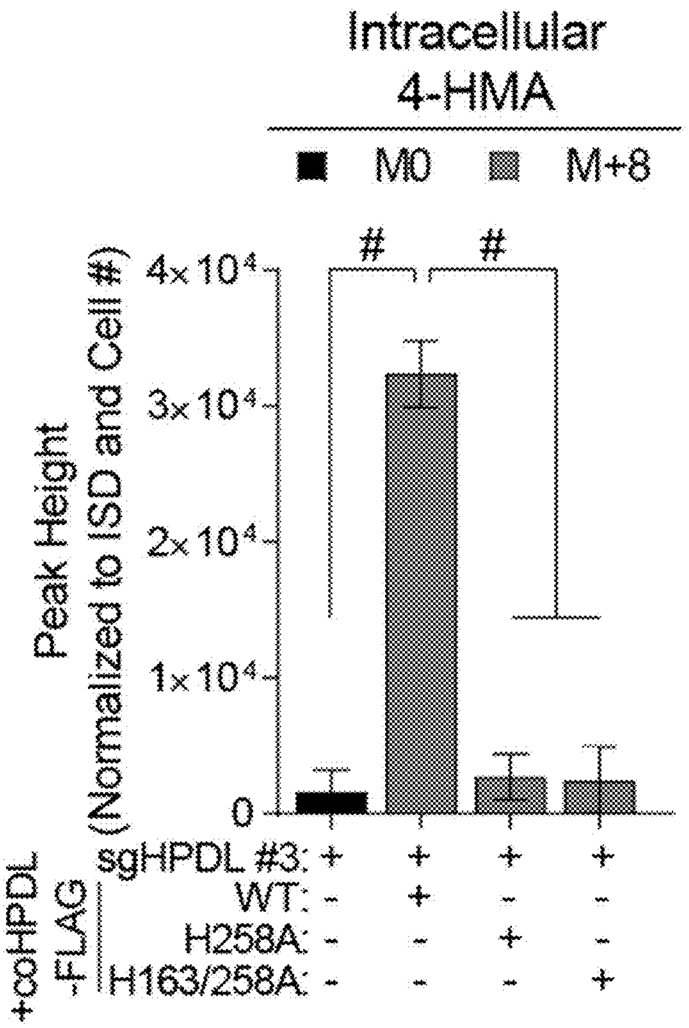
Figure 3E:
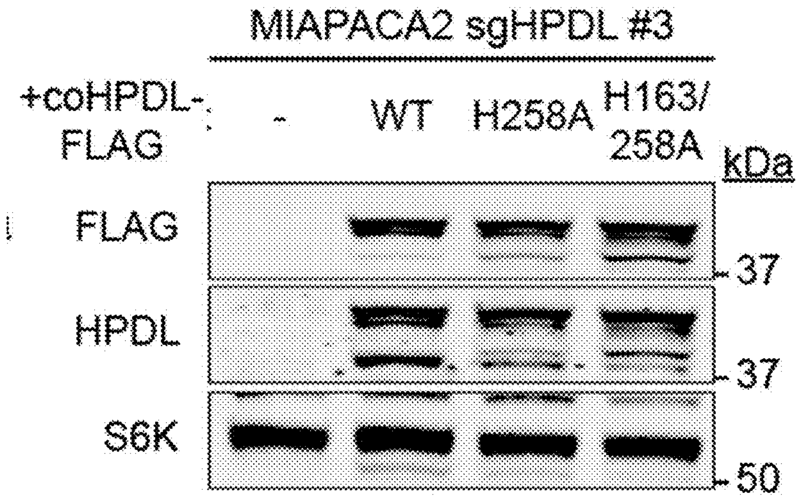

Genetic ablation of HPDL by pooled CRISPR/Cas9 deletion had no effect on proliferation in 2D culture, but induced decreased levels of $^{13}C_9$-Tyr-labelled 4-HMA (FIG. 3D and FIGS. 10D-10G) in human cells. Expression of sgRNA-resistant codon-optimized HPDL (coHPDL) wild-type (WT), but not catalytically inactive HPDL mutants (H258A and H163/258A), restored 4-HMA levels in HPDL-knock-out (KO) cells (FIG. 3E). This genetically linked HPDL catalytic activity to 4-HMA biosynthesis in human cells. In addition, HPDL KO also increased the levels of 4-HPPA and 4-HPLA, which was restored by coHPDL-FLAG WT (FIGS. 10E-10F). Increased levels of these metabolites upon HPDL KO may reflect their roles as HPDL substrates.

Figure 3F:
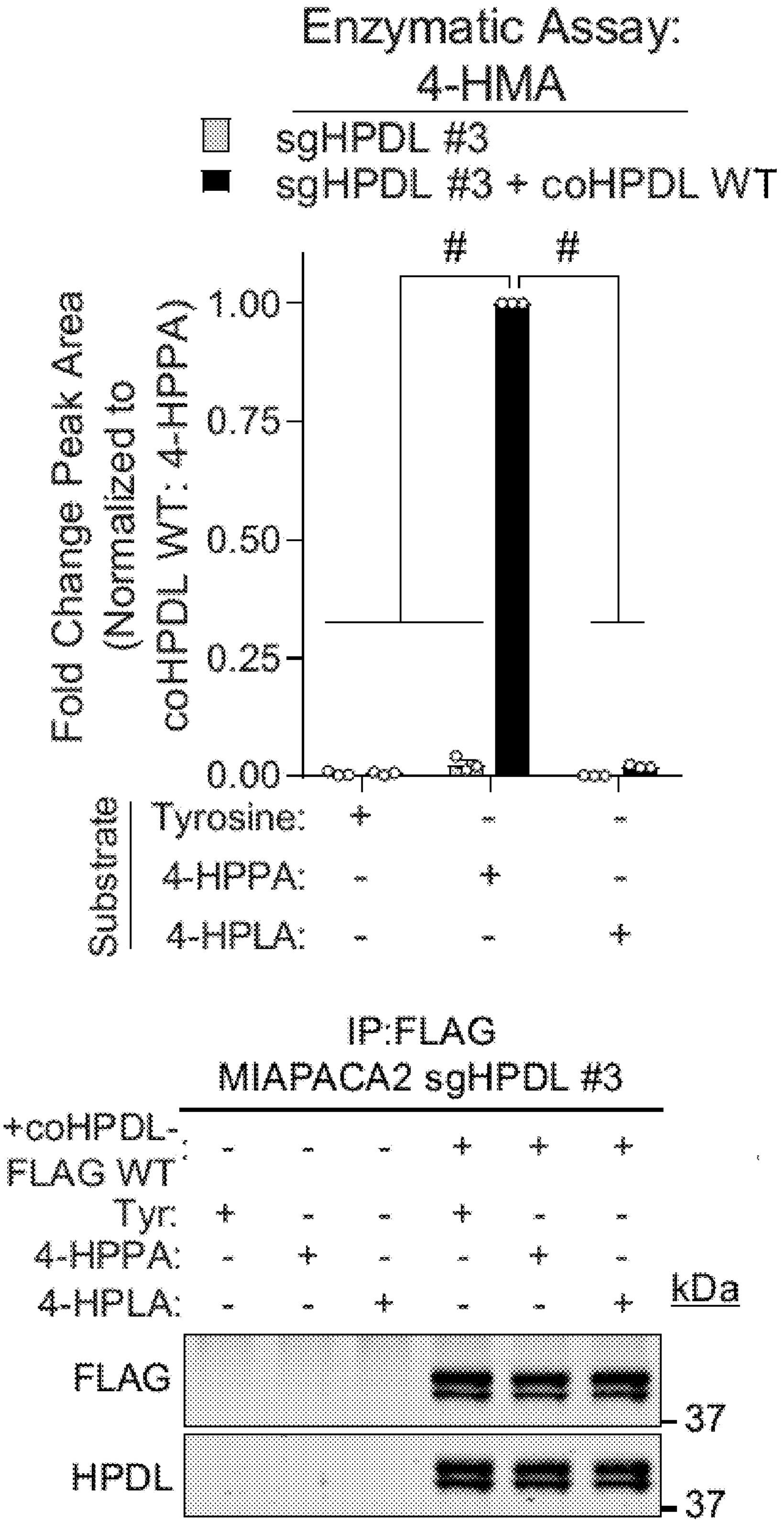
Figure 3G:
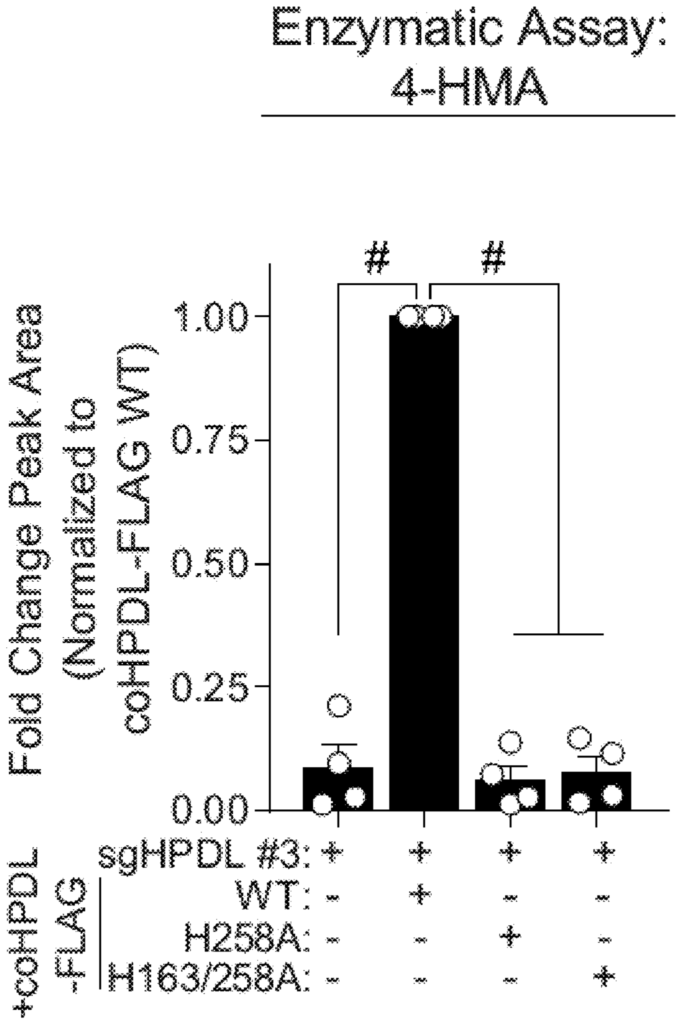
Figure 3G:
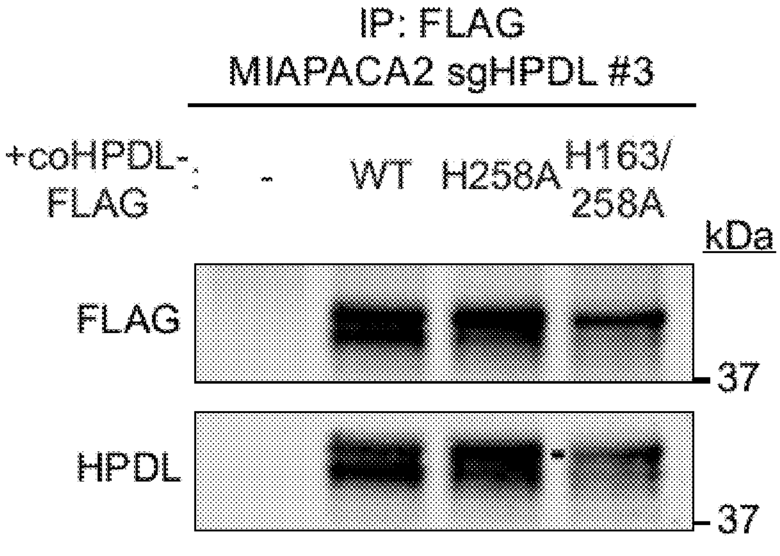
Figure 3H:
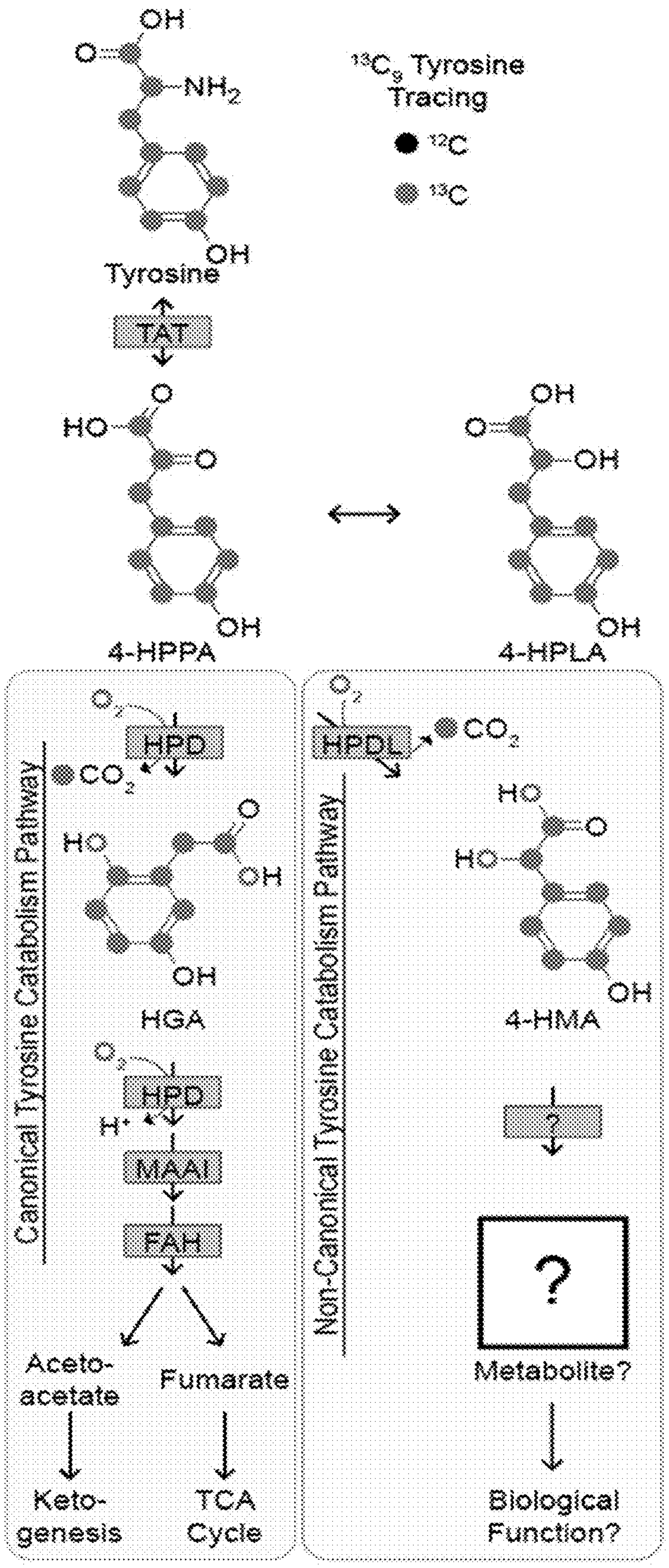

To directly assess the ability of HDPL to produce 4-HMA, WT coHPDL-FLAG was immunopurified from human cells and enzymatic assays were performed using Tyr, 4-HPPA and 4-HPLA as substrates. Homogentisate, the product of HPD, was not produced in any of the present enzymatic assays. Similar to reports with HmaS, it was found that HPDL synthesized 4-HMA from 4-HPPA, but not Tyr and 4-HPLA (FIG. 3F). This showed that 4-HPPA was a substrate of HPDL. It was also confirmed that WT HPDL-FLAG, but not catalytically-impaired HPDL mutants, produced 4-HMA from 4-HPPA (FIG. 3G). This directly confirmed that HPDL activity, and not a potential HPDL-interacting enzyme, was needed for 4-HMA synthesis. Therefore, in addition to the canonical Tyr catabolism pathway that requires HPD, humans have a previously undescribed, non-canonical tyrosine catabolism pathway in which HPDL converts 4-HPPA to 4-HMA (FIG. 3H).

In other species, 4-HMA is the precursor of chloroeremomycin (a glycopeptide antibiotic)[15,16] norcardicin A (monocyclic β-lactam antibiotic)[17], and an antioxidant, protocatechuate[18]. During the synthesis of protocatechuate, 4-HMA is degraded into 4-hydroxybenzoate (4-TB). In human cells, 4-HB is required for the synthesis of the headgroup of coenzyme Q10 (CoQ10), an essential component of the electron transport chain and an antioxidant (FIG. 11A). Tyr and 4-HPPA are known 4-HB precursors in yeast and mammals. However, the intermediates between 4-HPPA and 4-HB, which would constitute the CoQ10 headgroup biosynthesis pathway, have long been elusive in higher eukaryotic cells (FIG. 11A)[19]. Whether 4-HMA produced by human cells could be used for the synthesis of 4-HB and CoQ10 was asked.

Endogenous 4-HB in mammalian cells was below the limit of detection using the present Liquid Chromatography Mass Spectrometry (LC-MS) methods, suggesting very low intracellular levels in human cells. Therefore, CoQ10 was used as an indirect readout of 4-HB production. To assess the ability of human cells to biosynthesize CoQ10, cells were labelled with $^{13}C_6$-Phe or $^{13}C_9$-Tyr. CoQ10 was completely biosynthesized from Tyr, but not Phe, in human cells (FIG. 11B). Additionally, CoQ10 biosynthesis exhibited dose-dependent changes correlating with oxygen levels (FIG. 11C). CoQ10 labelling from $^{13}C_9$-Tyr was completely blocked with IOX1 and DFO (FIG. 11D). This was consistent with the fact that the final steps of CoQ10 biosynthesis rely on several monooxygenases, in particular COQ7, a di-iron-containing monooxygenase (FIG. 11A)[20,21], but also suggested that an unknown dioxygenase was involved in the pathway. Initial experiments did not identify significant differences in Tyr-derived CoQ10 in HPDL KO cells. However, expression of HPDL WT, but not catalytically inactive HPDL, increased $^{13}C$-labelled CoQ10 (FIGS. 11E-11F). Together, these data suggested that HPDL and 4-HMA were involved in CoQ10 biosynthesis, but that any effects of HPDL loss on tyrosine incorporation into the CoQ10 headgroup may be masked under the present experimental conditions.

Figure 4A:
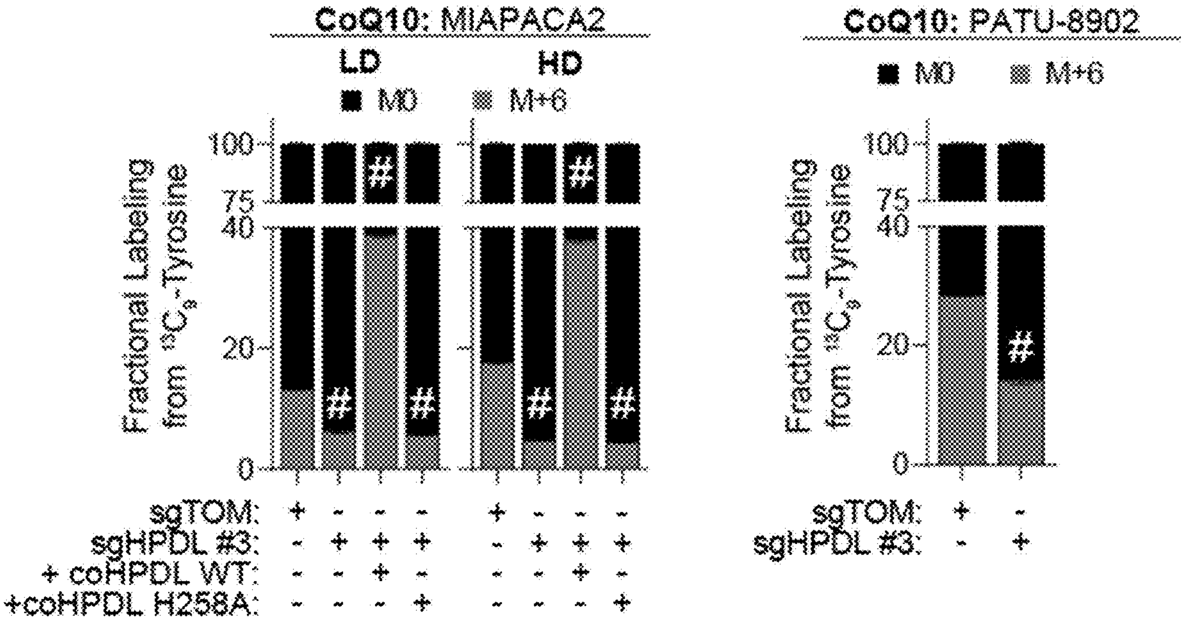
FIGS. 4A-4K show HPDL and 4-HMA participation in the human CoQ10 headgroup biosynthesis pathway and PDAC tumorigenesis. Total intracellular levels of unlabelled and 13C6-labelled CoQ10 from MIAPACA2 and PATU-8902 cells expressing control or HPDL sgRNA with or without sgRNA-resistant codon-optimized HPDL-FLAG (coHPDL) WT or catalytically inactive mutant (H258A) coHPDL (FIG. 4A). Cells were grown in $^{13}C_9$-Tyr media for 24 hours at low (LD) and high density (HD) (n=3 for each group). HPDL was required for $^{13}C_9$-Tyr-labelled CoQ10 synthesis at high densities. 3D growth assays in MIAPACA2 cells expressing control or HPDL sgRNA with or without coHPDL WT or catalytically inactive mutant (H258A) coHPDL. Growth was measured after 3 days (n=4 for each group) (FIG. 4B). HPDL loss in PDAC cells decreased 3D growth. Fractional labelling of CoQ10 from $^{13}C_9$-Tyr in MIAPACA2 cells grown in 3D conditions (n=4) (FIG. 4C). Representative images of confocal fluorescent imaging of MIAPACA2 cells expressing empty vector or coHPDL-EGFP (FIG. 4D). Mitochondria were stained using CMXROS dye. HPDL colocalized to the mitochondria. Fractional labelling of intracellular and mitochondrial CoQ10 from $^{13}C_9$-Tyr from MIAPACA2 cells expressing control or HPDL sgRNA with or without coHPDL WT and catalytically inactive mutant (n=4 for each group) (FIG. 4E). For mitochondrial purity see FIG. 12G. Loss of HPDL significantly decreased total and mitochondrial $^{13}C_9$-Tyr-derived CoQ10. Oxygen consumption rates (OCR) from MIAPACA2 cells expressing control or HPDL sgRNA with or without coHPDL WT and catalytically inactive mutant grown in 3D conditions for 3 days (n=5 for each group) (FIG. 4F). HPDL KO significantly decreased OCR. 3D growth assays (FIG. 4G) or OCR (FIG. 4H) in MIAPACA2 cells treated with or without 1 mM 4-HMA or 4-HB (n=4) (FIGS. 4G-4H). MIAPACA2 orthotopic pancreatic tumour weight from cells expressing control or HPDL sgRNA with or without coHPDL WT and catalytically inactive mutant after 5 weeks post-injection (FIG. 4I). Loss of HPDL significantly decreased tumour burden in mice. The death to proliferation ratio of tumours from FIG. 4I (FIG. 4J). Death and proliferation were measured using cleaved caspase 3 (CC3) and phospho-histone H3 (p-HH3) staining from immunohistochemistry images (see FIG. 12H). Loss of HPDL significantly increased the death to proliferation ratio in mice. Overall survival of patients with HPDL high (n=44) and low (n=96) expressing PDAC tumours from the TCGA dataset (FIG. 4K). Survival curve was compared using the Log-rank (Mantel-Cox) test. HPDL high PDAC tumours predicted poor overall survival in patients. Summary of the roles of HPDL and 4-HMA in the human CoQ10 headgroup biosynthesis pathway (FIG. 4L). More details can be found in FIG. 13. "n" and each individual point (FIG. 4I-FIG. 4J) represent the number of biologically independent experiments for each group and condition. Survival curves (FIG.

Example 4. HPDL and 4-HMA Participate in the Human CoQ10 Headgroup Biosynthesis Pathway and PDAC Tumorigenesis Whether 4-HMA could be shared between cells in which HPDL was KO in a pooled setting was tested. Control cells were able to secrete 4-HMA at high cell densities. However, HPDL KO cells did not release detectable levels of 4-HMA (FIG. 11G). This indicated that metabolite sharing was not occurring in a pooled HPDL KO setting. CoQ10 biosynthesis was higher in control cells cultured at higher densities (FIG. 11H). Under these conditions, HPDL KO significantly decreased the labelling of CoQ10 by $^{13}C_9$-Tyr (FIG. 4A and FIG. 11H). CoQ10 labelling was restored upon expression of coHPDL WT, but not catalytically impaired mutant coHPDL. These data suggested that HPDL was important for upregulation of CoQ10 biosynthesis in cells grown at high densities.

To test if the 4-HMA pathway was directly involved in CoQ10 biosynthesis, cells were labelled with $^{13}C_9$-Tyr for two weeks, followed by a chase with non-labelled (12C)-Tyr, (12C)-4-HPPA, (12C)-4-HPLA, (12C)-4-HMA and (12C)-4-HB for 24 hours (FIG. 11I). Addition of exogenous Tyr-derived intermediates did not affect the proliferation of human cells (FIG. 11J). Treatment with exogenous 4-HPPA, 4-HPLA, 4-HMA, and 4-HB resulted in a substantial intracellular accumulation of the respective unlabelled metabolite and downstream products of each metabolite inside cells labelled with $^{13}C_9$-Tyr for two weeks (FIG. 11K). Exogenous 4-HPPA increased the downstream metabolites 4-HPLA, 4-HMA, but not Tyr. This was consistent with 4-HPPA being downstream of Tyr and upstream of intermediates involved in 4-HB synthesis. Adding 4-HPLA slightly increased 4-HPPA, but did not significantly increase Tyr or 4-HMA levels. This indicated that there was very minimal conversion of 4-HPLA back to 4-HPPA, and that 4-HPLA was not a major contributor to the 4-HMA synthesis pathway. Exogenous 4-HMA had no effect on Tyr, 4-HPPA and 4-HPLA levels. This placed 4-HMA downstream of 4-HPPA. Addition of 4-HB did not change Tyr, 4-HPPA, 4-HPLA, and 4-HMA levels, indicating that 4-HB is downstream of these metabolites. The minimal effect of 4-HPPA, 4-HPLA, and 4-HMA on 4-HB levels suggested that the synthesis of endogenous 4-HB was highly regulated. Together, these data positioned 4-HMA between 4-HPPA and 4-HB, and revealed the unidirectional order of the 4-HMA CoQ10 headgroup biosynthesis pathway as Tyr-HPPA-HMA-HB (FIG. 11L).

Using the same experimental scheme, the incorporation of Tyr-derived metabolites into CoQ10 was measured. After cells were grown for two weeks in $^{13}C_9$-Tyr media, approximately 60% of the intracellular CoQ10 pool was labelled. Based on previous 24 hour labelling experiments, CoQ10 was expected to be fully labelled with $^{13}C_9$-Tyr after two weeks at 21% $O_2$. The inability to fully label CoQ10 by two weeks suggested that 40% of the intracellular CoQ10 pools were derived from a $^{13}C_9$-Tyr-independent source. After switching two-week $^{13}C_9$-Tyr labelled cells from $^{13}C_9$- to $^{12}C_9$-Tyr for 24 hours, a 20% increase in non-labelled CoQ10 was observed. Addition of 4-HPPA, 4-HMA and 4-HB in the presence of $^{13}C_9$-Tyr increased the fraction and levels of unlabelled CoQ10 by 30% (FIG. 11K). Surprisingly, 4-HPLA was also able to increase the fraction of non-labelled CoQ10 by 16%. That ~70% of 4-HPPA was derived from $^{13}C_9$-Tyr in the HPLA treated cells suggested two possibilities: either the small fraction of 4-HPLA-derived 4-HPPA was more efficiently incorporated into CoQ10, or that there was an HPLA-dependent pathway that contributed to CoQ10 pools. The data demonstrated that 4-HMA was incorporated into CoQ10.

To understand the functional role of CoQ10 synthesis in human cells, enzymes upstream (e.g. TAT) and downstream (e.g. COQ2) of HPDL in the CoQ10 biosynthesis pathway were genetically suppressed. In addition, if loss of mammalian enzymes such as ALDH3A1 and LDHD, which are the orthologs of yeast CoQ10 synthesis enzymes Hfd and Dld1/2, respectively, affected the growth of mammalian cells (FIG. 12A)[22-24] was also tested. TAT and LDHD KO cells had small decreases in CoQ10 levels, but loss of these enzymes did not affect 2D growth. ALDH3A1 knockout did not affect CoQ10 levels or 2D growth. The lack of effect of ALDH3A1 KO on CoQ10 levels may be masked by promiscuous activity of other aldehyde dehydrogenases in human cells. COQ2 knockout significantly decreased CoQ10 levels, but had no effect on 2D growth (FIGS. 12B-12E). This indicated that partial loss of CoQ10 was not sufficient to affect growth in 2D culture.

Figure 4B:
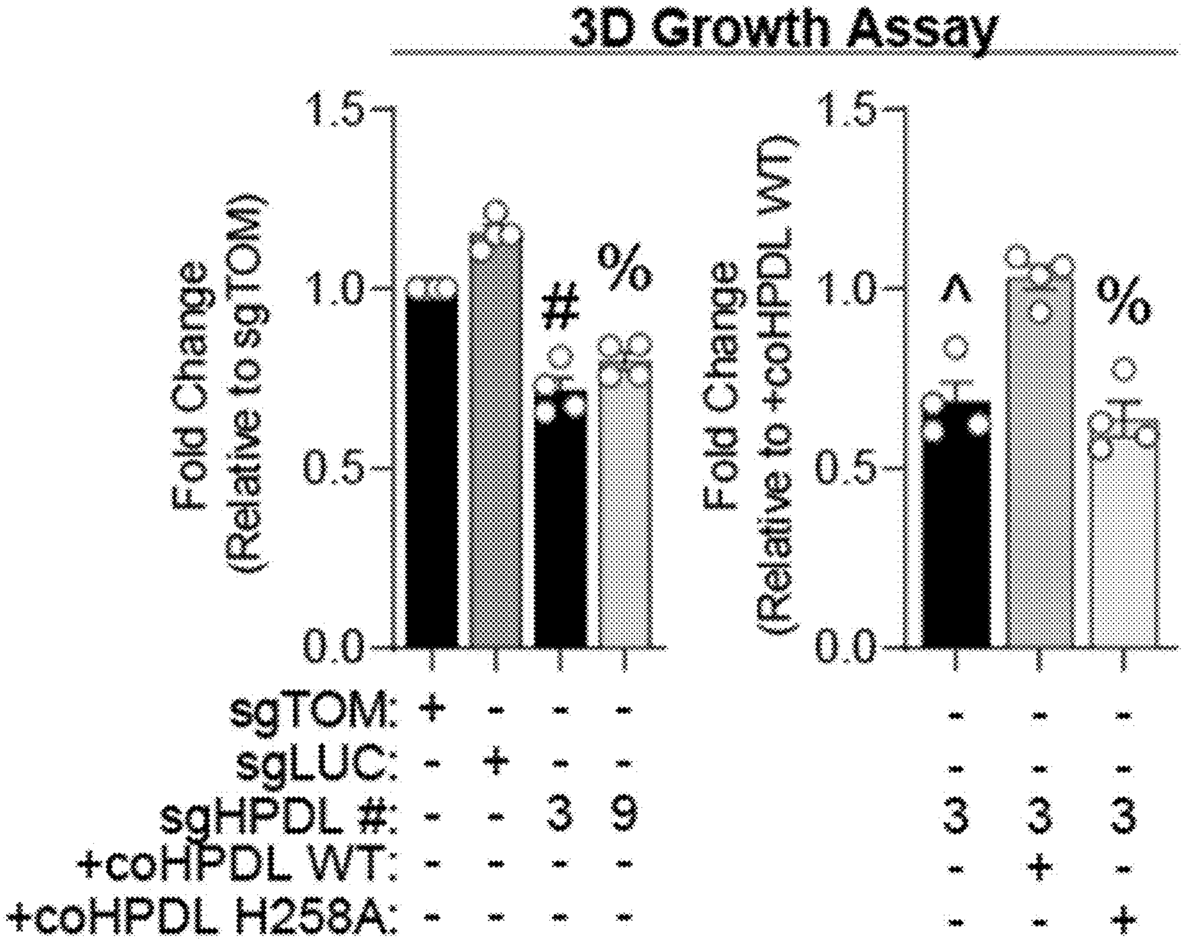
Figure 4C:
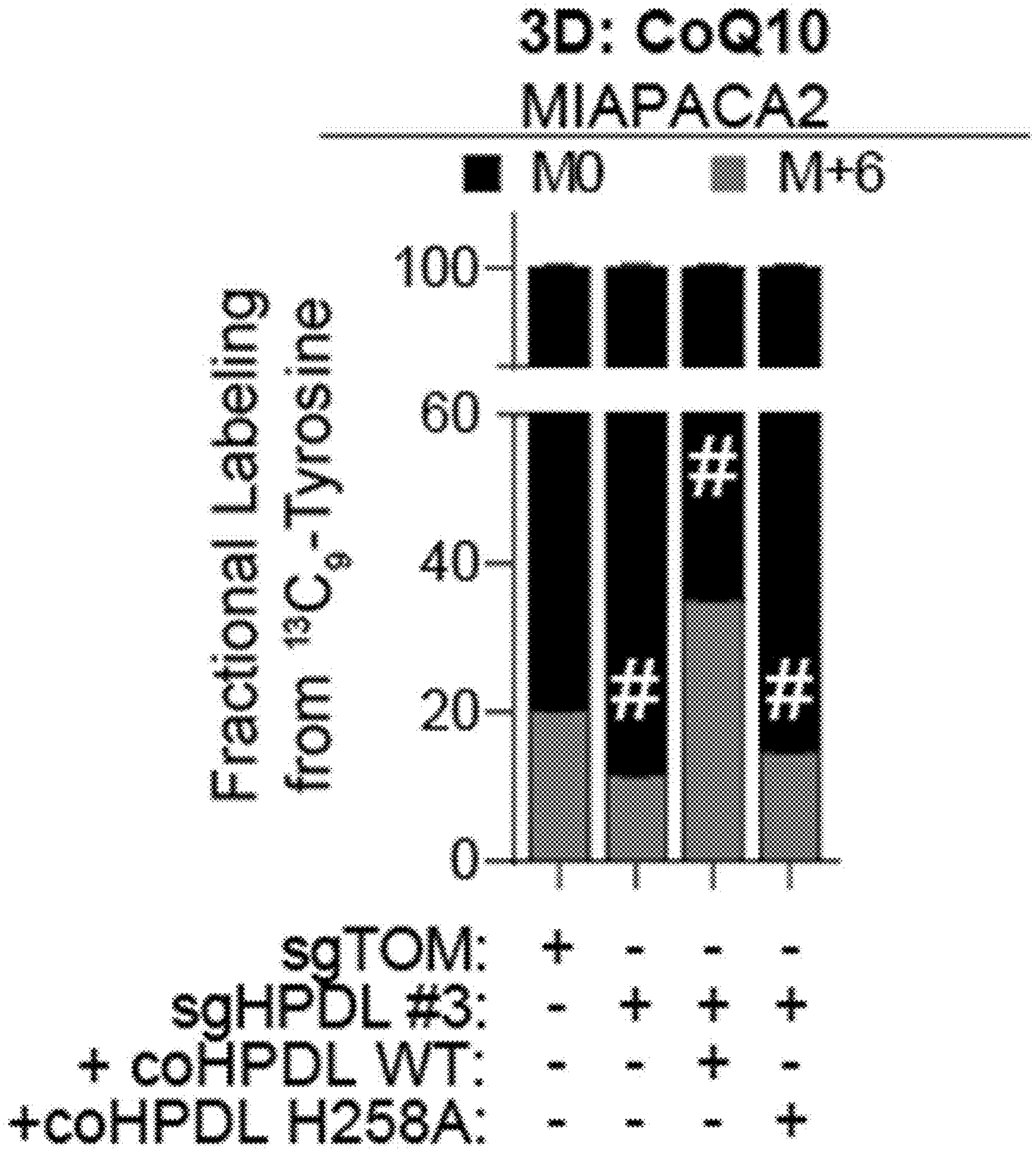

In contrast to its lack of effect in 2D growth, CoQ10 has been reported to be important for cancer cell proliferation in 3D culture[25]. 3D growth was impaired in HPDL KO cells, and restored by expression of coHPDL WT, but not catalytically impaired mutant coHPDL (FIG. 4B). Similarly, KO of other enzymes in the pathway also decreased growth in 3D culture (FIG. 12F). HPDL KO cells exhibited lower fractional labelling of CoQ10 from $^{13}C_9$-Tyr, which was restored by expression of WT, but not catalytically impaired coHPDL (FIG. 4C). These results indicated that PDAC cells required CoQ10 for optimal growth in 3D, but not 2D, culture, and were consistent with the observation that CoQ10 synthesis was increased in cells cultured at high density[26], which is mimicked by 3D culture.

Figure 4D:
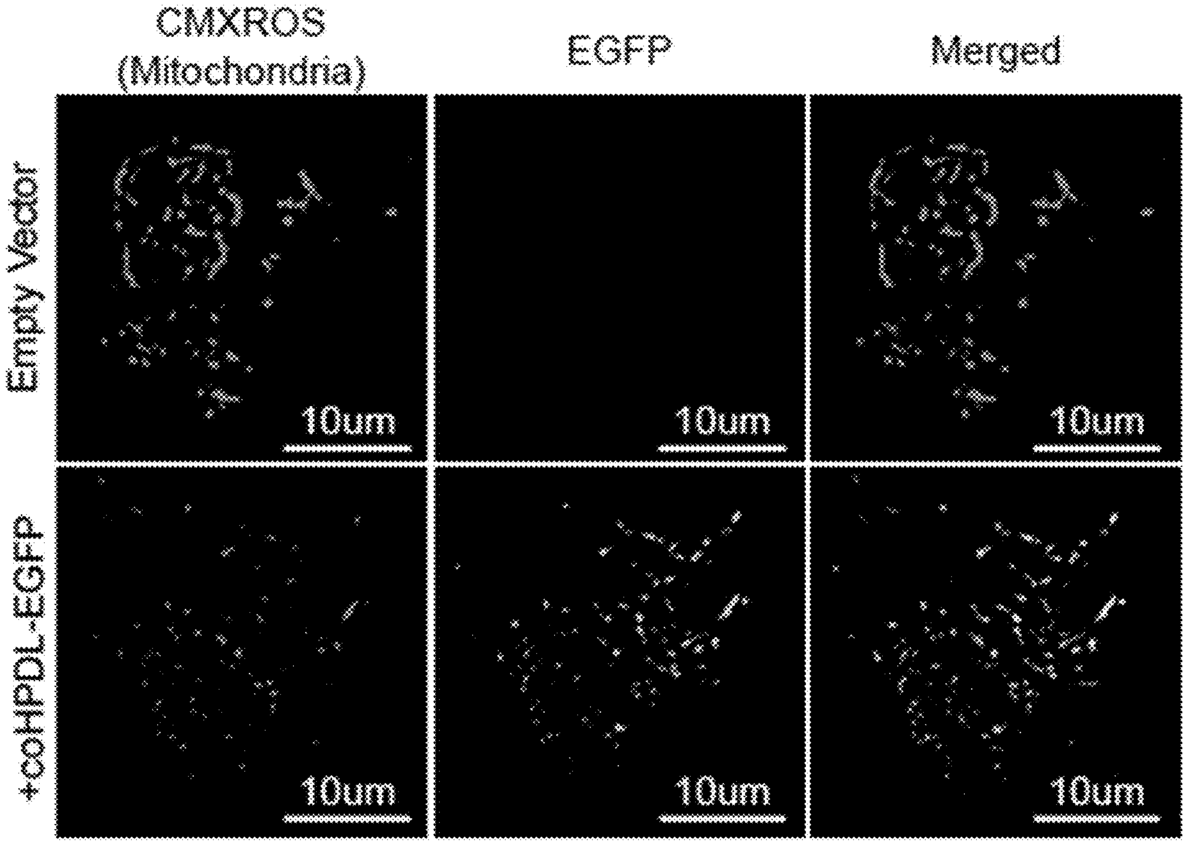
Figure 4E:
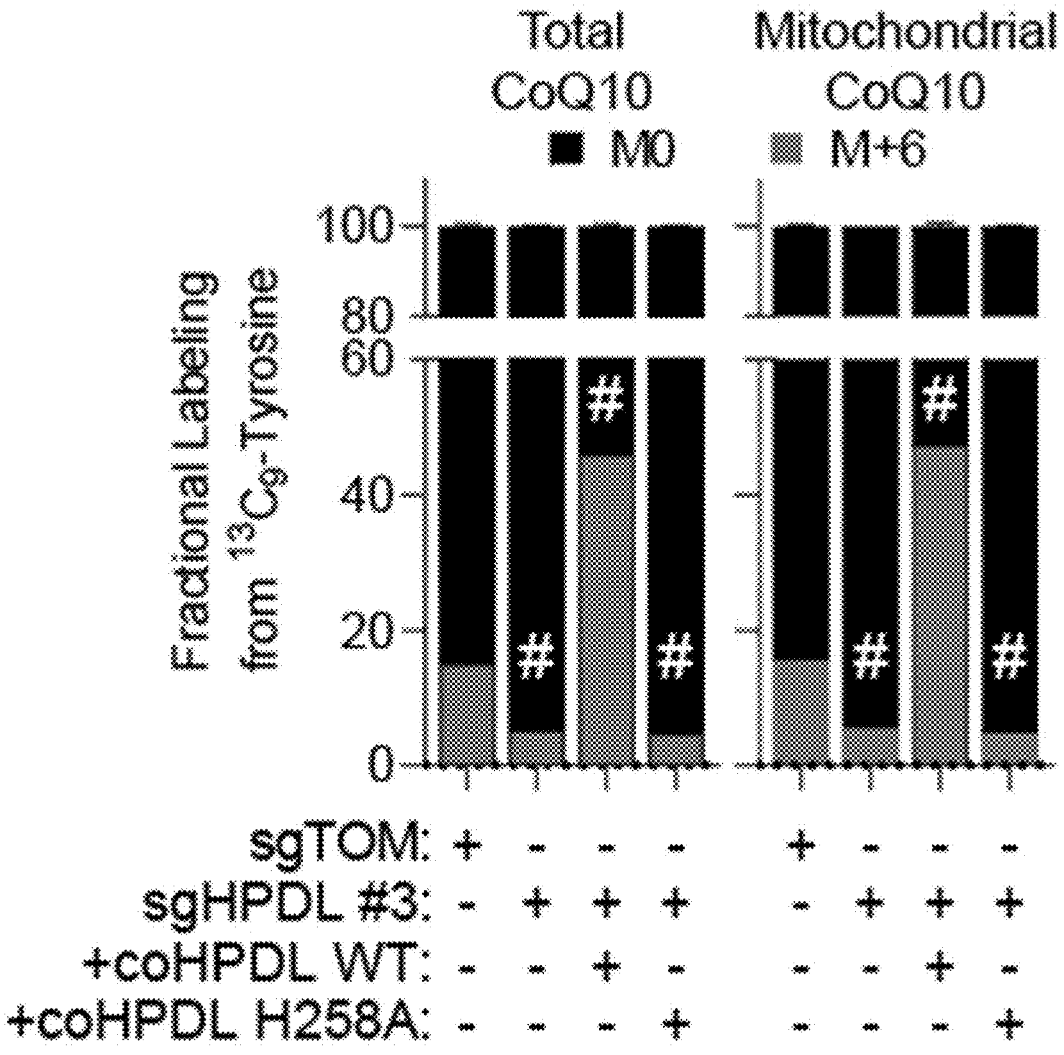
Figure 4F:
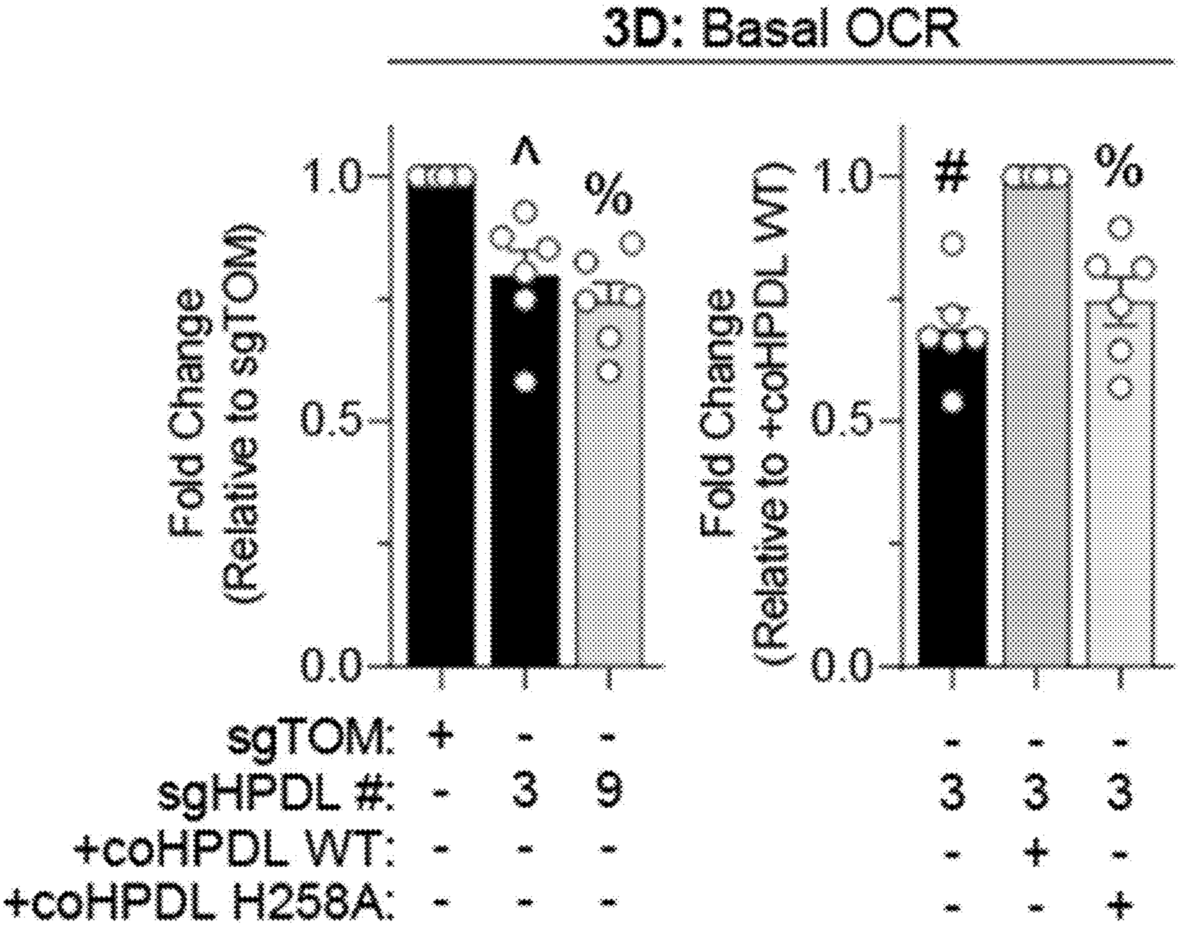
Figure 4G:
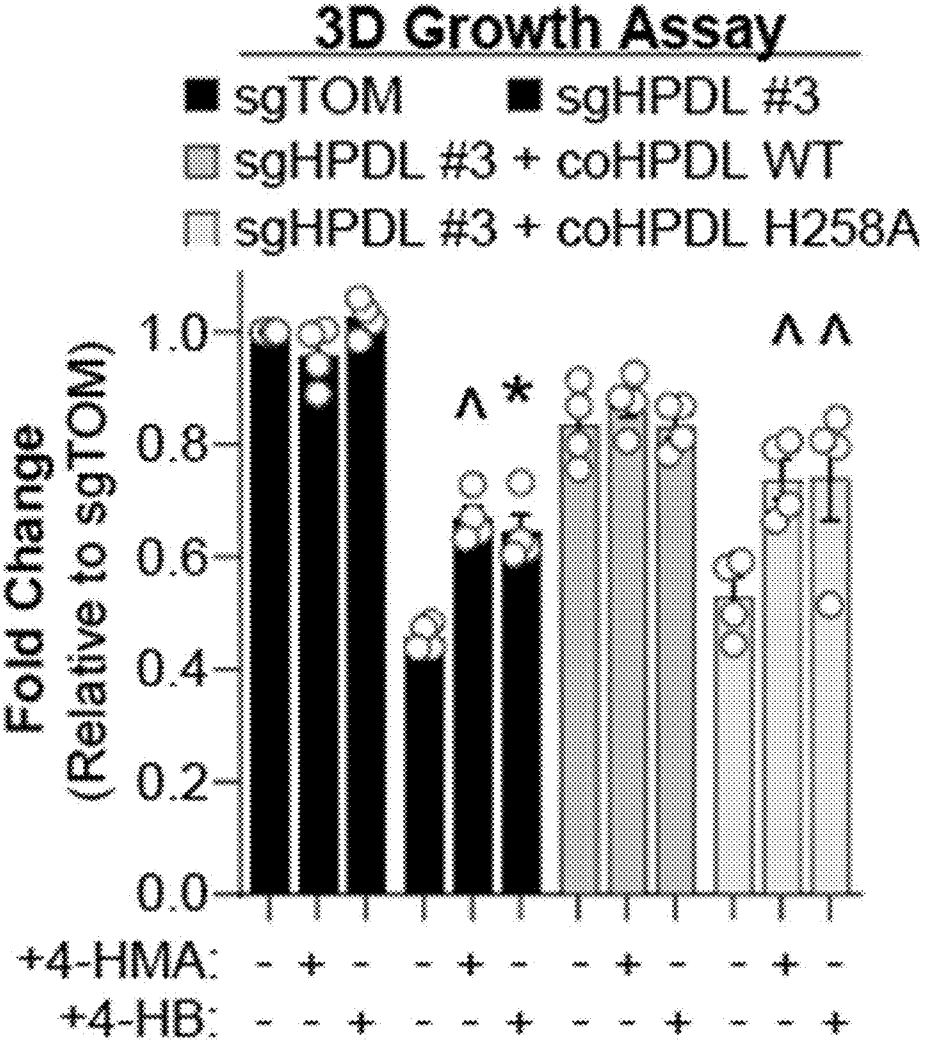
Figure 4H:
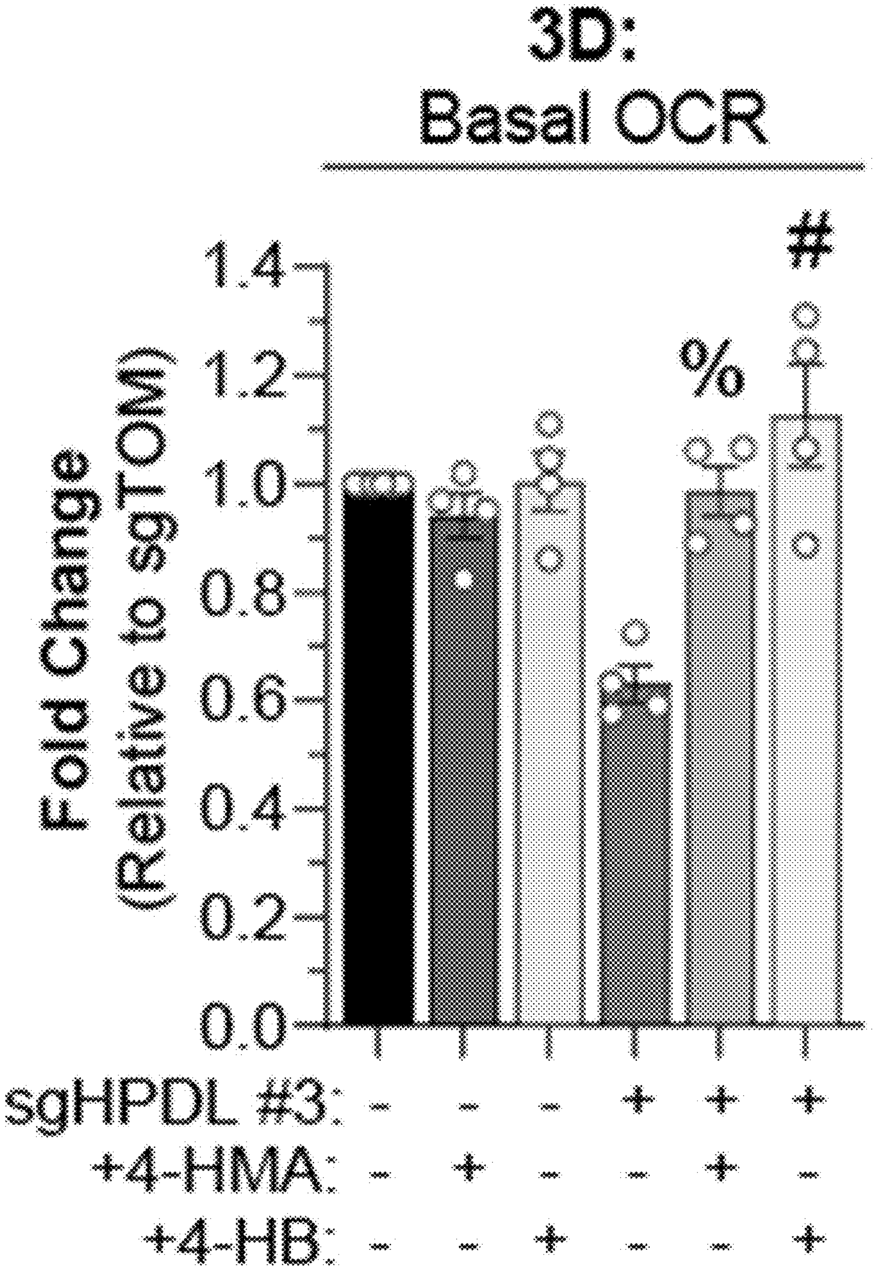

Many of the CoQ10 biosynthesis enzymes reside in the mitochondria and are important for supplying CoQ10 to the electron transport chain needed for cellular respiration?. It was found that HPDL was located in the mitochondria (FIG. 4D and FIG. 12G). To assess the role of HPDL in mitochondrial CoQ10 biosynthesis, Tyr-derived CoQ10 was measured from cells and isolated mitochondria. Mitochondrial CoQ10 labelling from $^{13}C_9$-Tyr was significantly reduced to the same extent as total intracellular CoQ10 in HPDL KO cells (FIG. 4E). Mitochondrial CoQ10 labelling was increased upon expression of coHPDL WT, but not catalytically impaired mutant coHPDL (FIG. 4E). Next, the effects of HPDL loss on cellular respiration was tested by measuring the oxygen consumption rate (OCR) in wild type and HPDL KO cells. Consistent with HPDL's role in mitochondrial CoQ10 synthesis, HPDL KO cells exhibited lower OCR than control cells (FIG. 4F). Furthermore, expression of coHPDL WT, but not catalytically impaired mutant coHPDL, restored OCR. Treatment of HPDL KO cells with exogenous 4-HMA or 4-HB increased 3D growth and OCR (FIG. 4G-4H). These data indicated that HPDL activity and its product, 4-HMA, are important for mitochondrial CoQ10 synthesis and respiration, and cell growth.

Figure 4I:
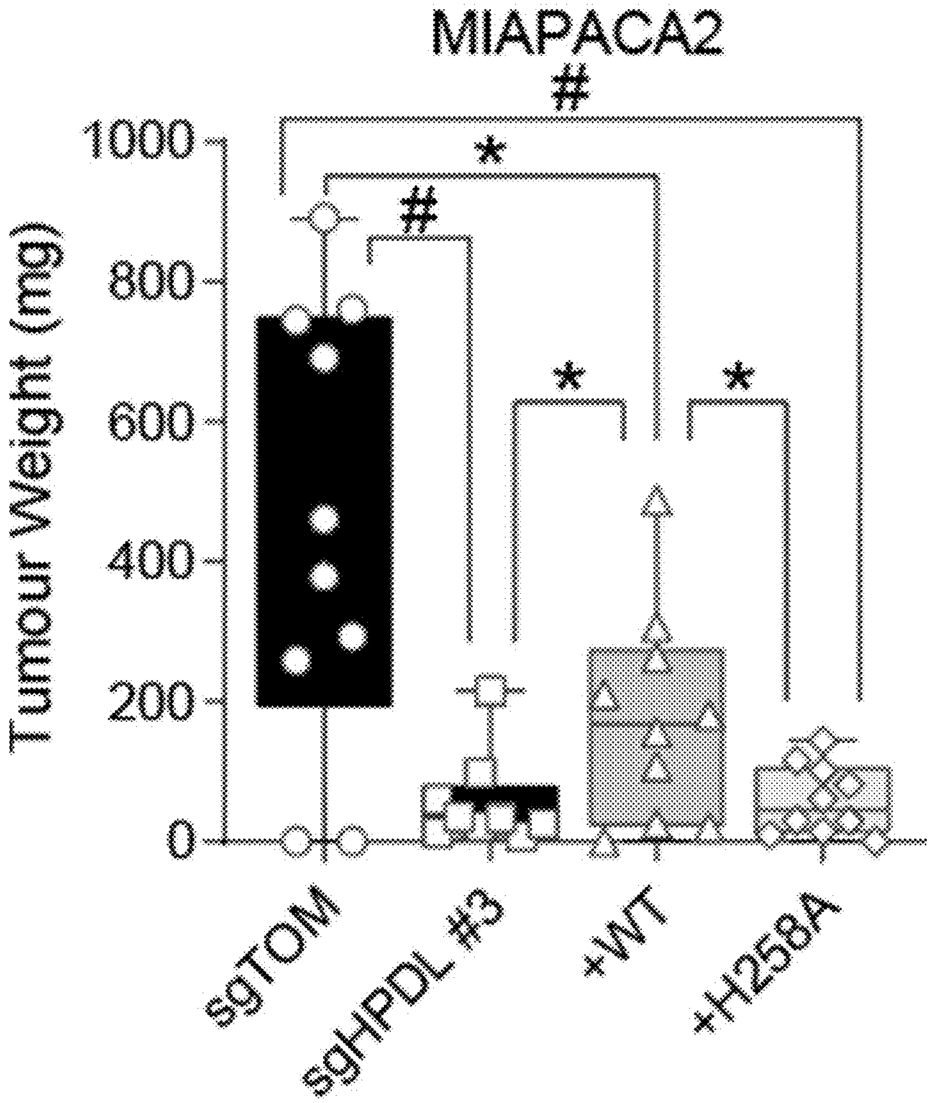
Figure 4J:
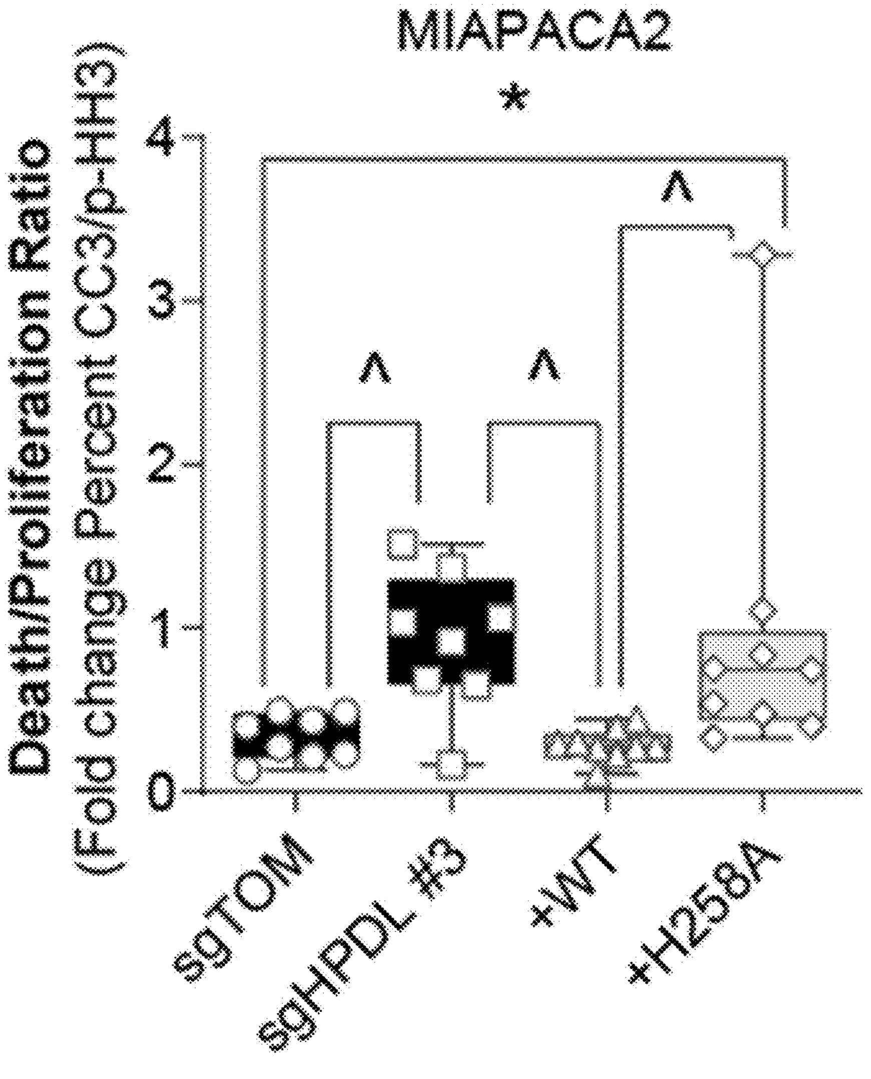
Figure 4K:
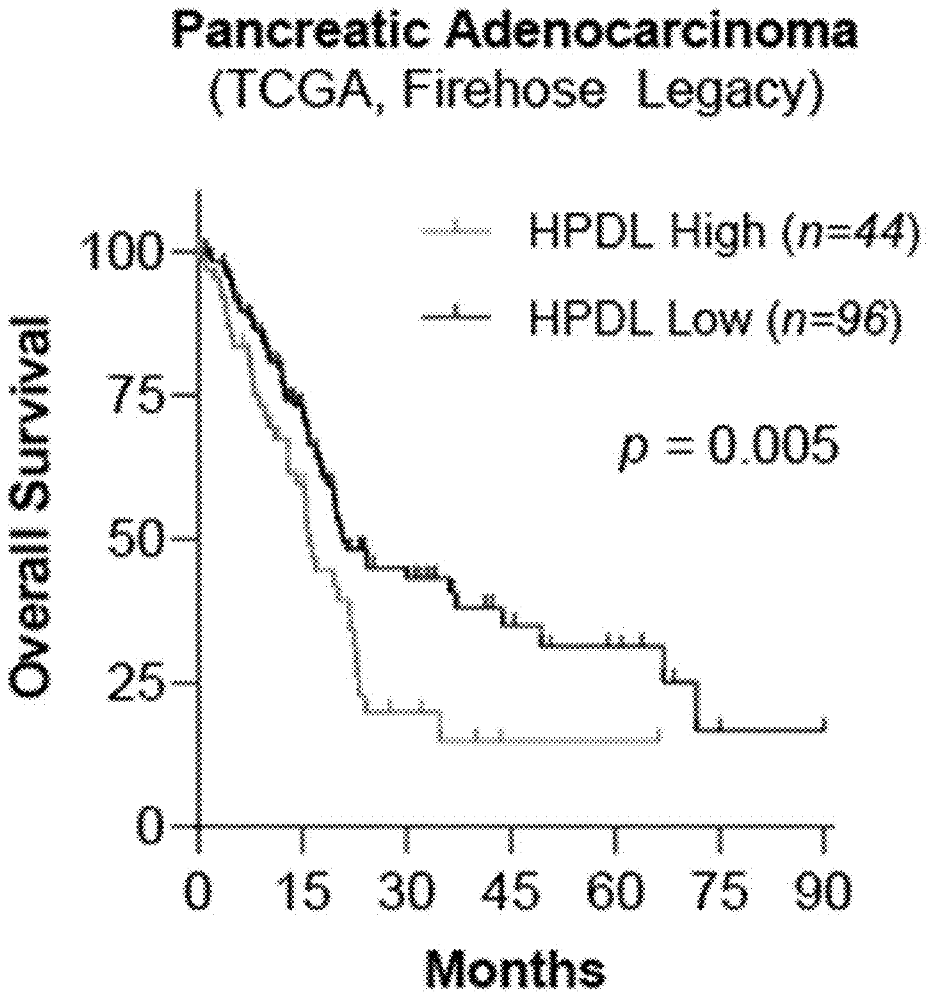

Because CoQ10 has been reported to be important for tumour growth[28], the role of HPDL and the 4-HMA pathway on PDAC tumour growth was evaluated. PDAC cells expressing control and HPDL sgRNAs, with or without coHPDL WT or catalytically impaired mutant, were orthotopically injected into the pancreatic head or the flank of nude mice (FIGS. 4I, FIGS. 12H-12M). After 6 weeks, HPDL KO tumours were significantly smaller than controls. Tumour burden was increased in HPDL KO tumours by expression of coHPDL WT, but not catalytically impaired mutant coHPDL (FIG. 4I). MIAPACA2 HPDL KO tumours exhibited increased proliferation by phospho-histone H3 (p-HH3) staining, but also had higher levels of cell death by cleaved caspase 3 (CC3) (FIGS. 12N-12O). Decreased tumour burden following HPDL KO was likely due to a higher cell death to proliferation ratio (FIG. 4J). Although HPDL was important for MIAPACA2 tumours implanted orthotopically, loss of HPDL was dispensable for orthotopic and subcutaneous PATU-8902 tumour growth. PDAC patients with high expression of HPDL have significantly lower overall and progression-free survival (FIG. 4K and FIG. 12P). These results show that HPDL activity promotes the growth and survival of a subset of PDAC tumours, and that there is heterogeneity in PDAC dependence on HPDL.

GASSP, a simple, robust, and cost-efficient system was demonstrated for gaseous labelling of cultured cells. A standard closed-system chamber was used to label cells with $^{18}O_2$ at different oxygen concentrations and to compare multiple treatment conditions with minimal usage of costly $^{18}O_2$. Using $^{18}O_2$-GASSP, a list of predicted, unexpected, and unknown metabolites that were labelled with $^{18}O$ was identified and generated. The majority of these metabolites were labelled with $^{18}O$ and are unknown in human metabolism. Certain metabolites, such as mannose 6-phosphate, N-acetyl glucosamine, were labelled with $^{18}O$, suggesting that such metabolites are biosynthesized via a step that directly consumes gaseous $^{18}O_2$ or incorporate $^{18}O$ indirectly by reacting with an $^{18}O$ labeled metabolite. In addition, there were many $^{18}O$ labelled metabolites that were not identified. This suggested that gaseous labelling of cells can reveal new biology and pathways that have not been studied in humans.

Figure 4L:
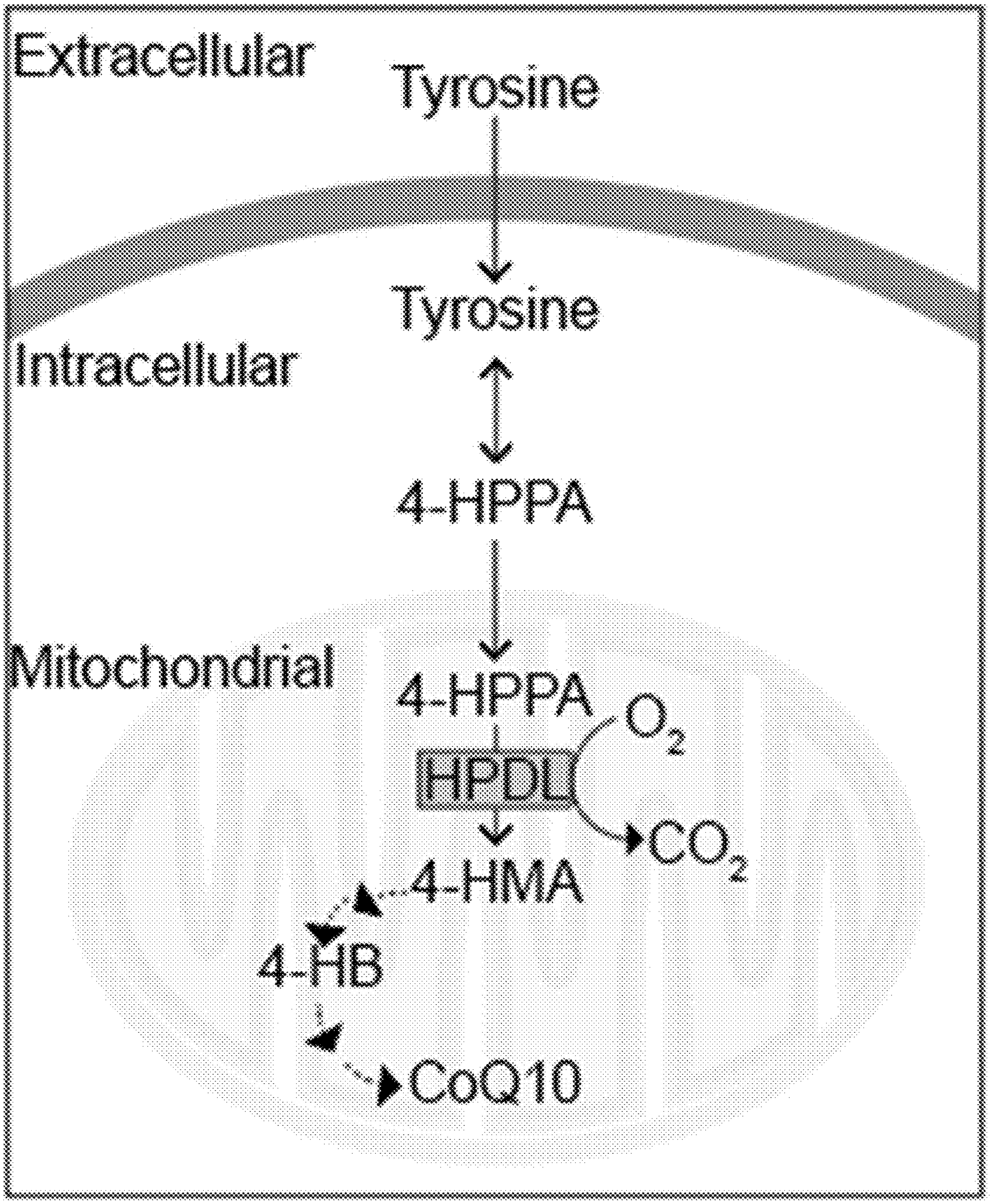

In this study, 4-HMA was identified as the most highly oxygen-labelled metabolite in three of four human cell lines tested. Differential labelling at different oxygen tensions, fragmentation patterns of $^{18}O$ labelled 4-HMA, and dioxygenase inhibitor treatments indicated that 4-HMA was produced by an iron-dependent dioxygenase. HPDL was genetically and biochemically identified as the human dioxygenase involved in the biosynthesis of 4-HMA, and HPDL and 4-HMA were involved in the biosynthesis of Tyr-derived CoQ10 (FIG. 4L and FIG. 13). Evolutionary studies of HPDL show that this enzyme is present in other eukaryotes[37]. Human HPDL aligns to an HPDL homolog in all higher eukaryotes, including other mammals (e.g., monkeys, horses), birds, fish, and a subset of bacteria. It may be speculated that HPDL generates 4-HB in species that no longer have the aromatic amino acid synthesis pathways needed to make other 4-HB precursors, such as chorismate. The HPDL and the 4-HMA biosynthesis pathway was important for PDAC tumorigenesis. HPDL may be a novel therapeutic target for the treatment of patients with PDAC or other cancers. Because statins are known to decrease CoQ10 levels in patients with cardiovascular diseases and these drugs are well tolerated in humans[29], there may be a therapeutic window for targeting HPDL or other enzymes in the CoQ10 biosynthesis pathway as novel cancer treatments.

Although statin-dependent inhibition of CoQ10 biosynthesis does not appear to be detrimental in adults, it may be important for early development. Mutations in COQ enzymes have been linked to CoQ10 deficiency and a wide variety of clinical pathologies[27]. Deleterious mutations occurring in HPDL have not been reported in humans. This may reflect reduced sequencing coverage of this gene, redundant pathways that compensate for poor HPDL function, or low tolerance to loss of HPDL activity during embryonic development.

Recently, HPDL variants were associated with childhood spastic cerebral palsy and severe neurodevelopmental delay with myelination defects[37-40]. Hpdl KO mice exhibited epilepsy, smaller brain sizes due to apoptosis, and perinatal lethality, which phenocopied neurodegenerative disease in patients with HPDL variants[37]. The data presented here suggest HPDL mutations may impair mitochondrial CoQ10 synthesis, and that treatment of patients who carry HPDL mutations with 4-HMA, 4-HB, or CoQ10 may stabilize or ameliorate some of their symptoms.

Tyr is required for the synthesis of 4-HB and the CoQ10 headgroup. However, the steps involved in converting Tyr to 4-HB in human cells have long been elusive[19]. Mammalian cells have been reported to incorporate exogenous p-coumarate, resveratrol, and kaempferol into the headgroup of CoQ10[30,31]. The conversion of 4-HPLA to p-coumarate and 4-HB has been proposed in rats (FIG. 13)[32], however the enzymes involved are not known. High-throughput yeast metabolomic and proteomic efforts have shown that 4-hydroxybenzaldehyde (4-HBz) is converted to 4-HB by Hfd (ALDH3A1 in humans), an aldehyde dehydrogenase[22,23]. These studies noted that 4-HBz was not directly made from 4-HPPA, indicating that there were additional intermediates and enzymes that were not identified in the CoQ10 headgroup synthesis pathway. The present study showed that ALDH3A1 KO did not affect CoQ10 levels or labelling in human cells.

In addition to the proposed HPLA-dependent mechanism of generating 4-HB, 4-HMA was identified as a Tyr-derived intermediate involved in 4-HB synthesis. The ability of human cells to naturally generate 4-HMA revealed one of the intermediates involved in converting 4-HPPA to 4-HB. Consistent with the ability of cells to convert 4-HMA to 4-HB, it was noted that a slow conversion of 4-HMA to 4-HBz occurred in *E. coli* expressing HmaS, presumably by a promiscuous oxidase[16]. In bacteria, 4-HMA is converted to 4-hydroxybenzoylformate (4-HBF) before being converted to 4-HBz and 4-HB[18]. Furthermore, it has been reported that yeast synthesize 4-HBF via Dld1/2 (LDHD and D2HGDH in humans), which were hypothesized to use 4-HMA as a substrate[24]. Yeast do not have an HPDL or HMS ortholog, and it is not clear how they synthesize 4-HMA. CoQ10 biosynthesis was a regulated process that increased at high cellular densities, and was dependent on HPDL and the 4-HMA pathway.

Only 60% of the intracellular CoQ10 pools were labelled with $^{13}C_9$-Tyr after two weeks, even though ~20% $^{13}C$-labelling of CoQ10 occurs after 24 hours. This suggested that there was a Tyr-independent pathway that contributed to CoQ10 synthesis. These data suggested that there were multiple independent pathways capable of biosynthesizing the headgroup of CoQ10, which explains how these pathways have long remained elusive.

Example 5. Coupled Enzymatic Assays

Four different enzymatic assays were performed to assess if HmaS and HPDL were producing the same product.

HmaS (A): $FeSO_4$ (20 μM), 4-Hydroxyphenylpyruvic acid (400 μM), 3-ME (1 mM), Sodium ascorbate (500 μM) and HmaS (1 μM) were mixed in PBS pH 7.4 and incubated at 37° C. under sacking for 90 minutes.

HPDL (B): $FeSO_4$ (20 μM), 4-Hydroxyphenylpyruvic acid (400 μM), 3-ME (1 mM), Sodium ascorbate (500 μM) and HPDL (1 μM) were mixed in PBS pH 7.4 and incubated at 37° C. under sacking for 90 minutes.

4-Hydroxymandelate oxidase (HMAO) and HmaS (C): $FeSO_4$ (20 μM), 4-Hydroxyphenylpyruvic acid (400 μM), 3-ME (1 mM), Sodium ascorbate (500 μM) HmaS (1 μM) and HMAO (1 μM) were mixed in PBS pH 7.4 and incubated at 37° C. under sacking for 90 minutes.

HMAO and HPDL (D): $FeSO_4$ (20 μM), 4-Hydroxyphenylpyruvic acid (400 μM), β-ME (1 mM), Sodium ascorbate (500 μM) HmaS (1 μM) and HMAO (1 μM) were mixed in PBS pH 7.4 and incubated at 37° C. under sacking for 90 minutes.

After the completion of these enzymatic assays, the mixture was dried over vacuum then a methoxyamine (MOX)/tert-butyldimethylsily (TBDMS) derivatization was performed. The derivatised product was then injected into a gas chromatography mass spectrometry (GCMS) and the 3 peaks corresponding to 4-HMA ions were quantified (351-425-453).

The results of the coupled enzymatic assays are presented in FIGS. 14A-14B. The same peaks were observed for A and B, indicating that HmaS and HPDL were both producing 4-HMA as expected. However, when HMAO was added, only C showed a significant decrease in the signal indicating that HMAO was only able to convert the 4-HMA produced by HmaS and not by HPDL. These data demonstrated that the enantiomer of 4-HMA produces by HPDL is not the same than the one produced by HmaS which has been already described in the literature as ((S)-2-hydroxy-2-(4- hydroxyphenyl)acetic acid). Therefore, HPDL is likely producing the (R)-2-hydroxy-2-(4-hydroxyphenyl)acetic acid.

Example 6. 4-HMA and 4-HB Supplementation in HPDL Knockout Mouse Pups

Hpdl+/−mice (C57BL/6 background) were obtained from the international mouse knockout consortium/knockout mouse project. Mating pairs were established and pups were genotyped at 3 days postpartum (P3) by PCR. Solutions of 4-HMA and 4-HB were prepared in water to a concentration of 10 mM. Pups were fed at either day 3 or day 7 postpartup with 10 μL of this solution every day or every other day, 5 days per week, until weaning, at which point the water was replaced with water containing 4-HMA or 4-HB.

The effect of treating a mouse with 4-HMA (10 μL of a 10 mM solution in water; 18.6 μg mouse; final dose is ~10 mg/kg) starting on postpartum day 3 or postpartum day 8 is shown in FIG. 23. The untreated mouse was dead on postpartum day 12. The treated mouse was dosed with 4-HMA on days 7, 9, 10, 11, and every day until postpartum day 21, when 4-HMA was added to the drinking water. Survival data for an untreated mouse pup and mouse pups treated with 4-HMA are shown in FIG. 24. Similar results have been observed with 4-HB supplementation (10 mg/kg) (FIG. 25). Once the mice are weaned, supplementation of 4-HB or 4-HMA in the drinking water continues (assuming 5 mL of water consumed per mouse per day, the concentration of 4-HB or 4-HMA is adjusted to 10 mg/kg/5 mL water).

Below are the methods used in the Examples described above.

For equipment and reagants, a modular incubator chamber and dual flow meter were purchased from Billups-Rothenberg inc. $^{18}O_2$:$CO_2$:$N_2$ gas mixtures were purchased from Icon Isotopes. $N_2$ and $^{16}O_2$:$CO_2$:$N_2$ were purchased from Airgas. An oxygen sensor (Altair 4 XR) was purchased from and calibrated by MSA. 4-hydroxyphenylpyruvate, 4-DL-hydroxyphenyllactate, and sodium ascorbate were purchased from Millipore Sigma. 4-DL-hydroxymandelate and 4-hydroxybenzoate were purchased from Alfa Aesar. MG132 and IOX1 were purchased from Tocris. $^{13}C_9$-tyrosine, $^{13}C_6$-phenylalanine and labelled amino acid internal standards were purchased from Cambridge Isotopes Laboratories. Antibodies were purchased and used for immunoblotting at the manufacturer-recommended concentrations. Non-limiting examples of antibodies of the present disclosure are provided in Table 2. Non-limiting examples of chemicals of the present disclosure are provided in Table 3. Non-limiting examples of kits of the present disclosure are provided in Table 4. Non-limiting examples of cell lines of the present disclosure are provided in Table 5. Non-limiting examples of recombinant DNA of the present disclosure are provided in Table 6. Non-limiting examples of oligonucleotides of the present disclosure are provided in Table 7. Non-limiting examples of software of the present disclosure are provided in Table 8. Non-limiting examples of software of the present disclosure are provided in Table 9.

TABLE 2

| Antibodies | |
|---|---|
| Description | Source |
| Mouse anti-HIF1α | BD Transduction Laboratories |
| Rabbit anti-HIF1α-P564-OH | Cell Signaling |

TABLE 2-continued

| Antibodies | |
|---|---|
| Description | Source |
| Mouse anti-ERK2 | Santacruz |
| Rabbit anti-HPDL | Sigma: Protein Atlas |
| Mouse anti-Flag M2 | Sigma |
| Rabbit anti-S6K | Cell Signaling |
| Mouse anti-Flag M2 Magnetic Beads | Sigma |
| Rabbit anti-ATTY | Abcam |
| Rabbit anti-LDHD | Sigma: Protein Atlas |
| Rabbit anti-ALDH3A1 | Sigma: Protein Atlas |
| Rabbit anti-COQ2 | Sigma: Protein Atlas |
| Rabbit anti-Golgin-97 | Cell Signaling |
| Rabbit anti-Calnexin | Cell Signaling |
| Mouse anti-Rab5A | Cell Signaling |
| Rabbit anti-LC3B | Cell Signaling |
| Rabbit anti-β-tubulin | Cell Signaling |
| Rabbit anti-Histone H2A | Cell Signaling |
| Rabbit anti-Histone H3 | Cell Signaling |
| Mouse anti-TUFM | Sigma: Protein Atlas |
| Rabbit anti-COX IV | Cell Signaling |
| Rabbit anti-phospho-Histone H3 (S10) | Cell Signaling |
| Rabbit anti-Cleaved Caspase 3 | Cell Signaling |
| IRDye ® 680RD Goat anti-Mouse IgG (H + L) | LiCOR |
| IRDye ® 800CW Goat anti-Rabbit IgG (H + L) | LiCOR |

TABLE 3

| Chemicals | |
|---|---|
| Description | Source |
| MG132 | TOCRIS |
| IOX1 | TOCRIS |
| Sodium L-Ascorbate | Sigma |
| Homogentisate (HGA) | Sigma |
| L-Tyrosine | Sigma |
| 4-Hydroxyphenylpyruvic acid | Sigma |
| DL-4-Hydroxyphenyllactatic acid | Sigma |
| DL-4-Hydroxymandelic acid | Alfa Aesar |
| 4-Hydroxybenzoic acid | Alfa Aesar |
| p-coumarate (trans-4-Hydroxycinnamic acid) | Alfa Aesar |
| (±)-Octopamine hydrochloride | Alfa Aesar |
| Tyramine hydrochloride | Alfa Aesar |
| L-Tyrosine (13C9, 99%) | Cambridge Isotope Laboratories |
| L-Phenylalanine (RING-13C6, 99%) | Cambridge Isotope Laboratories |
| COENZYME Q10 (UBIQUINONE) (DIMETHOXY-D6, METHYL-D3, 98%) | Cambridge Isotope Laboratories |
| Metabolomics Amino Acid Mix Standard | Cambridge Isotope Laboratories |
| 2-Mercaptoethanol, 99%, extra pure, ACROS Organics | Fisher |
| Iron(II) sulfate heptahydrate | Sigma |
| HEPES | Sigma |
| Methoxyamine Hydrochloride | Sigma |
| Pyridine | Fisher |
| N-tert-Butyldimethylsilyl-N-methyltrifluoroacetamide with 1% tert-Butyldimethylchlorosilane | Sigma |
| Growth factor-reduced Matrigel | Fisher Scientific |

TABLE 4

| Kits | |
|---|---|
| Description | Source |
| CyQUANT ™ Cell Proliferation Assay, for cells in culture | ThermoFisher |
| Seahorse XFe96 Spheroid FluxPak | Agilent |
| MitoTracker ™ Red CMXRos | ThermoFisher |
| Qproteome Mitochondria Isolation Kit | Qiagen |

TABLE 5

| Cell Lines | | |
|---|---|---|
| Description | Source | Catalog # |
| MIAPACA2 | ATCC | CRL-1420 ™ |
| A498 | ATCC | HTB-44 ™ |
| HepG2 | ATCC | HB-8065 ™ |

TABLE 5-continued

| Cell Lines | | |
|---|---|---|
| Description | Source | Catalog # |
| SKNDZ | ATCC | CRL-2149 ™ |
| 293T | ATCC | CRL-3216 ™ |

TABLE 6

| Recombinant DNA | |
|---|---|
| Description | Source |
| TLCV2 | Addgene |
| TLCV2-sgTomato (sgTOM) | This study |
| TLCV2-sgLuciferase (sgLUC) | This study |
| TLCV2-sgHPDL #3 (sgHPDL #3) | This study |
| TLCV2-sgHPDL #9 (sgHPDL #9) | This study |
| pLenti6.2-HPDL WT-3xFlag-V5 | This study |
| pLenti6.2-HPDL H258A-3xFLAG-V5 | This study |
| pLenti6.2-HPDL H163/258A-3xFLAG-V5 | This study |
| pLenti6.2-HPDL WT-EGFP | This study |
| psPAX2 | Addgene |
| pMD2.G | Addgene |

TABLE 7

| Oligonucleotides | | |
|---|---|---|
| Description | Sequence | SEQ ID NO. |
| sgTOM F | 5'-CACCGGGCCACGAGTTCGAGATCGA-3' | 1 |
| sgTOM R | 5'-AAACTCGATCTCGAACTCGTGGCCC-3' | 2 |
| sgLUC F | 5'-CACCGACAACTTTACCGACCGCGCC-3' | 3 |
| sgLUC_R | 5'-AAACGGCGCGGTCGGTAAAGTTGTC-3' | 4 |
| Human sgHPDL 3F | 5'-CACCGGACTCAGCCAGAACAAGAGT-3' | 5 |
| Human sgHPDL_3R | 5'-AAACACTCTTGTTCTGGCTGAGTCC-3' | 6 |
| Human sgHPDL 9F | 5'-CACCGGTGGAACCAGCGCAAAAGTG-3' | 7 |
| Human sgHPDL_9R | 5'-AAACCACTTTTGCGCTGGTTCCACC-3' | 8 |
| Human sgTAT_10F | 5'-CACCGTGGCCAACACAGCTAAACAA-3' | 9 |
| Human sgTAT_10R | 5'-AAACTTGTTTAGCTGTGTTGGCCAC-3' | 10 |
| Human sgLDHD 4F | 5'-CACCGGGCCACACCACAGCATCAGG-3' | 11 |
| Human sgLDHD_4R | 5'-AAACCCTGATGCTGTGGTGTGGCCC-3' | 12 |
| Human sgLDHD_6F | 5'-CACCGGGACAACGTGCTCAACCTGG-3' | 13 |
| Human sgLDHD_6R | 5'-AAACCCAGGTTGAGCACGTTGTCCC-3' | 14 |
| Human sgALDH3A1_2_F | 5'-CACCGGAAGCTCCCTGAGTGGGCCG-3' | 15 |
| Human sgALDH3A1_2_R | 5'-AAACCGGCCCACTCAGGGAGCTTCC-3' | 16 |
| Human sgALDH3A1_4_F | 5'-CACCGGGTGGGGAAGATCATCATGA-3' | 17 |
| Human sgALDH3A1_4_R | 5'-AAACTCATGATGATCTTCCCCACCC-3' | 18 |
| Human sgCOQ2_2_F | 5'-CACCGGGGGCTGCAAGTCACCACCG-3' | 19 |
| Human sgCOQ2_2_R | 5'-AAACCGGTGGTGACTTGCAGCCCCC-3' | 20 |

TABLE 7-continued

| Oligonucleotides | | |
|---|---|---|
| Description | Sequence | SEQ ID NO. |
| Human sgCOQ2_3_F | 5'-CACCGCCAGCTCAGTTTGTCCGCGG-3' | 21 |
| Human sgCOQ2_3_R | 5'-AAACCCGCGGACAAACTGAGCTGGC-3' | 22 |

TABLE 8

| Software | |
|---|---|
| Description | Source |
| Xcalibur | ThermoFisher |
| Chromeleon | ThermoFisher |
| GraphPad Prism 9 | Graphpad Software, LLC |
| CLUSTALW | UCD Dublin |
| Jalview | Waterhouse, A.M., Procter, J.B., Martin, D.M.A, Clamp, M. and Barton, G. J. (2009) Jalview Version 2 a multiple sequence alignment editor and analysis workbench Bioinformatics doi: 10.1093/bioinformatics/btp033 |
| Imagescope | Leica |
| MATLAB | Math Works |

TABLE 9

| Gaseous Labelling Equipment | |
|---|---|
| Description | Source |
| Modular Incubator Chamber (MIC-101) | Billups-Rothenberg |
| Dual Flow Meter | Billups-Rothenberg |
| 5%:5%:90% $^{16}O_2$:$CO_2$:$N_2$ | Airgas |
| 0.5%:5%:94.5% $^{16}O_2$:$CO_2$:$N_2$ | Airgas |
| 5%:5%:90% $^{18}O_2$:$CO_2$:$N_2$ | Berry&Associates/ ICON Isotopes |
| 1.5%:5%:93.5% $^{18}O_2$:$CO_2$:$N_2$ | Berry&Associates/ ICON Isotopes |
| 0.5%:5%:94.5% $^{18}O_2$:$CO_2$:$N_2$ | Berry&Associates/ ICON Isotopes |
| MSA ALTAIR 4XR Multigas Detector (LEL, $O_2$, $CO_2$, $H_2S$) with Bluetooth | Amazon |

For cell culture and infection, MIAPACA2 cells were purchased from the American Type Culture Collection. No lines used were found in the ICLAC or NCBI Biosample databases of commonly misidentified cell lines. Cultures were routinely verified to be negative for *mycoplasma* by PCR. Cell lines were authenticated by periodic STR fingerprinting and visual inspection, and low passage cultures were carefully maintained in a central lab cell bank[33]. 293T cells were used to generate lentivirus for stable expression of constructs in cell lines. Cells were stably infected with an all-in-one pLentiCRISPRv2 (TLCV2)-lentiviral vector expressing a dox-inducible-Cas9-2A-eGFP and U6-driven sgRNA guides against Tomato (sgTOM), Luciferase (sgLUC), or HPDL (sgHPDL) (See Table 7 above for sequences). sgRNA-resistant coHPDL-FLAG wild-type (WT) and catalytically impaired mutants (H258A and H163/258A) were stably expressed in HPDL-KO cells using a lentiviral vector harboring a blasticidin resistance gene, pLenti6.2. Cells were selected with 2 μg/mL puromycin for 2 days or 10 μg/mL blasticidin for 10 days. All cell lines were maintained in DMEM+10% FBS. Growth curves and experiments were performed with DMEM (high glucose, no pyruvate)+10% dialyzed FBS, and measured with a CyQUANT Cell Proliferation Assay kit (ThermoFisher) following the manufacturer's instructions.

For the 3D growth assay, approximately 2,500 cells were seeded into a low-attachment 96-well plate containing DMEM+10% diaFBS and 5% Matrigel. Cells were grown for three days at 37° C. and 5% $CO_2$. Cells were also treated or without 1 mM 4-HMA or 4-HB for the duration of the assay. To measure 3D growth with the CyQUANT Cell Proliferation Assay kit, plates were frozen at −80° C., thawed at room temperature, and equal volumes of 2× CyQUANT reagent+lysis buffer was added to the wells. As a control, wells containing media+5% Matrigel and no cells were used as blanks. CyQUANT measurements were performed as described in the manufacturer's instructions.

All steps involved in setting up labelling with $^{18}O_2$ were performed at room temperature and inside a chemical fume hood. The procedure may vary depending on the type and number of tissue culture plates in the chamber and the amount of media in the plates. Users must test the system by using $^{16}O_2$:$CO_2$:$N_2$ or other unlabelled gases to optimize conditions for their needs and avoid consumption of costly labelled gases. Cells were treated with or without 5 μM MG132, 500 μM IOX1, 250 μM DFO, or 70 μM ascorbate, before placing tissue culture plates into the modular incubator chamber (MIC) containing a wireless oxygen sensor and a 15 cm dish of water to maintain humidity. Next, the clamps were closed to form an air-tight seal between the lid and platform of the MIC. To expel natural $O_2$ from the chamber, both the inlet and outlet valves of the MIC were opened, and $N_2$ was flushed into the system at a rate of 40 L/min for 2 minutes, after which both valves were quickly closed to allow the system to equilibrate for 10 minutes. $N_2$ flushing was repeated for a total of three times, or until the sensor in the chamber stabilized at 0% $O_2$ for 10 minutes.

Next, the inlet valve was opened and the $^{18}O_2$:5% $CO_2$:$N_2$ gaseous mixture was flushed into the system at a rate of 2.5 L/min. Subsequently, the outlet valve was immediately opened to allow gas flow out of the chamber, and to release the pressure in the system. The chamber was injected with the $^{18}O_2$:5% $CO_2$:$N_2$ gaseous mixture for 1 minute before the inlet and outlet valves were closed simultaneously. The chamber was allowed to equilibrate for 5 minutes. This process was repeated seven times, or until the desired oxygen concentration was reached and was stable. For 3%, 1%, and 0.2% $^{18}O_2$ labelling studies, the chamber was infused with 5%:5%:90%, 1.5%:5%:93.5%, and 0.5%:5%:94.5% $^{18}O_2$:$CO_2$:$N_2$, respectively. The $^{18}O_2$-infused MIC was then placed in a 37° C., 5% $CO_2$ tissue culture incubator for 24 hours. The oxygen concentration in the chamber was monitored regularly. Oxygen measurements after 20 hours was not feasible due to the battery life of the sensor. At the end of the experiment, the chamber was opened inside a chemical fume hood before metabolite extraction.

For the HPDL enzymatic assay, cell lysates were generated in TNE lysis buffer (50 mM Tris-HCl pH 8.0, 150 mM NaCl, 2 mM EDTA, and 1% NP-40, supplemented with protease (ThermoFisher Scientific) and phosphatase (10 mM NaF, 10 mM β-glycerophosphate, and 10 mM sodium pyrophosphate) inhibitors. HPDL-FLAG was immunoprecipitated using anti-FLAG M2 magnetic beads (Millipore Sigma, M8823). Cell lysates were incubated with anti-FLAG M2 magnetic beads for 1 hour at 4° C. on a rotating platform. Beads were washed four times with TNE lysis buffer, and then 10% and 90% of the immunopurified protein was used for immunoblotting or enzymatic assay, respectively. For the HPDL enzymatic assay, beads were incubated in assay buffer (20 mM HEPES pH 7.4, 20 μM $FeSO_4$, 0.5 mM sodium ascorbate, and 1 mM β-mercaptoethanol) containing 400 μM of substrate (tyrosine, 4-hydroxyphenylpyruvate, or 4-hydroxyphenyllactate) for 1 hour at 37° C. At the end of the assay, 10 uL of assay buffer was retrieved and prepared for analysis by gas chromatography-mass spectrometry (GC-MS, see Metabolomics section).

For immunoblotting and HIF1α immunoprecipitation, whole cell lysates were generated in modified radioimmunoprecipitation (RIPA) buffer (50 mM Tris-HCl pH 8.0, 150 mM NaCl, 2 mM EDTA, 1% NP-40, and 0.1% SDS, without sodium deoxycholate supplemented with protease (ThermoFisher Scientific) and phosphatase (10 mM NaF, 1 mM Na3VO4, 10 mM β-glycerophosphate, and 10 mM sodium pyrophosphate) inhibitors. Protein lysates for HIF1α immunoprecipitation were precleared with Protein G sepharose beads for 20 mins, and transferred to a new tube containing control IgG or mouse anti-HIF1α antibody. Lysates containing antibodies were incubated overnight at 4° C. on a rotating platform, followed by incubation with protein G sepharose beads for 3 hours. Immunoprecipitations were washed with modified RIPA buffer and analyzed by immunoblotting. Protein lysates were loaded into 4-12% gradient Bolt gels (Life Technologies) and transferred with 1× transfer buffer (Tris-glycine) and 10% methanol. Membranes were incubated with their respective primary antibodies, and visualized with TRDye infrared secondary antibodies using an Odyssey Infrared imaging system (Li-Cor Biosciences).

Mitochondria were purified from cells using a Qproteome Mitochondria Isolation Kit (Qiangen), following the manufacturer's instructions. Briefly, cells were trypsinized, washed, and resuspended in 0.9% saline. About 10% of the cell suspension was set aside for total protein analysis, and the remaining suspension was used for mitochondrial purification. The cytosolic fraction was kept for further downstream analysis. Purified mitochondria were washed and resuspended in 0.9% saline. 10% of the mitochondria suspension was transferred to a new tube for mitochondrial protein analysis, and the remaining suspension was extracted with 46% methanol:23% $H_2O$:31% chloroform as described in the Metabolomics section. The $CH_3Cl$ fraction was set aside for lipids. Protein lysates were generated from the total, cytosolic, and mitochondria fractions with modified RIPA buffer supplemented with protease and phosphatase inhibitors. Equal cell volumes of total, cytosolic and mitochondria protein were evaluated by immunoblotting to check mitochondrial purity.

For 4-hydroxymandelic acid derivatization, acetic anhydride (10.6 mg, 0.104 mmol, 3.5 equiv.) was added slowly to a solution of 4-hydroxymandelic acid (5.0 mg, 0.030 mmol, 1 equiv.) in pyridine (1 ml), and stirred at room temperature overnight. After completion of the reaction, the solvent was evaporated and the crude product was resuspended in water. The mixture was then extracted twice with $CHCl_3$ and the organic phase evaporated under vacuum to afford the bis-acetylated hydroxymandelic acid derivative. This derivative (5.0 mg, 0.020 mmol, 1 equiv.) and (−)-menthol (6.2 mg, 0.040 mmol, 2 equiv.) was dissolved in dry $CH_2Cl_2$ (0.5 ml) and the solution was cooled to 0° C. N-(3-Dimethylaminopropyl)-N'-ethylcarbodiimide hydrochloride (5.7 mg, 0.030 mmol, 1.5 equiv.) and 4-dimethylaminopyridine (1.2 mg, 0.010 mmol, 0.5 equiv.) were then added, and the reaction was warmed to room temperature and stirred for 10 hours. The solvent was evaporated under vacuum and the crude product was directly injected into the GC-MS.

For derivatization of 4-HMA from cells, polar metabolites were extracted with 46% methanol:23% $H_2O$:311% chloroform, vortexed, and centrifuged as described in the Metabolomics section. The aqueous phase was transferred to new Eppendorf tubes and dried down in a SpeedVac. The polar metabolite extract was resuspended in water, and separated by LC as described in the Metabolomics section. The fraction containing 4-HMA was derivatized as described above, and separated and analyzed by GC-MS.

For metabolomics, briefly, cells were washed in 4° C. 0.9% saline and metabolites were extracted with 46% methanol:23% H2O:311% chloroform that contained a labelled amino acid standard mix (MSK-A2-1.2, Cambridge Isotope Laboratories, Inc.). Enzymatic assay samples were extracted using 80% methanol: 20% H2O that contained labelled amino acid standards. Extracts were placed into 1.5 mL Eppendorf tubes, vortexed at 4° C. for 10 min and centrifuged at 4° C. for 10 min at 17,200×g in a microcentrifuge. The aqueous phase was transferred to vials for GC-MS or Eppendorf tubes for LC-MS. Polar samples were evaporated in a SpeedVac and samples were resolved by GC-MS or LC-MS. Lipid samples were dried using a stream of $N_2$ (for $^{18}O$ labelling studies) or air. Metabolite and lipid extracts were submitted to the NYULMC Metabolomics Core Resource Laboratory.

For GC-MS, the metabolite extracts were derivatized with a solution of methoxamine (Sigma) dissolved in pyridine (Sigma) for 30 min at 37° C. An equal volume of MSTB-STFA+1% tert-butyldimethylsilane chloride (TBDMSCl) was added to the mixture and incubated at 37° C. for 30 mins. For separation of RS-4-IMA, 4-hydroxymandelic acid derivatized samples were prepared as described above and resuspended in pyridine before injection. Samples were resolved by GC (Agilent, 122-3832UI), peaks were picked using OpenChrom34, and analyzed using MATLAB.

For polar metabolomics, the LC column was a Millipore ZIC-pHILIC (2.1×150 mM, 5 μm bead size) coupled to a Dionex UltiMate 3000 system. The column oven temperature was held at 25° C. The flow rate was 100 μL/min, and the injection volume was 1 μL. Buffer A was 10 mM ammonium carbonate in water, pH 9, and Buffer B was neat acetonitrile. The gradient profile was 80-20% B (0-30 min), 20-80% B (30-31 min), and 80-80% B (31-42 min). MS Analyses were carried out on a Thermo Q Exactive HF mass spectrometer using a heated electrospray ionization (HESI) source. The method duration was 30 min using a polarity-switching, top 5 method. The spray voltage for both positive and negative ion modes was 3.5 kV. The capillary temperature was 320° C. with a maximum spray current of 100 ρA. The full MS scan was carried out at 120,000 resolution with a scan range of 67-1000 m/z. For $^{18}O_2$ labelling experiments, full MS scans were carried out at 240,000 resolution at the same scan range. Tandem MS spectra were obtained at 15,000 resolution. All data were acquired in profile mode. Peak heights were analyzed using Xcalibur (ThermoFisher Scientific).

Lipid metabolomics were acquired using a Waters CSH-C18 (2.1×100 mm, 1.7 μm) column coupled to a Dionex UltiMate 3000 system. The column oven temperature was held at 55° C. The flow rate was 300 μL/min and the injection volume was 1 μL. Buffer A was 60:40 acetonitrile: water, 0.1% formic acid and Buffer B was 90:10 isopropanol:acetonitrile, 10 mM ammonium formate. The gradient profile was 40-43% B (0-1.25 min), 43-50% B (1.25-2 min), 50-54% B (2-11 min), 54-70% B (11-12 min), 70-99% B (12-18 min), 70-99% B (18-32 min), 99-40% B (23-24 min), hold at 40% B (1 min). MS Analyses were carried out on a Thermo Q Exactive HF mass spectrometer using a heated electrospray ionization (HESI) source. The method duration was 20 minutes using a polarity-switching, top 10 method. The spray voltage for both positive and negative ion modes was 3.5 kV. The capillary temperature was 320° C. with a maximum spray current of 100 ρA. The full MS scan was carried out at 120,000 resolution with a scan range of 350-2000 m/z. For $^{18}O_2$ labelling experiments, full MS scan was carried out at 240,000 resolution at the same scan range. Tandem MS spectra were obtained at 15,000 resolution. All data were acquired in profile mode. Peak heights were analyzed using Xcalibur (ThermoFisher Scientific).

Identification of $^{18}O_2$ labelled features and metabolites was performed as described in FIG. 1B. Briefly, all features with a minimum signal intensity of 10,000 and a signal-to-noise ratio of 10 were obtained from the $^{16}O_2$ (control) samples by the NYULMC Metabolomics Core. Background features from blank sample runs were removed from the total features in the samples if signalSample was less than two times the signalBlank. Features identified after 20 min were also removed. Using this list of $^{16}O$ features, the incorporation of $^{18}O_2$ into labelled samples for the unlabelled and labelled $^{18}O$ features was measured using a mass difference of +2.0042 m/z per $^{18}O$ atom. As the number of oxygen atoms per feature was not known, it was concluded that no more than three $^{18}O$ atoms would be incorporated per metabolite. Candidate features with $^{18}O$ labelling were selected based on observed fractional labelling in three replicates being greater than the natural abundance of one, two or three $^{18}O$ atoms for a given metabolite. For example, for the incorporation of one $^{18}O$, the fractional labelling cut-off was set to 0.25% fractional labelling to exceed the natural abundance of a single $^{18}O$ atom, which was 0.2%. In addition, the observed $^{18}O$ fractional labelling in the $^{18}O_2$ samples had to be two times higher than in the $^{16}O_2$ samples. The features list was manually curated by checking the peak shape and retention time of unlabelled and $^{18}O$ labelled features. Unique $^{18}O$ labelled features were manually annotated using MS2 fragmentation analysis, NIST database searching, and retention time matching with standards. A second set of $^{18}O_2$ labelling experiments was carried out to identify overlapping and high confidence $^{18}O$ labelled metabolites. A comprehensive list of 46 $^{18}O$-labelled metabolites was generated from these two datasets.

All metabolites were normalized to the closest labelled amino acid standard and to the respective fold difference in cell number of the samples per experiment.

For measurement of oxygen consumption in spheroids, oxygen consumption rate (OCR) was measured with an XF96 analyzer (Seahorse Bioscience) and the Seahorse XFe96 Spheroid FluxPak, as described by the manufacturer's protocol. Spheroids were generated by seeding 40,000 cells per well into a low-attachment U-bottom 96-well plate with DMEM+10% diaFBS and 5% Matrigel. If indicated, spheroids were treated with or without 1 mM 4-HMA or 4-HB for the duration of the assay. Spheroids were allowed to form for three days before measuring oxygen consumption measurement. Each spheroid was transferred to a Spheroid FluxPak plate containing DMEM (25 mM glucose, 4 mM glutamine, and without pyruvate, phenol red and bicarbonate), and allowed to equilibrate for 1 hr at 37° C., no $CO_2$. OCR measurements were normalized to size of the spheroid.

For mouse pancreas orthotopic xenografts, mice were 7-8 weeks old. Female immunocompromised athymic nude mice (CrTac:NCr-Foxnlnu) were orthotopically injected with tumor cells into the pancreas. Mice were anaesthetized with ketamine (120 mg/kg) and xylazine (10 mg/kg) before surgery. MIAPACA2 ($1\times10^4$) cells expressing control or HPDL sgRNA, with or without sgRNA-resistant codon-optimized HPDL (coHPDL) wild-type and catalytically impaired mutant were suspended in 20 uL of 50% growth factor-reduced Matrigel (BD Science), and injected into the pancreas. Mice were treated with buprenorphine every 12 hours after surgery for 48 hours. Mice were housed in a temperature controlled ABSL-2 facility with 12 hour day-night light cycles. Mice were cared for by the husbandry staff at NYULH DCM (division of comparative medicine), and diet and water were provided ad libitum.

For immunohistochemistry, paraffin sections were deparaffinized and antigens were unmasked with citrate (pH 6) and heat. Sections were treated with 3% hydrogen peroxide before being blocked with 1% goat serum in PBS. Samples that were unmasked with citrate buffer were stained with phospho-Histone H3, and cleaved caspase 3. Sections were then stained using a Vectastain anti-rabbit HRP kit (Vector Laboratories) and a DAB (3,3'-diaminobenzidine) peroxidase substrate kit (Vector Laboratories). Briefly, sections were then incubated with biotinylated anti-rabbit antibodies, then with streptavidin-HRP and developed with DAB. Slides were scanned and whole tissue staining was quantified by Aperio ImageScope software (Leica Biosystems) in non-necrotic areas.

For bioinformatics, The Cancer Genome Atlas (TCGA) PDAC dataset (RNA-seq and survival data) was obtained from cBioportal (TCGA, Firehose Legacy)[35,36]. For overall and progression-free survival, samples were grouped into HPDL high and low expressing tumors, using an expression cutoff of greater or less than the mean expression, respectively. Survival curves were compared using the Log-rank (Mantel-Cox) test.

For quantification and statistical analysis, sample sizes and statistical tests for each experiment were denoted in the figure legends. Each immunoblot was performed at least three times. All metabolomics data represented at least n=3 biological replicates for each group. The between-group variances were similar, and the data were normally distributed. All analyses and graphs were generated with GraphPad Prism 9. A p-value of <0.05 was considered significant. P values can be found in the figures. Venn diagrams were made using an online bioinformatics tool (bioinformatics.psb.ugent.be/webtools/Venn/).

REFERENCES

1. Tang, D., Kang, R., Berghe, T. V., Vandenabeele, P. & Kroemer, G. The molecular machinery of regulated cell death. Cell Res 29, 347-364, doi:10.1038/s41422-019-0164-5 (2019).

2. Hirsila, M., Koivunen, P., Gunzler, V., Kivirikko, K. I. & Myllyharju, J. Characterization of the human prolyl 4-hydroxylases that modify the hypoxia-inducible factor. J Biol Chem 278, 30772-30780, doi:10.1074/jbc.M304982200 (2003).
3. Masson, N. et al. Conserved N-terminal cysteine dioxygenases transduce responses to hypoxia in animals and plants. Science 365, 65-69, doi:10.1126/science.aaw0112 (2019).
4. Laukka, T. et al. Fumarate and Succinate Regulate Expression of Hypoxia-inducible Genes via TET Enzymes. J Biol Chem 291, 4256-4265, doi:10.1074/jbc.M115.688762 (2016).
5. Moran, G. R. 4-Hydroxyphenylpyruvate dioxygenase. Arch Biochem Biophys 433, 117-128, doi:10.1016/j.abb.2004.08.015 (2005).
6. Liu, X. et al. Acetate Production from Glucose and Coupling to Mitochondrial Metabolism in Mammals. Cell 175, 502-513 e513, doi:10.1016/j.cell.2018.08.040 (2018).
7. Ast, T. & Mootha, V. K. Oxygen and mammalian cell culture: are we repeating the experiment of Dr. Ox? Nature Metabolism 1, 858-860, doi:10.1038/s42255-019-0105-0 (2019).
8. Monfregola, J. et al. Functional analysis of TMLH variants and definition of domains required for catalytic activity and mitochondrial targeting. J Cell Physiol 204, 839-847, doi:10.1002/jcp.20332 (2005).
9. Deshpande, A. R., Wagenpfeil, K., Pochapsky, T. C., Petsko, G. A. & Ringe, D. Metal-Dependent Function of a Mammalian Acireductone Dioxygenase. Biochemistry 55, 1398-1407, doi:10.1021/acs.biochem.5b01319 (2016).
10. Drazic, A. & Winter, J. The physiological role of reversible methionine oxidation. Biochim Biophys Acta 1844, 1367-1382, doi:10.1016/j.bbapap.2014.01.001 (2014).
11. Choroba, O. W., Williams, D. H. & Spencer, J. B. Biosynthesis of the Vancomycin Group of Antibiotics: Involvement of an Unusual Dioxygenase in the Pathway to (S)-4-Hydroxyphenylglycine. Journal of the American Chemical Society 122, 5389-5390, doi:10.1021/ja000076v (2000).
12. Hubbard, B. K., Thomas, M. G. & Walsh, C. T. Biosynthesis of L-p-hydroxyphenylglycine, a non-proteinogenic amino acid constituent of peptide antibiotics. Chemistry & Biology 7, 931-942 (2000).
13. Lemberger, L., Klutch, A. & Kuntzman, R. THE METABOLISM OF TYRAMINE IN RABBITS. Journal of Pharmacology and Experimental Therapeutics 153, 183 (1966).
14. Lichter-Konecki, U., Hipke, C. M. & Konecki, D. S. Human phenylalanine hydroxylase gene expression in kidney and other nonhepatic tissues. Mol Genet Metab 67, 308-316, doi:10.1006/mgme.1999.2880 (1999).
15. Gunsior, M., Ravel, J., Challis, G. L. & Townsend, C. A. Engineering p-Hydroxyphenylpyruvate Dioxygenase to a p-Hydroxymandelate Synthase and Evidence for the Proposed Benzene Oxide Intermediate in Homogentisate Formation. Biochemistry 43, 663-674, doi:10.1021/bi035762w (2004).
16. O'Hare, H. M., Huang, F., Holding, A., Choroba, O. W. & Spencer, J. B. Conversion of hydroxyphenylpyruvate dioxygenases into hydroxymandelate synthases by directed evolution. FEBS Letters 580, 3445-3450, doi:10.1016/j.febslet.2006.05.018 (2006).
17. Gunsior, M. et al. The Biosynthetic Gene Cluster for a Monocyclic β-Lactam Antibiotic, Nocardicin A. Chemistry & Biology 11, 927-938, doi: doi.org/10.1016/j.chembiol.2004.04.012 (2004).
18. Bhat, S. G. & Vaidyanathan, C. S. Involvement of 4-hydroxymandelic acid in the degradation of mandelic acid by *Pseudomonas convexa*. J Bacteriol 127, 1108-1118 (1976).
19. Stefely, J. A. & Pagliarini, D. J. Biochemistry of Mitochondrial Coenzyme Q Biosynthesis. Trends Biochem Sci 42, 824-843, doi:10.1016/j.tibs.2017.06.008 (2017).
20. Lu, T.-T., Lee, S. J., Apfel, U.-P. & Lippard, S. J. Aging-Associated Enzyme Human Clock-1: Substrate-Mediated Reduction of the Diiron Center for 5-Demethoxyubiquinone Hydroxylation. Biochemistry 52, 2236-2244, doi:10.1021/bi301674p (2013).
21. Wang, Y. et al. The anti-neurodegeneration drug clioquinol inhibits the aging-associated protein CLK-1. J Biol Chem 284, 314-323, doi:10.1074/jbc.M807579200 (2009).
22. Payet, L.-A. et al. Mechanistic Details of Early Steps in Coenzyme Q Biosynthesis Pathway in Yeast. Cell Chemical Biology 23, 1241-1250, doi: doi.org/10.1016/j.chembiol.2016.08.008 (2016).
23. Stefely, J. A. et al. Mitochondrial protein functions elucidated by multi-omic mass spectrometry profiling. Nature Biotechnology 34, 1191-1197, doi:10.1038/nbt.3683 (2016).
24. Valera, M. J. et al. The Mandelate Pathway, an Alternative to the Phenylalanine Ammonia Lyase Pathway for the Synthesis of Benzenoids in Ascomycete Yeasts. Appl Environ Microbiol 86, doi:10.1128/AEM.00701-20 (2020).
25. Kaymak, I. et al. Mevalonate Pathway Provides Ubiquinone to Maintain Pyrimidine Synthesis and Survival in p53-Deficient Cancer Cells Exposed to Metabolic Stress. Cancer Res 80, 189-203, doi:10.1158/0008-5472.CAN-19-0650 (2020).
26. Kapalczynska, M. et al. 2D and 3D cell cultures—a comparison of different types of cancer cell cultures. Arch Med Sci 14, 910-919, doi:10.5114/aoms.2016.63743 (2018).
27. Doimo, M. et al. Genetics of coenzyme q10 deficiency. Mol Syndromol 5, 156-162, doi:10.1159/000362826 (2014).
28. Martinez-Reyes, I. et al. Mitochondrial ubiquinol oxidation is necessary for tumour growth. Nature 585, 288-292, doi:10.1038/s41586-020-2475-6 (2020).
29. Adhyaru, B. B. & Jacobson, T. A. Safety and efficacy of statin therapy. Nat Rev Cardiol 15, 757-769, doi:10.1038/s41569-018-0098-5 (2018).
30. Xie, L. X. et al. Resveratrol and para-coumarate serve as ring precursors for coenzyme Q biosynthesis. Journal of Lipid Research 56, 909-919, doi:10.1194/jlr.M057919 (2015).
31. Fernindez-del-Rio, L. et al. Kaempferol increases levels of coenzyme Q in kidney cells and serves as a biosynthetic ring precursor. Free Radical Biology and Medicine 110, 176-187, doi: doi.org/10.1016/j.freeradbiomed.2017.06.006 (2017).
32. Booth, A. N. et al. Urinary Phenolic Acid Metabolites of Tyrosine. Journal of Biological Chemistry 235, 2649-2652 (1960).
33. Uphoff, C. C. & Drexler, H. G. Detecting *mycoplasma* contamination in cell cultures by polymerase chain reaction. Methods Mol Biol 731, 93-103, doi:10.1007/978-1-61779-080-5_8 (2011).

34. Wenig, P. & Odermatt, J. OpenChrom: a cross-platform open source software for the mass spectrometric analysis of chromatographic data. BMC Bioinformatics 11, 405, doi:10.1186/1471-2105-11-405 (2010).

35. Gao, J. et al. Integrative analysis of complex cancer genomics and clinical profiles using the cBioPortal. Sci Signal 6, pl1, doi:10.1126/scisignal.2004088 (2013).

36. Cerami, E. et al. The cBio cancer genomics portal: an open platform for exploring multidimensional cancer genomics data. Cancer Discov 2, 401-404, doi:10.1158/2159-8290.CD-12-0095 (2012).

37. Ghosh, S. G. et al. Biallelic variants in HPDL, encoding 4-hydroxyphenylpyruvate dioxygenase-like protein, lead to an infantile neurodegenerative condition. Genet Med 23, 524-533, doi:10.1038/s41436-020-01010-y (2021).

38. Morgan, N. V. et al. Evidence that autosomal recessive spastic cerebral palsy-1 (CPSQ1) is caused by a missense variant in HPDL. Brain Commun 3, fcab002, doi:10.1093/braincomms/fcab002 (2021).

39. Husain, R. A. et al. Bi-allelic HPDL Variants Cause a Neurodegenerative Disease Ranging from Neonatal Encephalopathy to Adolescent-Onset Spastic Paraplegia. *Am J Hum Genet* 107, 364-373, doi:10.1016/j.ajhg.2020.06.015 (2020).

40. Wiessner M, Maroofian R, Ni M-Y, Pedroni A, Müller J S, Stucka R, et al. Biallelic variants in HPDL cause pure and complicated hereditary spastic paraplegia. Brain. 2021 May 10.

41. Hernández-Camacho J D, Bernier M, López-Lluch G, Navas P, et al. Coenzyme Q 10 Supplementation in Aging and Disease. Front Physiol. 2018 Feb. 5; 9:44.

42. Doimo M, Desbats M A, Cerqua C, Cassina M, Trevisson E, Salviati L. Genetics of coenzyme q10 deficiency. Mol Syndromol. 2014 July; 5(3-4):156-62.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A method of treating a 4-hydroxyphenylpyruvate dioxygenase-like (HPDL)-related disease or disorder in a subject in need thereof, comprising administering to the subject a therapeutically effective amount of 4-hydroxymandelic acid (4-HMA), or a metabolite, pharmaceutically acceptable salt, prodrug, solvate, hydrate, or combinations thereof.

2. The method of claim 1, wherein the metabolite is 4-hydroxybenzoylformate (4-HBF), 4-hydroxybenzaldehyde (4-HBz), 4-hydroxybenzoate (4-HB), and/or CoQ10.

3. The method of any one of claim 1, wherein the 4-HMA is enantioentriched (R)-4-HMA.

4. The method of claim 3, wherein the enantioentriched (R)-4-HMA has enantiomeric excess (ee) of at least about 20%, or at least about 30%, or at least about 40%, or at least about 50%, or at least about 60%, or at least about 70%, or at least about 80%, or at least about 85%, or at least about 90%, or at least about 95%, or at least about 98%, or at least about 99%.

5. The method of any one of claim 1, wherein the 4-HMA is enantiopure (R)-4-HMA.

6. A method of treating a 4-hydroxyphenylpyruvate dioxygenase-like (HPDL)-related disease or disorder in a subject in need thereof, comprising administering to the subject a therapeutically effective amount of an activator of HPDL.

7. The method of claim 6, wherein the activator of HPDL is vitamin C, or a pharmaceutically acceptable salt, prodrug, solvate, or hydrate thereof.

8. A method of determining whether a subject will benefit from a treatment with 4-hydroxymandelic acid (4-HMA), or a metabolite, pharmaceutically acceptable salt, prodrug, solvate, hydrate, or combinations thereof, comprising:

a. detecting the presence of one or more mutations in the HPDL gene and/or additional gene(s) involved in CoQ10 headgroup synthesis in a biological sample obtained from the subject, wherein the one or more mutations result in reduced or abolished activity and/or expression of the protein(s) produced by said gene(s);

b. (i) determining that the subject will benefit from said treatment, when the one or more mutations are present in the HPDL gene and/or additional gene(s) involved in CoQ10 headgroup synthesis; or (ii) determining that the subject will not benefit from said treatment, when the one or more mutations are absent in the HPDL gene and/or additional gene(s) involved in CoQ10 headgroup synthesis.

9. A method of treating a 4-hydroxyphenylpyruvate dioxygenase-like (HPDL)-related disease or disorder in a subject in need thereof, comprising:

a. detecting the presence of one or more mutations in the HPDL gene and/or additional gene(s) involved in CoQ10 headgroup synthesis in a biological sample obtained from the subject, wherein the one or more mutations result in reduced or abolished activity and/or expression of the protein(s) produced by said gene(s); and b. (i) when the one or more mutations are present in the HPDL gene and/or additional gene(s) involved in CoQ10 headgroup synthesis, administering to the subject a therapeutically effective amount of 4-hydroxymandelic acid (4-HMA), or a metabolite, pharmaceutically acceptable salt, prodrug, solvate, hydrate, or combinations thereof; or (ii) when the one or more mutations are absent in the HPDL gene and/or additional gene(s) involved in CoQ10 headgroup synthesis, not administering 4-hydroxymandelic acid (4-HMA), or a metabolite, pharmaceutically acceptable salt, prodrug, solvate, hydrate, or combinations thereof, to the subject.

10. The method of claim 8, wherein the metabolite is 4-hydroxybenzoylformate (4-HBF), 4-hydroxybenzaldehyde (4-HBz), 4-hydroxybenzoate (4-HB), and/or CoQ10.

11. A method of treating a 4-hydroxyphenylpyruvate dioxygenase-like (HPDL)-related disease or disorder in a subject in need thereof, comprising a. detecting the presence of one or more mutations in the HPDL gene and/or additional gene(s) involved in CoQ10 headgroup synthesis in a biological sample obtained from the subject, wherein the one or more mutations result in reduced or abolished activity and/or expression of the protein(s) produced by said gene(s); and b. (i) when the one or more mutations are present in the HPDL gene and/or additional gene(s) involved in CoQ10 headgroup synthesis, administering to the subject a therapeutically effective amount of an activator of HPDL; or (ii) when the one or more mutations are absent in the HPDL gene and/or additional gene(s) involved in CoQ10 headgroup synthesis, not administering the activator of HPDL to the subject.

12. The method of claim 11, wherein the activator of HPDL is vitamin C, or a pharmaceutically acceptable salt, prodrug, solvate, or hydrate thereof.

13. A method of inhibiting expression of 4-hydroxyphenylpyruvate dioxygenase-like (HPDL) in a subject in need thereof, comprising administering to the subject a therapeutically effective amount of(S)-4-HMA, or a metabolite, pharmaceutically acceptable salt, prodrug, solvate, hydrate, or combinations thereof.

14. The method of claim 9, wherein the metabolite is 4-hydroxybenzoylformate (4-HBF), 4-hydroxybenzaldehyde (4-HBz), 4-hydroxybenzoate (4-HB), and/or CoQ10.

* * * * *

SEQUENCE LISTING

```
<160> NUMBER OF SEQ ID NOS: 26

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

caccgggcca cgagttcgag atcga                                            25


<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

aaactcgatc tcgaactcgt ggccc                                            25


<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

caccgacaac tttaccgacc gcgcc                                            25


<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 4
aaacggcgcg gtcggtaaag ttgtc 25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
caccggactc agccagaaca agagt 25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
aaacactctt gttctggctg agtcc 25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
caccggtgga accagcgcaa aagtg 25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
aaaccacttt tgcgctggtt ccacc 25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
caccgtggcc aacacagcta aacaa 25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
aaacttgttt agctgtgttg gccac 25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11
caccgggcca caccacagca tcagg 25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
aaaccctgat gctgtggtgt ggccc 25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
caccgggaca acgtgctcaa cctgg 25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14
aaacccaggt tgagcacgtt gtccc 25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
caccggaagc tccctgagtg ggccg 25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16

-continued aaaccggccc actcagggag cttcc 25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
caccgggtgg ggaagatcat catga 25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
aaactcatga tgatcttccc caccc 25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
caccgggggc tgcaagtcac caccg 25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
aaaccggtgg tgacttgcag ccccc 25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
caccgccagc tcagtttgtc cgcgg 25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
aaacccgcgg acaaactgag ctggc 25

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
tgggccagca ttgtccccac tcttgttctg gctgagtc 38

<210> SEQ ID NO 24
<211> LENGTH: 393
<212> TYPE: PRT
<213> ORGANISM: Homo sapiens

<400> SEQUENCE: 24

Met Thr Thr Tyr Ser Asp Lys Gly Ala Lys Pro Glu Arg Gly Arg Phe
1 5 10 15

Leu His Phe His Ser Val Thr Phe Trp Val Gly Asn Ala Lys Gln Ala
20 25 30

Ala Ser Phe Tyr Cys Ser Lys Met Gly Phe Glu Pro Leu Ala Tyr Arg
35 40 45

Gly Leu Glu Thr Gly Ser Arg Glu Val Val Ser His Val Ile Lys Gln
50 55 60

Gly Lys Ile Val Phe Val Leu Ser Ser Ala Leu Asn Pro Trp Asn Lys
65 70 75 80

Glu Met Gly Asp His Leu Val Lys His Gly Asp Gly Val Lys Asp Ile
85 90 95

Ala Phe Glu Val Glu Asp Cys Asp Tyr Ile Val Gln Lys Ala Arg Glu
100 105 110

Arg Gly Ala Lys Ile Met Arg Glu Pro Trp Val Glu Gln Asp Lys Phe
115 120 125

Gly Lys Val Lys Phe Ala Val Leu Gln Thr Tyr Gly Asp Thr Thr His
130 135 140

Thr Leu Val Glu Lys Met Asn Tyr Ile Gly Gln Phe Leu Pro Gly Tyr
145 150 155 160

Glu Ala Pro Ala Phe Met Asp Pro Leu Leu Pro Lys Leu Pro Lys Cys
165 170 175

Ser Leu Glu Met Ile Asp His Ile Val Gly Asn Gln Pro Asp Gln Glu
180 185 190

Met Val Ser Ala Ser Glu Trp Tyr Leu Lys Asn Leu Gln Phe His Arg
195 200 205

Phe Trp Ser Val Asp Asp Thr Gln Val His Thr Glu Tyr Ser Ser Leu
210 215 220

Arg Ser Ile Val Val Ala Asn Tyr Glu Glu Ser Ile Lys Met Pro Ile
225 230 235 240

Asn Glu Pro Ala Pro Gly Lys Lys Lys Ser Gln Ile Gln Glu Tyr Val
245 250 255

Asp Tyr Asn Gly Gly Ala Gly Val Gln His Ile Ala Leu Lys Thr Glu
260 265 270

Asp Ile Ile Thr Ala Ile Arg His Leu Arg Glu Arg Gly Leu Glu Phe
275 280 285

Leu Ser Val Pro Ser Thr Tyr Tyr Lys Gln Leu Arg Glu Lys Leu Lys
290 295 300

-continued

```
Thr Ala Lys Ile Lys Val Lys Glu Asn Ile Asp Ala Leu Glu Glu Leu
305                 310                 315                 320

Lys Ile Leu Val Asp Tyr Asp Glu Lys Gly Tyr Leu Leu Gln Ile Phe
                325                 330                 335

Thr Lys Pro Val Gln Asp Arg Pro Thr Leu Phe Leu Glu Val Ile Gln
            340                 345                 350

Arg His Asn His Gln Gly Phe Gly Ala Gly Asn Phe Asn Ser Leu Phe
        355                 360                 365

Lys Ala Phe Glu Glu Glu Gln Asn Leu Arg Gly Asn Leu Thr Asn Met
    370                 375                 380

Glu Thr Asn Gly Val Val Pro Gly Met
385                 390


<210> SEQ ID NO 25
<211> LENGTH: 357
<212> TYPE: PRT
<213> ORGANISM: Amycolatopsis orientalis

<400> SEQUENCE: 25

Met Gln Asn Phe Glu Ile Asp Tyr Val Glu Met Tyr Val Glu Asn Leu
1               5                   10                  15

Glu Val Ala Ala Phe Ser Trp Val Asp Lys Tyr Ala Phe Ala Val Ala
            20                  25                  30

Gly Thr Ser Arg Ser Ala Asp His Arg Ser Ile Ala Leu Arg Gln Gly
        35                  40                  45

Gln Val Thr Leu Val Leu Thr Glu Pro Thr Ser Asp Arg His Pro Ala
    50                  55                  60

Ala Ala Tyr Leu Gln Thr His Gly Asp Gly Val Ala Asp Ile Ala Met
65                  70                  75                  80

Ala Thr Ser Asp Val Ala Ala Ala Tyr Glu Ala Ala Val Arg Ala Gly
                85                  90                  95

Ala Glu Ala Val Arg Ala Pro Gly Gln His Ser Glu Ala Ala Val Thr
            100                 105                 110

Thr Ala Thr Ile Gly Gly Phe Gly Asp Val Val His Thr Leu Ile Gln
        115                 120                 125

Arg Asp Gly Thr Ser Ala Glu Leu Pro Pro Gly Phe Thr Gly Ser Met
    130                 135                 140

Asp Val Thr Asn His Gly Lys Gly Asp Val Asp Leu Leu Gly Ile Asp
145                 150                 155                 160

His Phe Ala Ile Cys Leu Asn Ala Gly Asp Leu Gly Pro Thr Val Glu
                165                 170                 175

Tyr Tyr Glu Arg Ala Leu Gly Phe Arg Gln Ile Phe Asp Glu His Ile
            180                 185                 190

Val Val Gly Ala Gln Ala Met Asn Ser Thr Val Val Gln Ser Ala Ser
        195                 200                 205

Gly Ala Val Thr Leu Thr Leu Ile Glu Pro Asp Arg Asn Ala Asp Pro
    210                 215                 220

Gly Gln Ile Asp Glu Phe Leu Lys Asp His Gln Gly Ala Gly Val Gln
225                 230                 235                 240

His Ile Ala Phe Asn Ser Asn Asp Ala Val Arg Ala Val Lys Ala Leu
                245                 250                 255

Ser Glu Arg Gly Val Glu Phe Leu Lys Thr Pro Gly Ala Tyr Tyr Asp
            260                 265                 270

Leu Leu Gly Glu Arg Ile Thr Leu Gln Thr His Ser Leu Asp Asp Leu
        275                 280                 285
```

```
Arg Ala Thr Asn Val Leu Ala Asp Glu Asp His Gly Gly Gln Leu Phe
    290                 295                 300

Gln Ile Phe Thr Ala Ser Thr His Pro Arg His Thr Ile Phe Phe Glu
305                 310                 315                 320

Val Ile Glu Arg Gln Gly Ala Gly Thr Phe Gly Ser Ser Asn Ile Lys
                325                 330                 335

Ala Leu Tyr Glu Ala Val Glu Leu Glu Arg Thr Gly Gln Ser Glu Phe
            340                 345                 350

Gly Ala Ala Arg Arg
        355


<210> SEQ ID NO 26
<211> LENGTH: 371
<212> TYPE: PRT
<213> ORGANISM: Homo sapiens

<400> SEQUENCE: 26

Met Ala Ala Pro Ala Leu Arg Leu Cys His Ile Ala Phe His Val Pro
1               5                   10                  15

Ala Gly Gln Pro Leu Ala Arg Asn Leu Gln Arg Leu Phe Gly Phe Gln
            20                  25                  30

Pro Leu Ala Ser Arg Glu Val Asp Gly Trp Arg Gln Leu Ala Leu Arg
        35                  40                  45

Ser Gly Asp Ala Val Phe Leu Val Asn Glu Gly Ala Gly Ser Gly Glu
    50                  55                  60

Pro Leu Tyr Gly Leu Asp Pro Arg His Ala Val Pro Ser Ala Thr Asn
65                  70                  75                  80

Leu Cys Phe Asp Val Ala Asp Ala Gly Ala Ala Thr Arg Glu Leu Ala
                85                  90                  95

Ala Leu Gly Cys Ser Val Pro Val Pro Pro Val Arg Val Arg Asp Ala
            100                 105                 110

Gln Gly Ala Ala Thr Tyr Ala Val Val Ser Ser Pro Ala Gly Ile Leu
        115                 120                 125

Ser Leu Thr Leu Leu Glu Arg Ala Gly Tyr Arg Gly Pro Phe Leu Pro
    130                 135                 140

Gly Phe Arg Pro Val Ser Ser Ala Pro Gly Pro Gly Trp Val Ser Arg
145                 150                 155                 160

Val Asp His Leu Thr Leu Ala Cys Thr Pro Gly Ser Ser Pro Thr Leu
                165                 170                 175

Leu Arg Trp Phe His Asp Cys Leu Gly Phe Cys His Leu Pro Leu Ser
            180                 185                 190

Pro Gly Glu Asp Pro Glu Leu Gly Leu Glu Met Thr Ala Gly Phe Gly
        195                 200                 205

Leu Gly Gly Leu Arg Leu Thr Ala Leu Gln Ala Gln Pro Gly Ser Ile
    210                 215                 220

Val Pro Thr Leu Val Leu Ala Glu Ser Leu Pro Gly Ala Thr Thr Arg
225                 230                 235                 240

Gln Asp Gln Val Glu Gln Phe Leu Ala Arg His Lys Gly Pro Gly Leu
                245                 250                 255

Gln His Val Gly Leu Tyr Thr Pro Asn Ile Val Glu Ala Thr Glu Gly
            260                 265                 270

Val Ala Thr Ala Gly Gly Gln Phe Leu Ala Pro Pro Gly Ala Tyr Tyr
        275                 280                 285

Gln Gln Pro Gly Lys Glu Arg Gln Ile Arg Ala Ala Gly His Glu Pro
```

-continued

```
    290                 295                 300

His Leu Leu Ala Arg Gln Gly Ile Leu Leu Asp Gly Asp Lys Gly Lys
305                 310                 315                 320

Phe Leu Leu Gln Val Phe Thr Lys Ser Leu Phe Thr Glu Asp Thr Phe
                325                 330                 335

Phe Leu Glu Leu Ile Gln Arg Gln Gly Ala Thr Gly Phe Gly Gln Gly
            340                 345                 350

Asn Ile Arg Ala Leu Trp Gln Ser Val Gln Glu Gln Ser Ala Arg Ser
        355                 360                 365

Gln Glu Ala
    370
```